(12) United States Patent
Wang et al.

(10) Patent No.: US 6,897,275 B2
(45) Date of Patent: May 24, 2005

(54) CATALYSTS FOR OLEFIN POLYMERIZATION

(75) Inventors: Lin Wang, Hockessin, DE (US); Elisabeth Hauptman, Wilmington, DE (US); Lynda Kaye Johnson, Wilmington, DE (US); Elizabeth Forrester McCord, Hockessin, DE (US); Ying Wang, West Chester, PA (US); Steven Dale Ittel, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 195 days.

(21) Appl. No.: 09/871,099

(22) Filed: May 31, 2001

(65) Prior Publication Data

US 2002/0032289 A1 Mar. 14, 2002

Related U.S. Application Data

(60) Provisional application No. 60/264,537, filed on Jan. 26, 2001, provisional application No. 60/214,036, filed on Jun. 23, 2000, provisional application No. 60/211,601, filed on Jun. 15, 2000, and provisional application No. 60/208,087, filed on May 31, 2000.

(51) Int. Cl.$^7$ .............................. C08F 4/60; C08F 4/70; C08F 4/76
(52) U.S. Cl. .................... 526/161; 526/169; 526/169.1; 526/171; 526/172; 502/155; 502/208; 502/213; 502/162
(58) Field of Search ................................ 526/161, 172, 526/169, 169.1, 171

(56) References Cited

U.S. PATENT DOCUMENTS

| | | | |
|---|---|---|---|
| 3,278,495 A | | 10/1966 | Hagel et al. |
| 3,481,908 A | | 12/1969 | Mortimer |
| 5,714,556 A | | 2/1998 | Johnson et al. |
| 5,866,663 A | | 2/1999 | Brookhart et al. |
| 6,060,569 A | * | 5/2000 | Bennett et al. ............. 526/172 |
| 6,127,497 A | | 10/2000 | Matsunaga et al. |
| 6,174,975 B1 | | 1/2001 | Johnson et al. |

FOREIGN PATENT DOCUMENTS

| | | |
|---|---|---|
| JP | 99292918 A | 10/1999 |
| WO | WO 98/30609 A1 | 7/1998 |
| WO | WO 00/50470 A2 | 8/2000 |

OTHER PUBLICATIONS

Hitchcock, Peter B. et al, Use of a Highly Hindered Phosphino–alkoxide Ligand in the Formation of Monomeric Homoleptic Lanthanoid Metal Complexes: X–Ray Structures of [Ln(OCBu$^t{}_2$CH$_2$Pme$_2$)$_3$], J. Chem Soc., Chem. Commun., 1988, p. 1557–1558.

Klabunde, Ulrich et al., Nickel catalysts for ethylene homo–and co–polymerization, Journal of Molecular Catalysis, 1987, pp. 123–134, vol. 41, Elsevier Sequoia/Printed in The Netherlands.

Muller, Ulrich et al., [{Ph$_2$PCH$_2$C(CF$_3$)$_2$O}NiH(Pcy$_3$)]: Support for a Nickel Hydride Mechanism in Ethene Oligomerization, Angew. Chem. Int. Ed. Engl., 1989, pp. 1011–1013, vol. 28.

Ostoja Starzewski, K. Alexander et al., Control of the molecular weight of polyethene in syntheses with bis(ylide)nickel catalysts, Angew. Chem. Int. Ed. Engl., 1987, pp. 63–64, vol. 26.

Keim, Wilhelm et al., Novel nickel–oligomerization catalysts with arsenic–oxygen chelate ligands, Angew. Chem. Int. Ed. Engl., 1983, p. 503, vol. 22, Braunstein, Pierre et al., Phenyl nickel complexes with a chelating P,N ligand. Structures of Ph3P=CHC(=NPh)Ph and [NiPh Ph2PCH=C(=NPh)Ph)–{Ph$_3$P=CHC(=NPh-)Ph–N}], J. Chem. Soc., Dalton Trans., 1996, pp. 3571–3574.

Ittel, Steven D. et al., Late–metal catalysts for ethylene homo– and copolymerization, Chem. Rev., 2000, pp. 1169–1203, vol. 100, published on web Mar. 25, 2000.

Michalak, Arthur et al., DFT studies on the copolymerization of alpha–olefins with polar monomers: comonomer binding by nickel– and palladium–based catalysts with Brookhart and Grubbs ligand, American Chemical Society, 2001, pp. 1521–1532, vol. 20 published on web Mar. 16, 2001.

Peuckert, Marcell et al., A new nickel complex for the oligomeriztion of ethylene, Organometallics, 1983, pp. 594–597, vol. 2.

Hirose, Keiji et al., Olefin oligomerizaztion with nickel P O chelate complexes, Journal of Molecular Catalysis, 1992, pp. 271–276, vol. 73.

Soula, R. et al., Very active neutral P, O–chelated nickel catalysts for ethylene polymerization, Macromolecules, 2001, pp. 2438–2442, vol. 34, published on web Mar. 16, 2001.

Marques, Maria M. et al., Synthesis of polar vinyl monomer–olefin copolymers by alpha–diimine nickel catalyst, Polymer International, 2001, pp. 579–587, vol. 50.

* cited by examiner

Primary Examiner—Roberto Rabago

(57) ABSTRACT

Transition metal complexes of selected monoanionic phosphine ligands, which also contain a selected Group 15 or 16 (IUPAC) element and which are coordinated to a Group 3 to 11 (IUPAC) transition metal or a lanthanide metal, are polymerization catalysts for the (co)polymerization of olefins such as ethylene and α–olefins, and the copolymerization of such olefins with polar group-containing olefins. These and other nickel complexes of neutral and monoanionic bidentate ligands copolymerize ethylene and polar comonomers, especially acrylates, at relatively high ethylene pressures and surprisingly high temperatures, and give good incorporation of the polar comonomers and good polymer productivity. These copolymers are often unique structures, which are described.

8 Claims, 3 Drawing Sheets

CATALYSTS FOR OLEFIN POLYMERIZATION

CROSS-REFERENCE TO RELATED APPLICATION

This application claims priority under 35 U.S.C. §119 from U.S. Provisional Application Ser. Nos. 60/208,087 (filed May 31, 2000), 60/211,601 (filed Jun. 15, 2000), 60/214,036 (filed Jun. 23, 2000) and 60/264,537 (filed Jan. 26, 2001), all of which are incorporated by reference herein as if fully set forth.

FIELD OF THE INVENTION

Transition metal complexes of selected monoanionic phosphine ligands, which also contain a selected Group 15 or 16 (IUPAC) element and which are coordinated to a Group 3 to 11 (IUPAC) transition metal or a lanthanide metal, are polymerization catalysts for the (co)polymerization of olefins such as ethylene and α-olefins, and the copolymerization of such olefins with polar group-containing olefins. In general, nickel complexes of neutral and monoanionic bidentate ligands copolymerize ethylene and polar comonomers at relatively high ethylene pressures and surprisingly high temperatures.

TECHNICAL BACKGROUND

Polyolefins are very important items of commerce, large quantities of various grades of these polymers being produced annually for a large number of uses, such as packaging films, elastomers and moldings. There are many different methods for making such polymers, including many used commercially, such as free radical polymerization, and many so-called coordination catalysts such as Ziegler-Natta-type and metallocene-type catalysts. Each of these catalyst systems has its advantages and disadvantages, including cost of the polymerization and the particular monomers (co)polymerized, and structure of the polyolefin produced. Due to the importance of polyolefins, new catalyst systems which are economical and/or produce new types of polyolefins are constantly being sought.

U. Klabunde, et al., *J. Mol. Cat.*, vol. 41, p. 123–134 (1987) describes the polymerization of ethylene with nickel complex catalysts having certain phosphorous-oxygen ligands. The catalysts and processes of this reference are different than those of the present invention.

U. Muller, et al., *Angew. Chem. Int. Ed. Eng.*, vol. 28, p. 1011–1013 report on the interaction of Ni(COD)$_2$ (COD is cyclooctadiene), ethylene and a phosphorous-oxygen compound which may be a ligand. There is no evidence for polymerization.

K. A. Ostoja Starzewski, et al., *Angew. Chem., Intl. Ed. Engl.*, vol. 26, p. 63 (1987) report on the polymerization of ethylene using certain phosphorous-oxygen ylides and Ni(COD)$_2$. Ylides are not used herein.

W. Keim, *Angew. Chem. Int. Ed. Engl.*, vol. 22, p. 503 (1983) reports the use of nickel complexes of certainarsenic-oxygen compounds to oligomerize ethylene. Higher molecular weight polymers are not reported.

P. Braunstein, et al., *J. Chem. Soc., Dalton Trans.*, 1996, p. 3571–3574 report that nickel complexes of certain phosphorous-nitrogen compounds oligomerize ethylene to low molecular weight olefins. Higher molecular weight polymers are not reported.

U.S. Pat. No. 5,714,556, U.S. Pat. No. 6,060,569, U.S. Pat. No. 6,174,975 and S. D. Ittel, et al., *Chem. Rev.*, vol. 100, p. 1169–1203 (2000) (and references therein), report the use of transition metal complexes of various phosphorous-containing ligands as catalysts for olefin polymerizations. The catalysts and processes of these references are different than those of the present invention.

One of the advantages of some late transition metal catalysts is that they can incorporate polar comonomers, for example olefinic esters, in copolymerizations with hydrocarbon olefins, especially ethylene. Palladium complexes are particularly noted for this ability, while nickel complexes often do not copolymerize polar comonomers or do so only very poorly, see for example U.S. Pat. No. 5,866,663.

It has also been discovered that using relatively high temperatures and high hydrocarbon olefin (ethylene) pressures often improves the incorporation of the polar comonomer in the polymer formed as well as increasing the productivity of the polymerization catalyst. This is surprising in view of the observations in the literature that increasing temperatures usually decrease the productivity of many nickel polymerization catalysts, see for instance U.S. Pat. No. 6,127,497 and WO00/50470.

JP-A-11292918 reports the copolymerization of methyl acrylate and ethylene using certain nickel complexes as polymerization catalysts. These polymerization are carried out at low temperatures and pressures, and mostly the incorporation of methyl acrylate is reported to be very low, and the polymers have low branching levels.

A. Michalak, et al., *Organometallics*, vol. 20, p. 1521–1532 (2001) conclude that, using computational methods, nickel complexes having neutral bidentate ligands such as α-diimines should not copolymerize ethylene and polar comonomers such as methyl acrylate.

Other references of interest concerning transition metal complexes and/or their use as polymerization catalysts are Keim, *Organometallics*, vol. 2, p. 594 (1983); I. Hirose, et al., *J. Mol. Cat.*, vol. 73, p. 271 (1992); and R. Soula, et al., *Macromolecules*, vol. 34, p. 2438–2442. None of the complexes or processes with them are claimed herein.

Other references of interest concerning polar copolymers include U.S. Pat. No. 3,481,908, U.S. Pat. No. 3,278,495 and M. M. Marques, et al., *Poly. Int.*, 50, 579–587 (2001).

All of the above publications are incorporated by reference herein for all purposes as if fully set forth.

SUMMARY OF THE INVENTION

This invention concerns a "first" process for the polymerization of olefins, comprising the step of contacting, at a temperature of about −100° C. to about +200° C., at least one polymerizable olefin with an active polymerization catalyst comprising a Group 3 through 11 (IUPAC) transition metal or a lanthanide metal complex of a ligand of the formula (I), (II) or (XII)

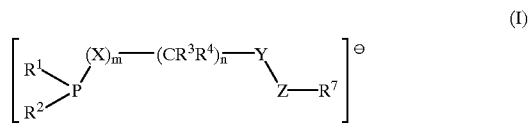

-continued

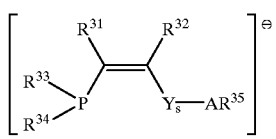

wherein:
- $R^1$ and $R^2$ are each independently hydrocarbyl, substituted hydrocarbyl or a functional group;
- Y is $CR^{11}R^{12}$, S(T), $S(T)_2$, P(T)Q, $NR^{36}$ or $NR^{36}NR^{36}$;
- X is O, $CR^5R^6$ or $NR^5$;
- A is O, S, Se, N, P or As;
- Z is O, Se, N, P or As;
- each Q is independently hydrocarbyl or substituted hydrocarbyl;
- $R^3$, $R^4$, $R^5$, $R^6$, $R^{11}$ and $R^{12}$ are each independently hydrogen, hydrocarbyl, substituted hydrocarbyl or a functional group;
- $R^7$ is hydrogen, hydrocarbyl, substituted hydrocarbyl or a functional group, provided that when Z is O or Se, $R^7$ is not present;
- $R^8$ and $R^9$ are each independently hydrogen, hydrocarbyl, substituted hydrocarbyl or a functional group;
- $R^{10}$ is hydrogen, hydrocarbyl, substituted hydrocarbyl or a functional group;
- each T is independently =O or $=NR^{30}$;
- $R^{30}$ is hydrogen, hydrocarbyl, substituted hydrocarbyl or a functional group;
- $R^{31}$ and $R^{32}$ are each independently hydrogen, hydrocarbyl, substituted hydrocarbyl or a functional group;
- $R^{33}$ and $R^{34}$ are each independently hydrocarbyl or substituted hydrocarbyl, provided that each is independently an aryl substituted in at least one position vicinal to the free bond of the aryl group, or each independently has an $E_s$ of $-1.0$ or less;
- $R^{35}$ is hydrogen, hydrocarbyl, substituted hydrocarbyl or a functional group, provided that when A is O, S or Se, $R^{35}$ is not present;
- each $R^{36}$ is independently hydrogen, hydrocarbyl, substituted hydrocarbyl or a functional group;
- m is 0 or 1;
- s is 0 or 1;
- n is 0 or 1; and
- q is 0 or 1;

and provided that:
- any two of $R^3$, $R^4$, $R^5$, $R^6$, $R^8$, $R^9$, $R^{11}$ and $R^{12}$ bonded to the same carbon atom taken together may form a functional group;
- any two of $R^1$, $R^2$, $R^3$, $R^4$, $R^5$, $R^6$, $R^7$, $R^8$, $R^9$, $R^{11}$, $R^{12}$, $R^{31}$, $R^{32}$, $R^{33}$, $R^{34}$, $R^{35}$ and $R^{36}$ bonded to the same atom or vicinal to one another taken together may form a ring; and
- when said ligand is (I), Y is C(O), Z is O, and $R^1$ and $R^2$ are each independently hydrocarbyl, then $R^1$ and $R^2$ are each independently an aryl substituted in one position vicinal to the free bond of the aryl group, or $R^1$ and $R^2$ each independently have an $E_s$ of $-1.0$ or less.

Also described herein is a "second" process for the polymerization of olefins, comprising the step of contacting, at a temperature of about $-100°$ C. to about $+200°$ C., at least one polymerizable olefin with a compound of the formula (IV), (V) or (XIII)

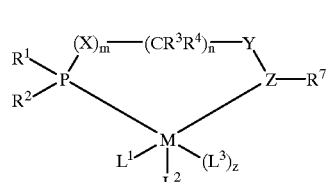

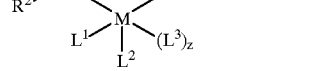

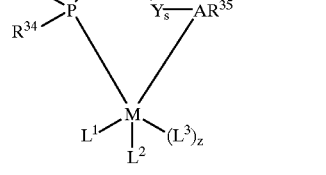

wherein $R^1$, $R^2$, $R^3$, $R^4$, $R^5$, $R^6$, $R^7$, $R^8$, $R^9$, $R^{10}$, $R^{11}$, $R^{12}$, $R^{30}$, $R^{31}$, $R^{32}$, $R^{33}$ $R^{34}$, $R^{35}$, $R^{36}$, Y, X, A, Z, Q, T, m, s, n and q are as defined above;

M is a Group 3 through Group 11 transition metal or a lanthanide metal; and $L^1$ is a monodentate monoanionic ligand into which an ethylene molecule may insert between $L^1$ and M, and $L^2$ is a monodentate neutral ligand which may be displaced by ethylene or an empty coordination site, or $L^1$ and $L^2$ taken together are a monoanionic bidentate ligand into which ethylene may insert between said monoanionic bidentate ligand and said nickel atom, and each $L^3$ is independently a monoanionic ligand and z is the oxidation state of M minus 2;

and provided that;
- any two of $R^3$, $R^4$, $R^5$, $R^6$, $R^8$, $R^9$, $R^{11}$ and $R^{12}$ bonded to the same carbon atom taken together may form a functional group;
- any two of $R^1$, $R^2$, $R^3$, $R^4$, $R^5$, $R^6$, $R^7$, $R^8$, $R^9$, $R^{11}$, $R^{12}$, $R^{31}$, $R^{32}$, $R^{33}$, $R^{34}$, $R^{35}$ and $R^{36}$ bonded to the same atom or vicinal to one another taken together may form a ring; and
- when said compound is (IV), Y is C(O), Z is O, and $R^1$ and $R^2$ are each independently hydrocarbyl, then $R^1$ and $R^2$ are each independently an aryl substituted in one position vicinal to the free bond of the aryl group, or $R^1$ and $R^2$ each independently have an $E_s$ of $-1.0$ or less.

In the above-mentioned processes, (IV), (V) and (XIII) and/or the transition metal complexes of (I), (II) or (XII) may in and of themselves be active catalysts, or may be "activated" by contact with a cocatalyst/activator as further described below.

The present invention also concerns the ligands of the formulas (I), (II) and (XII) above, transition metal complexes thereof, and polymerization catalyst components comprising these transition metal complexes.

Also disclosed herein is a "third" process for forming an ethylene/polar monomer copolymer, comprising the step of contacting, under polymerizing conditions, a nickel complex of a bidentate neutral ligand or a bidentate monoanionic ligand, with a monomer component comprising one or more hydrocarbon olefins and one or more polar comonomers (and other optional components such as, for example, one or more cocatalysts and/or other additives), at a temperature of about 60° C. to about 170° C., provided that when CO is present, at least one other polar monomer is present.

This third process also relates to an improved process for forming an ethylene/polar monomer copolymer, said process comprising the step of contacting, under polymerizing conditions, a transition metal complex of a bidentate neutral ligand or a bidentate monoanionic ligand, with a monomer component comprising one or more hydrocarbon olefins and one or more polar comonomers (and other optional components such as, for example, one or more cocatalysts and/or other additives), wherein the improvement comprises that the transition metal is nickel, and that the monomer component and complex are contacted at a temperature of about 60° C. to about 170° C., provided that when CO is present, at least one other polar monomer is present.

This invention further concerns a "first" polymer, consisting essentially of repeat units derived from ethylene, and one or more polar olefins of the formula $H_2C=CHC(O)R^{32}$, wherein $R^{32}$ is $-OR^{34}$ or any group readily derivable from it, and $R^{34}$ is hydrocarbyl or substituted hydrocarbyl, wherein:

said polymer contains "first branches" of the formula $-(CH_2)_nCH_3$ and "second branches" of the formula $-(CH_2)_mC(O)R^{32}$, wherein m and n are independently zero or an integer of 1 or more; and said polymer has the following structural characteristics:
(a) one or both of:
  (1) the ratio of first branches wherein n is 0 to first branches wherein n is 1 is about 3.0 or more; and
  (2) the ratio of first branches wherein n is 0 to first branches wherein n is 3 is 1.0 or more; and
(b) one or both of:
  (1) the total number of first branches in which n is 0, 1, 2 and 3 in said polymer is about 10 or more per 1000 $CH_2$ groups; and
  (2) the incorporation of repeat units derived from $H_2C=CHC(O)R^{32}$ is 0.3 mole percent or more based on the total repeat units derived from the hydrocarbonolefin and $H_2C=CHC(O)R^{32}$.

This invention also concerns a "second" polymer, consisting essentially of repeat units derived from:

one or more hydrocarbon olefins, such as ethylene, and
one or more polar olefins of the formula $H_2C=CHC(O)R^{32}$, wherein $R^{32}$ is $-OR^{34}$ or any group readily derivable from it, and $R^{34}$ is hydrocarbyl or substituted hydrocarbyl;

wherein in said polymer incorporation of repeat units derived from $H_2C=CHC(O)R^{32}$ is 0.3 mole percent or more based on the total repeat units; and wherein said polymer has one or both of the following structural characteristics:

at least 5 mole percent of said repeat units derived from $H_2C=CHC(O)R^{32}$ are present in said polymer as end groups; and said end groups are at least 0.001 mole percent of the total repeat units in said polymer;

and provided that said end groups have the formula

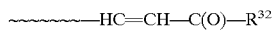

wherein ~~~~~~ is the remainder of the polymer chain of said end group.

This invention still further concerns a "third" polymer, consisting essentially of:

repeat units derived from ethylene;

repeat units derived from one or more monomers of the formula $H_2C=CHC(O)R^{32}$, wherein each $R^{32}$ is independently $-OR^{34}$ or any group readily derivable from it, and each $R^{34}$ is independently hydrocarbyl or substituted hydrocarbyl, and repeat units derived from one or more alpha-olefins of formulas $H_2C=CH-(CH_2)_t-H$ and/or $H_2C=CH-R^{75}-G$, wherein t is an integer of 1 to 20, $R^{75}$ is alkylene or substituted alkylene, and G is an inert functional group.

These and other features and advantages of the present invention will be more readily understood by those of ordinary skill in the art from a reading of the following detailed description. It is to be appreciated that certain features of the invention which are, for clarity, described below in the context of separate embodiments, may also be provided in combination in a single embodiment. Conversely, various features of the invention which are, for brevity, described in the context of a single embodiment, may also be provided separately or in any subcombination.

BRIEF DESCRIPTION OP THE DRAWINGS

DETAILED DESCRIPTION OF THE PREFERRED EMBODIMENTS

Figure 1:
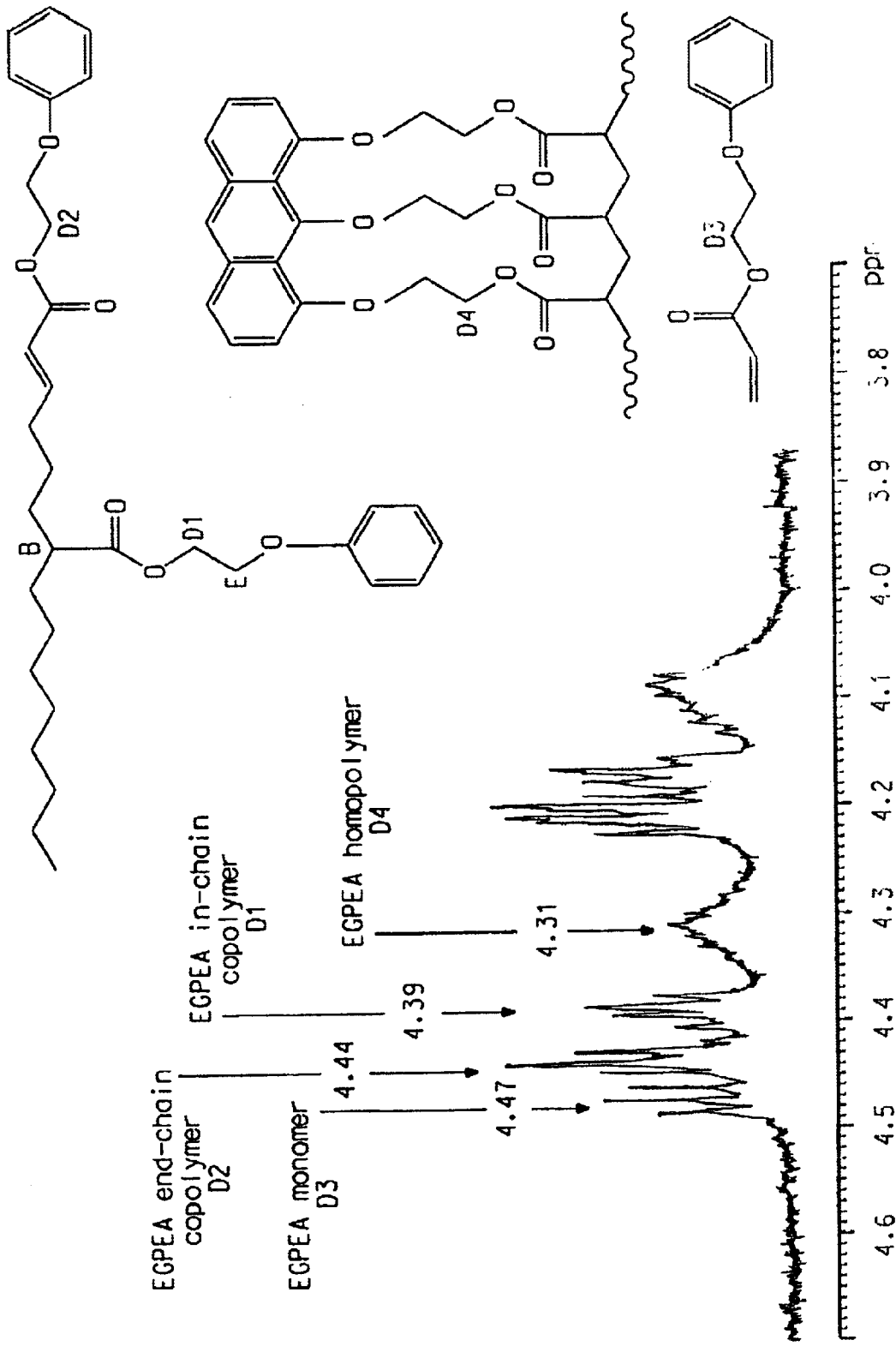
FIG. 1 shows the $^{13}C$ NMR of a copolymer of ethylene and 2-phenoxyethyl acrylate (EGPEA) which also contains some homopolymer of EGPEA, and which shows assignments of various NMR peaks.

Herein, certain terms are used. Some of them are:

A "hydrocarbyl group" is a univalent group containing only carbon and hydrogen. As examples of hydrocarbyls may be mentioned unsubstituted alkyls, cycloalkyls and aryls. If not otherwise stated, it is preferred that hydrocarbyl groups (and alkyl groups) herein contain 1 to about 30 carbon atoms.

By "substituted hydrocarbyl", herein is meant a hydrocarbyl group that contains one or more substituent groups which are inert under the process conditions to which the compound containing these groups is subjected (e.g., an inert functional group, see below). The substituent groups also do not substantially detrimentally interfere with the polymerization process or operation of the polymerization catalyst system. If not otherwise stated, it is preferred that substituted hydrocarbyl groups herein contain 1 to about 30 carbon atoms. Included in the meaning of "substituted" are chains or rings containing one or more heteroatoms, such as nitrogen, oxygen and/or sulfur, and the free valence of the substituted hydrocarbyl may be to the heteroatom. In a substituted hydrocarbyl, all of the hydrogens may be substituted, as in trifluoromethyl.

By "(inert) functional group" herein is meant a group other than hydrocarbyl or substituted hydrocarbyl that is inert under the process conditions to which the compound containing the group is subjected. The functional groups also do not substantially interfere with any process described herein that the compound in which they are present may take part in. Examples of functional groups include halo (fluoro, chloro, bromo and iodo), and ether such as —$OR^{22}$ wherein $R^{22}$ is hydrocarbyl or substituted hydrocarbyl. In cases in which the functional group may be near a transition metal atom the functional group should not coordinate to the metal atom more strongly than the groups in those compounds are shown as coordinating to the metal atom, that is they should not displace the desired coordinating group.

By a "cocatalyst" or a "catalyst activator" is meant a compound that reacts with a transition metal compound to form an activated catalyst species. One such catalyst activator is an "alkyl aluminum compound" which, herein, is meant a compound in which at least one alkyl group is bound to an aluminum atom. Other groups such as, for example, alkoxide, hydride and halogen may also be bound to aluminum atoms in the compound.

By "neutral Lewis base" is meant a compound, which is not an ion, that can act as a Lewis base. Examples of such compounds include ethers, amines, sulfides and organic nitriles.

By "neutral Lewis acid" is meant a compound, which is not an ion, that can act as a Lewis acid. Examples of such compounds include boranes, alkylaluminum compounds, aluminum halides and antimony [V] halides.

By "cationic Lewis acid" is meant a cation that can act as a Lewis acid. Examples of such cations are lithium, sodium and silver cations.

By an "empty coordination site" is meant a potential coordination site on a transition metal atom that does not have a ligand bound to it. Thus if an olefin molecule (such as an ethylene molecule) is in the proximity of the empty coordination site, the olefin molecule may coordinate to the metal atom.

By a "ligand into which an olefin molecule may insert between the ligand and a metal atom", or a "ligand that may add to an olefin", is meant a ligand coordinated to a metal atom which forms a bond (L—M) into which an olefin molecule (or a coordinated olefin molecule) may insert to start or continue a polymerization. For instance, with ethylene this may take the form of the reaction (wherein L is a ligand):

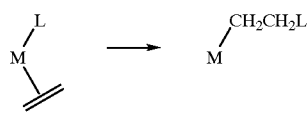

By a "ligand which may be displaced by an olefin" is meant a ligand coordinated to a transition metal which, when exposed to the olefin (such as ethylene), is displaced as the ligand by the olefin.

By a "monoanionic ligand" is meant a ligand with one negative charge.

By a "neutral ligand" is meant a ligand that is not charged.

By "aryl" is meant a monovalent aromatic group in which the free valence is to the carbon atom of an aromatic ring. An aryl may have one or more aromatic rings which may be fused, connected by single bonds or other groups.

By "substituted aryl" is meant a monovalent aromatic group substituted as set forth in the above definition of "substituted hydrocarbyl". Similar to an aryl, a substituted aryl may have one or more aromatic rings which may be fused, connected by single bonds or other groups; however, when the substituted aryl has a heteroaromatic ring, the free valence in the substituted aryl group can be to a heteroatom (such as nitrogen) of the heteroaromatic ring instead of a carbon.

By "aryl substituted in at least one position vicinal to the free bond of the aryl group," is meant the bond to one of the carbon atoms next to the free valence of the aryl group is something other than hydrogen. For example for a phenyl group, it would mean the 2 position of the phenyl group would have something other than hydrogen attached to it. A 1-naphthyl group already has something other than hydrogen attached to one of the vicinal carbon atoms at the fused ring junction, while a 2-napthyl group would have to be substituted in either the 1 or 3 positions to meet this limitation. A preferred aryl substituted in at least one position vicinal to the free bond of the aryl group is a phenyl group substituted in the 2 and 6 positions, and optionally in the other positions.

"Alkyl group" and "substituted alkyl group" have their usual meaning (see above for substituted under substituted hydrocarbyl). Unless otherwise stated, alkyl groups and substituted alkyl groups preferably have 1 to about 30 carbon atoms.

By a "styrene" herein is meant a compound of the formula (XXXIV)

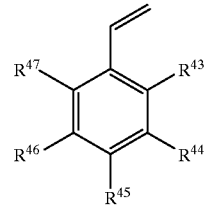

wherein $R^{43}$, $R^{44}$, $R^{45}$, $R^{46}$ and $R^{47}$ are each independently hydrogen, hydrocarbyl, substituted hydrocarbyl or a functional group, all of which are inert in the polymerization process. It is preferred that all of $R^{43}$, $R^{44}$, $R^{45}$, $R^{46}$ and $R^{47}$ are hydrogen. Styrene (itself) is a preferred styrene.

By a "norbornene" is meant a compound of the formula (XXXV)

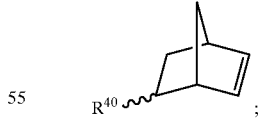

wherein $R^{40}$ is hydrogen or hydrocarbyl containing 1 to 20 carbon atoms. It is preferred that $R^{40}$ is hydrogen or alkyl, more preferably hydrogen or n-alkyl, and especially preferably hydrogen. The norbornene may be substituted by one or more hydrocarbyl, substituted hydrocarbyl or functional groups in the $R^{40}$ or other positions, with the exception of the vinylic hydrogens, which remain. Norbornene (itself), dimethyl endo-norbornene-2,3-dicarboxylate and t-butyl 5-norbornene-2-carboxylate are preferred norbornenes, with norbornene (itself) being especially preferred.

By a "π-allyl group" is meant a monoanionic ligand comprised of 1 sp³ and two sp² carbon atoms bound to a metal center in a delocalized η³ fashion indicated by

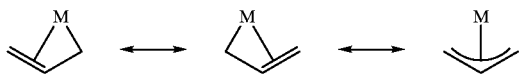

The three carbon atoms may be substituted with other hydrocarbyl groups or functional groups.

"Vinyl group" has its usual meaning.

By a "hydrocarbon olefin" is meant an olefin containing only carbon and hydrogen.

By a "polar (co)monomer" or "polar olefin" is meant an olefin which contains elements other than carbon and hydrogen. In a "vinyl polar comonomer," the polar group is attached directly to a vinylic carbon atom, as in acrylic monomers. When copolymerized into a polymer the polymer is termed a "polar copolymer". Useful polar comonomers are found in U.S. Pat. No. 5,866,663, WO9905189, WO9909078 and WO9837110, and S. D. Ittel, et al., *Chem. Rev.*, vol. 100, p. 1169–1203(2000), all of which are incorporated by reference herein for all purposes as if fully set forth. Also included as a polar comonomer is CO (carbon monoxide).

By a "bidentate" ligand is meant a ligand which occupies two coordination sites of the same transition metal atom in a complex.

By "under polymerization conditions" is meant the conditions for a polymerization that are usually used for the particular polymerization catalyst system being used. These conditions include things such as pressure, temperature, catalyst and cocatalyst (if present) concentrations, the type of process such as batch, semibatch, continuous, gas phase, solution or liquid slurry etc., except as modified by conditions specified or suggested herein. Conditions normally done or used with the particular polymerization catalyst system, such as the use of hydrogen for polymer molecular weight control, are also considered "under polymerization conditions". Other polymerization conditions such as add presence of hydrogen for molecular weight control, other polymerization catalysts, etc., are applicable with this polymerization process and may be found in the references cited herein.

By "$E_s$" is meant a parameter to quantify steric effects of various groupings, see R. W. Taft, Jr., *J. Am. Chem. Soc.*, vol. 74, p. 3120–3128 (1952), and M. S. Newman, *Steric Effects in Organic Chemistry*, John Wiley & Sons, New York, 1956, p. 598–603, which are both hereby included by reference. For the purposes herein, the $E_s$ values are those described for o-substituted benzoates in these publications. If the value of $E_s$ for a particular group is not known, it can be determined by methods described in these references.

The transition metals preferred herein in the first and second processes are in Groups 3 through 11 of the periodic table (IUPAC) and the lanthanides, especially those in the $4^{th}$, $5^{th}$, $6^{th}$ and $10^{th}$ periods. Suitable transition metals include Ni, Pd, Cu, Pt, Fe, Co, Ti, Zr, V, Hf, Cr, Ru, Rh and Re, with Ni, Ti, Zr, Cu and Pd being more preferred, and Ni, Ti and Zr being especially preferred. Preferred oxidation states for some of the transition metals are Ni[II], Ti[IV], Zr[IV], and Pd[II].

For ligand (I), Table 1 gives preferred structures. For ligand (II), Table 2 gives preferred structures. In both tables, H is hydrogen, HC is hydrocarbyl, SHC is substituted hydrocarbyl and FG is functional group.

TABLE 1

| m | n | X | Z | $R^3$ | $R^4$ | $R^5$ | $R^6$ | $R^7$ | $R^{11}$ | $R^{12}$ |
|---|---|---|---|---|---|---|---|---|---|---|
| Zero | Zero | | N | | | | | HC, SHC | HC, SHC | H, HC, SHC |
| Zero | Zero | | O | | | | | | HC, SHC | HC, SHC, FG |
| Zero | 1 | | O | H | H | | | | HC, SHC, FG | HC, SHC, FG |
| Zero | 1 | | N | H | H | | | HC, SHC | H, HC, SHC, FG | H, HC, SHC, FG |
| Zero | 1 | | S | H | H | | | | HC, SHC, FG | HC, SHC, FG |
| 1 | Zero | O | O | | | H, HC, SHC | H, HC, SHC | | H, HC, SHC | H, HC, SHC |
| 1 | 1 | $CR^5R^6$ | O | H, HC, SHC | H, HC, SHC | H | H | | H, HC, SHC | H, HC, SHC |
| 1 | 1 | $CR^5R^6$ | N | H, HC, SHC | H, HC, SHC | H | H | HC, SHC | H, HC, SHC | H, HC, SHC |

TABLE 2

| q | $R^8$ | $R^9$ | $R^{10}$ |
|---|---|---|---|
| Zero | | | HC, SHC |
| 1 | H, HC | H, HC | HC, SHC |

In all preferred (I) and (II) (and by reference corresponding structures (IV) and (V), respectively), $R^1$ and $R^2$ are t-butyl, aryl or substituted aryl, more preferably t-butyl, and 2,6-disubstituted phenyl, especially 2,6-dimethoxyphenyl. It is believed that in most of the ligands it is preferred that $R^1$ and $R^2$ be relatively sterically bulky groups, for example t-butyl. Thus, for instance, 2,6-dimethylphenyl would often be favored over phenyl for $R^1$ and $R^2$. Thus $R^1$ and $R^2$ may, for example, be isopropyl, phenyl, substituted phenyl, aryl, substituted aryl, cyclohexyl, t-butyl or 2-octyl. In another preferred form, $R^1$ and $R^2$ are independently aryl substituted in one position vicinal to the free bond of the aryl group, or $R^1$ and $R^2$ each independently have an $E_s$ of −1.0 or less, or both. By both means they may be aryl substituted in one position vicinal to the free bond of the aryl group, and also have an $E_s$ of −1.0 or less.

Any two of $R^3$, $R^4$, $R^5$, $R^6$, $R^8$, $R^9$, $R^{11}$ and $R^{12}$ bonded to the same carbon atom taken together may form a functional group. By this is meant, for instance, two of these bonds may form part of an oxo (keto) group, =O, or an imino =N—R, wherein R is hydrocarbyl group. Preferred types of functional groups (single or double bonded) include oxo, —C(O)R$^{13}$ and —CO$_2$R$^{13}$, wherein R$^{13}$ is hydrocarbyl or substituted hydrocarbyl.

In (I) or (IV) the following structures are preferred:

the transition metal is Ni, m is 0, n is 1, R$^3$ and R$^4$ are hydrogen, Y is CR$^{11}$R$^{12}$, R$^{11}$ is hydrocarbyl or substituted hydrocarbyl, R$^{12}$ is hydrocarbyl, substituted hydrocarbyl or a functional group, and Z is O; or the transition metal is Ti, m is 0, n is 1, R$^3$ and R$^4$ are hydrogen, Y is CR$^{11}$R$^{12}$, R$^{11}$ is hydrocarbyl or substituted hydrocarbyl, R$^{12}$ is hydrocarbyl, substituted hydrocarbyl or a functional group, and Z is O; or the transition metal is Zr, m is 0, n is 1, R$^3$ and R$^4$ are hydrogen, Y is CR$^{11}$R$^{12}$, R$^{11}$ is hydrocarbyl or substituted hydrocarbyl, R$^{12}$ is hydrocarbyl, substituted hydrocarbyl or a functional group, and Z is O; or the transition metal is Ni, m is 0, n is 1, R$^3$ and R$^4$ are hydrogen, R$^7$ is hydrocarbyl or substituted hydrocarbyl, Y is CR$^{11}$R$^{12}$, R$^{11}$ is hydrogen, R$^{12}$ is hydrocarbyl or substituted hydrocarbyl, and Z is N; or the transition metal is Ni, m is 0, n is 1, R$^3$ and R$^4$ are hydrogen, Y is CR$^{11}$R$^{12}$, R$^{11}$ and R$^{12}$ taken together are oxo, and Z is O; or the transition metal is Ni, m is 0, n is 1, R$^3$ and R$^4$ are hydrogen, R$^{11}$ is hydrocarbyl or substituted hydrocarbyl, Y is CR$^{11}$R$^{12}$, R$^{11}$ and R$^{12}$ taken together are oxo, and Z is N; or the transition metal is Ni, m is 0, n is 1, R$^3$ and R$^4$ are hydrogen, Y is S(T), T is =O and Z is O; or the transition metal is Ni, m is 0, n is 1, R$^3$ and R$^4$ are hydrogen, Y is S(T), T is =N-silyl, Z is N and R$^7$ is silyl; or the transition metal is Ni, m is 0, n is 1, R$^3$ and R$^4$ are hydrogen, Y is S(T), T is =O, Z is N, and R$^7$ is hydrocarbyl or substituted hydrocarbyl; or the transition metal is Ni, m is 0, n is 1, R$^3$ and R$^4$ are hydrogen, Y is CR$^{11}$R$^{12}$, R$^{11}$ and R$^{12}$ taken together are a ring and Z is O; or the transition metal is Ni, m is 0, n is 1, R$^3$ and R$^4$ are hydrogen, Y is CR$^{11}$R$^{12}$, R$^{11}$ and R$^{12}$ taken together are N-hydrocarbyl- or N-substituted hydrocarbylimino, Z is N and R$^7$ is hydrocarbyl or substituted hydrocarbyl; or the transition metal is Ni, m is 0, n is 1, R$^3$ and R$^4$ are hydrogen, Y is S(T), T is =O and Z is O; or the transition metal is Ni, m is 0, n is 1, R$^3$ and R$^4$ are hydrogen, Y is CR$^{11}$R$^{12}$, R$^{11}$ and R$^{12}$ taken together are sulfo, Z is N and R$^7$ is hydrocarbyl or substituted hydrocarbyl.

In (II) or (V), it is preferred that the transition metal is Ni, q is 0 or 1, R$^8$ and R$^9$ are hydrogen and R$^{10}$ is hydrocarbyl or substituted hydrocarbyl.

In (XII) (and by reference corresponding structure (XIII)), R$^{33}$ and R$^{34}$ are preferably t-butyl, aryl (other than phenyl) or substituted aryl, more preferably t-butyl and 2,6-disubstituted phenyl, especially 2,6-dimethoxyphenyl. It is believed that in most of the ligands it is preferred that R$^{33}$ and R$^{34}$ be relatively sterically bulky groups, for example t-butyl. Thus, for instance, 2,6-dimethylphenyl would often be favored over 2-methylphenyl for R$^{33}$ and R$^{34}$. Thus R$^{33}$ and R$^{34}$ may, for example, be isopropyl, aryl (other than phenyl), substituted aryl, cyclohexyl, t-butyl or 2-octyl. In another preferred form R$^{33}$ and R$^{34}$ are independently aryl substituted in one position vicinal to the free bond of the aryl group, or R$^{33}$ and R$^{34}$ each independently have an E$_s$ of −1.0 or less, or both. By both means they may be aryl substituted in one position vicinal to the free bond of the aryl group, and also have an E$_s$ of −1.0 or less.

As examples of useful groups R$^{31}$ and R$^{32}$ may be mentioned hydrogen, aryl, substitued aryl, oxygen and nitrogen based functional groups and SO$_3$Na, as well as when R$^{31}$ and R$^{32}$ taken together form a ring, for example, an aromatic or non-aromatic ring, which may include one or more heteroatoms.

Other preferences include when A is O and s is 0.

In (IV), (V) and (XIII), useful groups L$^1$ include hydrocarbyl and substituted hydrocarbyl (especially phenyl and alkyl, and particularly phenyl, methyl, hydride and acyl). Useful groups for L$^2$ include phosphine such as triphenylphosphine, nitrile such as acetonitrile, ethers such as ethyl ether, pyridine, and tertiary alkylamines such as triethylamine and TMEDA (N,N,N',N'-tetramethyl-1,2-ethylenediamine). Alternatively L$^1$ and L$^2$ taken together may be a π-allyl or π-benzyl group such as

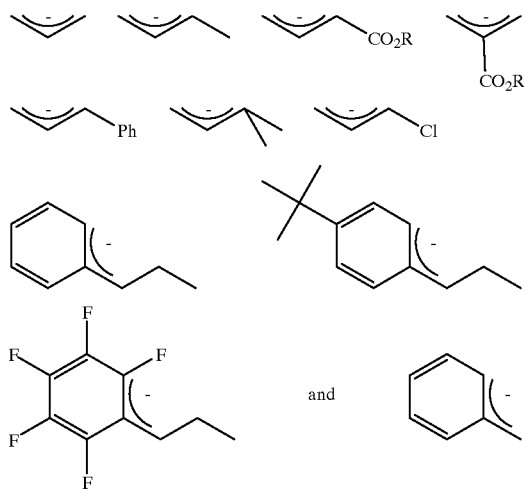

wherein R is hydrocarbyl, and π-allyl and π-benzyl groups are preferred.

In (IV), (V) and (XIII), when an olefin (such as ethylene) may insert between L$^1$ and the transition metal atom, and L$^2$ is an empty coordination site or is a ligand which may be displaced by an olefin (such as ethylene), or L$^1$ and L$^2$ taken together are a bidentate monoanionic ligand into which an olefin (such as ethylene) may be inserted between that ligand and the transition metal atom, (IV), (V) and (XIII) may by themselves catalyze the polymerization of an olefin.

Examples of L$^1$ which form a bond with the metal into which ethylene may insert between it and the transition metal atom are hydrocarbyl and substituted hydrocarbyl, especially phenyl and alkyl, and particularly methyl, hydride and acyl. Ligands L$^2$ which ethylene may displace include phosphine such as triphenylphosphine, nitrile such as acetonitrile, ether such as ethyl ether, pyridine, tertiary alkylamines such as TMEDA, and other olefins. Ligands in which L$^1$ and L$^2$ taken together are a bidentate monoanionic ligand into which ethylene may insert between that ligand and the transition metal atom include π-allyl- or π-benzyl-type ligands (in this instance, sometimes it may be necessary to add a neutral Lewis acid cocatalyst such as triphenylborane or tris(pentafluoro-phenyl)borane of a cationic Lewis acid such as Li$^+$ to initiate the polymerization, see for instance previously incorporated U.S. Pat. No. 6,174,975).

For a summary of which ligands ethylene may insert into (between the ligand and transition metal atom) see for instance J. P. Collman, et al., *Principles and Applications of Organotransition Metal Chemistry*, University Science Books, Mill Valley, Calif., 1987, included herein by reference.

If for instance the ligand in the location of $L^1$ is not a ligand into which ethylene may insert between it and the transition metal atom, it may be possible to add a cocatalyst which may convert it into $L^1$ a ligand which will undergo such an insertion. Thus if the ligand in the location of $L^1$ is halo such as chloride or bromide, a carboxylate, acetylacetonate or an alkoxide, it may be converted to hydrocarbyl such as alkyl by use of a suitable alkylating agent such as an alkylaluminum compound, a Grignard reagent or an alkyllithium compound. It may be converted to hydride by use of a compound such as sodium borohydride.

As indicated above, when $L^1$ and $L^2$ taken together are a monoanionic bidentate ligand, a cocatalyst (sometimes also called an activator) which is an alkylating or hydriding agent is also typically present in the olefin polymerization. A preferred cocatalyst is an alkylaluminum compound, and useful alkylaluminum compounds include trialkylaluminum compounds such as triethylaluminum, trimethylaluminum and tri-i-butylaluminum, alkyl aluminum halides such as diethylaluminum chloride and ethylaluminum dichloride, and aluminoxanes such as methylaluminoxane. More than one such cocatalyst may be used in combination.

Preferred for $L^3$ are ligands of the type above described for $L^1$.

The ligands (I), (II) and (XIII) may be synthesized by a variety of methods, depending on the particular ligand desired. The synthesis of many specific ligands is illustrated in the Examples. Many of these syntheses are accomplished through the use of $R_2PLi$ or $R_2PCH_2Li$. More generally speaking, the synthesis of various types of ligands is illustrated in the schemes shown below. In these schemes, each R independently represents hydrocarbyl or substituted hydrocarbyl, and each R' independently represent hydrogen, hydrocarbyl or substituted hydrocarbyl.

Scheme 1

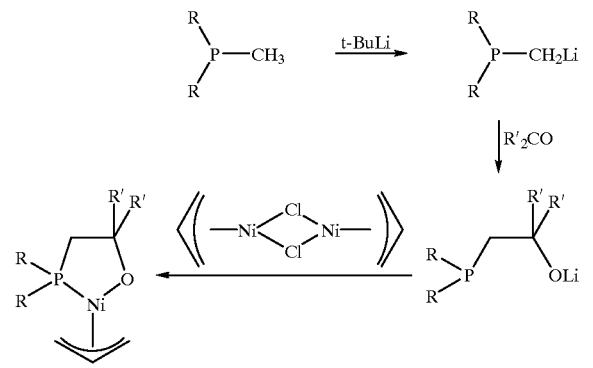

In Scheme 1 one may substitute an imine for the ketone $R'_2CO$ and obtain a final product in which Z is nitrogen rather than oxygen. In another variation of Scheme I one can react $R_2PH$ with an acrylonitrile, followed by reaction with R'MgX (addition across the nitrile bond) and then ((allyl)NiCl)$_2$ to form the 6-membered metallocycle in which Z is nitrogen. To obtain compounds in which Z is not nitrogen or oxygen, one can use analogous compounds containing the appropriate element for Z. As shown in Scheme 2, (II) can exist in isomeric forms, and the formula for any of the forms represents all of the isomeric forms.

Scheme 2

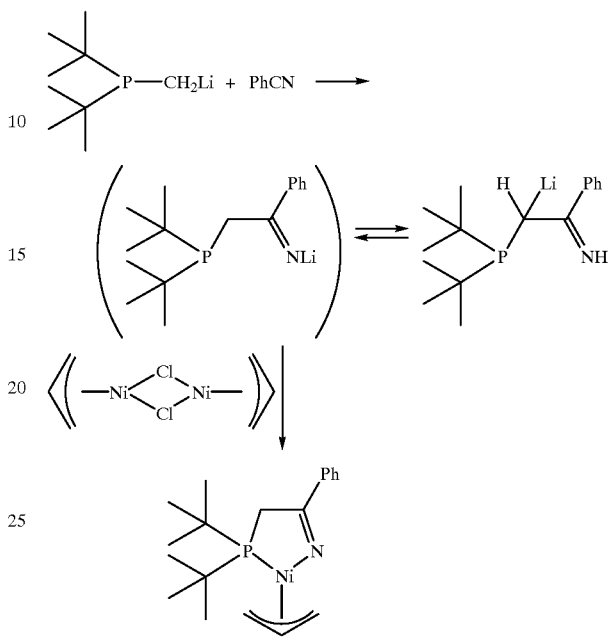

Scheme 2 shows the synthesis of (II). Appropriate substitution (as in all these synthesis schemes) in these compounds may be obtained by using appropriately substituted starting materials.

Scheme 3

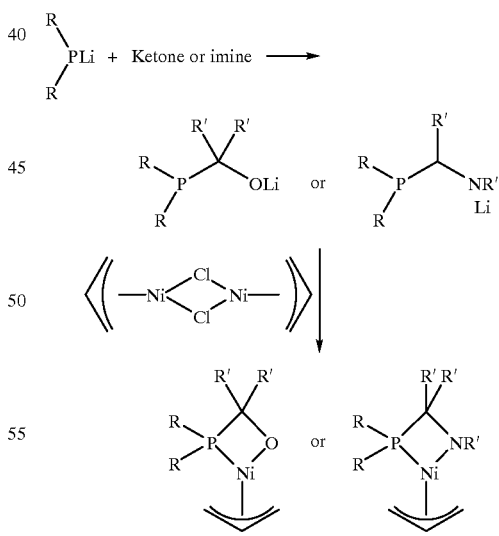

Scheme 3 shows the synthesis of 4-membered (or isomeric) metallocycles. Herein by isomeric is meant (and included in the definition of) that 4-membered heterocycles such as those shown in Scheme 3 may also be in the form of bridged dimers and/or oligomers. Z may be changed by using the appropriate starting material.

Scheme 4

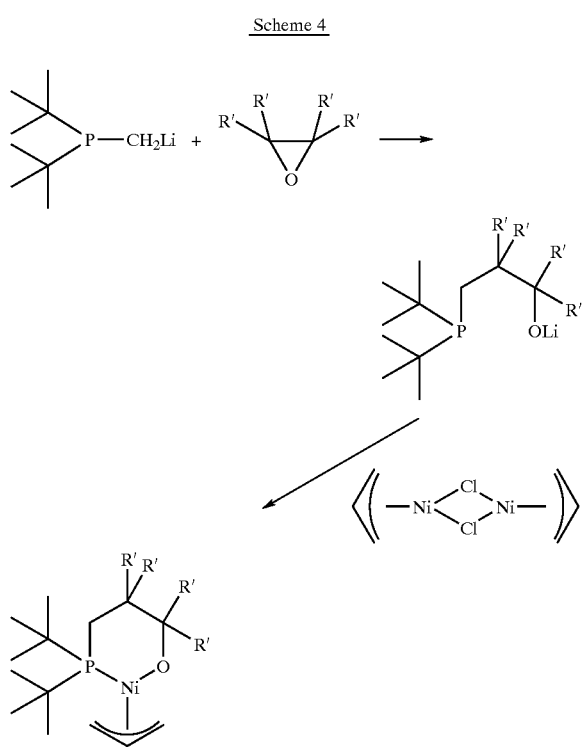

Scheme 4 illustrates the synthesis of a 6-membered metallocycle. The corresponding nitrogen compound may be made by using an aziridine as a starting material.

Scheme 5

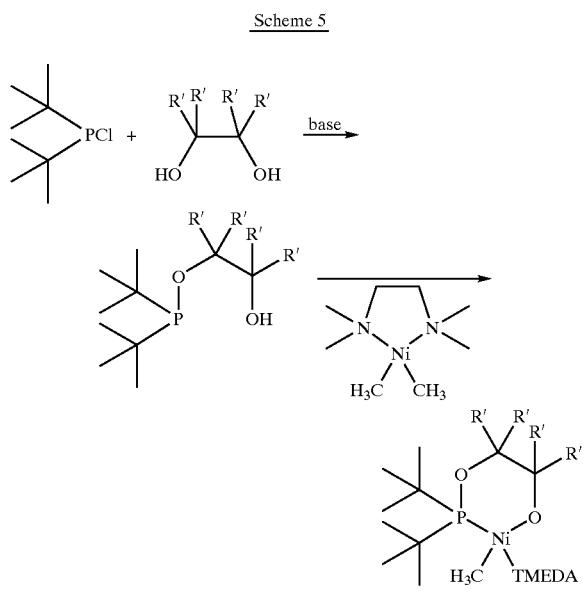

Scheme 5 illustrates a method for making (I) in which X is —O—. Herein TMEDA is tetramethylethylenediamine.

In Schemes 1–5 above Ni complexes are prepared, and for making late transition metal complexes other than Ni, similar reactions of metal compounds with an appropriate anion may be used to prepare the complex. Useful types of Ni compounds are listed below.

$(Ph_3P)_2Ni(Ph)(Cl)$ which gives as ligands (in addition to (I), (II) or (XIII)) Ph and $Ph_3P$.

$(TMEDA)_2Ni(Ph)(Cl)$ in the presence of a "trapping ligand" $L^2$ such as pyridine, which gives as ligands (in addition to (I), (II) or (XIII)) Ph and pyridine.

$(Ph_3P)_2NiCl_2$ which gives as ligands (in addition to (I), (II) or (XIII)) Cl and $Ph_3P$.

$((allyl)Ni(X))_2$ which gives as a ligand (in addition to (I), (II) or (XII)) π-allyl.

Other useful Ni precursors and methods of synthesis of these types of nickel complexes may also be found in previously incorporated U.S. Pat. No. 6,060,569, U.S. Pat. No. 6,174,975 and S. D. Ittel, et al., *Chem. Rev.*, vol. 100, p. 1169–1203 (2000), as well as WO98/42664, and R. H. Grubbs., et al., *Organometallics*, vol. 17, p. 3149 (1988), which are also incorporated herein by reference for all purposes as if fully set forth.

In preparing early transition metal complexes such as Zr and Ti complexes, the anion may be reacted with a simple metal compound such as a halide, for example $ZrCl_4$ or $TiCl_4$.

Useful monomers (olefins) include hydrocarbon olefins such as ethylene and α-olefins of the formula $H_2C=CH(CH_2)_tH$ (III) wherein t is an integer of 1 to 20, a styrene, a norbornene and cyclopentene; and polar comonomers such as CO and polar olefins. Useful polar olefins include those of the formula $H_2C=CHR^{13}E$, wherein $R^{13}$ is alkylene, alkylidene or a covalent bond, especially $—(CH_2)_x—$ wherein x is 0 or an integer of 1 to 20 and E is a polar group. Useful polar groups E include $—CO_2R^{14}$, $—OC(O)R^{14}—CO_2H$, $—C(O)NR^{14}_2$ and $—OR^{14}$, and $—CO_2R^{14}$ and $—OR^{14}$ are more preferred, wherein each $R^{14}$ is hydrogen, hydrocarbyl or substituted hydrocarbyl, preferably alkyl or substituted alkyl. For any olefin other than a norbornene, cyclopentene and a styrene, it is preferred that it be copolymerized with ethylene. An especially preferred olefin is ethylene (alone). Typically CO and polar comonomers will be used with a hydrocarbon olefin such as ethylene to form a copolymer, and often when CO is used at least one other polar monomer will also be present.

It will be understood that not every combination of every ligand with every transition metal will polymerize every (type of) olefin or combination of olefins described herein. For instance, late transition metals are believed to be more efficacious for polymerization of polar olefins than are early transition metals. The structure of the polyolefin produced will also vary with the particular transition metal and ligand chosen. For example late transition metals tend to produce polymers with an unusual branching pattern, while early transition metals give polymers with more "normal" branching patterns. For a description of unusual and normal branching patterns see U.S. Pat. No. 5,880,241, which is incorporated by reference herein for all purposes as if fully set forth. The combinations of ingredients to use in the polymerization and the products produced may be readily determined by experimentation.

It is preferred that the polymer produced by the first and second processes herein have a degree of polymerization (average number of monomer units in a polymer molecule) of at least about 20, more preferably at least about 40, and especially preferably at least about 100.

In the first and second polymerization processes herein, the temperature at which the polymerization is carried out is generally about −100° C. to about +200° C., preferably about −60° C. to about 150° C., and more preferably about −20° C. to about 100° C. The pressure of the olefin (if it is a gas) at which the polymerization is carried out is preferably atmospheric pressure to about 275 MPa.

The first and second polymerization processes herein may be run in the presence of various liquids, particularly aprotic organic liquids. The catalyst system, monomer(s), and polymer may be soluble or insoluble in these liquids, but obviously these liquids should not prevent the polymerization from occurring. Suitable liquids include alkanes, cycloalkanes, selected halogenated hydrocarbons, and aromatic hydrocarbons. Specific useful solvents include hexane, toluene, benzene, methylene chloride, chlorobenzene, p-xylene, and 1,2,4-trichlorobenzene.

Cocatalysts such as alkylaluminum compounds and/or boranes and/or other Lewis acids may optionally be present in the first and second processes. It is believed that the presence of certain Lewis acids may enhance the productivity of the catalyst and/or the rate of polymerization of the olefin(s). Also Lewis acids may form so-called Zwitterionic complexes which are also useful in these processes. For an explanation of Zwitterionic complexes, see U.S. patent application Ser. No. 09/871,100 filed 31 May 2001, now U.S. Pat. No. 6,506,861 which is hereby incorporated by reference herein for all purposes as if fully set forth.

In the third polymerization process described herein one or more polar comonomers are used with one or more hydrocarbon olefins, and preferably ethylene, to form a polar copolymer. Useful polar comonomers include, but are not limited to compounds of the formula $H_2C=CHR^{20}C(O)Y$ (X), $H_2C=CHR^{20}CN$ (XI), $H_2C=CR^{25}C(O)Y$ (XII), or $H_2C=CHR^{20}CCN$, wherein $R^{20}$ is alkylene or substituted alkylene, $R^{25}$ is hydrogen, and Y is $-OH$, $-NR^{21}R^{22}$, $-OR^{23}$, and $-SR^{24}$, wherein $R^{21}$ and $R^{22}$ are each independently hydrogen, hydrocarbyl or substituted hydrocarbyl, $R^{23}$ and $R^{24}$ are each hydrocarbyl or substitute hydrocarbyl, and $R^{25}$ is hydrogen. More generally vinyl polar monomers of the formula $H_2C=CHX$, wherein X is a polar group, are preferred. Other more specific preferred polar comonomers are (X) wherein $R^{20}$ is $-(CH_2)_q-$ wherein q is 0 or an integer of 1 to 20 and Y is $-OR^{23}$, and (XII), wherein it is especially preferred that q is zero. Norbornenes containing functional groups are also useful polar comonomers.

Some of Ni complexes which may contain bidentate ligands and may be useful in the third process herein may be found in JP-A-11158214, JP-A-11158213, JP-A-10017617, JP-A-09255713, JP-A-11180991, JP-A-256414(2000), JP-A-10007718, JP-A-10182679, JP-A-128922(2000), JP-A-10324709, JP-A-344821(2000), JP-A-11292917, JP-A-11181014, WO00/56744, WO96/37522, WO96/37523, WO98/49208, WO00/18776, WO00/56785, WO00/06620, WO99/50320, WO00/68280, WO00/59956, WO00/50475, WO00/50470, WO98/42665, WO99/54364, WO98/33823, WO99/32226, WO99/49969, WO99/15569, WO99/46271, WO98/03521, WO00/59961, DE-A-19929131, U.S. Pat. No. 5,886,224, U.S. Pat. No. 5,714,556, U.S. Pat. No. 6,060,569, U.S. Pat. No. 6,069,110, U.S. Pat. No. 6,174,976, U.S. Pat. No. 6,103,658, U.S. Pat. No. 6,200,925, U.S. Pat. No. 5,929,181, U.S. Pat. No. 5,932,670, U.S. Pat. No. 6,030,917, U.S. Pat. No. 4,689,437, EP-A-0950667 and EP-A-0942010, and S. D. Ittel, et al., *Chem. Rev.*, vol. 100, p. 1169–1203 (2000) (and references therein), all of which are hereby incorporated by reference for all purposes as if fully set forth, as well as the complexes described herein derived from (I), (II) or (XII).

All of the complexes mentioned in these publications, and all nickel complexes of bidentate neutral and monoanionic ligands, may not in general be catalysts for the copolymerization of ethylene and one or more polar comonomers, but the conditions described herein give a good chance for them to be such catalysts. To determine whether such a complex is a polar olefin copolymerization catalyst, one may simply try a copolymerization of ethylene and a polar comonomer such as methyl acrylate or ethyl-10-undecylenoate under the conditions described herein. These conditions include principally temperature and ethylene pressure. During most polymerizations there are other conditions usually present, such as activation of the polymerization catalyst, exclusion of polymerization catalyst poisons, use of a molecular weight regulating compound such as hydrogen, agitation, supportation, etc. Except for those conditions specifically described herein for the third polymerization, the other conditions described, for example, in the above references may be used in such test polymerizations and in polymerizations of the third process in general, and reference may be had thereto for further details.

In the third process herein a preferred low temperature is about 80° C., more preferably about 90° C., and a preferred high temperature is about 150° C., more preferably about 130° C. A preferred lower ethylene pressure is about 5 MPa or more. A preferred upper limit on ethylene pressure is about 200 MPa, more preferably about 20 MPa.

Preferred bidentate ligands in the third process herein are:

(XIV)

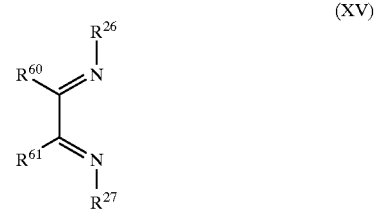

(XV)

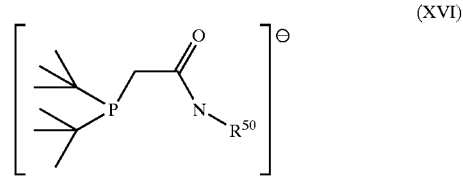

(XVI)

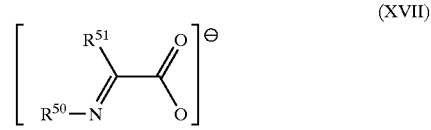

(XVII)

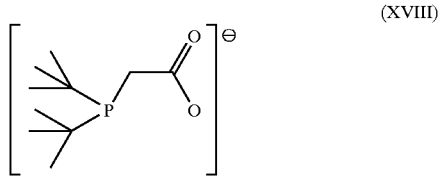

(XVIII)

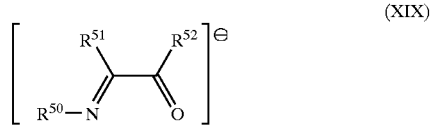

(XIX)

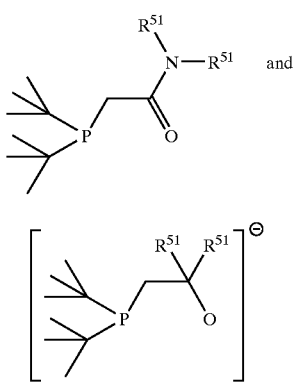

wherein:
R²⁶ and R²⁷ are each independently hydrocarbyl or substituted hydrocarbyl, provided that the carbon atom bound to the imino nitrogen atom has at least two carbon atoms bound to it;

R²⁸ and R²⁹ are each independently hydrogen, hydrocarbyl, substituted hydrocarbyl, or R²⁸ and R²⁹ taken together are hydrocarbylene or substituted hydrocarbylene to form a carbocyclic ring;

R⁶⁰ and R⁶¹ are each independently functional groups bound to the rest of (XV) through heteroatoms (for example O, S or N), or R⁶⁰ and R⁶¹ (still containing their heteroatoms) taken together form a ring.

each R⁵⁰ is independently hydrocarbyl or substituted hydrocarbyl;

each R⁵¹ is independently hydrogen, hydrocarbyl or substituted hydrocarbyl; and each R⁵² is hydrocarbyl, substituted hydrocarbyl, hydrocarbyloxy, or substituted hydrocarbyloxy.

When (XVI), (XVII) and (XVIII) are used as the complexes, especially as their nickel complexes it is preferred that they be used as their complexes with Lewis acids ("Zwitterionic complexes") such as tris(pentafluorophenyl)borane. These Zwitterionic complexes are sometimes better polymerization catalysts than the complexes which are do not contain the Lewis acid. These Zwitterionic compounds may be formed before the complex is added to the polymerization process, or may be formed in situ by reaction with Lewis acid which is present.

Other copolymerizable olefins may also be present in the third process. α-Olefins of the formula H₂C═CH(CH₂)$_z$CH₃ wherein z is 0 or an integer of 1 to 21, for example propylene or 1-butene, may be used. It is preferred that any other comonomers present constitute less than 50 mole percent, more preferably less than 25 mole percent of the product copolymer.

One problem noted with using some polar comonomers, for example acrylate-type comonomers, under certain conditions is the tendency of these comonomers to form homopolymers. It is believed that these homopolymers arise from a "competitive" free radical-type polymerization "originating" from some free radicals which may be present or generated in the third process polymerization. Some types of polar comonomers such as acrylates are well known to readily undergo such polymerizations. These usually unwanted free radical polymerizations may be suppressed to varying extents by the presence of free radical polymerization inhibitors such as phenothiazine in the third polymerization process, but these may interfere with the desired polymerization process, or cause other problems. This may be particularly acute in the third polymerization process herein because of the relatively high process temperatures. It has been found that the presence of alkali metal or ammonium salts, preferably alkali metal salts, of relatively noncoordinating anions in the third polymerization process retards or eliminates the formation of homopolymer of the polar comonomer (or copolymers containing only polar comonomers if more than one polar comonomer is used). Particularly preferred alkali metal cations are Li, Na and K, and Li and Na are especially preferred. Useful weakly coordinating anions include BAF, tetrakis(pentafluorophenyl)borate, N(S(O)₂CF₃)₂⁻, tetraphenylborate, trifluoromethanesulfonate, and hexafluoroantimonate, and preferred anions are BAF, tetrakis(pentafluorophenyl)borate, and N(S(O)₂CF₃)₂⁻. A useful molar ratio of these salts to the number of moles of Ni compounds present is about 10,000 to about 5 to 1.0, more preferably about 1,000 to about 50 to 1.0. These salts will preferably be used in a third polymerization process in which there is a liquid phase present, for example a polymerization which is a solution or liquid suspension polymerization.

In any of the polymerization processes herein in which a polar comonomer is copolymerized, and any formation of any polar copolymer, it is preferred that the molar ratio of the total of the polar comonomers present to any added Lewis acid is at least 2:1, preferably at least 10:1. Polar comonomers, such acrylic-type monomers, have been copolymerized in certain situations by destroying their Lewis basic (or coordinating) character by reacting them with a Lewis acid, to form a Lewis acid "salt" of the polar comonomer. While this may often help to form the polar copolymer, later removal of the stoichiometric amount (of polar comonomer) of Lewis acid is difficult and expensive.

The olefin polymerizations herein may also initially be carried out in the "solid state" by, for instance, supporting the transition metal compound on a substrate such as silica or alumina, activating it if necessary with one or more cocatalysts and contacting it with the olefin(s). Alternatively, the support may first be contacted (reacted) with one or more cocatalysts (if needed) such as an alkylaluminum compound, and then contacted with an appropriate Ni compound. The support may also be able to take the place of a Lewis or Bronsted acid, for instance, an acidic clay such as montmorillonite, if needed. Another method of making a supported catalyst is to start a polymerization or at least make a transition metal complex of another olefin or oligomer of an olefin such as cyclopentene on a support such as silica or alumina. These "heterogeneous" catalysts may be used to catalyze polymerization in the gas phase or the liquid phase. By gas phase is meant that a gaseous olefin is transported to contact with the catalyst particle. For the copolymerization of polar olefins using supported catalysts, especially in a liquid medium, a preferred case is when the ligand is covalently attached to the supports, which helps prevent leaching of the transition metal complex from the support.

In all of the polymerization processes described herein oligomers and polymers of the various olefins are made. They may range in molecular weight from oligomeric olefins, to lower molecular weight oils and waxes, to higher molecular weight polyolefins. One preferred product is a polymer with a degree of polymerization (DP) of about 10 or more, preferably about 40 or more. By "DP" is meant the average number of repeat (monomer) units in a polymer molecule.

Depending on their properties, the polymers made by the first and second processes described herein are useful in many ways. For instance if they are thermoplastics, they may be used as molding resins, for extrusion, films, etc. If they are elastomeric, they may be used as elastomers. If they contain functionalized monomers such as acrylate esters, they are useful for other purposes, see for instance previously incorporated U.S. Pat. No. 5,880,241.

Depending on the process conditions used and the polymerization catalyst system chosen, polymers, even those made from the same monomer(s) may have varying properties. Some of the properties that may change are molecular weight and molecular weight distribution, crystallinity, melting point, and glass transition temperature. Except for molecular weight and molecular weight distribution, branching can affect all the other properties mentioned, and branching may be varied (using the same transition metal compound) using methods described in previously incorporated U.S. Pat. No. 5,880,241.

It is known that blends of distinct polymers, varying for instance in the properties listed above, may have advantageous properties compared to "single" polymers. For instance it is known that polymers with broad or bimodal molecular weight distributions may be melt processed (be shaped) more easily than narrower molecular weight distribution polymers. Thermoplastics such as crystalline polymers may often be toughened by blending with elastomeric polymers.

Therefore, methods of producing polymers which inherently produce polymer blends are useful especially if a later separate (and expensive) polymer mixing step can be avoided. However in such polymerizations one should be aware that two different catalysts may interfere with one another, or interact in such a way as to give a single polymer.

In such a process the transition metal containing polymerization catalyst disclosed herein can be termed the first active polymerization catalyst. Monomers useful with these catalysts are those described (and also preferred) above. A second active polymerization catalyst (and optionally one or more others) is used in conjunction with the first active polymerization catalyst. The second active polymerization catalyst may be a late transition metal catalyst, for example as described herein, in previously incorporated U.S. Pat. No. 5,880,241, U.S. Pat. No. 6,060,569, U.S. Pat. No. 6,174,975 and U.S. Pat. No. 5,714,556, and/or in U.S. Pat. No. 5,955,555 (also incorporated by reference herein for all purposes as if fully set forth). Other useful types of catalysts may also be used for the second active polymerization catalyst. For instance so-called Ziegler-Natta and/or metallocene-type catalysts may also be used. These types of catalysts are well known in the polyolefin field, see for instance *Angew. Chem., Int. Ed. Engl.*, vol. 34, p. 1143–1170 (1995), EP-A-0416815 and U.S. Pat. No. 5,198,401 for information about metallocene-type catalysts; and J. Boor Jr., *Ziegler-Natta Catalysts and Polymerizations*, Academic Press, New York, 1979 for information about Ziegler-Natta-type catalysts, all of which are hereby included by reference. Many of the useful polymerization conditions for all of these types of catalysts and the first active polymerization catalysts coincide, so conditions for the polymerizations with first and second active polymerization catalysts are easily accessible. Oftentimes the "co-catalyst" or "activator" is needed for metallocene or Ziegler-Natta-type polymerizations. In many instances the same compound, such as an alkylaluminum compound, may be used as an "activator" for some or all of these various polymerization catalysts.

In one preferred process described herein the first olefin(s) (the monomer(s) polymerized by the first active polymerization catalyst) and second olefin(s) (the monomer(s) polymerized by the second active polymerization catalyst) are identical, and preferred olefins in such a process are the same as described immediately above. The first and/or second olefins may also be a single olefin or a mixture of olefins to make a copolymer. Again it is preferred that they be identical particularly in a process in which polymerization by the first and second active polymerization catalysts make polymer simultaneously.

In some processes herein the first active polymerization catalyst may polymerize a monomer that may not be polymerized by said second active polymerization catalyst, and/or vice versa. In that instance two chemically distinct polymers may be produced. In another scenario two monomers would be present, with one polymerization catalyst producing a copolymer, and the other polymerization catalyst producing a homopolymer, or two copolymers may be produced which vary in the molar proportion or repeat units from the various monomers. Other analogous combinations will be evident to the artisan.

In another variation of this process one of the polymerization catalysts makes an oligomer of an olefin, preferably ethylene, which oligomer has the formula $R^{70}CH=CH_2$, wherein $R^{70}$ is n-alkyl, preferably with an even number of carbon atoms. The other polymerization catalyst in the process then (co)polymerizes this olefin, either by itself or preferably with at least one other olefin, preferably ethylene, to form a branched polyolefin. Preparation of the oligomer (which is sometimes called an α-olefin) by a second active polymerization-type of catalyst can be found in previously incorporated U.S. Pat. No. 5,880,241, as well as in WO99/02472 (also incorporated by reference herein).

Likewise, conditions for such polymerizations, using catalysts of the second active polymerization type, will also be found in the appropriate above-mentioned references.

Two chemically different active polymerization catalysts are used in this polymerization process. The first active polymerization catalyst is described in detail above. The second active polymerization catalyst may also meet the limitations of the first active polymerization catalyst, but must be chemically distinct. For instance, it may have a different transition metal present, and/or utilize a different type of ligand and/or the same type of ligand that differs in structure between the first and second active polymerization catalysts. In one preferred process, the ligand type and the metal are the same, but the ligands differ in their substituents.

Included within the definition of two active polymerization catalysts are systems in which a single polymerization catalyst is added together with another ligand, preferably the same type of ligand, which can displace the original ligand coordinated to the metal of the original active polymerization catalyst, to produce in situ two different polymerization catalysts.

The molar ratio of the first active polymerization catalyst to the second active polymerization catalyst used will depend on the ratio of polymer from each catalyst desired, and the relative rate of polymerization of each catalyst under the process conditions. For instance, if one wanted to prepare a "toughened" thermoplastic polyethylene that contained 80% crystalline polyethylene and 20% rubbery polyethylene, and the rates of polymerization of the two catalysts were equal, then one would use a 4:1 molar ratio of the catalyst that gave crystalline polyethylene to the catalyst that gave rubbery polyethylene. More than two active polymerization catalysts may also be used if the desired product is to contain more than two different types of polymer.

The polymers made by the first active polymerization catalyst and the second active polymerization catalyst may be made in sequence, i.e., a polymerization with one (either first or second) of the catalysts followed by a polymerization with the other catalyst, as by using two polymerization vessels in series. However it is preferred to carry out the polymerization using the first and second active polymerization catalysts in the same vessel(s), i.e., simultaneously. This is possible because in most instances the first and second active polymerization catalysts are compatible with each other, and they produce their distinctive polymers in the other catalyst's presence. Any of the processes applicable to the individual catalysts may be used in this polymerization process with 2 or more catalysts, i.e., gas phase, liquid phase, continuous, etc.

Catalyst components which include transition metal complexes of (I), (II) or (XII), with or without other materials such as one or more cocatalysts and/or other polymerization catalysts are also disclosed herein. For example, such a catalyst component could include the transition metal complex supported on a support such as alumina, silica, a polymer, magnesium chloride, sodium chloride, etc., with or without other components being present. It may simply be a solution of the transition metal complex, or a slurry of the is transition metal complex in a liquid, with or without a support being present.

The polymers produced by this process may vary in molecular weight and/or molecular weight distribution and/or melting point and/or level of crystallinity, and/or glass transition temperature and/or other factors. For copolymers the polymers may differ in ratios of comonomers if the different polymerization catalysts polymerize the monomers present at different relative rates. The polymers produced are useful as molding and extrusion resins and in films as for packaging. They may have advantages such as improved melt processing, toughness and improved low temperature properties.

Hydrogen or other chain transfer agents such as silanes (for example trimethylsilane or triethylsilane) may be used to lower the molecular weight of polyolefin produced in the polymerization process herein. It is preferred that the amount of hydrogen present be about 0.01 to about 50 mole percent of the olefin present, preferably about 1 to about 20 mole percent. When liquid monomers (olefins) are present, one may need to experiment briefly to find the relative amounts of liquid monomers and hydrogen (as a gas). If both the hydrogen and monomer(s) are gaseous, their relative concentrations may be regulated by their partial pressures.

Copolymers of ethylene and certain polar comonomers such as $H_2C$=$CHC(O)R^{32}$ are described herein (first and second polymers), and they contain first branches of the formula —$(CH_2)_nCH_3$ and second branches of the formula —$(CH_2)_mC(O)R^{33}$, wherein $R^{32}$ is —$OR^{34}$ or any group readily derivable from it, $R^{33}$ is $R^{32}$ or any group readily derivable from it, $R^{34}$ is hydrocarbyl or substituted hydrocarbyl, and each $R^{35}$ is hydrogen, hydrocarbyl or substituted hydrocarbyl. By "any group readily derivable from it" is meant any derivative of a carboxylic acid which is readily interconverted from the carboxylic acid itself or a derivative of a carboxylic acid. For example a carboxylic acid ester may be converted to a carboxylic acid by hydrolysis, an amide by reaction with a primary or secondary amine, a carboxylate salt (for example with an alkali or alkaline earth metal) by hydrolysis and neutralization, an acyl halide by hydrolysis and reaction with a compound such as thionyl chloride, nitrites, and others.

The first and/or second polymers, and/or third polymers in some instances, have the following characteristics in various combinations that separates them from other copolymers made from the same monomers. These characteristics are:

the ratio of first branches wherein n is 0 to first branches wherein n is 1 is about 3.0 or more, preferably about 4.0 or more;

the ratio of first branches wherein n is 0 to first branches wherein n is 3 is 1.0 or more, preferably 1.5 or more;

the ratio of second branches wherein m is 0 to second branches wherein m is one or more is at least about 3.0, more preferably at least about 5.0;

the total number of first branches where n is 0, 1, 2 and 3 in said polymer is about 10 or more per 1000 $CH_2$ groups, preferably about 20 or more;

the incorporation of repeat units derived from $H_2C$=$CHC(O)R^{33}$ is 0.3 mole percent or more based on the total repeat units derived from ethylene and $H_2C$=$CHC(O)R^{33}$, preferably about 0.5 mole percent or more, especially preferably 1.1 mole percent or more, and very preferably about 1.5 mole percent or more (if there are repeat units in which $R^{33}$ varies, the total of such units shall be used);

the polymers have end groups of the formula ~~~~~~~HC=CH—C(O)—$R^{32}$ and at least about 5 mole percent, preferably at least about 10 mole percent, of said monomer incorporated is present in said polymer as end groups of the formula ~~~~~~~—HC=CH—C(O)—$R^{33}$, wherein ~~~~~~~ is the remainder of the polymer chain of said end group (the polymer chain the end group is attached to); and/or the said unsaturated end groups are at least 0.001 mole percent, preferably at least about 0.01 mole percent, and more preferably at least 0.1 mole percent, of the total repeat units (ethylene and polar comonomer(s)) in said polymer.

In these polymers any number of these characteristics can be combined as features of these polymers, including the preferred characteristics.

The first, second and third polymers may also contain "saturated" end groups of the formula ~~~~~~C(O)$R^{33}$, which with present analytical techniques may be indistinguishable from second branches where m is $\geq 5$. In some instances end groups may have the formula ~~~~~~CH=$CH_2$ (a vinyl end group). Such end groups may sometimes be polymerizable, and therefore polymers with such end groups may be useful as macromonomers.

It is difficult, and sometimes not possible, to distinguish between ester groups which are saturated polymer ends (no olefin bond associated with the end group), and ester groups at the ends of long branches by $^{13}C$ NMR spectroscopy (created by chain walking event, a CWE). In both cases the carbonyl group is shifted from about 175.5 ppm for the inchain comonomer to 170–174 ppm for the saturated end group or CWE. Usually the saturated ester end group or CWE peak in the region 170–174 ppm is very small and present in only trace quantities. Because of the very low levels of this peak, it is difficult to confirm by 2D NMR this hypothesis, Lie and the assignment should be considered tentative. Review of many of the experimental results obtained show that in many examples no saturated end groups and/or CWE are present. However in some examples up to 50 mole percent, more commonly up to 20 mole percent, of the total amount of acrylate ester appears to be present as saturated end groups and/or CWE. These numbers are very approximate, since the contents of the saturated end groups and/or CWE are typically so small the error in the measurement is relatively large.

Some NMR and separations evidence exists that these copolymers may sometimes be capped by short runs of acrylate homopolymers, presumably by free radical polymerization of acrylate ester at the beginning and/or end of the coordination polymerization of a polymer chain.

The first, second and third polymers are useful in many ways, for instance,

1. Tackifiers for low strength adhesives (U, vol. A1, p. 235–236) are a use for these polymers. Elastomeric and/or relatively low molecular weight polymers are preferred.

2. The polymers are useful as base resins for hot melt adhesives (U, vol. A1, p. 233–234), pressure sensitive adhesives (U, vol. A1, p. 235–236) or solvent applied adhesives. Thermoplastics are preferred for hot melt adhesives. The polymers may also be used in a carpet installation adhesive.

3. Base polymer for caulking of various kinds is another use. An elastomer is preferred. Lower molecular weight polymers are often used.

4. The polymers, particularly elastomers, may be used for modifying asphalt, to improve the physical properties of the asphalt and/or extend the life of asphalt paving, see U.S. Pat. No. 3,980,598.

5. Wire insulation and jacketing may be made from any of the polymers (see EPSE, vol. 17, p. 828–842). In the case of elastomers it may be preferable to crosslink the polymer after the insulation or jacketing is formed, for example by free radicals.

6. The polymers, especially the branched polymers, are useful as base resins for carpet backing, especially for automobile carpeting.

7. The polymers may be used for extrusion or coextrusion coatings onto plastics, metals, textiles or paper webs.

8. The polymers may be used as a laminating adhesive for glass.

9. The polymers are useful for blown or cast films or as sheet (see EPSE, vol. 7 p. 88–106; ECT4, vol. 11, p. 843–856; PM, p. 252 and p. 432ff). The films may be single layer or multilayer, the multilayer films may include other polymers, adhesives, etc. For packaging the films may be stretch-wrap, shrink-wrap or cling wrap. The films are useful for many applications such as packaging foods, geomembranes and pond liners. It is preferred that these polymers have some crystallinity.

10. The polymers may be used to form flexible or rigid foamed objects, such as cores for various sports items such as surf boards and liners for protective headgear. Structural foams may also be made. It is preferred that the polymers have some crystallinity. The polymer of the foams may be crosslinked.

11. In powdered form the polymers may be used to coat objects by using plasma, flame spray or fluidized bed techniques.

12. Extruded films may be formed from these polymers, and these films may be treated, for example drawn. Such extruded films are useful for packaging of various sorts.

13. The polymers, especially those that are elastomeric, may be used in various types of hoses, such as automotive heater hose.

14. The polymers may be used as reactive diluents in automotive finishes, and for this purpose it is preferred that they have a relatively low molecular weight and/or have some crystallinity.

15. The polymers can be converted to ionomers, which when they possess crystallinity can be used as molding resins. Exemplary uses for these ionomeric molding resins are golf ball covers, perfume caps, sporting goods, film packaging applications, as tougheners in other polymers, and usually extruded) detonator cords.

16. The functional groups on the polymers can be used to initiate the polymerization of other types of monomers or to copolymerize with other types of monomers. If the polymers are elastomeric, they can act as toughening agents.

17. The polymers can act as compatibilizing agents between various other polymers.

18. The polymers can act as tougheners for various other polymers, such as thermoplastics and thermosets, particularly if the olefin/polar monomer polymers are elastomeric.

19. The polymers may act as internal plasticizers for other polymers in blends. A polymer which may be plasticized is poly(vinyl chloride).

20. The polymers can serve as adhesives between other polymers.

21. With the appropriate functional groups, the polymers may serve as curing agents for other polymers with complimentary functional groups (i.e., the functional groups of the two polymers react with each other).

22. The polymers, especially those that are branched, are useful as pour point depressants for fuels and oils.

23. Lubricating oil additives as Viscosity Index Improvers for multigrade engine oil (ECT3, Vol 14, p. 495–496) are another use. Branched polymers are preferred. Ethylene copolymer with acrylates or other polar monomers will also function as Viscosity Index Improvers for multigrade engine oil with the additional advantage of providing some dispersancy.

24. The polymers may be used for roofing membranes.

25. The polymers may be used as additives to various molding resins such as the so-called thermoplastic olefins to improve paint adhesion, as in automotive uses.

26. A flexible pouch made from a single layer or multilayer film (as described above) which may be used for packaging various liquid products such as milk, or powder such as hot chocolate mix. The pouch may be heat sealed. It may also have a barrier layer, such as a metal foil layer.

27. A wrap packaging film having differential cling is provided by a film laminate, comprising at least two layers; an outer reverse which is a polymer (or a blend thereof) described herein, which contains a tackifier in sufficient amount to impart cling properties; and an outer obverse which has a density of at least about 0.916 g/mL which has little or no cling, provided that a density of the outer reverse layer is at least 0.008 g/mL less than that of the density of the outer obverse layer. It is preferred that the outer obverse layer is linear low density polyethylene, and the polymer of the outer obverse layer have a density of less than 0.90 g/mL. All densities are measured at 25° C.

28. Fine denier fibers and/or multifilaments. These may be melt spun. They may be in the form of a filament bundle, a non-woven web, a woven fabric, a knitted fabric or staple fiber.

29. A composition comprising a mixture of the polymers herein and an antifogging agent. This composition is especially useful in film or sheet form because of its antifogging properties.

30. If the polymers are functionalized with monomers such as fluoroalkyl acrylate esters or other fluorine-containing monomers, they are useful for selectively imparting surface activity to polyolefins. This would be of use reducing fluid penetration in flash-spun polyolefin films for medical and other applications. The fluoro-functionalized polyolefins would also be useful for dispersing fluoropolymers in lubricant applications.

31. Mixtures of ethylene homopolymers or oligomers together with copolymers of ethylene and acrylates and optionally other monomers are useful as adhesion promoters, surface active agents, tougheners, and compatibilizers for additives.

In the above use listings, sometimes a reference is given which discusses such uses for polymers in general. All of these references are hereby included by reference. For the references, "U" refers to, W. Gerhartz, et al., Ed., *Ullmann's Encyclopedia of Industrial Chemistry*, 5th Ed. VCH Verlagsgesellschaft mBH, Weinheim, for which the volume and page number are given, "ECT3" refers to the H. F. Mark, et al., Ed., *Kirk-Othmer Encyclopedia of Chemical Technology*, 4th Ed., John Wiley & Sons, New York, "ECT4" refers to the J. I Kroschwitz, et al., Ed., *Kirk-Othmer Encyclopedia of Chemical Technology*, 4th Ed., John Wiley & Sons, New York, for which the volume and page number are given, "EPSE" refers to H. F. Mark, et al., Ed., *Encyclopedia of Polymer Science and Engineering*, 2nd Ed., John Wiley & Sons, New York, for which volume and page numbers are given, and "PM" refers to J. A. Brydson, ed., *Plastics Materials*, 5th Ed., Butterworth-Heinemann, Oxford, UK, 1989, and the page is given.

In the Examples, all pressures are gauge pressures. The following abbreviations are used:

$\Delta H_f$—heat of fusion (in J/g)
BAF—tetrakis(bis-3,5-(trifluoromethyl)phenyl)borate
DSC—differential scanning calorimetry
GPC—gel permeation chromatography
PMAO-IP—improved processing methylaluminoxane from Akzo-Nobel
RB—round-bottomed
RT—room temperature
TCB—1,2,4-trichlorobenzene
THF—tetrahydrofuran
Am—amyl
Ar—aryl
BAF—tetrakis(3,5-trifluoromethylphenyl)borate
BArF—tetrakis(pentafluorophenyl)borate
BHT—2,6-di-t-butyl-4-methylphenol
Bu—butyl
$Bu_2O$—dibutyl ether
CB—chlorobenzene
Cmpd—compound
E—ethylene
EG—end-group, refers to the ester group of the acrylate being located in an unsaturated end group of the ethylene copolymer
EGPEA—2-phenoxyethyl acrylate
Eoc—end-of-chain
Equiv—equivalent
Et—ethyl
$Et_{sBu}$—percent of ethyl branches occurring in sec-butyl ended branches
GPC—gel permeation chromatography
HA—hexyl acrylate
Hex—hexyl
IC—in-chain, refers to the ester group of the acrylate being bound to the main-chain of the ethylene copolymer
IDA—isodecyl acrylate
Incorp—incorporation
i-Pr—iso-propyl
M.W.—molecular weight
MA—methyl acrylate
Me—methyl
MeOH—methanol
$Me_{sBu}$—percent of methyl branches occurring in sec-butyl ended branches
MI—melt index
Mn—number average molecular weight
Mp—peak average molecular weight
Mw—weight average molecular weight
N:—not determined
PDI—polydispersity; Mw/Mn
PE—polyethylene
Ph—phenyl
Press—pressure
RI—refractive index
Rt or RT—room temperature
t-Bu—t-butyl
TCB—1,2,4-trichlorobenzene
Temp—temperature
THA—3,5,5-trimethylhexyl acrylate
THF—tetrahydrofuran
TO—number of turnovers per metal center=(moles monomer consumed, as determined by the weight of the isolated polymer or oligomers) divided by (moles catalyst)
tol—toluene
Total Me—Total number of methyl groups per 1000 methylene groups as determined by $^1H$ or $^{13}C$ NMR analysis
UV—ultraviolet

EXAMPLES 1–89

Ligand Precursor and Catalyst Synthesis

All operations related to the catalyst synthesis were performed in a nitrogen drybox or using a Schlenk line with nitrogen protection. Anhydrous solvents were used in all cases. Solvents were distilled from drying agents under nitrogen using standard procedures: chlorobenzene from $P_2O_5$; THF from sodium benzophenone ketyl. Ni[II] allyl chloride and NaBAF were prepared according to the literature.

(Tert-butyl)$_2$PCH$_2$Li was synthesized by reacting (tert-butyl)$_2$PCH$_3$ with tert-butyl lithium in heptane in a 109° C. bath for a few hours. The product was filtered and washed with pentane. (Tert-butyl)$_2$PLi was synthesized by reacting (tert-butyl)$_2$PH with n-butyl lithium in heptane at 90° C. for 6 h. Ph$_2$PLi was made by reacting Ph$_2$PH with n-butyl lithium at RT for 3 d at RT. The NMR spectra were recorded using a Bruker 500 MHz spectrometer or a Bruker 300 MHz spectrometer.

In the Examples 1–89 the following catalysts were used:

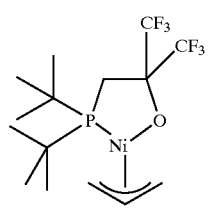

1

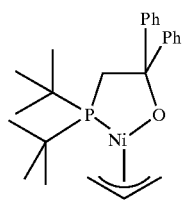
2
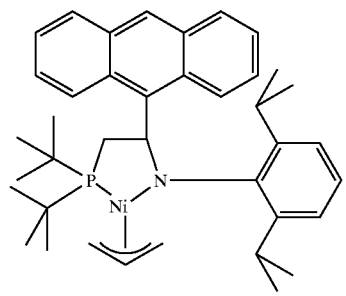
3
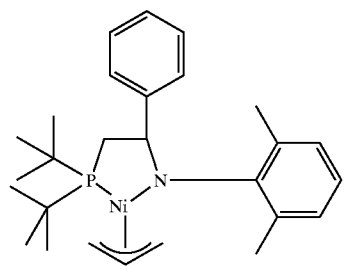
4
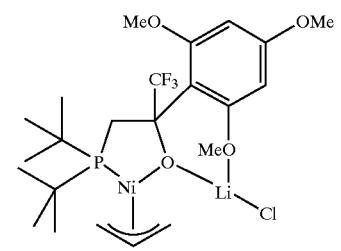
5
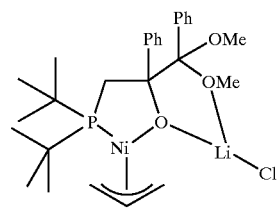
7
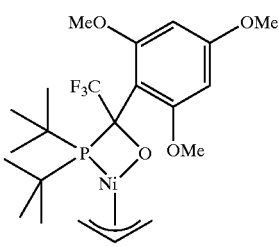
8
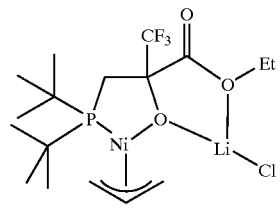
9
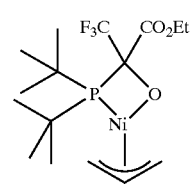
10
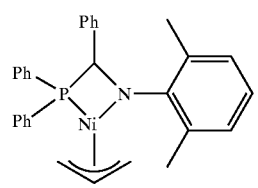
11
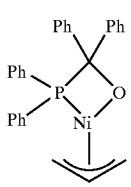
12
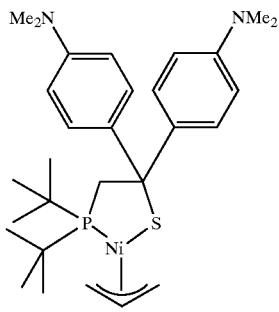
13
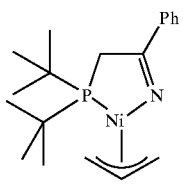
14

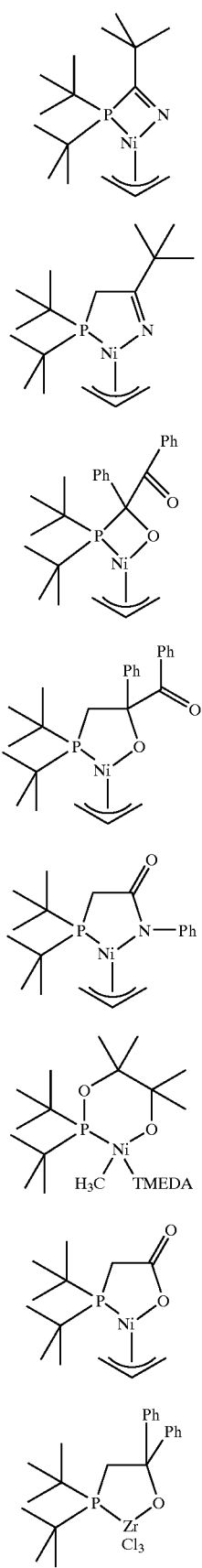

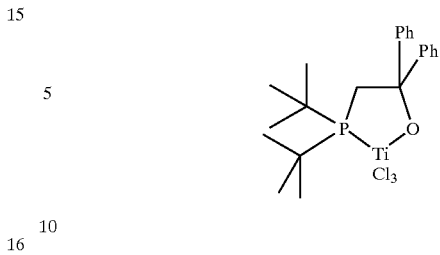

EXAMPLE 1

Synthesis of Catalyst 1

In a drybox, 0.50 g (tert-butyl)$_2$PCH$_2$Li was mixed with 20 mL THF in a Schlenk flask. It was brought out of the drybox and placed in an ice-water bath. One atmosphere of hexafluoroacetone was applied to the flask. The mixture was allowed to stir at 0° C. under 1 atm of hexafluoroacetone for 1 h. The hexafluoroacetone flow was stopped. The reaction mixture was allowed to warm up to RT, during which time gas evolution was seen. The mixture was then stirred at RT for 1 h and was transferred back to the drybox. The THF was evaporated. The product was dried under full vacuum overnight. A yellow solid was obtained. $^{31}$PNMR in THP-d$_8$: singlet peak at 13.07 ppm. $^1$HNMR in THF-d$_8$: 2.08 ppm (2H, d, JPH=4.6 Hz, P—CH$_2$—); 1.22 ppm (18H, d, JPH= 11.2 Hz, —C(CH$_3$)$_3$). A small amount of THF (~0.2 eq) existed in the solid product. To this product was added 0.405 g ((allyl)NiCl)$_2$ and 15 mL THF. The mixture was allowed to stir at RT over the weekend. The mixture was evaporated to dryness, extracted with 30 mL toluene, filtered through Celite®, followed by 3×5 mL toluene wash. Solvent was evaporated. The product was dried under full vacuum overnight. The product became powdery after triturating with pentane. Yellow brown solid (0.82 9) was obtained. $^{31}$PNMR in CD$_2$Cl$_2$: singlet peak at 78.81 ppm.

EXAMPLE 2

Synthesis of Catalyst 2

A 100-mL round-bottomed flask was charged with 292 mg (1.60 mmol) of benzophenone dissolved in ca. 15 mL THF. Then the (t-Bu)$_2$P—CH$_2$Li (266 mg, 1.60 mmol) dissolved in ca. 15 mL THF was added. The solution turns from colorless to dark blue. It was stirred for one hour after which time, a solution of (Ni(C$_3$H$_5$)Cl)$_2$ (217 mg, 0.80 mmol) in 15 mL THF was added. It was stirred for an additional 1 h and the solvent removed. The residue was extracted with hexane and toluene and the solvent removed. The residue was washed with small amounts of hexane and dried. The yield was 395 mg (71%). $^1$HNMR (CD2Cl2, 23° C., 300 MHz) d 8.2–7.9 (m, 4H, Ar); 7.4–6.9 (m, 6H, Ar); 5.10 (m, 1H); 4.26 (brs, 1H); 3.25 (dd, J=14 Hz, J=5 Hz, 1H), 2.80 (m, 2H), 2.24 (brs, 1H), 1.16 (d, J=13 Hz, 1H), 0.97 (d, JP—H=13 Hz, 9H); 0.80 (d, JP—H=13 Hz). $^{31}$PNMR (CD2Cl2, 23° C.,): d 84.0. $^{13}$CNMR (CD2Cl2, 23° C., 75 MHz) d 156.1 (s); Ar C—H signals overlapping with C6D6 signal; 127.2 (s); 125.7 (d, JP—C=6 Hz); 109.3 (d, JC—H=157 Hz); 86.7 (d, JP—C=10 Hz); 69.1 (m, JP—C= 22 Hz); 41.2 (dt, JP—C=25 Hz, JC—H=127 Hz); 37.6 (m, JP—C=6 Hz); 33.8 (m); 29.9 (q, JC—H=124 Hz).

A single red-orange crystal was grown from CH$_2$Cl$_2$/hexane at ambient temperature, and X-ray diffraction data confirmed the structure. No LiCl was present in the structure based X-ray single crystal diffraction analysis.

EXAMPLE 3

Synthesis of Catalyst 3

In a drybox, 0.2273 g (tert-butyl)$_2$PCH$_2$Li was mixed with 20 mL THF in a 100 mL RB flask. The mixture was cooled at −30° C. for 30 min. Under stirring, 0.50 g monoimine-A was added to the solution while the solution was still cold. The reaction mixture turned yellow blue right away. The mixture was allowed to warm up to RT and to stir at this temperature overnight. THF was evaporated. The product was dried under vacuum for 7 h. A deep yellow green solid (0.912 g) was isolated. $^{31}$PNMR in THF-d$_8$: singlet peak at 18.56 ppm. To the product was added 0.1847 g ((allyl)NiCl)$_2$ and 20 mL THF in a RB flask. The mixture was allowed to stir for 6.5 h at RT. The mixture was evaporated to dryness. The residue was extracted with 25 mL toluene. It was filtered through Celite®, followed by 3×5 mL toluene wash. The solution was evaporated to dryness. The product was then dried under full vacuum overnight. Dark green solid (0.92 g) was isolated.

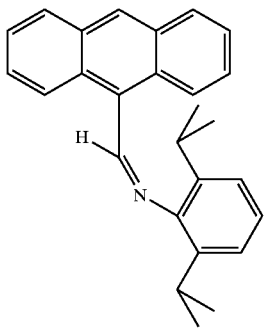

A

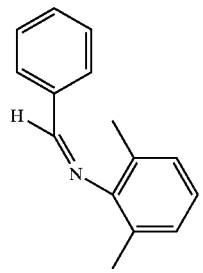

B

EXAMPLE 4

Synthesis of Catalyst 4

In a drybox, 0.35 g (tert-butyl)$_2$PCH$_2$Li was added to the −30° C. solution of 0.4409 g monoimine-B in 30 mL THF in a 100 mL RB flask. The reaction mixture turned yellow blue immediately. The mixture was allowed to warm up to RT and stirred at this temperature for 19 h. THF was evaporated. The product was dried under vacuum. $^{31}$PNMR in THF-d$_8$: Two singlet peaks. One was a sharp and tall peak at 20.54 ppm and another was a wide and short peak at 18.74 ppm. To the product was added 0.2812 g ((allyl)NiCl)$_2$ and 30 mL THF in a RB flask. The mixture was allowed to stir for 18 h at RT. The mixture was evaporated to dryness. The residue was extracted with 30 mL toluene. It was filtered through Celite®, followed by 3×5 mL toluene wash. The solution was evaporated to dryness. The solid product was then dried under vacuum for 8 h. $^{31}$PNMR in C$_6$D$_6$: two major singlet peak at 81.75 ppm and 79.92 ppm, as well as a minor singlet peak at 20.05 ppm. Electron spray mass spectroscopy showed major peaks at 468 and 470 (due to $^{58}$Ni and $^{60}$Ni isotopes), which indicated that the desired product picked up a proton in the spray process. X-ray single crystal diffraction analysis confirmed the structure. No LiCl was present in the structure.

EXAMPLE 5

Synthesis of Catalyst 5

A 100 mL RB flask was charged with 217 mg(0.82 mmol) of 2,2,2-trifluoro-2',4',6'-trimethoxyacetophenone dissolved in ca. 10–15 mL THF. Then (t-Bu)$_2$P—CH$_2$Li (136 mg, 0.82 mmol) dissolved in ca. 10–15 mL THF was added. The initially purple solution (color came from traces impurities in starting ketone) turned clear yellow. It was stirred for one h after which time, a solution of (Ni(C$_3$H$_5$)Cl)$_2$ (111 mg, 0.41 mmol) in 10–15 mL THF was added. It was stirred for an additional one h and the solvent removed. The residue was washed with hexane and dried in vacuo to yield 362 mg (78%). Key NMR signals (incomplete): $^1$H-NMR (CD$_2$Cl$_2$, 23° C., 300 MHz) δ 6.5–6.2 (brm, 2H, Ar); 5.3 (brm, 1H), 4.8 (brs, 1H); 4.1 (brs, 2H); 3.8 (brs, 9H); 3.7–2.0 (brm); 2.0–0.8 (brm, t-Bu signals). Two isomers (50:50) by $^{31}$PNMR (CD$_2$Cl$_2$, 23° C., 300 MHz). δ 81.4; 80.2. $^{13}$CNMR (CD$_2$Cl2, 23° C., 125 MHz): δ 161.3 (s); ca. 112 (brs); ca. 94.0 (brm, J=158 Hz); 93.2 (br); ca. 86; 68.1; 58.4; 56.3; 55.6. A single red-orange crystal was grown from CH$_2$Cl$_2$/hexane at ambient temperature, and the structure confirmed by X-ray diffraction. The complex contained one equivalent of LiCl, and existed as a dimer bridged by LiCl.

EXAMPLE 6

Synthesis of Catalyst 6

A 200 mL RB flask was charged with 300 mg (1.10 mmol) of 2,4,6-trimethoxybenzophenone dissolved in ca. 20 mL THF. Then (t-Bu)$_2$P—CH$_2$Li (183 mg, 1.10 mmol) dissolved in ca. 20 mL THF was added. It was stirred for one h, after which time, a solution of (Ni(C$_3$H$_5$)Cl)$_2$ (149 mg, 0.55 mmol) in THF (ca. 20 mL) was added. It was stirred for an additional one h and the solvent removed. The residue was washed with hexane and dried in vacuo to yield 664 mg product. Key NMR signals (incomplete): $^1$HNMR (CD$_2$Cl$_2$, 23° C., 300 MHz) δ 7.64 (brs, 1H, Ar); 7.51 (brs, 1H, Ar); 7.14 (brt, 2H, Ar); 7.00 (brt, 1H, Ar); 6.14 (s, 2H); 5.28 (m, 1H); 5.0–4.5 (brm, 2H); 3.67 (s, 3H, OCH3); 3.64 (s, 6H, OCH$_3$); 3.26 (brs, 1H); 2.87 (dd, 1H, J=14 Hz, J=5 Hz); 2.8–2.4 (brm, 2H); 1.7–0.7 (brm, 18H, t-Bu). Two isomers (50:50) by $^{31}$PNMR (CD$_2$Cl$_2$, 23° C., 75 MHz): δ 79.0; 78.2. $^{13}$CNMR (CD$_2$Cl$_2$, 23C, 125 MHz): δ 167.9 (d, J$_{P-C}$=4.5 Hz); 159.9 (s); 158.5 (brs); 154.4 (brs); 127.6 (dd, J$_{C-H}$=158 Hz, J=7.5 Hz); 126.1 (dt); 125.7 (dt, J=150 Hz); 111.0 (brd); 95.0 (dd, J$_{C-H}$=159 Hz, J=4.7 Hz); 87.2 (brs); 67.0 (brdt, J$_{P-C}$=22 Hz); 57.7 (q, J$_{C-H}$=145 Hz); 55.6 (q, J$_{C-H}$=144 Hz); ca. 40.0 (brs); 39.7 (dt, J$_{P-C}$=25 Hz); 35.3 (d, J$_{P-C}$=18 Hz); 33.7 (d, J$_{P-C}$=16 Hz); 30.0 (brq, J$_{C-H}$=127 Hz). A single red-orange crystal was grown from CH$_2$Cl$_2$/hexane at ambient temperature, and an X-ray diffraction confirmed the structure. The complex contained one equivalent of LiCl, and existed as a dimer bridged by LiCl.

EXAMPLE 7

Synthesis of Catalyst 7

A 200 mL RB flask was charged with 300 mg (1.17 mmol) of 2,2-dimethoxy-2-phenylacetophenone dissolved in ca. 20 mL THF. Then (t-Bu)$_2$P—CH$_2$Li (195 mg, 1.17 mmol) dissolved in ca. 20 mL THF was added. It was stirred for one h, after which time a solution of (Ni(C$_3$H$_5$)Cl)$_2$ (158 mg, 0.59 mmol) in THF (ca. 20 mL) was added. It was stirred for an additional h and the solvent removed. The residue was washed with hexane and dried in vacuo to yield 438 mg (67%). Two isomers (50:50) by $^{31}$PNMR (CD$_2$Cl$_2$, 23° C., 300 MHz): δ 82.1 (s) and δ 81.5 (s). A single red-orange crystal was grown from CH$_2$Cl$_2$/hexane at ambient temperature, and X-ray diffraction data confirmed the structure. The complex contained one equivalent of LiCl, and existed as a dimer bridged by LiCl.

EXAMPLE 8

Synthesis of Catalyst 8

In a drybox, 0.3043 g (tert-butyl)$_2$PLi was added to a −30° C. solution of 0.5284 g 2,2,2-trifluoro-2',4',6'-trimethoxyacetophenone (Aldrich) in 15 mL THF in a 100 mL RB flask. The reaction mixture turned yellow. The mixture was allowed to warm up to RT and stir at this temperature overnight. THF was evaporated. The product was dried under vacuum for 6 h. $^{31}$PNMR in THF-d$_8$: a singlet peak at 41.28 ppm. The product was mixed with 0.1608 g ((allyl)NiCl)$_2$ and 15 mL THF in a RB flask. The mixture was allowed to stir for 2 h at RT. It was then evaporated to dryness. The residue was mixed with 10 mL toluene. Pentane (40 mL) was then added into the flask. The brown solid was filtered, followed by 3× pentane wash and dried in vacuo. Brown solid (0.445 g) was obtained. $^{31}$PNMR in THF-d$_8$: two singlet peak at 50.31 ppm and 50.05 ppm.

EXAMPLE 9

Synthesis of Catalyst 9

In a drybox, 0.30 g (tert-butyl)$_2$PCH$_2$Li was added to a −30° C. solution of 0.3072 g ethyl trifluoropyruvate (Lancaster) in 15 mL THF in a 100 mL RB flask. The reaction mixture turned golden yellow. The mixture was allowed to warm up to RT and stir at this temperature for 1 h. THF was evaporated. The product was dried under vacuum overnight. The product was mixed with 0.247 g ((allyl)NiCl)$_2$ and 15 mL THF in a RB flask. The mixture was allowed to stir for 1 h at RT. The mixture was then evaporated to dryness. The residue was dissolved by adding 10 mL toluene. Pentane (40 mL) was then added into the flask. The yellow solid was filtered, followed by 3× pentane wash and dried in vacuo. Yellow solid (0.36 g) was obtained. $^{31}$PNMR in THF-d$_8$: The major singlet peak at 78.24 ppm and two small singlet peaks at 96.72 ppm and 218.21 ppm. A single crystal was grown and the structure was confirmed synchrotron diffraction analysis. The complex contained one equivalent of LiCl, and existed as a dimer bridged by LiCl.

EXAMPLE 10

Synthesis of Catalyst 10

In a drybox, 0.502 g (tert-butyl)$_2$PLi was added to a −30° C. solution of 0.5613 g ethyl trifluoropyruvate (Lancaster) in 25 mL THF in a 100 mL RB flask. The reaction mixture turned yellow and then copper color. The mixture was allowed to warm up to RT and to stir at this temperature overnight. THF was evaporated. The product was dried under vacuum. $^{31}$PNMR in THF-d$_8$: singlet peak at 41.22 ppm. The product was mixed with 0.453 g ((allyl)NiCl)$_2$ and 25 mL THF in a RB flask. The mixture was allowed to stir for 1 h at RT. The mixture was evaporated to dryness. The residue was mixed with 5 mL toluene. Pentane (40 mL) was then added into the flask. The brown solid was filtered, followed by 3× pentane wash and dried in vacuo. Brown solid (0.745 g) was obtained. $^{31}$PNMR in THF-d$_8$: Singlet peak at 46.04 ppm.

EXAMPLE 11

Synthesis of Catalyst 11

In a drybox, 0.40 g Ph$_2$PLi was added to a −30° C. solution of 0.4357 g monoimine-B in 25 mL THF in a 100 mL RB flask. The reaction mixture turned orange. The mixture was allowed to warm up to RT and stir at this temperature for 1 h. THF was evaporated. The product was dried under vacuum. $^{31}$PNMR in THF-d$_8$: A major singlet peak at −22.60 and two small singlet peaks at −16.15 ppm and −82.25 ppm. The product was mixed with 0.2798 g ((allyl)NiCl)$_2$ and 25 mL THF in a RB flask. The mixture was allowed to stir for 2 h at RT. The mixture was evaporated to dryness. The residue was extracted with toluene, filtered and washed with toluene. Solvent was evaporated. The product was dried in vacuo.

EXAMPLE 12

Synthesis of Catalyst 12

In a drybox, 0.40 g Ph$_2$PLi was added to a −30° C. solution of 0.3794 g benzophenone in 25 mL THF in a 100 mL RB flask. The reaction mixture turned blue-green. The mixture was allowed to warm up to RT and to stir at this temperature for 1 h. THF was evaporated. The product was dried under vacuum. $^{31}$PNMR in THF-d$_8$: A major singlet peak at −14.28 and a small singlet peaks at −26.30 ppm, as well as a tiny singlet peak at −39.62 ppm. The product was mixed with 0.2796 g ((allyl)NiCl)$_2$ and 25 mL THF in a RB flask. The mixture was allowed to stir for 2 h at RT. The mixture was evaporated to dryness. The residue was extracted with toluene, filtered and washed with toluene. Solvent was evaporated. The product was dried in vacuo.

EXAMPLE 13

Synthesis of Catalyst 13

In a drybox, 0.30 g (tert-butyl)$_2$PCH$_2$Li was added to a −30° C. solution of 0.5137 g 4,4'-bis(dimethylamino) thiobenzophenone in 20 mL THF in a 100 mL RB flask. The reaction mixture turned golden yellow. The mixture was allowed to warm up to RT and to stir at this temperature for a few h. THF was evaporated. The product was dried under vacuum overnight. $^{31}$PNMR in THF-d$_8$: A major singlet peak at 21.53 ppm and some minor peaks at 26.05 ppm, 24.34 ppm, 16.58 ppm and 12.74 ppm. The product was mixed with 0.148 g ((allyl)NiCl)$_2$ and 15 mL THF in a RB flask. The mixture was allowed to stir for 2 h at RT. The mixture was evaporated to dryness. The solid product was dried in vacuo overnight. $^{31}$PNMR in THF-d$_8$: A singlet peak at 101.84 ppm.

EXAMPLE 14

Synthesis of Catalyst 14

In a drybox, 0.40 g (tert-butyl)$_2$PCH$_2$Li was added to a −30° C. solution of 0.2485 g benzonitrile in 20 mL THF in a 100 mL RB flask. The reaction mixture turned red-orange.

The mixture was allowed to warm up to RT and stir at this temperature for a few hours. THF was evaporated. The product was dried under vacuum overnight. $^{31}$PNMR in THF-$d_8$: A broad singlet peak at 7.26 ppm. $^1$HNMR in THF-$d_8$ indicated that it was (t-Bu)$_2$PCH(Li)C(Ph)=NH: 1.14 ppm (18H, (CH$_3$)$_3$C—, d, $^3$JPH=10.8 Hz); 3.71 ppm (1H, broad singlet); 4.23 ppm (1H, broad singlet, —C(Ph)=NH); 7.11 ppm (1H, ArH, t); 7.18 ppm (2H, ArH, t); 7.64 ppm (2H, ArH, d). The product was mixed with 0.327 g ((allyl)NiCl)$_2$ and 20 mL THF in a RB flask. The mixture was allowed to stir for 2.5 h at RT. The mixture was evaporated to dryness. The solid product was extracted with 10 mL toluene and was filtered through Celite®, followed by 3×10 mL toluene wash. Toluene was evaporated. The solid product was dried in vacuo overnight. Dark brown solid (0.379 g) was obtained. $^{31}$PNMR in THF-$d_8$: A singlet peak at 73.06 ppm. $^1$HNMR in THF-$d_8$ indicated that it is the expected ((t-Bu)$_2$PCH$_2$C(Ph)=NNi(allyl)) complex: 1.26 and 1.41 ppm (9H each, (CH$_3$)$_3$C—, d, $^3$JPH=12.9 Hz for both); 1.59 and 2.49 ppm (1H each, d, PCHH'); 3.11, 3.59, 3.68, 4.24 ppm (1H each, broad singlets, allyl-H); 5.02 ppm (1H, m, central allyl-H); 7.26 ppm (3H, s, ArH); 7.53 ppm (2H, s, ArH).

EXAMPLE 15

Synthesis of Catalyst 15

In a drybox, 0.40 g (tert-butyl)$_2$PLi was added to a −30° C. solution of 0.2186 g trimethylacetonitrile in 20 mL THF in a 100 mL RB flask. The reaction mixture turned yellow. The mixture was allowed to warm up to RT and to stir at this temperature for 3 d. THF was evaporated. The product was dried under vacuum overnight. $^{31}$PNMR in THF-$d_8$: 45.93 ppm and a minor peak at 21.13 ppm. The product was mixed with 0.357 g ((allyl)NiCl)$_2$ and 20 mL THF in a RB flask. The mixture was allowed to stir for 1 h at RT. The mixture was evaporated to dryness. The solid product was extracted with toluene and was filtered through Celite®, followed by 3× toluene wash. Toluene was evaporated. The solid product was dried in vacuo overnight. Red-brown solid (0.476 g) was obtained.

EXAMPLE 16

Synthesis of Catalyst 16

In a drybox, 0.40 g (tert-butyl)$_2$PCH$_2$Li was added to a −30° C. solution of 0.2003 g trimethylacetonitrile in 20 mL THF in a 100 mL RB flask. The reaction mixture turned yellow. The mixture was allowed to warm up to RT and stir at this temperature for 3 d. THF was evaporated. The product was dried under vacuum overnight. $^{31}$PNMR in THF-$d_8$: A major singlet peak at 17.67 ppm and a minor peak at 12.78. The product was mixed with 0.327 g ((allyl)NiCl)$_2$ and 20 mL THF in a RB flask. The mixture was allowed to stir for 1 h at RT. The mixture was evaporated to dryness. The solid product was mixed with 10 mL toluene first and then 40 mL pentane. The solid was filtered, followed by 3× pentane wash and dried in vacuo overnight. $^{31}$PNMR in THF-$d_8$: A singlet peak at 73.48 ppm. $^1$HNMR in THF-$d_8$: 1.18 ppm (d, —P(CH$_3$)$_3$, 18H); 1.34 ppm (d, —C(CH$_3$)$_3$, 9H); 1.49 ppm, 2.38 ppm (1H each, d, PCHH'); 3.01 ppm, 3.23 ppm, 3.44 ppm, 3.97 ppm (1H each, brs, allyl-H); 4.92 ppm (1H, central allyl-H, m).

EXAMPLE 17

Synthesis of Catalyst 17

In a drybox, 0.40 g (tert-butyl)$_2$PLi was added to a −30° C. solution of 0.5529 g benzil in 20 mL THF in a 100 mL RB flask. The reaction mixture turned dark red-brown. The mixture was allowed to warm up to RT and stir at this temperature overnight. THF was evaporated. The product was dried under vacuum overnight. $^{31}$PNMR in THF-$d_8$: A major singlet peak at 41.09 ppm and a minor peak at 2.45 ppm. The product was mixed with 0.359 g ((allyl)NiCl)$_2$ and 20 mL THF in a RB flask. The mixture was allowed to stir for 1 h at RT. The mixture was evaporated to dryness. The solid product was mixed with 10 mL toluene first and then 90 mL pentane. The solid was filtered, followed by 3× pentane wash and dried in vacuo overnight. Light brown solid (0.59 g) was obtained.

EXAMPLE 18

Synthesis of Catalyst 18

In a drybox, 0.40 g (tert-butyl)$_2$CH$_2$PLi was added to a −30° C. solution of 0.5066 g benzil in 20 mL THF in a 100 mL RB flask. The reaction mixture turned dark red-brown. The mixture was allowed to warm up to RT and to stir at this temperature overnight. THF was evaporated. The product was dried under vacuum overnight. $^{31}$PNMR in THF-$d_8$: A major singlet peak at 14.28 ppm and several minor peaks were observed. The product was mixed with 0.329 g ((allyl)NiCl)$_2$ and 20 mL THF in a RB flask. The mixture was allowed to stir for 1 h at RT. The mixture was evaporated to dryness. The solid product was mixed with 10 mL toluene first and then 90 mL pentane. The solid was filtered, followed by 3× pentane wash and dried in vacuo overnight. Yellow solid (0.285 g) was obtained. $^{31}$PNMR in THF-$d_8$: A major singlet peak at 94.03 ppm and minor peaks at 67.51, 66.72 and 62.29 ppm were observed.

EXAMPLE 19

Synthesis of Catalyst 19

A 100 mL RB flask was charged with 102 mg (0.86 mmol) 9 of phenyl isocyanate dissolved in ca. 10 mL THF. Then (t-Bu)$_2$P—CH$_2$Li (143 mg, 0.86 mmol) dissolved in ca. 10 mL THF was added. The solution is clear yellow. It was stirred for one h, after which time a solution of (Ni(C$_3$H$_5$)Cl)$_2$ (116 mg, 0.43 mmol) in 15 mL THF was added. The solution turned brown-yellow. It was stirred for an additional one h and the solvent removed. The residue was washed with hexane and dried in vacuo. The yield was 207 mg (57%). Key NMR signals (incomplete) $^1$HNMR (CD$_2$Cl$_2$, 23° C., 300 MHz) δ 7.7–6.5 (brm, Ar); 5.32 (brs), 5.09 (m); 3.64 (brm); 3.01 (brm); 3.0–2.3 (brm); 2.0–0.6 overlapping signals+two doublets (J=14 Hz) at 1.42 ppm and 1.27 ppm corresponding to t-Bu signals). $^{31}$PNMR (CD$_2$Cl$_2$, 23° C., 300 MHz) δ 50.6.

EXAMPLE 20A

Synthesis of (t-Bu)$_2$POC(CH$_3$)$_2$C(CH$_3$)$_2$OH

In a drybox, 0.623 g pinacol and 2.0 g (t-Bu)$_2$PCl were dissolved in 20 mL THF. To this mixture was added over 10 min 0.4438 g KH in portions. The mixture was allowed to stir at RT for 12 d. The mixture was filtered through Celite®, followed by 3×5 mL THF wash. Solvent was evaporated. The viscous liquid was dried overnight. Light tan viscous liquid was obtained. $^{31}$PNMR in CD$_2$Cl$_2$: A singlet peak at 135.29 ppm and a few minor peaks. Crystals grew out of the liquid in several days. X-ray single crystal analysis indicated that it was the desired product. It existed as tetramer in the solid state through hydrogen bonding.

39

EXAMPLE 20B

Synthesis of Catalyst 20

Catalyst 20 was generated in-situ by adding 13.9 mg of $(t\text{-}Bu)_2POC(CH_3)_2C(CH_3)_2OH$ to a chlorobenzene solution of $(TMEDA)NiMe_2$ (10.2 mg in 5 mL chlorobenzene, TMEDA=tetramethylethylenediamine).

EXAMPLE 20C

Polymerization Using Catalyst 20

The in-situ prepared Catalyst 20 (0.05 mmol, see Example 20B) was screened for ethylene polymerization at 6.9 MPa of ethylene at 50° C. for 18 h in a shaker tube. Polyethylene (0.067 g) was obtained. It had melting points of 131° C. (166.7 J/g) and 114° C. (33.5 J/g).

EXAMPLE 21

Synthesis of Catalyst 21

In a drybox, 0.489 g $(tert\text{-}butyl)_2PCH_2Li$ was mixed with 25 mL THF in a Schlenk flask. It was brought out of the drybox and placed in an ice-water bath. One atmosphere of carbon dioxide was applied to the flask. The mixture was allowed to stir at 0° C. under 1 atm of carbon dioxide for 15 min and then at RT for 45 min. The $CO_2$ flow was stopped. THF was evaporated. The product was dried under full vacuum overnight. Tan yellow solid was obtained. Part of the product (0.4204 g) was mixed with 0.2704 g ((allyl) $NiCl)_2$ in 20 mL THF. The mixture was allowed to stir at RT for 40 min. The mixture was evaporated to dryness and was added to 5 mL toluene to dissolve, followed by addition of about 70 mL pentane. The solid was filtered, followed by 3×5 mL pentane wash. The product was dried under full vacuum overnight. Orange solid (0.48 g) was obtained. $^{31}PNMR$ in $THF\text{-}d_8$: singlet peak at 51.70 ppm. $^1HNMR$ in $THF\text{-}d_8$: 5.34 ppm (bm, central allyl-H, 1H); 2.67–2.95 (bm, allyl-$CH_2$ and $PCH_2$—, 6H); 1.34 ppm (d, $J_{PH}$=12.4 Hz, $C(CH_3)_3$, 18H). Lithium NMR in $C_6D_6$ of 21 and a crystal structure of the Zwitterion tetrafluoroborate derivative indicate that one equivalent of $Li^+$ present which can potentially complex to 21 does not in fact complex to 21.

EXAMPLE 22

Synthesis of Catalyst 22

In a drybox, 0.1009 g $(tert\text{-}butyl)_2PCH_2C(Ph)_2OLi.THF$ (see Example 2) was dissolved in 5 mL THF in a 20 mL vial. To this was added 56 mg of $ZrCl_4$. The solution turned a peach color. It was allowed to stir overnight. Solvent was evaporated and the resulting solid was dried in vacuo.

EXAMPLE 23

Synthesis of Catalyst 23

In a drybox, 0.1009 g $(tert\text{-}butyl)_2PCH_2C(Ph)_2OLi.THF$ (see Example 2) was dissolved in 5 mL THF in a 20 mL vial. To this was added 45.5 mg of $TiCl_4$. The solution turned dark amber. It was stirred overnight. Solvent was evaporated and the resulting tan solid was dried in vacuo.

Ethylene Polymerization Screening Using the Nickel Catalysts 1–21

In a drybox, a glass insert was loaded with the isolated Ni catalysts (except Catalyst 20 in Example 20, which was generated in-situ). Solvent (TCB or chlorobenzene), optionally comonomers were added to the glass insert. A Lewis acid cocatalyst (typically $BPh_3$ or $B(C_6F_5)_3$) was often added to the solution. The insert was then capped and sealed. Outside of the drybox, the tube was placed under ethylene and was shaken mechanically at desired temperature listed in Table 3 for about 18 h. Sometimes an aliquot of the solution was used to acquire a $^1HNMR$ spectrum. The remaining portion was added to about 20 mL of methanol in order to precipitate the polymer. The polymer was isolated, washed with methanol several times and dried in vacuo.

Ethylene Polymerization Screening by the Catalysts 22 and 23, in the Presence of MAO In a drybox, a glass insert was loaded with 0.02 mmol of the isolated Zr or Ti catalyst and 9 mL of 1,2,4-trichlorobenzene. It was then cooled to −30° C. PMAO-IP (1 mL 12.9 wt % (in Al) toluene solution) was added to the frozen solution. It was put in a −30° C. freezer. The insert was then capped and sealed. Outside of the drybox, the cold tube was placed under ethylene and was shaken mechanically at desired temperature listed in Table 3, condition V, for about 18 h. Methanol (about 15 mL) and 2 mL conc. hydrochloric acid was added to the mixture. The polymer was isolated, washed with methanol several times and dried in vacuo.

Polymer Characterization

The results of ethylene polymerization and copolymerization catalyzed by Catalysts 1–23 under different reaction conditions (See Table 3) are reported in Tables 4–13. The polymers were characterized by NMR, GPC and DSC analysis. A description of the methods used to analyze the amount and type of branching in polyethylene is given in previously in corporated U.S. Pat. No. 5,880,241. GPC's were run in trichlorobenzene at 135° C. and calibrated against polyethylene using universal calibration based on polystyrene narrow fraction standards. DSC was recorded between −100° C. to 150° C. at a heating rate of 10° C./min. Data reported here are all based on second heat. $^1HNMR$ of the polymer samples was run in tetrachloroethane-$d_2$ at 120° C. using a 500 MHz Bruker spectrometer.

TABLE 3

Conditions for Ethylene Polymerization and Copolymerization Screening.

| | |
|---|---|
| I | 0.02 mmol catalyst, 10 mL TCB, RT, 18 h, 6.9 MPa ethylene, 10 eq $B(C_6F_5)_3$ |
| II | 0.02 mmol catalyst, 10 mL TCB, RT, 18 h, 1.0 MPa ethylene, 10 eq $B(C_6F_5)_3$ |
| III | 0.02 mmol catalyst, 10 mL TCB, 60° C., 18 h, 1.0 MPa ethylene, 10 eq $B(C_6F_5)_3$ |
| IV | 0.02 mmol catalyst, 3 mL TCB, 2 mL E-10-U*, 60° C., 18 h, 1.0 MPa ethylene, 40 eq $B(C_6F_5)_3$ |
| V | 0.02 mmol catalyst, 9 mL TCB, 1 mL PMAO-IP (12.9 wt % (in Al) in toluene), RT, 18 h, 6.9 MPa ethylene |
| VI | 0.02 mmol catalyst, 4 mL TCB, 1 mL n-hexyl acrylate, 120° C., 18 h, 6.9 MPa ethylene, 40 eq $B(C_6F_5)_3$ |
| VII | 0.02 mmol catalyst, 10 mL TCB, 60° C., 18 h, 1.0 MPa ethylene, 10 eq $B(C_6F_5)_3$, 1 eq NaBAF |

*Ethyl-10-Undecylenate.

TABLE 4

Ethylene Polymerization at 6.4 MPa Ethylene in Shaker Tubes
(0.05 mmol catalyst, 5 mL chlorobenzene, 18 h)

| Ex. | Catalyst | Cocatalyst/amt | T (° C.) | Yield (g) | #Me/1000CH$_2$ | m.p. (° C.) | Mw/PDI | TON** |
|---|---|---|---|---|---|---|---|---|
| 24 | 1 | BPh$_3$/5eq | 25 | 10.202 | <1 | 136 (162*) | 737,803/3.5 | 7,287 |
| 25 | 1 | B(C$_6$F$_5$)$_3$/5eq | 25 | 4.764 | 9 | 128 | 134,256/60.2 | 3,403 |
| 26 | 1 | none | 25 | 0 | | | | |
| 27 | 1 | BPh$_3$/5eq | 80 | 4.990 | 6 | 133 | 47,301/3.3 | 3,564 |
| 28 | 1 | B(C$_6$F$_5$)$_3$/5eq | 80 | 1.710 | 12 | 124 | 15,813/14.0 | 1,221 |
| 29 | 2 | B(C$_6$F$_5$)$_3$/5eq | 80 | 2.280 | 31 | 125 | 4,759/3.0 | 1,629 |
| 30 | 2 | BPh$_3$/5eq | 80 | 0 | | | | |
| 31 | 4 | B(C$_6$F$_5$)$_3$/10eq | 50 | 4.862 | 86 | 114, 106 | 28,765/41.8 | 3,466 |
| 32 | 11 | B(C$_6$F$_5$)$_3$/10eq | 50 | 0.117 | 25 | 119, 102 | | 209 |
| 33 | 12 | B(C$_6$F$_5$)$_3$/2eq | 50 | 0.046 | 19 | 119, 102 | | 82 |

*Heat of fusion (in J/g)

TABLE 5

Ethylene (Co)polymerization at 2.1 MPa Ethylene in
Shaker Tubes (0.05 mmol catalyst, 5 mL solvent/comonomer, 18 h)

| Ex. | Catalyst | Cocatalyst/eq | Solvent/Comonomer | T (° C.) | Yield (g) | Mole % Comonomer | #Me/1000 CH$_2$ | m.p. (° C.) | Mw/PDI | TON E/Comonomer |
|---|---|---|---|---|---|---|---|---|---|---|
| 34 | 1 | BPh$_3$/2 | C$_6$H$_5$Cl | 50 | 5.518 | | <1$^{a)}$ | 136 | 173,568/3.1 | 3941 |
| 35 | 1 | BPh$_3$/5 | C$_6$H$_5$Cl | 50 | 4.56 | | 2 | 135 | 191,589/5.1 | 3,321 |
| 36 | 1 | BPh$_3$/10 | C$_6$H$_5$Cl | 50 | 5.132 | | 2 | 137 | 268,453/3.5 | 3,666 |
| 37 | 1 | BPh$_3$/10 | 1-Hexene | 50 | 1.295 | | 12 | 111 | 121,450/2.4 | / |
| 38 | 1 | BPh$_3$/10 | E-4-P* | 50 | 4.972 | 3.0 | 1$^{b)}$ | 117 | 62,753/3.7 | 3,100/97 |
| 39 | 2 | B(C$_6$F$_5$)$_3$/2 | C$_6$H$_5$Cl | 50 | 1.816 | | 8 | 127 | 20,100/9.2 | 1,297 |
| 40 | 2 | B(C$_6$F$_5$)$_3$/10 | C$_6$H$_5$Cl | 50 | 12.314 | | 12 | 125*** | 19,712/5.1 | 8,796 |
| 41 | 2 | B(C$_6$F$_5$)$_3$/10 | 1-Hexene | 50 | 3.662 | | 48$^{c)}$ | 99 | 14,611/5.2 | / |
| 42 | 2 | B(C$_6$F$_5$)$_3$/30 | E-10-U** | 80 | 5.616 | 9.9 | 24 | −10 | 7,298/6.0 | 2,189/240 |
| 43 | 3 | B(C$_6$F$_5$)$_3$/10 | C$_6$H$_5$Cl | 50 | 1.799 | | 28 | 113 | 189,503/16.6 | 1,285 |
| 44 | 3 | BPh$_3$/10 | C$_6$H$_5$Cl | 50 | 0 | | | | | |
| 45 | 3 | B(C$_6$F$_5$)$_3$/10 | 1-Hexene | 50 | 0.738 | | 87 | 72 | 146,422/3.4 | / |
| 46 | 3 | B(C$_6$F$_5$)$_3$/30 | E-10-U | 80 | 3.427 | 2.2 | 105 | 117, 106 | 264,357107.9 | 2,089/47 |

*Ethyl-4-pentenoate
**Ethyl-10-Undecylenate
***Heat of fusion: 200 J/g.
$^{a)}$No alkyl branches based on $^{13}$CNMR.
$^{b)}$No alkyl branches, 2.6 mole % ethyl-4-pentenoate based on $^{13}$CNMR.
$^{c)}$Based on $^{13}$CNMR, total Me was 34.4 (1.7Me, 2.7Et, 0.7Pr, 25.9Bu, 0.5Am, 2.9Hex+). The enriched butyl branch is consistent with the significant 1-hexene incorporation in ethylene copolymerization.

TABLE 6

Ethylene (Co)polymerization 1.0 MPa Ethylene at 50° C. in
Shaker Tubes (0.05 mmol catalyst, 5 mL solvent/comonomer, 18 hr)

| Ex | Catalyst | Cocatalyst/eq | Solvent/Comonomer | Yield (g) | Mole % Comonomer | #Me/1000CH$_2$ | Mw/PDI | TON E/Co-monomer |
|---|---|---|---|---|---|---|---|---|
| 47 | 2 | B(C$_6$F$_5$)$_3$/30 | MUE* | 1.928 | 6.3 | 11 | 7,674/3.7 | 952/64 |
| 48 | 4 | B(C$_6$F$_5$)$_3$/30 | MUE | 0.102 | 6.0 | 24 | 17,303/11.7 | 51/3 |

*Methyl undecenyl ether (CH$_2$=CH(CH$_2$)$_9$OCH$_3$).

TABLE 7

Condition I in Table 3

| Ex | Catalyst | Yield (g) | #Me/1000 CH$_2$ | m.p. (° C.)(ΔH$_f$) | Mw/PDI | TON |
|---|---|---|---|---|---|---|
| 49 | 2 | 7.264 | 6 | 128 (234) | 32,932/3.82 | 12,947 |
| 50 | 5 | 15.560 | 10 | 125 (218) | 13,921/4.91 | 27,734 |
| 51 | 6 | 11.718 | 14 | 124 (206) | 10,411/3.68 | 20,886 |
| 52 | 7 | 10.619 | 20 | 117 (185) | 2,792/2.57 | 18,927 |
| 53 | 13 | 0.029 | 7 | 131 (161) | 49,268/4.1 | 52 |
| 54 | 8 | 8.970 | 22 | 125 (142) | 187,705/4.9 | 15,988 |
| 55 | 9 | 9.728 | 12 | 130 (194) | 30,547/18.3 | 17,339 |
| 56 | 10 | 0.112 | 22 | 127 (182) | 190,093/182.7 | 200 |

TABLE 7-continued

Condition I in Table 3

| Ex | Catalyst | Yield (g) | #Me/ 1000 CH$_2$ | m.p. (° C.)($\Delta H_f$) | Mw/PDI | TON |
|---|---|---|---|---|---|---|
| 57 | 14 | 6.401 | 121 | 120 (81) | trimodal 67,779/251.5 | 11,409 |
| 58 | 15 | 8.407 | 16 | 126 (102) | trimodal 93,871/3.1 | 14,985 |
| 59 | 16 | 0.088 | 73 | 123 (99) | 25,262/24.7 | 157 |
| 60 | 17 | 1.250 | 30 | 129 (141) | 73,164/2.4 | 2228 |
| 61 | 18 | 14.279 | 33 | 118 (148) | 4,162/4.7 | 25,450 |
| 62 | 19 | 11.233 | 21 | 121 (169) | 14,451/7.0 | 20,022 |
| 63 | 21 | 19.292 | 52 | 114 (169), 108 | 4,593/3.9 | 34,386 |

TABLE 8

Condition II in Table 3

| Ex | Catalyst | Yield (g) | #Me/ 1000 CH$_2$ | m.p. (° C.)($\Delta H_f$) | Mw/PDI | TON |
|---|---|---|---|---|---|---|
| 64 | 2 | 2.492 | 19 | 120 (140) | 46,024/4.5 | 4,442 |
| 65 | 5 | 1.202 | 10 | 127 (181) | 52,542/4.3 | 2,142 |
| 66 | 6 | 2.631 | 30 | 120 (130) | 11,521/3.2 | 4,689 |
| 67 | 7 | 1.188 | 21 | 122 (207) | 6,405/3.2 | 2,117 |
| 68 | 9 | 2.057 | 22 | 125 (175) | 32,505/37.8 | 3,666 |

TABLE 9

Condition III in Table 3

| Ex | Catalyst | Yield (g) | #Me/ 1000 CH$_2$ | m.p. (° C.)($\Delta H_f$) | Mw/PDI | TON |
|---|---|---|---|---|---|---|
| 69 | 2 | 1.934 | 11 | 125 (164) | 13,263/3.1 | 3447 |
| 70 | 5 | 6.624 | 13 | 124 (194) | 10,468/3.2 | 11,807 |
| 71 | 6 | 6.276 | 30 | 115 (198) | 5,285/3.6 | 11,186 |
| 72 | 7 | 4.196 | 32 | 115 (172) | 2,688/2.6 | 7,479 |
| 73 | 18 | 5.629 | 38 | 108 (88) | 8,381/9.1 | 10,033 |
| 74 | 19 | 9.868 | 50 | 100 (63) | 7,784/9.8 | 17,589 |
| 75 | 21 | 6.560 | 31 | 113 (112) | 5,581/5.5 | 11,692 |

TABLE 10

Condition IV in Table 3

| Ex | Catalyst | Yield (g) | #Me/ 1000CH$_2$ | Mole % Comonomer | m.p. (° C.) ($\Delta H_f$) | Mw/PDI | TON E/EU* |
|---|---|---|---|---|---|---|---|
| 76 | 2 | 0.648 | 6 | 2.8 | 112 (124) | 5,737/2.6 | 947/28 |
| 77 | 5 | 3.861 | 6 | 4.9 | 108 (92) | 6,315/2.5 | 4,939/257 |
| 78 | 6 | 0.129 | 12 | 5.1 | 124, 108 (124) | 7,435/4.0 | 164/9 |
| 79 | 7 | 0.268 | 16 | 4.8 | 88 (116) | 1,665/2.9 | 347/17 |
| 80 | 15 | 0.060 | 15 | 2.6 | 114 (132) | 29,070/6.8 | 89/2 |
| 81 | 18 | 2.360 | 11 | 15.0 | | 3,017/2.5 | 1,798/318 |
| 82 | 19 | 1.165 | 21 | 10.6 | | 7,057/4.0 | 1,095/130 |

*Ethylene/Ethyl-10-undecylenate

TABLE 11

Condition V in Table 3

| Ex | Catalyst | Yield (g) | #Me/ 1000 CH$_2$ | m.p. (° C.)($\Delta H_f$) | TON |
|---|---|---|---|---|---|
| 83 | 22 | 5.50 | 21 | 132 (157) | 9,803 |
| 84 | 23 | 4.520 | 18 | 134 (136) | 8,056 |
| 85 | 23* | 4.543 | 8 | 134 (125) | 8,097 |

*One equivalent of (tert-butyl)2PCH2CPh$_2$OLi.THF was added to Catalyst 23.

TABLE 12

Condition VI in Table 3

| Ex | Catalyst | Yield (g) | #Me/ 1000CH$_2$ | Mole % Comonomer | m.p. (° C.) ($\Delta H_f$) | Mw/PDI | TON E/HA |
|---|---|---|---|---|---|---|---|
| 86 | 21 | 14.07 | 27 | 0.74* | 114 (184) | 2,757/3.0 | 24,079, 179 |

*0.42 mole% in chain acrylate branch and 0.32 mole% unsaturated chain end.

TABLE 13

Condition VII in Table 3

| Ex. | Catalyst | Yield (g) | #Me/ 1000 CH$_2$ | m.p. (° C.)($\Delta H_f$) | Mw/PDI | TON |
|---|---|---|---|---|---|---|
| 87 | 2 | 6.902 | 29 | 121 (145) | 15,842/5.6 | 12,302 |
| 88 | 5 | 13.547 | 18 | 122 (167) | 8,675/4.6 | 24,146 |
| 89 | 7 | 13.858 | 59 | 106 (110) | 3,033/3.3 | 24,700 |

As noted above, one potential problem with the copolymerization of ethylene (and/or other olefins) and a polar comonomer such as an acrylate is the possibility of obtaining a homopolymer of the polar comonomer because of free radical polymerization of that polar comonomer. One method of determining whether such a homopolymer is present is to run an NMR spectrum of the polymer(s). Unfortunately, using $^1$H-NMR for some of the more common acrylate monomers such as methyl acrylate the $^1$H spectra of the homopolymer and ethylene copolymers overlap, so a quantitative analysis is difficult. Although this analysis can be done by $^{13}$C-NMR, it is more difficult, expensive and time consuming. However, when an acrylate of the formula $H_2C=CHC(O)OR^{36}$, wherein $R^{36}$ is —$CH_2CH_2OR^{37}$, and $R^{37}$ is aryl or substituted aryl, preferably aryl, is used, the peaks do not overlap at all in the $^1$H-NMR spectra, and that is a great advantage in determining whether the copolymer is "contaminated" with homopolymer.

Total methyls per 1000 CH$_2$ are measured using different NMR resonances in 1H and 13C NMR. Because of accidental overlaps of peaks and different methods of correcting the calculations, the values measured by $^1$H and $^{13}$C NMR will usually not be exactly the same, but they will be close, normally within 10–20% at low levels of acrylate comonomer. In $^{13}$C NMR the total methyls per 1000 CH2 are the sums of the 1B$_1$, 1B$_2$, 1B$_3$, and 1B$_{4+}$, EOC resonances per 1000 CH$_2$, where the CH$_2$'s do not include the CH$_2$'s in the alcohol portions of the ester group. The total methyls measured by 13C NMR do not include the minor amounts of methyls from the methyl vinyl ends or the methyls in the alcohol portion of the ester group. By $^1$H NMR the total methyls are measured from the integration of the resonances from 0.6 to 1.08 and the $CH_2$'s are determined from the integral of the region from 1.08 to 2.49 ppm. It is assumed that there is 1 methine for every methyl group, and ⅓ of the methyl integral is subtracted from the methylene integral to remove the methine contribution. The methyl and methylene integrals are also usually corrected to exclude the values of the methyls and methylenes in the alcohol portion of the ester group, if this is practical. Because of the low levels of incorporation, this is usually a minor correction.

FIG. 1 shows the $^1$H-NMR spectrum of a mixture of an EGPEA (Z=1, $R^{37}$ is phenyl) homopolymer in a mixture with an EGPEA compolymer with ethylene. The spectrum was obtained on a 500 MHz Bruker Avance spectrometer on a 5 mm QNP probe on samples diluted ~10 mg/0.5 ml in tce-$d_2$ at 120° C. using a 90 degree pulse of 14 μsec, a spectral width of 12.8 kHz, an acquisition time of 2.6 sec and a recycle delay of 30 sec. A total of 8 transients were acquired. Spectra were referenced to tce-$d_2$ at 5.928 ppm. FIG. 1 also indicates the assignments of the various peaks. Using EGPEA (and other acrylates described above) separation of the homopolymer and copolymer peaks is clear and quantitative analysis of the mixture is possible.

Another NMR analysis used below is end group analysis of ethylene copolymers with acrylates. 100 MHz $^{13}$C NMR spectra were obtained on a Varian® Unity 400 MHz spectrometer on typically 10 wt % solutions of the polymers and 0.05 M CrAcAc in 1,2,4-trichlorobenzene (TCB) in a 10 mm probe unlocked at 120° C. using a 90 degree pulse of 19.2 μsec, a spectral width of 35 kHz, a relaxation delay of 5 s, an acquisition time of 0.64 s. and inverse gated decoupling (decoupling only during acquisition). A few samples were run under similar conditions on a Bruker Avance 500 MHz NMR. A typical sample contained 310 mg polymer and 60 mg CrAcAc in TCB with a total volume of 3.1 mL (Varian recommended volume) in a 10 mm NMR tube; care was taken that the sample was very well mixed and uniform in consistency. Samples were preheated for at least 15 min. in the NMR before acquiring data. Data acquisition time was typically 10.5 hr per sample. The T1 values of the carbons of an ethylene/methyl acrylate copolymer sample were measured under these conditions to be all less than 0.9 s. The longest T1 measured was for the Bu+, EOC resonance at 14 ppm, which was 0.84 s. Spectra are referenced to the solvent—the TCB high field resonance at 127.918 ppm.

Figure 2:
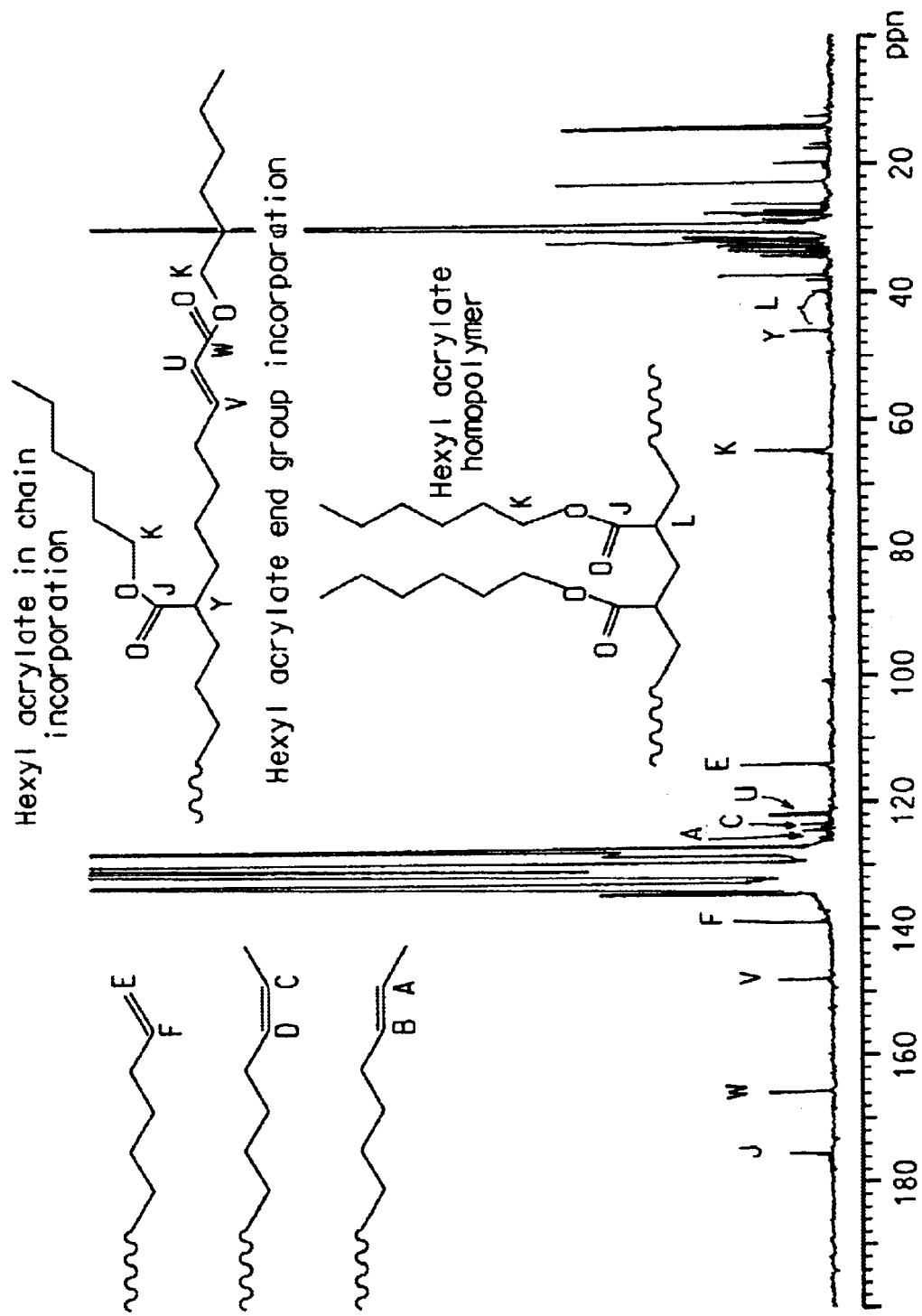
FIG. 2 shows the $^{13}C$ NMR of a copolymer of ethylene and hexyl acrylate (HA) which also contains some homopolymer of HA, and which shows assignments of various NMR peaks.

Integrals of unique carbons in each branch were measured and were reported as number of branches per 1000 methylenes. Counted in these methylenes are those in the backbone (main chain) and branches, but not methylenes in the alcohol portions of esters, for example the —O$\underline{CH_2}$$CH_3$ methylene in an ethyl ester. These integrals are accurate to +/−5% relative for abundant branches and +/−10 or 20% relative for branches present at less than 10 per 1000 methylenes. FIG. 2 shows such a spectrum together with assignments of various carbon atoms.

| INDEX | FREQUENCY | PPM | HEIGHT | |
|---|---|---|---|---|
| 1 | 17613.645 | 175.137 | 8.7 | J |
| 2 | 16655.651 | 165.612 | 12.6 | W |
| 3 | 14882.774 | 147.983 | 10.5 | V |
| 4 | 13969.102 | 138.898 | 19.1 | F |
| 5 | 13546.174 | 134.693 | 44.9 | |
| 6 | 13489.570 | 134.130 | 43.0 | |
| 7 | 13483.697 | 134.072 | 52.0 | |

-continued

| INDEX | FREQUENCY | PPM | HEIGHT | |
|---|---|---|---|---|
| 8 | 13448.453 | 133.721 | 5119.1 | |
| 9 | 13401.995 | 133.260 | 5131.0 | |
| 10 | 13369.955 | 132.941 | 93.1 | |
| 11 | 13359.275 | 132.835 | 41.8 | |
| 12 | 13319.759 | 132.442 | 16.6 | |
| 13 | 13270.631 | 131.953 | 36.9 | |
| 14 | 13244.999 | 131.699 | 75.8 | |
| 15 | 13215.095 | 131.401 | 5189.6 | |
| 16 | 13181.453 | 131.067 | 4823.7 | TCB solvent |
| 17 | 13154.219 | 130.796 | 84.7 | |
| 18 | 13138.199 | 130.637 | 62.3 | |
| 19 | 13130.189 | 130.557 | 113.2 | |
| 20 | 13101.887 | 130.276 | 5124.1 | |
| 21 | 13063.439 | 129.893 | 68.1 | |
| 22 | 12993.485 | 129.198 | 8.3 | |
| 23 | 12938.484 | 128.651 | 43.9 | |
| 24 | 12864.792 | 127.918 | 4827.4 | |
| 25 | 12831.684 | 127.589 | 55.7 | |
| 26 | 12822.072 | 127.493 | 36.1 | |
| 27 | 12806.586 | 127.339 | 25.5 | |
| 28 | 12504.876 | 124.339 | 5.6 | A |
| 29 | 12418.368 | 123.479 | 5.7 | C |
| 30 | 12269.383 | 121.998 | 12.3 | U |
| 31 | 11479.598 | 114.145 | 17.7 | E |
| 32 | 6439.715 | 64.032 | 14.7 | K |
| 33 | 6424.764 | 63.883 | 9.9 | |
| 34 | 4611.303 | 45.851 | 7.9 | Y |
| 35 | 3817.780 | 37.961 | 4.1 | |
| 36 | 3755.302 | 37.340 | 21.6 | $\alpha B_1$ |
| 37 | 3452.525 | 34.329 | 12.7 | |
| 38 | 3422.087 | 34.027 | 4.3 | |
| 39 | 3395.921 | 33.767 | 18.6 | $\alpha B_2$ |
| 40 | 3322.229 | 33.034 | 11.4 | MB1 |
| 41 | 3280.043 | 32.614 | 21.7 | |
| 42 | 3237.857 | 32.195 | 14.6 | |
| 43 | 3220.769 | 32.025 | 54.8 | 3B6+, EOC |
| 44 | 3177.515 | 31.595 | 27.6 | |
| 45 | 3048.822 | 30.315 | 23.2 | |
| 46 | 3037.608 | 30.204 | 35.5 | |
| 47 | 3000.228 | 29.832 | 2905.6 | $CH_2$'s |
| 48 | 2968.188 | 29.513 | 39.1 | |
| 49 | 2958.576 | 29.418 | 76.7 | |
| 50 | 2931.342 | 29.147 | 36.8 | |
| 51 | 2926.002 | 29.094 | 27.5 | |
| 52 | 2856.048 | 28.398 | 13.0 | |
| 53 | 2777.550 | 27.618 | 17.4 | |
| 54 | 2752.986 | 27.374 | 6.7 | |
| 55 | 2741.238 | 27.257 | 24.4 | $\beta B2+$ |
| 56 | 2725.752 | 27.103 | 17.3 | |
| 57 | 2599.195 | 25.844 | 18.7 | |
| 58 | 2286.271 | 22.733 | 53.2 | 2B5+, EOC |
| 59 | 2271.319 | 22.584 | 27.7 | |
| 60 | 1993.640 | 19.823 | 11.6 | 1B1 |
| 61 | 1774.166 | 17.641 | 4.4 | |
| 62 | 1405.173 | 13.972 | 52.3 | 1B4+, EOC |
| 63 | 1390.755 | 13.829 | 30.2 | |
| 64 | 1265.799 | 12.586 | 5.4 | |

Details about NMR nomenclature (e.g., $2B_{5+}$) and other details of NMR polymer analysis, will be found in previously incorporated U.S. Pat. No. 5,880,241.

GPC molecular weights are reported versus polystyrene standards. Unless noted otherwise, GPC's were run with RI detection at a flow rate of 1 mL/min at 135° C. with a run time of 30 min. Two columns were used: AT-806MS and WA/P/N 34200. A Waters RI detector was used and the solvent was TBC with 5 grams of BHT per 3.79 L. Dual UV/RI detection GCP was run in THF at rt using a Waters 2690 separation module with a Waters 2410 RI detector and a Waters 2487 dual absorbance detector. Two Shodex columns, KF-806M, were used along with one guard column, KF-G. In addition to GPC, molecular weight information was at times determined by $^1$H NMR spectroscopy (olefin end group analysis) and by melt index measurements (g/10 min at 190° C.).
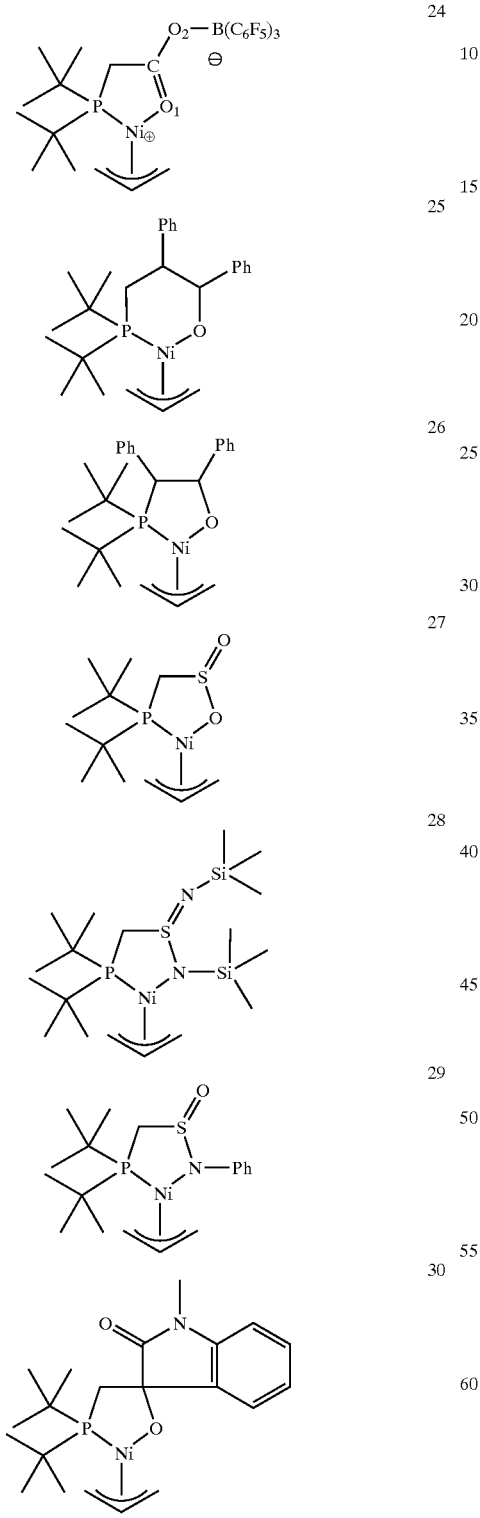
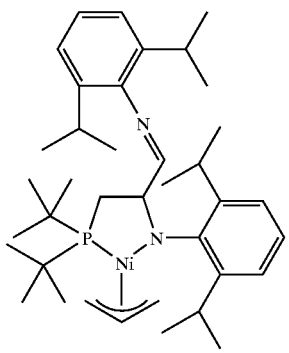
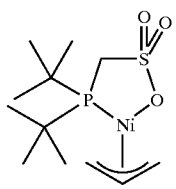
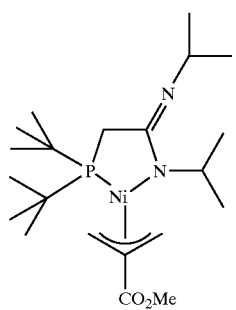
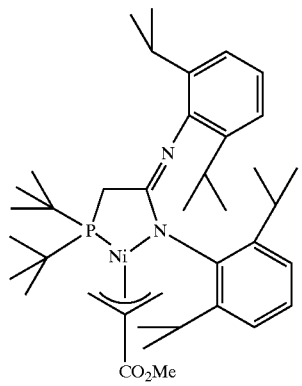
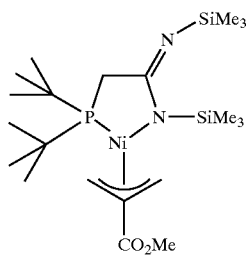

49

-continued

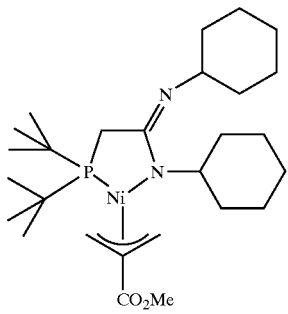

36

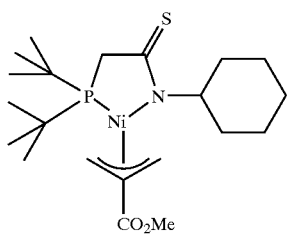

37

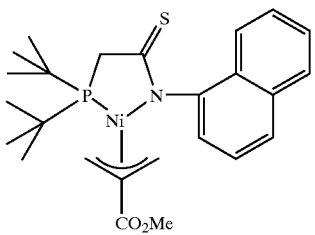

38

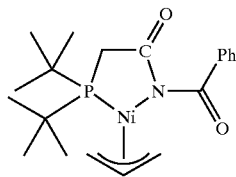

39

EXAMPLE 90

Synthesis of Catalyst 24

In a drybox, 0.100 g Catalyst 21 and 15 mL toluene were combined. To this orange solution was added 0.177 g tris(pentafluorophenyl)boron at RT. The cloudy orange solution was stirred at RT overnight. The reaction mixture was filtered through Celite®, followed by 3×5 mL toluene wash. The filtrate was evaporated to ca. 2 mL and was added 50 mL pentane. The yellow precipitate was filtered and washed with 3×5 mL pentane. The product was dried in vacuo. Final yield of the yellow solid was 0.088 g (33%). X-ray single crystal analysis confirmed the proposed structure (Zwitterionic complex). $^{31}$PNMR in $CD_2Cl_2$: δ 60.05 (s). $^1$HNMR in $CD_2Cl_2$: (obtained by 1D NOE, 2D $^1$H-$^{13}$C correlation (HMQC) and NOESY experiments): δ 5.42 (sept, central allyl-H, 1H); 4.18 (vd, J=7.9 Hz, syn-terminal allyl-H, on the C═O side, 1H); 3.04–3.07 (m, overlapped peaks of syn-terminal-allyl proton that is close to (t-Bu)$_2$P and anti-terminal-allyl proton that is close to C═O, 2H total); 2.82–2.98 (ABX pattern (X is phosphorus), $J_{AB}$=18.4 Hz, $^2J_{PH}$=8.3 Hz, PCHH', 2H total); 1.77 (d, $^2J_{PH}$=12.9 Hz, anti-terminal-allyl-H that is close to (t-Bu)$_2$P, 1H); 1.35 (d, $^3J_{PH}$=14.7 Hz, C(CH$_3$)$_3$, 9H); 1.18 (d, $^3J_{PH}$=14.7 Hz, C(CH$_3$)$_3$, 9H). $^{19}$FNMR in $CD_2Cl_2$: δ −134.89 (d, J=20.2 Hz, ortho-F, 6F); −159.75 (t, para-F, 3F); −165.63 (t, meta-F, 6F).

50

EXAMPLE 91

Synthesis of Catalyst 25

In a drybox, 0.3545 g (1.806 mmole) trans-stilbene oxide and 20 mL THF were combined. The clear solution was cooled at −30° C. for 0.5 h. Then 0.3 g (1.806 mmole) (t-Bu)$_2$PCH$_2$Li was added. The resulting pale yellow reaction was stirred at RT for 3 h. The reaction was evaporated under full vacuum overnight. $^{31}$PNMR of the ligand precursor in THF-d$_8$: δ 12.00 (s, major); 26.73 (s, minor). Then 0.6443 g (1.778 mmole) ligand precursor and 20 mL THF were combined. To this solution was added 0.2404 g (0.889 mmole) nickel allyl chloride dimer. After stirring overnight, the reaction was evaporated under full vacuum. To the resulting residue was added 20 mL toluene. The solution was filtered through Celite®, followed by 3×10 mL toluene wash. The filtrate was evaporated under full vacuum. To the residue was added 30 mL pentane and the resulting solid was stirred for several minutes. The solid was filtered and was washed with 3×10 mL pentane. The sample was dried in vacuo for several hours. Final weight of the light brown solid was 51.4 mg (6%).

EXAMPLE 92

Synthesis of Catalyst 26

In a drybox, 0.387 g (1.972 mmole) trans-stilbene oxide and 20 mL THF were combined. The clear solution was cooled to −30° C. for 0.5 h. Then 0.3 g (1.972 mmole) (t-Bu)$_2$PLi was added. The amber reaction was stirred at RT for 2.5 h. The reaction was then evaporated under full vacuum. Then 0.6769 g (1.943 mmole) ligand precursor and 20 mL THF were combined. To the reaction was added 0.2627 g (0.9715 mmole) nickel allyl chloride dimer. After stirring overnight, the reaction was evaporated under full vacuum. To the resulting residue was added 20 mL toluene. The solution was filtered through Celite®, followed by 3×10 mL toluene wash. The filtrate was evaporated under full vacuum to dryness. Final weight of the dark brown solid was 0.5148 g (60%).

EXAMPLE 93

Synthesis of Catalyst 27

In a drybox, 0.300 g (1.806 mmole) (t-Bu)$_2$PCH$_2$Li and 20 mL THF were combined in a 50 mL Schlenk flask. The flask was removed from the drybox, placed on the Schlenk line, and degassed. After cooling the pale yellow solution to 0° C. with an ice bath, SO$_2$ was applied at 1 atm. The ice bath was removed after 20 min and the reaction was allowed to warm to RT. After 15 min, SO$_2$ was discontinued. The reaction mixture was stirred for an additional 25 min. The reaction mixture was then evaporated to remove excess SO$_2$. The reaction mixture was transferred into a drybox. The solution was evaporated under full vacuum overnight. Then 0.4058 g (1.763 mmole) ligand precursor and 20 mL THF were combined. To this yellow solution was added 0.2385 g (0.882 mmole) nickel allyl chloride dimer. The dark red reaction mixture was stirred at RT for 2 h. The reaction mixture was then evaporated under full vacuum. The resulting red residue was triturated with 25 mL pentane. The solid was filtered and washed with 3×10 mL pentane. The sample was dried in vacuo for 45 minutes.

EXAMPLE 94

Synthesis of Catalyst 28

In a drybox, 0.6214 g (3.01 mmole) bis(trimethylsilyl) sulfur diimide and 20 mL THF were combined. The yellow solution was cooled at −30° C. for 45 min. Then 0.5 g (3.01 mmole) (t-Bu)$_2$PCH$_2$Li was added. The orange-brown reaction mixture was stirred at RT for 1 h. To the reaction mixture was added 0.407 g (1.505 mmole) nickel allyl chloride dimer. The red solution was stirred at RT for 3 h. The reaction mixture was then evaporated under full vacuum overnight. To the residue was added 20 mL toluene. The solution was filtered through Celite®, followed by 3×10 mL toluene wash. The filtrate was evaporated under full vacuum. Final weight of the orange-brown solid was 1.0114 g (72%). $^{31}$PNMR in THF-d$_8$: δ 93.78 (s).

EXAMPLE 95

Synthesis of Catalyst 29

In a drybox, 0.4189 g (3.01 mmole) N-thionylaniline and 20 mL THF were combined. The clear solution was cooled at −30° C. for 0.5 h. Then 0.5 g (3.01 mmole) (t-Bu)$_2$PCH$_2$Li was added. The resulting orange-brown reaction was stirred at RT for 1 h. To the reaction mixture was added 0.407 g (1.505 mmole) nickel allyl chloride dimer. The red solution was stirred for 3 h at RT. The reaction mixture was then evaporated under full vacuum. To the residue was added 5 mL toluene, followed by 50 mL pentane. The resulting solid was stirred for several min, filtered, and washed with 3×10 mL pentane. Final weight of the dull orange-yellow solid was 0.884 g (67%). $^{31}$PNMR in THF-d$_8$: 77.18 (s).

EXAMPLE 96

Synthesis of Catalyst 30

In a drybox, 0.485 g (3.01 mmole) 1-methylisatin and 20 mL THF were combined. The orange solution was cooled at −30° C. for 45 min. Then 0.500 g (3.01 mmole) (t-Bu)$_2$PCH$_2$Li was added. The reaction mixture turned purple and it was stirred at RT for 1 h. To the reaction mixture was added 0.407 g (1.505 mmole) nickel allyl chloride dimer. The red solution was stirred at RT for 3 h. The reaction mixture was then evaporated under full vacuum overnight. To the residue was added 20 mL toluene. The solution was filtered through Celite®, followed by 3×10 mL toluene wash. The filtrate was evaporated under full vacuum. Final weight of the dark brown solid was 1.463 g.

EXAMPLE 97

Synthesis of Catalyst 31

In a drybox, 0.6646 9 (1.765 mmole) ArN═C(H)—C(H)═NAr (Ar=2,6-diisopropylphenyl) and 20 mL THF were combined. The yellow solution was cooled at −30° C. for 0.5 h. Then 0.2932 g (1.765 mmole) (t-Bu)$_2$PCH$_2$Li was added. The resulting orange-red reaction was stirred at RT for 1 h. To the reaction was added 0.2386 g (0.8825 mmole) nickel allyl chloride dimer. The red solution was stirred at RT for 3 h. The reaction was then evaporated under full vacuum. To the residue mixture was added 20 mL toluene. The solution was filtered through Celite®, followed by 3×10 mL toluene wash. The filtrate was evaporated under full vacuum. Final weight of the dark brown solid was 0.6937 g (62%).

EXAMPLE 98

Synthesis Catalyst 32

In a drybox, 0.250 g (1.64 mmole) sodium chloromethylsulfonate and 20 mL THP were combined. The mixture was cooled to −30° C. for 0.5 h. Then 0.25 g (1.64 mmole) (t-Bu)$_2$PLi was added and the mixture was stirred and allowed to slowly warm up to RT. As it warmed, the reaction mixture became cloudy orange. The reaction mixture was stirred at RT for two days. The resulting cloudy brown solution was evaporated under full vacuum. Then 0.425 g (1.62 mmole) ligand precursor and 20 mL THF were combined. To this brown suspension was added 0.219 g (0.81 mmole) nickel allyl chloride dimer. The resulting red-brown reaction mixture was stirred at RT for 3 h. The reaction mixture was then evaporated under full vacuum to dryness. The sample was triturated with 25 mL pentane. The solid was filtered and washed with 3×10 mL pentane. It was dried in vacuo for 1.5 h. Final weight of the light brown solid was 0.369 g (67%).

EXAMPLE 99

Synthesis of Catalyst 33

In a dry box, to a 100 mL flask containing 10 mL of THF solution of 1,3-diisopropylcarbodiimide (0.0816 g, 0.64 mmole), was slowly added the THF solution of (t-Bu)$_2$PCH$_2$Li (0.107 g, 0.64 mmole). The solution changed from yellow to colorless upon stirring overnight. Solvent was removed. The residue was rinsed with pentane. White powder (0.136 g, 0.467 mmole) was obtained in 72% yield. $^1$H NMR of the ligand precursor (in C$_6$D$_6$): δ 0.98 (d, 18H, t-Bu-H); 1.3 (dd, 12H, —CH(CH$_3$)$_2$); 1.96 (s, d, 2H, PCH$_2$); 3.80 (m, 2H, —CH(CH$_3$)$_2$). It contained one equivalent of hydrolyzed product that might be resulted of hydrolysis of the lithium salt during the period outside of the drybox. $^{31}$PNMR (C$_6$D$_6$): δ 21.837 (s); 13.177 (s). In the dry box, 0.0542 g (0.185 mmole) of the ligand precursor and 0.0441 g (0.092 mmole) allyl-Ni-bromide dimer {((2-MeO$_2$C—C$_3$H$_4$)NiBr)$_2$} were mixed in 10 mL THF in a 50 mL flask. The mixture was stirred for 1 h. THF was removed in vacuo and the residue was extracted with ether. After removal of ether, the product was washed with pentane. Light brown solid (0.0434 g, 0.098 mmole) was obtained in 53% yield. $^{31}$PNMR (C$_6$D$_6$) δ 61.89 (s).

EXAMPLE 100

Synthesis of Catalyst 34

In a dry box, to a 100 mL RB flask containing 10 mL THF solution of 1,3-bis-(2,6-diisopropylphenyl)carbodiimide (0.245 g, 0.675 mmole), was slowly added THF solution of (t-Bu)$_2$PCH$_2$Li (0.112 g, 0.675 mmole). Upon stirring overnight, the solution turned from yellow to colorless. Solvent was removed and the product was washed with pentane. White powder (0.272 g, 0.514 mmole) was obtained in 76% yield. $^1$HNMR (C$_6$D$_6$): δ 0.98 (d, 24H, —CH(CH$_3$)$_2$); 1.37 (d, 18H, t-Bu-H); 2.41 (d, 2H, PCH$_2$); 3.26 (m, 2H, —CH(CH$_3$)$_2$); 3.56 (m, 2H, —CH(CH$_3$)$_2$); 6.92–7.60 (m, 6H, Ar—H). $^{31}$PNMR (C$_6$D$_6$): δ 19.12 (s). In the dry box, 0.0814 g (0.154 mmole) of the ligand precursor and 0.0366 g (0.077 mmole) of the allyl-Ni-bromide dimer (((2-MeO$_2$C—C$_3$H$_4$)NiBr)$_2$) were mixed in 10 mL THF in a 50 ml RB flask and the mixture was stirred for 1 h. THF was removed in vacuo and the residue was extracted with ether. Upon removal of the ether, the product was washed with pentane. Yellow powder (0.0906 g, 0.133 mmole) was obtained in 87% yield. $^{31}$PNMR (C$_6$D$_6$): δ 59.68 (s).

EXAMPLE 101

Synthesis of Catalyst 35

In a dry box, to the 100 mL RB flask containing 10 mL of THF solution of 1,3-bis(trimethylsilyl)carbodiimide (0.0813 g, 0.436 mmole), was added slowly a THF solution of (t-Bu)$_2$PCH$_2$Li (0.0725 g, 0.436 mmole). The solution turned from yellow to colorless after stirring overnight. Solvent was removed. The white solid residue, which is soluble in pentane, was mixed with 0.1036 g (0.218 mmole) of allyl-Ni-bromide complex (((2-MeO$_2$C—C$_3$H$_4$)NiBr)$_2$) in 30 mL THF. The mixture was stirred for an hour. Solvent was then removed under vacuum. The residue was extracted with ether. Solvent was removed. The solid was rinsed with pentane. Orange powder (0.0515 g, 0.102 mmole) was obtained in 23% yield. $^1$HNMR (C$_6$D$_6$): δ 0.21 (s, 1H, allyl-H); 0.25 (s, 18H, —Si(CH$_3$)$_3$); 0.94 (d, 19H, t-Bu-H and allyl-H); 1.28 (s, 2H, PCH$_2$); 3.0 (s, 1H, allyl-H); 3.3 (s, 3H, —OCH$_3$); 3.62 (s, 1H, allyl-H). $^{31}$PNMR (C$_6$D$_6$): δ 57.65.

EXAMPLE 102

Synthesis of Catalyst 36

In a dry box, to a 100 mL RB flask containing 10 mL of THF solution of 1,3-dicyclohexylcarbodiimide (0.143 g, 0.694 mmole), was added slowly a THF solution of (t-Bu)$_2$PCH$_2$Li (0.115 g, 0.694 mmole) at RT. The color of the solution turned yellow and the mixture was stirred overnight. Solvent was removed under vacuum and the white solid residue was mixed with 0.1649 g (0.348 mmole) of allyl-Ni-bromide complex (((2-MeO$_2$C—C$_3$H$_4$)NiBr)$_2$) in 30 mL of THF. The mixture was stirred for 1 h. Solvent was then removed under vacuum. The residue was extracted with ether. Ether was then removed. The solid was rinsed with pentane. Orange powder (0.150 g, 0.287 mmole) was obtained in 41% yield. $^{31}$PNMR (C$_6$D$_6$): δ 62.55 (s).

EXAMPLE 103

Synthesis of Catalyst 37

In a dry box, to a 100 mL RB flask containing 10 mL THF solution of 1-naphthylisothiocyanate (0.079 g, 0.426 mmole), was slowly added a THF solution of (t-Bu)$_2$PCH$_2$Li (0.0709 g, 0.426 mmole) at −30° C. The solution turned yellow orange and it was stirred for one h while the solution warmed up to RT. Solvent was removed. The solid residue was mixed with 0.101 g (0.312 mmole) of allyl-Ni-bromide complex (((2-MeO$_2$C—C$_3$H$_4$)NiBr)$_2$) in 30 mL THF. The mixture was stirred for 1 h. Solvent was removed under vacuum. The residue was extracted with ether. Solvent was evaporated and the product was rinsed with pentane. Brown powder (0.176 g, 0.351 mmole) was obtained in 82% yield. $^{31}$PNMR (C$_6$D$_6$): δ 73.43 (s, major).

EXAMPLE 104

Synthesis of Catalyst 38

In a dry box, to a 100 mL RB flask containing 10 mL THF solution of cyclohexylisothiocyanate (0.0439 g, 0.311 mmole), was added slowly a THF solution of (t-Bu)$_2$PCH$_2$Li (0.0568 g, 0.311 mmole) at −30° C. The solution turned yellow orange it was stirred for 1 h, during which time the solution warmed up to RT. Solvent was removed. The solid residue was mixed with 0.0739 g (0.156 mmole) of allyl-Ni-bromide complex (((2-MeO$_2$C—C$_3$H$_4$)NiBr)$_2$) in 30 mL THF. The mixture was stirred for 1 h. Solvent was removed under vacuum. The residue was extracted with ether. The solvent was removed. The product was rinsed with pentane. Brown powder (0.0773 g, 0.169 mmole) was obtained in 54% yield. $^{31}$PNMR (C$_6$D$_6$): δ 66.69 (s, major).

EXAMPLE 105

Synthesis of Catalyst 39

In a dry box, benzoylisocyanate (0.1966 g, 1.336 mmole) was dissolved in 20 mL THF in a 100 mL RB flask. The solution was cooled to ca. −30° C. in a freezer. (t-Bu)$_2$PCH$_2$Li (0.2220 g, 1.336 mmole) was added to the above cold solution under stirring. The mixture turned dark red. It was allowed to stir at RT for 4 h. The solution was then evaporated to dryness. To the ligand precursor (ca. 1.300 mmole) was added 20 mL THF. Under stirring, nickel allyl chloride dimer (0.1760 g, 0.6500 mmole) was added to the mixture. The solution became dark red. It was allowed to stir at RT for 2 h. Solvent was evaporated. Toluene (ca. 8 mL) was added to the brick red residue. Upon brief stirring, large excess of pentane was added. The resulting solid was filtered, followed by 3× pentane wash, and dried in vacuo. pale orange solid (0.4223 g, 72%) was obtained.

EXAMPLES 106–120

Polymerizations with catalysts 24 through 38 are shown in Tables 14 and 15.

TABLE 14

| | | | Condition I in Table 3 | | | |
|---|---|---|---|---|---|---|
| Ex | Cata-lyst | Yield (g) | #Me/1000 CH$_2$ | m.p. (° C.)(ΔH$_f$) | Mw/PDI | TON |
| 106 | 24* | 7.81 | 26 | 118 (52.2) | 4,495/4.9 | 13,900 |
| 107 | 25 | 2.89 | 15 | 123 (0.6) | 17,614/8.9 | 5,150 |
| 108 | 26 | 8.26 | 21 | 122 (173.1) | 19,394/11.2 | 14,700 |
| 109 | 27 | 4.66 | 33 | 129 (147.6) | 226,688/8.8 | 8,300 |
| 110 | 28 | 1.07 | 20 | 127 (182.2) | 34,420/33.5 | 1,900 |
| 111 | 29 | 6.14 | 17 | 123 (159.3) | 12,964/5.2 | 10,900 |
| 112 | 30 | 9.71 | 32 | 123 (172.2) | 4,898/8.1 | 17,300 |
| 113 | 31 | 7.82 | 13 | 121 (126.8) | 563,495/5.1 | 13,900 |
| 114 | 32 | 11.75 | 12 | 131 (225.5) | 254,365/106.4 | 20,940 |

*No B(C$_6$F$_5$)$_3$ was used. The catalyst self-initiated ethylene polymerization.

TABLE 15

Ethylene Polymerization Using 0.02 mmole Catalyst, 5 mL TCB and 10 eq $B(C_6F_5)_3$, at RT under 6.9 MPa Ethylene for 18 h

| Ex | Catalyst | Yield (g) | #Me/ 1000 $CH_2$ | m.p. (° C.) ($\Delta H_f$) | Mw | TON |
|---|---|---|---|---|---|---|
| 115 | 33 | 4.427 | 27 | 129 (173.8) | Trimodal | 7604 |
| 116 | 34 | 0.181 | 25 | 117 (116.9) | Trimodal | 343 |
| 117 | 35 | 0.698 | 15 | 126 (190.1) | 67,352 | 1160 |
| 118 | 36 | 3.388 | 27 | 128 (165.6) | Insoluble in TCB | 4452 |
| 119 | 37 | 0.083 | 35 | 130 (137.2) | Trimodal | 140 |
| 120 | 38 | 0.321 | 21 | 129 (168.5) | 70,329 | 535 |

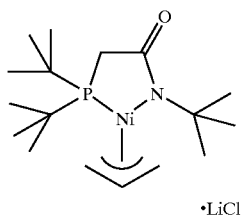

40

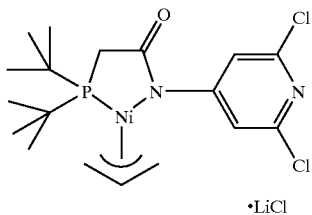

44

-continued

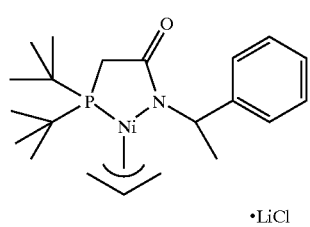

41

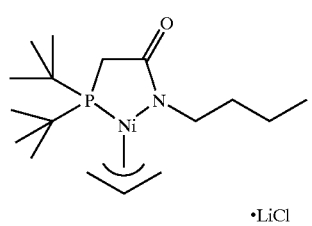

42

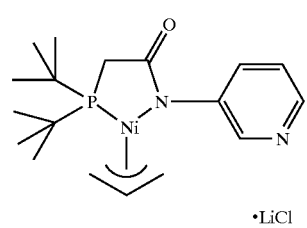

43

EXAMPLES 121–150

Examples 121–150 are listed in Tables 16–20 below. The structures for these compounds illustrate just one of the possible products and binding modes that may have formed during the synthesis of the ligand and the subsequent synthesis of the nickel compound and are not meant to be restrictive. The polymerizations were carried out according to General Polymerization Procedure A. Varying amounts of acrylate homopolymer are present in some of the samples. In Tables 16–20, the yield of the polymer is reported in grams and includes the yield of the dominant ethylene/acrylate copolymer as well as the yield of any acrylate homopolymer that was formed. Molecular weights were determined by GPC, unless indicated otherwise. All copolymerizations were run for 18 h, unless otherwise noted.

General Polymerization Procedure A: In a drybox, a glass insert was loaded with the nickel compound and, optionally, a Lewis acid (e.g., $BPh_3$ or $B(C_6F_5)_3$) and borate (e.g., NaBAF or LiBArF) and any other specified cocatalysts. Next, the solvent was added to the glass insert followed by the addition of any co-solvents and then comonomers. The insert was greased and capped. The glass insert was then loaded in a pressure tube inside the drybox. The pressure tube was then sealed, brought outside of the drybox, connected to the pressure reactor, placed under the desired ethylene pressure and shaken mechanically. After the stated reaction time, the ethylene pressure was released and the glass insert was removed from the pressure tube. The polymer was precipitated by the addition of MeOH (~20 mL). The polymer was then collected on a frit and rinsed with MeOH and, optionally, acetone. The polymer was transferred to a pre-weighed vial and dried under vacuum overnight. The polymer yield and characterization were then obtained.

TABLE 16

Ethylene Homopolymerizations, (0.02 mmol Cmpd, 25° C., 1.0 MPa, 10 mL TCB, 10 equiv B(C$_6$F$_5$)$_3$)

| Ex. | Cmpd | NaBAF equiv | PE g | PE TO | M.W. | Total Me |
|---|---|---|---|---|---|---|
| 121 | 40 | 10 | 1.08[a] | 1,920 | $M_w$ = 37,044; $M_n$ = 4,989; $M_w/M_n$ = 7.43 | 22.4 |
| 122 | 40 | 1 | 2.49[a] | 4,440 | $M_w$ = 34,072; $M_n$ = 4,693; $M_w/M_n$ = 7.26 | 44.6 |
| 123 | 42 | 0 | 1.01 | 1,800 | $M_w$ = 25,754; $M_n$ = 905 $M_w/M_n$ = 28.46 | 79.2 |
| 124 | 43 | 0 | 1.79 | 3,190 | $M_w$ = 12,361; $M_n$ = 519; $M_w/M_n$ = 23.80 | 59.4 |

[a]Formation of a surface polymer film on the reaction mixture appeared to limit the productivity of these polymerizations.

TABLE 17

Ethylene/Acrylate Copolymerizations (6.9 MPa, 100° C.) (0.02 mmol Cmpd, 10 mL total of TCB + Acrylate, 20 equiv B(C$_6$F$_5$)$_3$)

| Ex. | Cmpd | Acrylate mL | NaBAF equiv | Yield g | Acrylate Incorp. mol % | M.W. | Total Me |
|---|---|---|---|---|---|---|---|
| 125 | 42 | EGPEA 1 | 0 | 0.38 | 0.5 | $M_w(^1H)$ = 3,531 | 19.7 |
| 126 | 41 | EGPEA 1 | 0 | 0.077 | 0.3 | $M_n(^1H)$ = 16,192 | 17.7 |
| 127 | 43 | EGPEA 1 | 0 | 0 | | | |
| 128 | 44 | EGPEA 1 | 0 | 0.094 | 0.4 | $M_w$ = 3,259; $M_p$ = 1,067; $M_n$ = 988; $M_w/M_n$ = 3.30 | nd |
| 129 | 40 | EGPEA 1 | 0 | 0.10 | 1.3[a] | $M_w$ = 11,396; $M_p$ = 7,282; $M_n$ = 4,581; $M_w/M_n$ = 2.49 | 6.9 |
| 130 | 40 | EGPEA 1 | 1 | 2.40 | 0.66 $^{13}$C 0.33 IC 0.33 EG | $M_w$ = 6,649; $M_p$ = 6,271 $M_n$ = 3,104; $M_w/M_n$ = 2.14 | nd |
| 131 | 40 | EGPEA 1 | 20 | 8.61 | 0.38 $^{13}$C 0.19 IC 0.19 EG | $M_w$ = 6,674; $M_p$ = 5,860; $M_n$ = 3,209; $M_w/M_n$ = 2.08 | nd |
| 132 | 40 | EGPEA 2 | 20 | 5.50 | 0.77 $^{13}$C 0.39 IC 0.38 EG | $M_n$ = 5,238; $M_p$ = 4,484; $M_n$ = 2,423; $M_w/M_n$ = 2.16 | nd |
| 133 | 41 | EGPEA 2 | 20 | 0.61 | A | $M_w$ = 5,032; $M_p$ = 4,711; $M_n$ = 2,330; $M_w/M_n$ = 2.16 | nd |
| 134 | 42 | EGPEA 2 | 20 | 1.06 | 1.0 | $M_w$ = 4,237; $M_p$ = 3,286; $M_n$ = 1,548; $M_w/M_n$ = 2.74 | 14.2 |
| 135 | 43 | EGPEA 2 | 20 | 0.70 | A | nd | nd |
| 136 | 40 | EGPEA 4 | 20 | 2.02 | 0.70 | $M_w$ = 3,201; $M_p$ = 2,755; $M_n$ = 1,688; $M_w/M_n$ = 1.90 | 11.0 |
| 137 | 40 | MA 0.5 | 10 | 13.21 | 0.41 $^{13}$C 0.21 IC 0.20 EG | $M_w$ = 5,008; $M_p$ = 4,932; $M_n$ = 1,582; $M_w/M_n$ = 3.16 | 8.6 |
| 138 | 40 | MA 0.5 | 20 | 11.45 | 0.57 $^{13}$C 0.33 IC 0.24 EG | $M_w$ = 4,461; $M_p$ = 3,994; $M_n$ = 1,755; $M_w/M_n$ = 2.54 | 10.2 |
| 139 | 40 | HA 2 | 20 | 1.48 | 0.60 $^{13}$C 0.21 IC 0.39 EG | $M_w$ = 4,034; $M_p$ = 3,699; $M_n$ = 1,849; $M_w/M_n$ = 2.18 | 7.4 |
| 140 | 40 | HA 1 | 20 | 9.88 | 0.36 $^{13}$C 0.15 IC 0.21 EG | $M_w$ = 5,834; $M_p$ = 5,525; $M_n$ = 2,251; $M_w/M_n$ = 2.59 | 8.2 |
| 141 | 40 .005 mmol | EGPEA 1 | 10 | 0.40 | 0.5 | $M_w$ = 7,123; $M_n$ = 3,183; $M_p$ = 6,843; $M_w/M_n$ = 2.24 | 8.5 |

[a]Large amount of homopolymer was formed: overlaps with any copolymer resonances in the $^1$H NMR spectrum.

TABLE 18

Ethylene/Acrylate Copolymerizations (6.9 MPa) (0.02 mmol Cmpd, 18 h, 10 mL total of TCB + EGPEA, 20 equiv B(C$_6$F$_5$)$_3$, 10 equiv NaBAF)

| Ex. | Cmpd | EGPEA mL | Temp. ° C. | Yield g | Acrylate Incorp. mol % | M.W. | Total Me |
|---|---|---|---|---|---|---|---|
| 142 | 40 | 2 | 120 | 12.40 | 0.69 $^{13}$C 0.37 IC 0.32 EG | $M_w$ = 3,813; $M_n$ = 1,577; $M_p$ = 3,234; $M_w/M_n$ = 2.42 | nd |

TABLE 18-continued

Ethylene/Acrylate Copolymerizations (6.9 MPa)
(0.02 mmol Cmpd, 18 h, 10 mL total of TCB + EGPEA, 20 equiv
$B(C_6F_5)_3$, 10 equiv NaBAF)

| Ex. | Cmpd | EGPEA mL | Temp. °C. | Yield g | Acrylate Incorp. mol % | M.W. | Total Me |
|---|---|---|---|---|---|---|---|
| 143 | 40 | 4 | 120 | 5.16 | Trace[a] | $M_w$ = 2,660; $M_p$ = 2,528; $M_n$ = 1,305; $M_w/M_n$ = 2.04 | nd |
| 144 | 41 | 2 | 120 | 5.30 | 1.1 | $M_w$ = 3,331; $M_p$ = 3,047; $M_n$ = 1,386; $M_w/M_n$ = 2.40 | 13.8 |
| 145 | 40 | 4 | 120 | 3.30 | 1.5 | $M_w$ = 3,125; $M_p$ = 3,139; $M_n$ = 1,476; $M_w/M_n$ = 2.12 | 16.8 |
| 146 | 40 | 4 | 120 | 4.10 | 2.2 | | |
| 147 | 40 | 2 | 130 | 8.99 | 2.8 | $M_w$ = 3,479; $M_p$ = 3,202; $M_n$ = 1,510; $M_w/M_n$ = 2.30 | 25.7 |
| 148 | 40 0.001 mmol | 2 | 120 | 4.57 | 2.2 | $M_w$ = 3,914; $M_p$ = 3,592; $M_n$ = 1,761; $M_w/M_n$ = 2.22 | 32 |

[a]Large amount of acrylate homopolymer was formed, preventing quantitative determination of percent acrylate incorporation in the copolymer. Ester groups incorporated both in branches and in unsaturated end groups.

TABLE 19

Ethylene/Acrylate Copolymerizations (3.5 MPa, 120° C.) (18 h, 10 mL total of TCB + EGPEA, 20 equiv $B(C_6F_5)_3$, 10 equiv NaBAF)

| Ex. | Cmpd | EGPEA mL | Temp. °C. | Yield G | Acrylate Incorp. mol % | M.W. | Total Me |
|---|---|---|---|---|---|---|---|
| 149 | 40 0.01 mmol | 1 | 120 | 2.48 | 0.69 $^{13}$C 0.37 IC 0.32 EG | $M_w$ = 3,675; $M_p$ = 3,403; $M_n$ = 1,701; $M_w/M_n$ = 2.16 | nd |
| 150 | 40 0.005 mmol | 1 | 120 | 0.21 | Trace[a] | $M_w$ = 3,272; $M_p$ = 3,403; $M_n$ = 1,701; $M_w/M_n$ = 2.01 | nd |

[a]Large amount of acrylate homopolymer was formed, preventing quantitative determination of percent acrylate incorporation in the copolymer.

TABLE 20

Branching Analysis for Some MA and HA Copolymers of Table 17[a]

| Ex. | Total Me | Me | Et | Hex+ & eoc | Am+ & eoc | Bu+ & eoc | Me ester |
|---|---|---|---|---|---|---|---|
| 137 | 8.6 | 2.4 | 1.0 | 6.4 | 5.8 | 5.2 | 2.5 |
| 138 | 10.2 | 2.5 | 2.1 | 7.5 | 6.1 | 5.6 | 3.9 |
| 139 | 7.4 | 2.4 | 0.6 | | 5.3 | 5.0 | |
| 140 | 8.2 | 3.1 | | | 5.1 | 5.1 | |

[a]Pr and Bu branches were not detected in these copolymers.

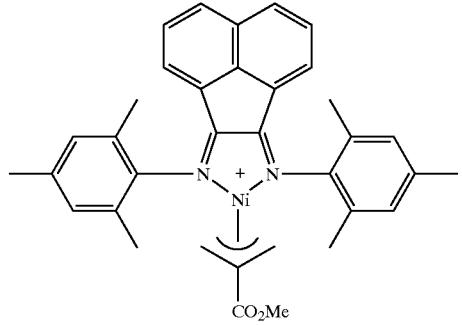

50

45

55

60

-continued

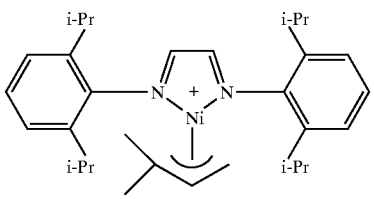

46

47
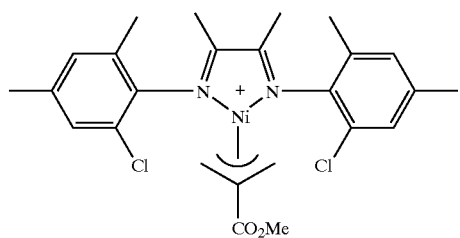
48
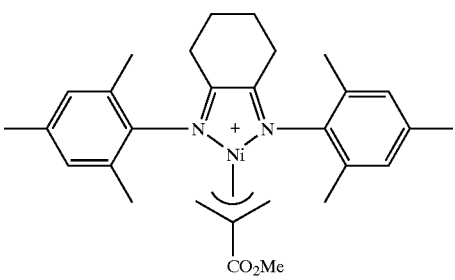 (appears later)
49
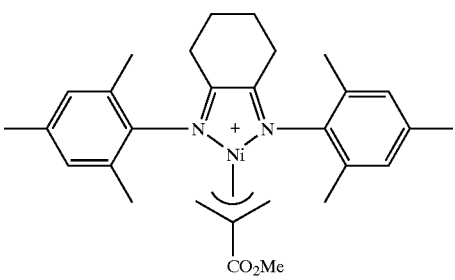
50
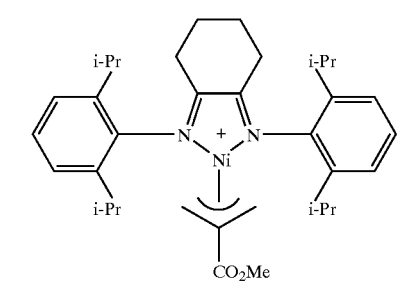
51
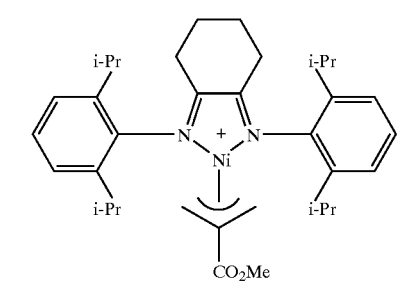
52
53
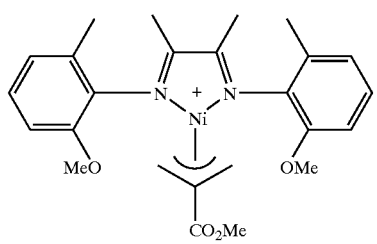
54
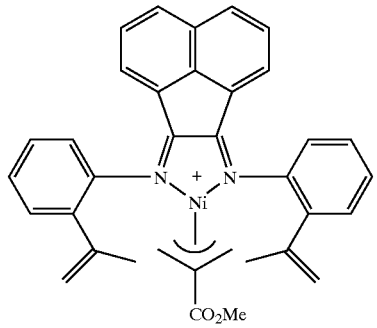
55
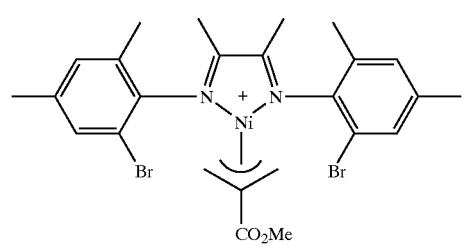
56
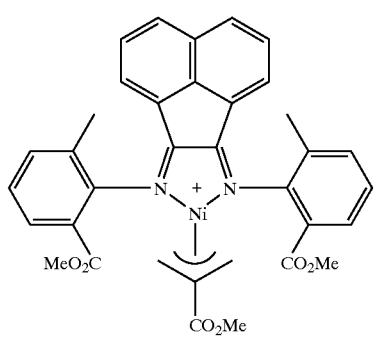
57
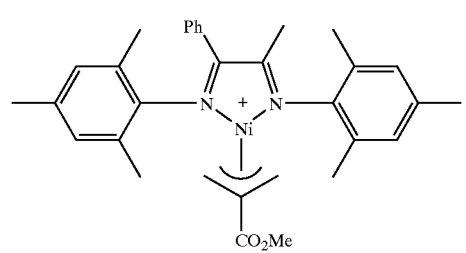

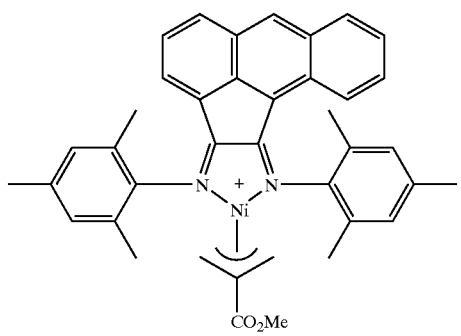
58
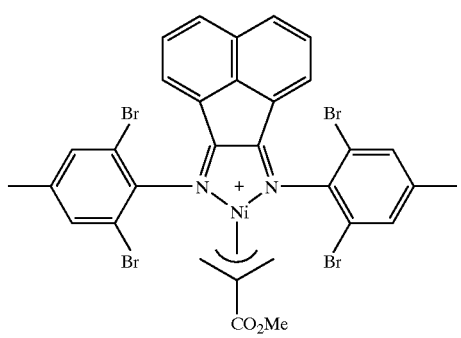
59
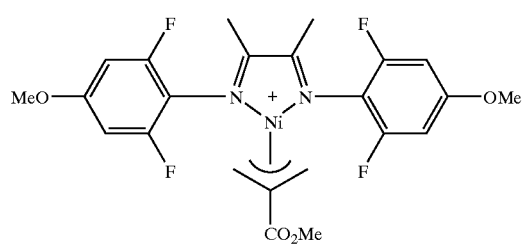
60
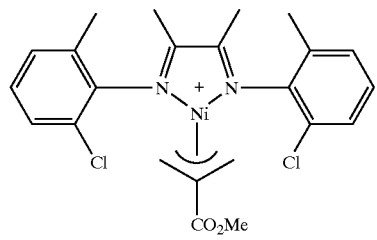
61
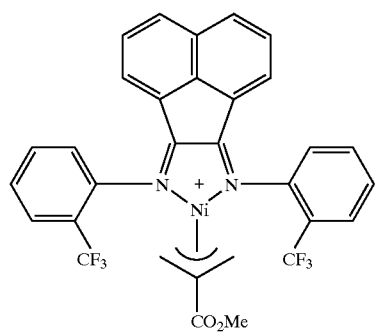
62
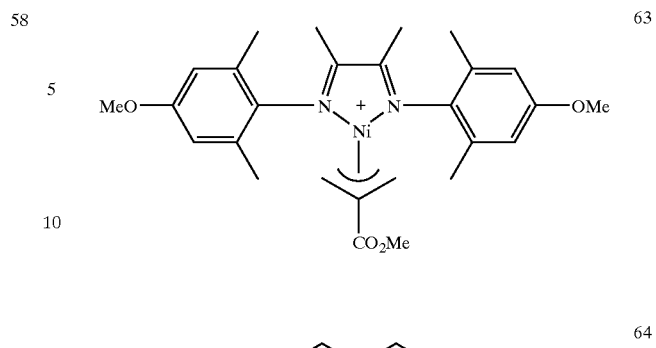
63
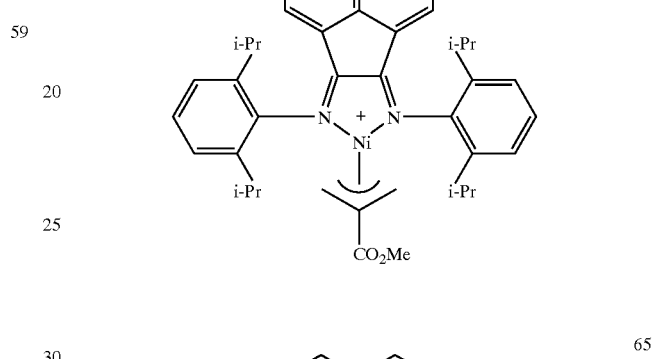
64
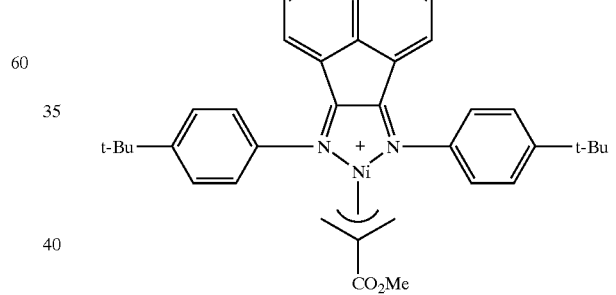
65
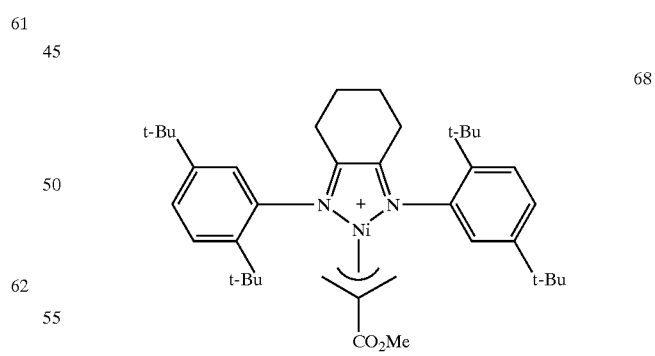
68
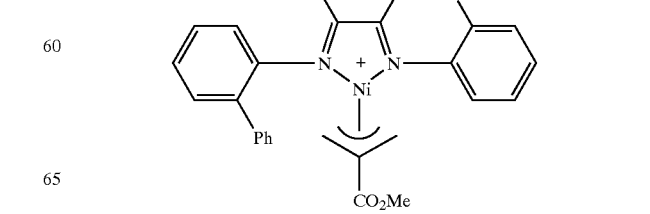
69

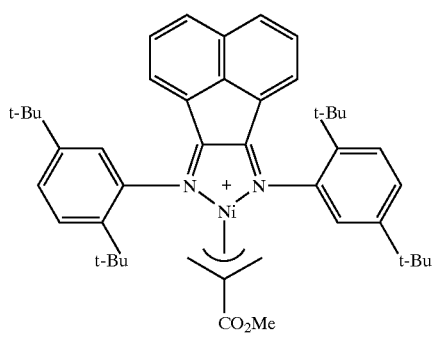
71
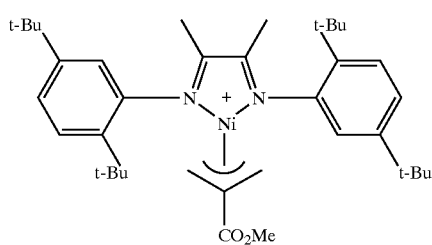
72
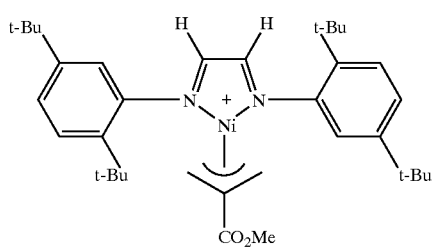
73
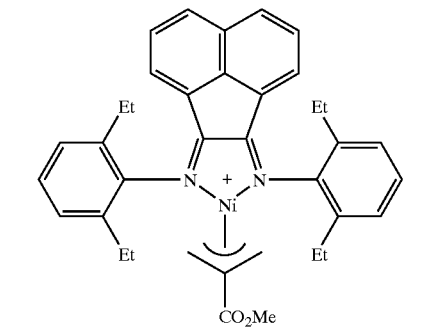
74
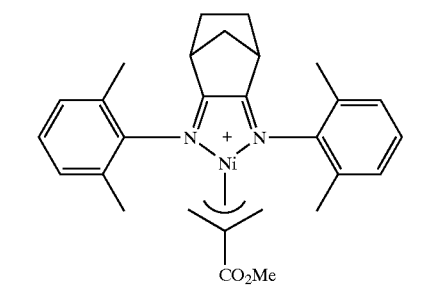
75
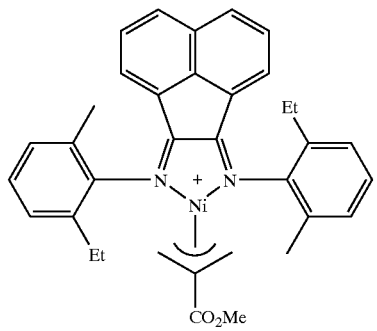
76
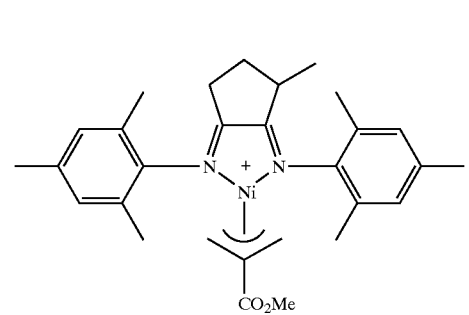
77
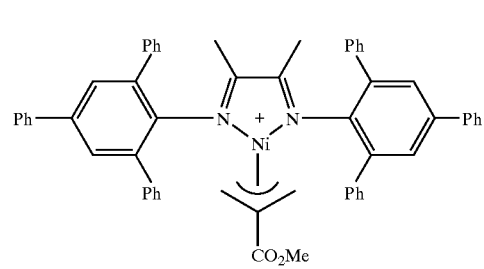
78
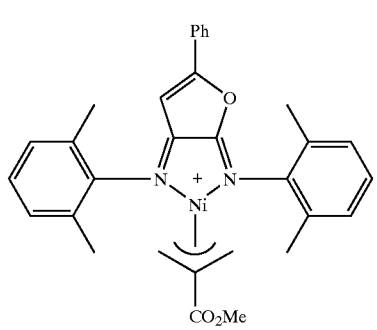
79
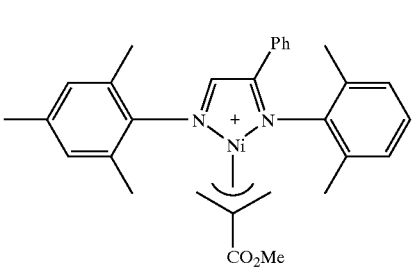
80

91 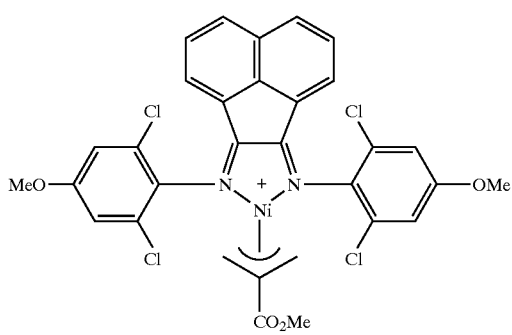

92 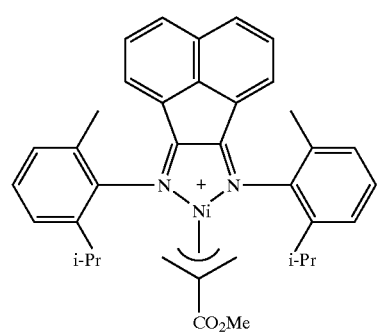

93 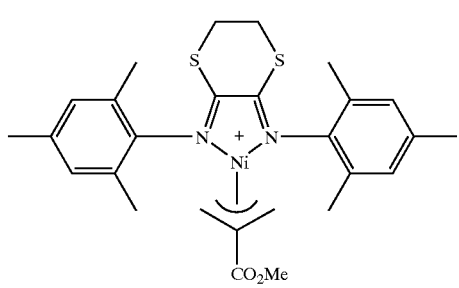

94 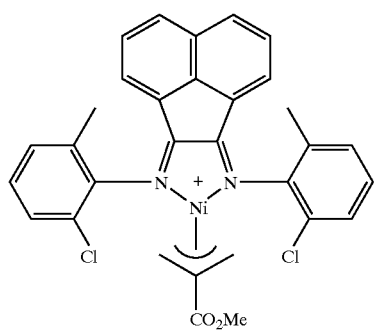

95 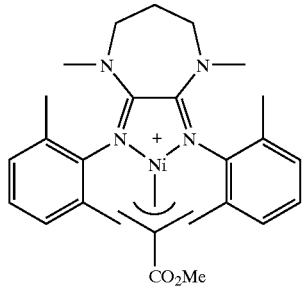

96 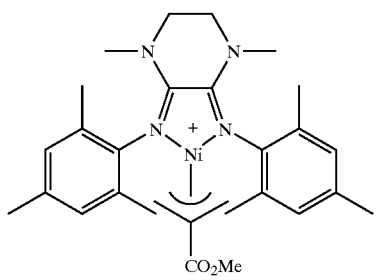

97 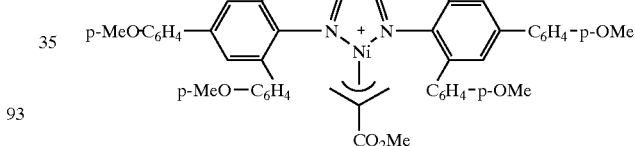

EXAMPLES 151–439

Examples 151–439 are listed in Tables 21–57 below. They were carried out with nickel complexes 45–97 shown above. For each of 45–97 the counterion is BAF. The polymerizations were carried out according to General Polymerization Procedure A. Varying amounts of acrylate homopolymer are present in some of the isolated polymers. In Tables 21–58, the yield of the polymer is reported in grams and includes the yield of the dominant ethylene/acrylate copolymer as well as the yield of any acrylate homopolymer that was formed. Molecular weights were determined by GPC, unless indicated otherwise. Mole percent acrylate incorporation and total Me were determined by $^1$H NMR spectroscopy, unless indicated otherwise. Mole percent acrylate incorporation is typically predominantly IC, unless indicated otherwise. The $LiB(C_6F_5)_4$ used (LiBArF) included 2.5 equiv of $Et_2O$. All copolymerizations were run for 18 h, unless otherwise noted.

TABLE 21

Reproducibility of Ethylene/Acrylate Copolymerizations Using 45 (0.02 mmol Cmpd, 6.9 MPa., 120° C., 18 h, 10 mL Total of TCB + Acrylate, 40 equiv B(C$_6$F$_5$)$_3$)

| Ex. | Acrylate mL | Yield g | Acrylate Incorp. mol % | M.W. | Total Me |
|---|---|---|---|---|---|
| 151 | EGPEA 2 | 9.77 | 1.20 ($^{13}$C) | $M_p$ = 8,651; $M_w$ = 8,930; $M_n$ = 3,983; PDI = 2.24 | 54.6 |
| 152 | EGPEA 2 | 12.47 | 1.4 | $M_p$ = 12,036; $M_w$ = 12,662; $M_n$ = 4,449; PDI = 2.85 | 51.8 |
| 153 | EGPEA 2 | 10.73 | 2.0 | $M_p$ = 13,657; $M_w$ = 14,740; $M_n$ = 5,348; PDI = 2.76 | 54.5 |
| 154 | HA 2 | 2.08 | 1.28 ($^{13}$C) | $M_p$ = 6,838; $M_w$ = 6,534; $M_n$ = 1,331; PDI = 4.91 | 53.2 |
| 155 | HA 2 | 2.42 | 1.16 ($^{13}$C) | $M_p$ = 6,625; $M_w$ = 7,524; $M_n$ = 3,305; PDI = 2.28 | 54.9 |

TABLE 22

Variation of Acrylate Concentration, Acrylate Structure, Solvent and Temperature in Ethylene/Acrylate Copolymerizations Using 45 (0.02 mmol Cmpd, 6.9 MPa E, 18 h, 10 mL Total of TCB + Acrylate, 40 equiv B(C$_6$F$_5$)$_3$)

| Ex. | Acrylate mL | Temp ° C. | Yield g | Acryl. Incorp. (mol %) | M.W. | Total Me |
|---|---|---|---|---|---|---|
| 156 | EGPEA 1 | 120 | 16.72 | 0.7 | $M_p$ = 12,452; $M_w$ = 13,952; $M_n$ = 4,319; PDI = 3.23 | 69.8 |
| 157 | EGPEA 2 | 120 | 12.47 | 1.4 | $M_p$ = 12,036; $M_w$ = 12,662; $M_n$ = 4,449; PDI = 2.85 | 51.8 |
| 158 | EGPEA 4 | 120 | 5.37 | 2.70 ($^{13}$C) | $M_p$ = 6,623; $M_w$ = 9,878; $M_n$ = 3,388; PDI = 2.92 | 42.6 ($^{13}$C) |
| 159 | EGPEA 2 | 100 | 4.21 | 1.60 ($^{13}$C) | $M_p$ = 20,949; $M_w$ = 21,275; $M_n$ = 9,605; PDI = 2.21 | 26.1 ($^{13}$C) |
| 160 | EGPEA 4 | 100 | 3.13 | 3.60 ($^{13}$C) | $M_p$ = 12,760; $M_w$ = 14,733; $M_n$ = 6,092; PDI = 2.42 | 20.6 ($^{13}$C) |
| 161 | IDA[a] 2 | 80 | 0.89 | 1.6 ($^{13}$C) | nd | nd |
| 162 | IDA[b] 1 | 80 | 1.75 | nd | $M_p$ = 30,258; $M_w$ = 32,201; $M_n$ = 13,047; PDI = 2.47 | nd |
| 163 | HA 1 | 120 | 2.70 | 0.66 ($^{13}$C) | $M_p$ = 8,851; $M_w$ = 9,678; $M_n$ = 2,252; PDI = 4.30 | 54.7 |
| 164 | HA 2 | 120 | 2.08 | 1.28 ($^{13}$C) | $M_p$ = 6,838; $M_w$ = 6,534; $M_n$ = 1,331; PDI = 4.91 | 53.2 |
| 165 | MA 0.25 | 120 | 13.08 | 0.10 ($^{13}$C)[c] | $M_p$ = 10,797; $M_w$ = 12,929; $M_n$ = 4,798; PDI = 2.69 | 76.0 |
| 166 | MA 0.5 | 120 | 13.17 | 0.17 ($^{13}$C)[d] | $M_p$ = 12,267; $M_w$ = 13,485; $M_n$ = 4,587; PDI = 2.94 | 72.0 |
| 167 | MA 1 | 120 | 15.45 | 0.19 ($^{13}$C)[d] | $M_p$ = 13,376; $M_w$ = 13,971; $M_n$ = 4,694; PDI = 2.98 | 78.6 |

[a]Total Volume = 5 mL: 2 mL IDA + 3 mL Bu$_2$O; No TCB used.
[b]Total Volume = 5 mL: 4 mL TCB and 1 mL IDA;
[c]Acrylate homopolymer not detected by $^{13}$C NMR spectroscopy.
[d]Acrylate homopolymer detected by $^{13}$C NMR spectroscopy.

TABLE 23

Variation of Acrylate Concentration and Temperature in Ethylene/EGPEA Copolymerizations with Cmpd. 46 (0.02 mmol Cmpd, 6.9 MPa E, 18 h, 10 mL Total of TCB + EGPEA, 40 equiv B(C$_6$F$_5$)$_3$)

| Ex. | EGPEA mL | Temp ° C. | Yield g | Acrylate Incorp. mol % | M.W. | Total Me |
|---|---|---|---|---|---|---|
| 168 | 2 | 120 | 2.17 | 0.03 ($^{13}$C) | $M_p$ = 12,550; $M_w$ = 13,744; $M_n$ = 5,936; PDI = 2.32 | |
| 169 | 2 | 100 | 1.88 | 0.44 ($^{13}$C) | $M_p$ = 17,362; $M_w$ = 17,905; $M_n$ = 8,075; PDI = 2.16 | 28.6 |

TABLE 23-continued

Variation of Acrylate Concentration and Temperature in
Ethylene/EGPEA Copolymerizations with Cmpd. 46 (0.02 mmol Cmpd,
6.9 MPa E, 18 h, 10 mL Total of TCB + EGPEA, 40 equiv
$B(C_6F_5)_3$)

| Ex. | EGPEA mL | Temp °C. | Yield g | Acrylate Incorp. mol % | M.W. | Total Me |
|---|---|---|---|---|---|---|
| 170 | 4 | 120 | 1.22 | Nd[a] | $M_p$ = 8,651; $M_w$ = 8,930; $M_n$ = 3,983; PDI = 2.24 | |
| 171 | 4 | 100 | 0.032 | 1.1 | $M_p$ = 13,111; $M_w$ = 13,076; $M_n$ = 6,062; PDI = 2.16 | 24.3 |

[a]Due to significant homopolymer formation, percent acrylate incorporation in the copolymer was not determined by $^1$H NMR spectroscopy.

TABLE 24

Effect of Counterion on Ethylene/EGPEA Copolymerizations
Using Cmpd 45 (0.02 mmol Cmpd, 6.9 MPa E, 120° C., 18 h, 8 mL
TCB, 2 mL EGPEA, 40 equiv $B(C_6F_5)_3$)

| Ex. | Counterion | Yield g | Acrylate Incorp. mol % | M.W. | Total Me |
|---|---|---|---|---|---|
| 172 | $[B[3,5-C_6H_3-(CF_3)_2]_4]^-$ | 12.47 | 1.4 | $M_p$ = 12,036; $M_w$ = 12,662; $M_n$ = 4,449; PDI = 2.85 | 51.8 |
| 173 | $[B(C_6F_5)_4]^-$ | 16.72 | 1.5 | $M_p$ = 15,316; $M_w$ = 17,100; $M_n$ = 6,108; PDI = 2.80 | 57.1 |
| 174 | $[N(SO_2CF_3)_2]^-$ | 5.38 | 1.9 | $M_p$ = 12,551; $M_w$ = 13,097; $M_n$ = 4,949; PDI = 1.78 | 52.6 |

TABLE 25

Effect of $Bu_2O$ Addition on Ethylene/Acrylate Copolymerizations Using Cmpd 45 (0.02 mmol Cmpd, 6.9 MPa E, 120° C., 18 h, 8 mL Total of TCB + $Bu_2O$, 2 mL EGPEA, 40 equiv $B(C_6F_5)_3$)

| Ex. | $Bu_2O$[a] mL | Yield g | Acrylate Incorp. mol % | M.W. | Total Me |
|---|---|---|---|---|---|
| 175 | 0 | 12.47 | 1.4 | $M_p$ = 12,036; $M_w$ = 12,662; $M_n$ = 4,449; PDI = 2.85 | 51.8 |
| 176 | 2 | 5.10 | 1.72 ($^{13}$C) | $M_p$ = 6,952; $M_w$ = 8,846; $M_n$ = 3,044; PDI = 2.91 | 65.0 |
| 177 | 4 | 8.73 | 1.08 ($^{13}$C) | $M_p$ = 7,135; $M_w$ = 8,894; $M_n$ = 3,313; PDI = 2.68 | 66.5 |
| 178 | 8 | 11.94 | b | Dual UV/RI. UV: $M_p$ = 7,616; $M_w$ = 50,244; $M_n$ = 1,819; PDI = 27.62; RI: $M_p$ = 12,075; $M_w$ = 14,395; $M_n$ = 5,150; PDI = 2.80 | Nd |

[a]Amount of acrylate homopolymer formation increases as the amount of $Bu_2O$ increases.
[b]According to $^{13}$C NMR spectroscopy, the polymer was a mixture of polyethylene and poly(EGPEA); no copolymer resonances were observed.

TABLE 26

Variation of the Lewis Acid (LA) Cocatalyst in Ethylene/Acrylate
Copolymerizations, Including Copolymerization in the Absence of a Lewis Acid
Cocatalyst (0.02 mmol Cmpd, 6.9 MPa E; 120° C., 18 h, 10 mL Total of TCB + Acrylate)

| Ex. | Cmpd | Acrylate mL | LA/equiv | Yield g | Acrylate Incorp. Mol % | M.W. | Total Me |
|---|---|---|---|---|---|---|---|
| 179 | 45 | EGPEA 2 | $B(C_6F_5)_3$ 40 | 12.47 | 1.4 | $M_p$ = 12,036; $M_w$ = 12,662, $M_n$ = 4,449; PDI = 2.85 | 51.8 |
| 180 | 45 | EGPEA 2 | $BPh_3$ 40 | 2.73 | 2.2 | $M_p$ = 11,442; $M_w$ = 13,348; $M_n$ = 4,897; PDI = 2.73 | 49.5 |

TABLE 26-continued

Variation of the Lewis Acid (LA) Cocatalyst in Ethylene/Acrylate Copolymerizations, Including Copolymerization in the Absence of a Lewis Acid Cocatalyst (0.02 mmol Cmpd, 6.9 MPa E; 120° C., 18 h, 10 mL Total of TCB + Acrylate)

| Ex. | Cmpd | Acrylate mL | LA/equiv | Yield g | Acrylate Incorp. Mol % | M.W. | Total Me |
|---|---|---|---|---|---|---|---|
| 181 | 45 | EGPEA 2 | $AlPh_3$ 40 | 1.15 | a | $M_p$ = 3,207; $M_w$ = 4,233; $M_n$ = 1,723; PDI = 2.46 | Nd |
| 182 | 45 | EGPEA 1 | $B(C_6F_5)_3$ 40 | 16.72 | 0.7 | $M_p$ = 12,452; $M_w$ = 13,952; $M_n$ = 4,319; PDI = 3.23 | 69.8 |
| 183 | 45 | EGPEA 1 | $B(C_6F_5)_3$ 5 | 2.62 | 0.23 ($^{13}$C) | $M_p$ = 12,529; $M_w$ = 12,302; $M_n$ = 5,147; PDI = 2.39 | 55.8 |
| 184 | 46 | THA 2 | $B(C_6F_5)_3$ 40 | 2.37 | 0.23 | $M_p$ = 12,775; $M_w$ = 13,777; $M_n$ = 7,165; PDI = 1.92 | |
| 185 | 46 | THA 2 | None | 0.63 | 0.64 ($^{13}$C) | Dual UV/RI. UV: $M_p$ = 8,098; $M_w$ = 687,552, $M_n$ = 6,306; PDI = 109.04; RI: $M_p$ = 9,383; $M_w$ = 12,732; $M_n$ = 5,694; PDI = 2.24 | 34.0 |

[a] Due to significant homopolymer formation, percent acrylate incorporation in the copolymer was not determined by $^1$H NMR spectroscopy.

TABLE 27

Effect of alpha-Diimine Structure on Ethylene/Acrylate Copolymerizations (0.02 mmol Cmpd, 6.9 MPa E, 120° C., 18 h, 9 mL TCB, 1 mL EGPEA, 40 equiv $B(C_6F_5)_3$)

| Ex. | Cmpd | Yield g | Acrylate Incorp. mol % | M.W. | Total Me |
|---|---|---|---|---|---|
| 186 | 45 | 16.72 | 0.7 | $M_p$ = 12,452; $M_w$ = 13,952; $M_n$ = 4,319; PDI = 3.23 | 69.8 |
| 187 | 47 | 14.02 | 0.8 | $M_p$ = 9,915; $M_w$ = 13,027; $M_n$ = 3,660; PDI = 3.56 | 69.5 |
| 188 | 48 | 0 | — | — | — |
| 189 | 50 | 3.96 | 0.55 ($^{13}$C) | $M_p$ = 14,350; $M_w$ = 15,584; $M_n$ = 7,421 | 72.0 ($^{13}$C) |
| 190 | 51 | 2.28 | 1.8 | $M_p$ = 15,543; $M_w$ = 17,651; $M_n$ = 7,561; PDI = 2.33 | 64.8 |
| 191 | 55 | 7.64 | 1.6 | $M_p$ = 14,350; $M_w$ = 15,584; $M_n$ = 7,421 | 68.6 |
| 192 | 56 | 8.81 | Nd[c] | $M_p$ = 946; $M_w$ = 7,044; $M_n$ = 911; PDI = 7.73 | Nd |
| 193 | 57 | 12.28 | 1.1 | $M_p$ = 14,408; $M_w$ = 16,770; $M_n$ = 6,740; PDI = 2.49 | 71.7 |
| 194 | 58 | 18.19 | 1.0 | $M_p$ = 14,315; $M_w$ = 15,940; $M_n$ = 5,887; PDI = 2.71 | 85.6 |
| 195 | 59 | 15.30 | 0.8 | $M_p$ = 12,221; $M_w$ = 16,421; $M_n$ = 5,647; PDI = 2.91 | 78.6 |
| 196 | 60 | 0 | — | — | — |
| 197 | 61 | 16.78 | 0.8 | $M_p$ = 13,852; $M_w$ = 16,074; $M_n$ = 4,701; PDI = 3.42 | 77.0 |
| 198 | 62 | 2.28 | 0.9 | $M_p$ = 1,162; $M_w$ = 1,609; $M_n$ = 642; PDI = 2.51 | 75.2 |
| 199 | 63 | 1.08 | 1.6 | $M_p$ = 10,915; $M_w$ = 12,370; $M_n$ = 5,370; PDI = 2.30 | 74.2 |
| 200 | 64 | 5.32 | 1.6 | $M_p$ = 42,905; $M_w$ = 43,993; $M_n$ = 16,290; PDI = 2.70 | 105.0 |
| 201[a] | 64 | 5.55 | 0.3 | RI (THF, rt): $M_p$ = 101,394; $M_w$ = 1,154,459; $M_n$ = 5,516; PDI = 209.31 | 101.5 |
| 202[a] | 64 | 1.66[b] | 0.3 | RI (THF, rt): $M_p$ = 94,326; $M_w$ = 5,952,749; $M_n$ = 8,304; PDI = 716.88 | 99.5 |

[a] Ex 201 and 202 include 20 equiv $B(C_6F_5)_3$; Ex. 201 also includes 20 equiv $LiB(C_6F_5)_4$ and Ex. 202 includes 20 equiv NaBAF;
[b] Some polymer was lost in isolation;
[c] Not determined due to broad $^1$H NMR spectrum.

TABLE 28

Effect of alpha-Diimine Structure on Ethylene/Acrylate Copolymerizations (0.02 mmol Cmpd, 6.9 MPa E; 120° C., 18 h, 8 mL TCB, 2 mL of EGPEA, 40 equiv $B(C_6F_5)_3$)

| Ex. | Cmpd | Yield g | Acrylate Incorp. mol % | M.W. | Total Me |
|---|---|---|---|---|---|
| 203 | 45 | 12.47 | 1.4 | $M_p = 12,036$; $M_w = 12,662$; $M_n = 4,449$; PDI = 2.85 | 51.8 |
| 204 | 46 | 2.17 | 0.03 ($^{13}$C) | $M_p = 12,550$; $M_w = 13,744$; $M_n = 5,936$; PDI = 2.32 | |
| 205 | 47 | 4.10 | 2.0 | $M_p = 8,181$; $M_w = 9,903$; $M_n = 3,243$; PDI = 3.05 | 59.9 |
| 206 | 48 | 0 | — | — | — |
| 207 | 49 | 0 | — | — | — |
| 208 | 50 | 1.10 | 1.7 | Dual UV/RI. UV: $M_p = 19,292$; $M_w = 374,248$; $M_n = 7,268$; PDI = 51.49; RI: $M_p = 22,404$; $M_w = 26,916$; $M_n = 11,257$; PDI = 2.39 | 60.5 |
| 209 | 51 | 2.32 | 3.1 | $M_p = 14,689$; $M_w = 17,651$; $M_n = 4,327$; PDI = 2.29 | 77.8 |
| 210 | 52 | 0.087 | a | Dual UV/RI. UV: $M_p = 21,556$; $M_w = 47,428$; $M_n = 6,142$; PDI = 7.72; RI: $M_p = 40,121$; $M_w = 40,676$; $M_n = 18,309$; PDI = 2.22 | a |
| 211 | 53 | 9.41 | 2.9 ($^{13}$C) | $M_p = 485$; $M_w = 1,035$; $M_n = 317$; PDI = 3.27 | 84.2 ($^{13}$C) |
| 212 | 56 | 0.49 | | Dual UV/RI. UV: $M_p = 2,195$ and 75; $M_w = 1,301,735$; $M_n = 3,351$; PDI = 388.41; RI: $M_p = 2,652$; $M_w = 84,063$; $M_n = 3,608$; PDI = 23.30 | |
| 213 | 57 | 2.94 | | $M_p = 9,779$; $M_w = 12,435$; $M_n = 4,519$; PDI = 2.75 | |
| 214 | 58 | 7.77 | 1.7 | Dual UV/RI. UV: $M_p = 21,192$; $M_w = 201,274$; $M_n = 10,087$; PDI = 19.95; RI: $M_p = 22,402$; $M_w = 95,991$; $M_n = 11,047$; PDI = 8.69 | 60.3 |
| 215 | 61 | 5.77 | 2.4 | $M_p = 9,535$; $M_w = 11,659$; $M_n = 4,357$; PDI = 2.68 | 56.1 |
| Examples 216–221 below include 20 equiv of $B(C_6F_5)_3$ | | | | | |
| 216 | 71 | 3.45 | 0.6 | $M_p = 20,054$; $M_w = 19,855$; $M_n = 9,070$; PDI = 2.19 | 63.4 |
| 217 | 72 | 1.32 | 1.6 | $M_p = 14,328$; $M_w = 16,242$; $M_n = 6,327$; PDI = 2.57 | 66.2 |
| 218 | 73 | 0.27 | | | |
| 219 | 69 | 1.79 | 1.5 | Dual UV/RI. UV: $M_p = 15,033$; $M_w = 21,410$; $M_n = 6,666$; PDI = 3.21; RI: $M_p = 8,520$; $M_w = 16,322$; $M_n = 2,159$; PDI = 7.56 | 62.1 |
| 220[b] | 45 | 7.50 | 1.0 | $M_p = 13,125$; $M_w = 14,026$; $M_n = 6,211$ PDI = 2.26 | 51.0 |
| 221[c] | 55 | 3.07 | 1.3 | $M_p = 7,458$; $M_w = 10,026$; $M_n = 3,566$; PDI = 2.81 | 58.2 |

[a] $^1$H NMR spectrum is broad;
[b] 20 equiv NaBAF present;
[c] 20 equiv LiBArF present.

TABLE 29

Effect of Pressure on Ethylene/EGPEA Copolymerizations (0.02 mmol Cmpd, 120° C., 18 h, 8 mL TCB, 2 mL EGPEA, 40 equiv $B(C_6F_5)_3$)

| Ex. | Cmpd | Press. MPa | Yield g | Acrylate Incorp. mol % | M.W. | Total Me |
|---|---|---|---|---|---|---|
| 222 | 45 | 6.9 | 12.47 | 1.4 | $M_p = 12,036$; $M_w = 12,662$; $M_n = 4,449$; PDI = 2.85 | 51.8 |

TABLE 29-continued

Effect of Pressure on Ethylene/EGPEA Copolymerizations (0.02 mmol Cmpd, 120° C., 18 h, 8 mL TCB, 2 mL EGPEA, 40 equiv $B(C_6F_5)_3$)

| Ex. | Cmpd | Press. MPa | Yield g | Acrylate Incorp. mol % | M.W. | Total Me |
|---|---|---|---|---|---|---|
| 223 | 45 | 4.1 | 4.30 | 2.9 | $M_p$ = 7,492; $M_w$ = 11,174; $M_n$ = 3,738; PDI = 2.99 | 57.7 |
| 224 | 47 | 6.9 | 4.10 | 2.0 | $M_p$ = 8,181; $M_w$ = 9,903; $M_n$ = 3,243; PDI = 3.05 | 59.9 |
| 225 | 47 | 4.1 | 0.70 | 3.3 | Dual UV/RI. UV: $M_p$ = 8,392; $M_n$ = 4,579; $M_w$ = 174,212; PDI = 38.05; RI: $M_p$ = 9,874; $M_n$ = 5,504; $M_w$ = 18,139; PDI = 3.30 | 59.8 |

TABLE 30

$^{13}$C NMR Branching Analysis for EGPEA Copolymers

| Ex. | Total Me | Me | Et | Pr | Bu | Hex+ & eoc | Am+ & eoc | Bu+ & eoc | $Me_{sBu}$ (%) | $Me_{sBu}$ (%) |
|---|---|---|---|---|---|---|---|---|---|---|
| 151 | 51.4 | 32.2 | 6.5 | 2.8 | 2.1 | 5.5 | 7.3 | 9.9 | 3.68 | 19.86 |
| 158 | 42.6 | 23.7 | 6.9 | 3.8 | 2.1 | 4.6 | 8.1 | 8.3 | Nd | Nd |
| 169 | 27.3 | 19.0 | 1.7 | 1.7 | 1.0 | 3.2 | 3.4 | 4.8 | Nd | Nd |
| 159 | 26.1 | 17.7 | 2.9 | 1.2 | 1.0 | 1.9 | 2.5 | 4.2 | Nd | Nd |
| 160 | 20.6 | 14.2 | 2.0 | 1.6 | 0.9 | 2.0 | 3.8 | 2.8 | Nd | Nd |
| 211 | 84.2 | 36.9 | 10.2 | 3.1 | 4.1 | 21.8 | 31.0 | 34.0 | 9 | 54.8 |
| 199 | 72.0 | 45.1 | 6.2 | 3.3 | 4.3 | 7.8 | 13.4 | 17.4 | Nd | Nd |

TABLE 31

$^{13}$C NMR Branching Analysis for MA Copolymers

| Ex. | Total Me | Me | Et | Pr | Bu | Hex+ & eoc | Am+ & eoc | Bu+ & eoc | $Me_{sBu}$ (%) | $Me_{sBu}$ (%) |
|---|---|---|---|---|---|---|---|---|---|---|
| 167 | 78.2 | 45.2 | 9.9 | 4.1 | 4.7 | 9.8 | 14.5 | 19.0 | 4.4 | 19.9 |
| 166 | 72.0 | 41.7 | 10.0 | 3.9 | | 8.5 | 11.9 | 16.3 | 4.2 | 18.9 |
| 165 | 76.0 | 42.7 | 11.0 | 4.0 | | 8.7 | 12.8 | 18.3 | 5.8 | 23.1 |
| 250 | 52.2 | 30.1 | 8.0 | 2.4 | 2.8 | 6.2 | 8.4 | 11.7 | Nd | Nd |
| 251 | 62.4 | 35.1 | 8.7 | 3.6 | 4.6 | 7.4 | 11.3 | 15.0 | Nd | Nd |
| 252 | 65.5 | 39.1 | 8.5 | 2.6 | 3.8 | 7.7 | 12.7 | 15.3 | Nd | Nd |
| 253 | 79.6 | 44.9 | 11.1 | 3.4 | 4.1 | 10.0 | 14.7 | 20.1 | Nd | Nd |
| 254 | 61.9 | 47.5 | 9.0 | 3.6 | 5.0 | 8.9 | 14.0 | 1.8 | Nd | Nd |
| 255 | 35.7 | 23.1 | 4.2 | 1.9 | 1.4 | 3.0 | 5.8 | 6.9 | Nd | Nd |
| 256 | 43.9 | 27.1 | 5.5 | 2.6 | 1.9 | 4.4 | 6.4 | 8.7 | Nd | Nd |

TABLE 32

$^{13}$C NMR Branching Analysis for HA Copolymers

| Ex. | Total Me | Me | Et | Pr | Bu | AM+ & eoc | Bu+ & eoc | $Me_{sBu}$ (%) | $Me_{sBu}$ (%) |
|---|---|---|---|---|---|---|---|---|---|
| 154 | 53.2 | 27.5 | 5.3 | 3.1 | 2.8 | 16.4 | 17.3 | trace | trace |
| 163 | 54.7 | 29.4 | 6.4 | 3.5 | 3.3 | 13.4 | 15.4 | 3.8 | 14.2 |
| 155 | 54.9 | 32.2 | 6.4 | 3.0 | 2.2 | 13.6 | 13.3 | Nd | Nd |
| 253 | 32.8 | 22.1 | 3.2 | 1.5 | 1.1 | 6.2 | 6.0 | Nd | Nd |
| 257 | 23.9 | 16.7 | 1.7 | 1.5 | 1.8 | 5.9 | 4.0 | Nd | Nd |
| 258 | 28.3 | 19.7 | 3.2 | 1.4 | 1.4 | 3.7 | 4.0 | Nd | Nd |

TABLE 33

$^{13}$C NMR Branching Analysis for THA Copolymers

| Ex. | Total Me | Me | Et | Pr | Bu | Hex+ & eoc | Am+ & eoc | Bu+ & eoc | Me$_{sBu}$ (%) | Me$_{sBu}$ (%) |
|---|---|---|---|---|---|---|---|---|---|---|
| 184 | 34.0 | 22.7 | 3.2 | 2.3 | 1.8 | 3.7 | 4.1 | 5.8 | 3.3 | 15.7 |

TABLE 34

Effect of Counterion on Ethylene/EGPEA Copolymerizations Using Cmpd 45 (0.02 mmol Cmpd, 6.9 MPa E, 100° C., 18 h, 9 mL TCB, 1 mL EGPEA, 20 equiv B(C$_6$F$_5$)$_3$)

| Ex. | Counterion | Yield g | Acrylate Incorp. mol % | M.W. | Total Me |
|---|---|---|---|---|---|
| 226 | [B[3,5-C$_6$H$_3$—(CF$_3$)$_2$]$_4$]$^-$ | 7.55 | 0.7 | M$_p$ = 24,874; M$_w$ = 27,982; M$_n$ = 11,277; PDI = 2.48 | 46.4 |
| 227 | [B(C$_6$F$_5$)$_4$]$^-$ | 5.41 | 0.9 | M$_p$ = 18,648; M$_w$ = 20,469; M$_n$ = 8,130; PDI = 2.52 | 44.3 |

TABLE 35

Effect of Solvent on Ethylene/EGPEA Copolymerizations Using Cmpd 45 (0.02 mmol Cmpd, 6.9 MPa E, 100° C., 18 h, 9 mL Solvent, 1 mL EGPEA, 20 equiv B(C$_6$F$_5$)$_3$)

| Ex. | Solvent | Yield g | Acrylate Incorp. mol % | M.W. | Total Me |
|---|---|---|---|---|---|
| 228 | TCB | 7.55 | 0.7 | M$_p$ = 24,874; M$_w$ = 27,982; M$_n$ = 11,277; PDI = 2.48 | 46.4 |
| 229 | p-Xylene | 11.32 | 0.6 | M$_p$ = 21,849; M$_w$ = 21,579; M$_n$ = 9,271; PDI = 2.33 | 52.7 |
| 230 | 2,2,4-Trimethylpentane | 2.04 | 1.6 | M$_p$ = 12,625; M$_w$ = 13,906; M$_n$ = 5,591; PDI = 2.74 | 44.3 |
| 231 | FC-75 | 1.04 | 5.4 | M$_p$ = 1,837; M$_w$ = 3,468; M$_n$ = 1,265; PDI = 2.74 | 18.7 |

TABLE 36

Effect of B(C$_6$F$_5$)$_3$ and NaBAF Concentrations on Ethylene/EGPEA Copolymerizations Using Cmpd 45 (0.02 mmol Cmpd, 6.9 MPa E, 100° C., 18 h, 8 mL TCB, 2 mL of EGPEA)

| Ex. | B(C$_6$F$_5$)$_3$ equiv | NaBAF equiv | Yield g | Acrylate Incorp. mol % | M.W. | Total Me |
|---|---|---|---|---|---|---|
| 232 | 40 | 20 | 7.53 | 1.2 | M$_p$ = 16,054; M$_w$ = 19,338; M$_n$ = 8,066; PDI = 2.40 | 38.6 |
| 233 | 40 | 10 | 5.38 | 1.3 | M$_p$ = 17,925; M$_w$ = 18,882; M$_n$ = 8,495; PDI = 2.22 | 27.5 |
| 234 | 20 | 10 | 7.01 | 1.5 | M$_p$ = 17,546; M$_w$ = 18,485; M$_n$ = 7,769; PDI = 2.38 | 29.6 |
| 235 | 20 | 10 | 6.29 | 1.2 | M$_p$ = 14,365; M$_w$ = 16,722; M$_n$ = 6,646; PDI = 2.52 | 29.5 |
| 236[a] | 20 | 10 | 4.69 | 1.3 | M$_p$ = 16,912; M$_w$ = 18,207; M$_n$ = 7,126; PDI = 2.57 | 33.6 |

[a]250 ppm phenothiazine was added to the acrylate; For entries 1–4, the acrylate contained 250 ppm 1,4-benzoquinone.

TABLE 37

Effect of Solvent on Ethylene/Acrylate Copolymerizations Using
Cmpd 45 (0.02 mmol Cmpd, 6.9 MPa, 100° C., 18 h, 8 mL Solvent, 2 mL of EGPEA)

| Ex. | Solvent | $B(C_6F_5)_3$ equiv | NaBAF equiv | Yield g | Acrylate Incorp. mol % | M.W. | Total Me |
|---|---|---|---|---|---|---|---|
| 237 | TCB | 40 | 20 | 7.53 | 1.2 | $M_p$ = 16,054; $M_w$ = 19,338; $M_n$ = 8,066; PDI = 2.40 | 38.6 |
| 238 | TCB | 20 | 10 | 7.01 | 1.5 | $M_p$ = 17,546; $M_w$ = 18,485; M = 7,769; PDI = 2.38 | 29.6 |
| 239 | Toluene | 40 | 20 | 6.05 | 1.0 | $M_p$ = 14,852; $M_w$ = 16,995; $M_n$ = 7,853; PDI = 2.16 | 48.2 |
| 240 | 2,2,4-Tri-methyl-pentane | 40 | 20 | 1.51 | 1.7 | $M_p$ = 6,633; $M_w$ = 7,942; $M_n$ = 4,157; PDI = 1.91 | 41.8 |
| 241 | 2,2,4-Tri-methyl-pentane | 40 | 20 | 2.09 | 1.3 | $M_p$ = 12,923; $M_w$ = 16,462; $M_n$ = 6,313; PDI = 2.61 | 42.7 |
| 242 | Chloro-benzene | 20 | 10 | 9.16 | 1.0 | $M_p$ = 16,417; $M_w$ = 18,316; $M_n$ = 7,496; PDI = 2.44 | 33.3 |
| 243 | p-Xylene | 20 | 10 | 7.46 | 1.0 | $M_p$ = 16,975; $M_w$ = 18,211; $M_n$ = 7,246; PDI = 1.84 | 33.1 |

TABLE 38

Effect of Acrylate Concentration, Acrylate Structure and
Temperature on Ethylene/Acrylate Copolymerizations (0.02 mmol Cmpd,
6.9 MPa E, 18 h, 10 mL Total of TCB + Acrylate, 20 equiv $B(C_6F_5)_3$)

| Ex. | Cmpd | Acrylate mL | Temp ° C. | Yield g | Acrylate Incorp. mol % | M.W. | Total Me |
|---|---|---|---|---|---|---|---|
| 244 | 45 | EGPEA 1 | 100 | 7.55 | 0.7 | $M_p$ = 24,874; $M_w$ = 27,982; $M_n$ = 11,277; PDI = 2.48 | 46.4 |
| 245 | 45 | EGPEA 1 | 80 | 2.20 | 0.6 | $M_p$ = 38,136; $M_w$ = 39,514; $M_n$ = 20,849; PDI = 1.90 | 49.6 |
| 246 | 45 | EGPEA 0.5 | 80 | 5.41 | 0.4 | $M_p$ = 45,864; $M_w$ = 45,281; $M_n$ = 23,339; PDI = 1.94 | 81.7 |
| 247 | 45 | HA 1 | 100 | 5.68 | 0.66 ($^{13}$C) | $M_p$ = 22,173; $M_w$ = 21,451; $M_n$ = 9,298; PDI = 2.31 | 32.8 ($^{13}$C) |
| 248 | 45 | HA 1 | 80 | 1.65 | 1.0 | $M_p$ = 27,677; $M_w$ = 29,086; $M_n$ = 12,715; PDI = 2.29 | 26.3 |
| 249 | 47 | EGPEA 1 | 80 | 0.08 | 0.8 | $M_p$ = 17,915; $M_w$ = 17,005; $M_n$ = 6,567; PDI = | 51.4 |
| 250 | 45 | MA 0.25 | 100–135 | 10.58 | 0.31 ($^{13}$C) | $M_p$ = 28,080; $M_w$ = 21,336; $M_n$ = 4,233; PDI = 5.04 | 52.1 |
| 251 | 45 | MA 0.5 | 100–135 | 8.36 | 0.51 ($^{13}$C) | $M_p$ = 20,078; $M_w$ = 17,262; $M_n$ = 3,831; PDI = 4.51 | 62.1 |
| 252 | 47 | MA 0.25 | 100–135 | 3.61 | 0.57 ($^{13}$C) | $M_p$ = 4,716; $M_w$ = 6,741; $M_n$ = 1,796; PDI = 3.75 | 65.1 |
| 253 | 47 | MA 0.5 | 100–135 | 1.90 | 0.61 ($^{13}$C) | Dual UV/RI UV: $M_p$ = 3,803; $M_w$ = 5,095; $M_n$ = 1,350; PDI = 3.77; RI: $M_p$ = 5,237; $M_w$ = 6,717; $M_n$ = 3,805; PDI = 2.39 | 78.8 |
| 254 | 57 | MA 0.25 | 100–135 | 4.22 | 0.37 ($^{13}$C) | $M_p$ = 8,697; $M_w$ = 14,347; $M_n$ = 3,656; PDI = 3.92 | 61.5 |

10 equiv of NaBAF was added to Ex. 255 below and 20 equiv of NaBAF were added to entries 256–261 below.

| Ex. | Cmpd | Acrylate mL | Temp ° C. | Yield g | Acrylate Incorp. mol % | M.W. | Total Me |
|---|---|---|---|---|---|---|---|
| 255 | 45 | MA 0.5 | 100 | 4.28 | 1.09 ($^{13}$C) | $M_p$ = 13,677; $M_w$ = 15,046; $M_n$ = 7,270; PDI = 2.07 | 35.7 |
| 256 | 45 | MA 0.5 | 100 | 9.36 | 0.53 ($^{13}$C) | $M_p$ = 16,828; $M_w$ = 17,679; $M_n$ = 7,546; PDI = 2.34 | 43.7 |
| 257 | 45 | HA 2 | 100 | 1.07 | 1.20 ($^{13}$C) | $M_p$ = 8,501; $M_w$ = 9,737; $M_n$ = 4,703; PDI = 2.07 | 23.9 |
| 258 | 45 | HA 1 | 100 | 4.76 | 0.53 ($^{13}$C) | $M_p$ = 16,421; $M_w$ = 17,244; $M_n$ = 7,900; PDI = 2.18 | 28.3 |
| 259 | 45 | EGPEA 2 | 135 | 1.20 | 1.1 | $M_p$ = 7,174; $M_w$ = 8,652; $M_n$ = 3,719; PDI = 2.33 | 74.9 |
| 260 | 45 | EGPEA 2 | 130 | 5.59 | 1.2 | $M_p$ = 9,545; $M_w$ = 10,772; $M_n$ = 4,927; PDI = 2.19 | 58.2 |

TABLE 38-continued

Effect of Acrylate Concentration, Acrylate Structure and Temperature on Ethylene/Acrylate Copolymerizations (0.02 mmol Cmpd, 6.9 MPa E, 18 h, 10 mL Total of TCB + Acrylate, 20 equiv $B(C_6F_5)_3$)

| Ex. | Cmpd | Acrylate mL | Temp °C. | Yield g | Acrylate Incorp. mol % | M.W. | Total Me |
|---|---|---|---|---|---|---|---|
| 261 | 45 | EGPEA 2 | 120 | 7.01 | 1.5 | $M_p = 17{,}546$; $M_w = 18{,}485$; $M_n = 7{,}769$; PDI = 2.38 | 29.6 |

TABLE 39

Effect of alpha-Diimine Structure on Ethylene/EGPEA Copolymerization (0.02 mmol Cmpd, 6.9 MPa E, 100° C. 18 h, 9 mL TCB, 1 mL EGPEA, 20 equiv $B(C_6F_5)_3$)

| Ex. | Cmpd | Yield g | Acrylate Incorp. mol % | M.W. | Total Me |
|---|---|---|---|---|---|
| 262 | 55 | 7.55 | 0.7 | $M_p = 24{,}874$; $M_w = 27{,}982$; $M_n = 11{,}277$; PDI = 2.48 | 46.4 |
| 263 | 68 | 0.32 | 0.5 | $M_p = 13{,}743$; $M_w = 18{,}058$; $M_n = 5{,}435$; PDI = 3.32 | 60.3 |
| 264 | 69 | 1.48 | 0.3 | $M_p = 838$; $M_w = 1{,}731$; $M_n = 796$; PDI = 2.17 | 57.5 |

TABLE 40

Effect of alpha-Diimine Structure on Ethylene/Acrylate Co-polymerizations (0.02 mmol Cmpd, 6.9 MPa E, 18 h, 8 mL TCB, 2 mL of EGPEA)

| Ex. | Cmpd | Temp (° C.) | $B(C_6F_5)_3$ (equiv) | NaBAF (equiv) | Yield (g) | Acrylate Incorp. (mol %) | M.W. | Total Me |
|---|---|---|---|---|---|---|---|---|
| 265 | 45 | 100 | 40 | 20 | 7.53 | 1.2 | $M_p = 16{,}054$; $M_w = 19{,}338$; $M_n = 8{,}066$; PDI = 2.40 | 38.6 |
| 266 | 76 | 100 | 40 | 20 | 4.22 | 1.0 | $M_p = 24{,}124$; $M_w = 27{,}307$; $M_n = 14{,}435$; PDI = 1.89 | 31.4 |
| 267 | 75 | 100 | 40 | 20 | 5.68 | 1.2 | $M_p = 14{,}987$; $M_w = 16{,}393$; $M_n = 6{,}919$; PDI = 2.37 | 79.2 |
| 268 | 74 | 100 | 40 | 20 | 3.42 | 0.6 | $M_p = 31{,}607$; $M_w = 34{,}104$; $M_n = 17{,}087$; PDI = 2.00 | 41.2 |
| 269 | 77 | 100 | 40 | 20 | 0.025 | 1.9 | $M_n(^1H)$: No olefins detected | 33.5 |
| 270 | 45 | 135 | 20 | 10 | 1.20 | 1.1 | $M_p = 7{,}174$; $M_w = 8{,}652$; $M_n = 3{,}719$; PDI = 2.33 | 74.9 |
| 271 | 64 | 135 | 20 | 10 | 1.05 | 0.5 | $M_p = 25{,}027$; $M_w = 30{,}553$; $M_n = 12{,}666$; PDI = 2.41 | 111.4 |
| 272 | 45 | 135 | 20 | 10 | 2.55 | 1.0 | $M_p = 6{,}743$; $M_w = 8{,}241$; $M_n = 887$; PDI = 9.29 | 85.8 |

TABLE 41

Effect of Borone Concentration and Inhibitor on Ethylene/EGPEA Copolymerizations (0.02 mmol Cmpd 45, 6.9 MPa E, 120° C., 18 h, 6 mL TCB, 4 mL EGPEA)

| Ex. | $B(C_6F_5)_3$ equiv | Inhibitor | Yield g | Acrylate Incorp. mol % | % Ester in Copolymer[a] | M.W. | Total Me |
|---|---|---|---|---|---|---|---|
| 273 | 40 | None | 5.37 | 2.70($^{13}$C) | 12% | $M_p = 6{,}623$; $M_w = 9{,}878$; | 42.6 ($^{13}$C) |

TABLE 41-continued

Effect of Borone Concentration and Inhibitor on Ethylene/EGPEA Copolymerizations (0.02 mmol Cmpd 45, 6.9 MPa E, 120° C., 18 h, 6 mL TCB, 4 mL EGPEA)

| Ex. | $B(C_6F_5)_3$ equiv | Inhibitor | Yield g | Acrylate Incorp. mol % | % Ester in Copolymer[a] | M.W. | Total Me |
|---|---|---|---|---|---|---|---|
| 274 | 20 | NaBAF 20 equiv | 3.02 | 2.2 | 20% | $M_n$ = 3,388; PDI = 2.92 $M_p$ = 12,928; $M_w$ = 13,956; $M_n$ = 5,371; PDI = 2.60 | 28.4 |
| 275 | 20 | BQ 250 ppm | 2.59 | 2.6 | 16% | $M_p$ = 8,739; $M_w$ = 10,424; $M_n$ = 3,480; PDI = 3.00 | 27.5 |
| 276 | 20 | NaBAF 20 equiv BQ 250 ppm | 3.07 | 2.4 | 23% | $M_p$ = 11,454; $M_w$ = 12,303; $M_n$ = 4,114; PDI = | 29.9 |

[a]The percent of the ester groups in the $^1$H NMR spectrum of the isolated polymer sample that belong to copolymer. Due to the high acrylate concentration, the isolated polymers all contained some homopolymer. The EGPEA used contained 100 ppm hydroquinone in addition to the NaBAF and 1,4-benzoquinone (BQ) inhibitors that were added to the individual runs.

TABLE 42

Steric Effects on Ethylene/MA Copolymerizations Utilizing Long Reaction Times (90 h) and Low Catalyst Concentrations (0.019 mmol Cmpd), (211 equiv $B(C_6F_5)_3$ and 105 equiv NaBAF were used. Mole % incorp. and total Me determined by $^{13}$C NMR spectroscopy.)

| Ex | Cmpd | MA mL (p-Xylene mL) | Press MPa | Temp ° C. | Yield g | Acrylate Incorp mol % | M.W. | Total Me |
|---|---|---|---|---|---|---|---|---|
| 277 | 45 | 0.5 (9.5) | 3.5 | 120 | 0.892 | 1.33 | $M_p$ = 6,812; $M_w$ = 7,201; $M_n$ = 3,410; PDI = 2.05 | 72.5 |
| 278 | 76 | 0.5 (9.5) | 3.5 | 120 | 0.937 | 1.02 | $M_p$ = 7,911; $M_w$ = 8,993; $M_n$ = 4,499; PDI = 2.00 | 82.7 |
| 279 | 74 | 0.5 (9.5) | 3.5 | 120 | 0.840 | 0.93 | $M_p$ = 8,726; $M_w$ = 9,799; $M_n$ = 4,511; PDI = 2.00 | 94.9 |
| 280 | 64 | 0.5 (9.5) | 3.5 | 120 | 0.106 | nd | $M_p$ = 13,521; $M_w$ = 14,744; $M_n$ = 6,125; PDI = 2.41 | nd |
| 281 | 45 | 1.0 (14.0) | 3.5 | 120 | 0.007 | nd | nd | nd |
| 282 | 45 | 0.5 (9.5) | 6.9 | 120 | 3.340 | 0.82 | $M_p$ = 12,403; $M_w$ = 13,853; $M_n$ = 5,681; PDI = 2.44 | 50.4 |
| 283 | 76 | 0.5 (9.5) | 6.9 | 120 | 4.221 | 0.48 | $M_p$ = 20,376; $M_w$ = 20,960; $M_n$ = 9,659; PDI = 2.17 | 58.1 |
| 284 | 74 | 0.5 (9.5) | 6.9 | 120 | 5.424 | 0.43 | $M_p$ = 28,364; $M_w$ = 30,997; $M_n$ = 12,568; PDI = 2.47 | 68.5 |
| 285 | 64 | 0.5 (9.5) | 6.9 | 120 | 0.95 | 0.30 | $M_p$ = 47,858; $M_w$ = 47,408; $M_n$ = 20,796; PDI = 2.28 | 97.2 |
| 286 | 45 | 1.0 (14.0) | 6.9 | 120 | 2.518 | 0.97 | $M_p$ = 13,043; $M_w$ = 14,076; $M_n$ = 5,931; PDI = 2.37 | 46.3 |
| 287 | 45 | 0.5 (9.5) | 6.9 | 100 | 3.865 | 0.62 | $M_p$ = 23,142; $M_w$ = 24,270; $M_n$ = 10,544; PDI = 2.30 | 30.9 |
| 288 | 76 | 0.5 (9.5) | 6.9 | 100 | 3.720 | 0.45 | $M_p$ = 34,987; $M_w$ = 36,412; $M_n$ = 16,929; PDI = 2.15 | 37.4 |
| 289 | 74 | 0.5 (9.5) | 6.9 | 100 | 4.041 | 0.51 | $M_p$ = 53,630; $M_w$ = 50,877; $M_n$ = 24,819; PDI = 2.05 | 48.0 |
| 290 | 64 | 0.5 (9.5) | 6.9 | 100 | 0.860 | 0.50 | $M_p$ = 64,690; $M_w$ = 60,660; $M_n$ = 31,328; PDI = 1.94 | 78.1 |
| 291 | 45 | 1.0 (14.0) | 6.9 | 100 | 1.631 | 0.83 | $M_p$ = 17,935; $M_w$ = 17,277; $M_n$ = 7,070; PDI = 2.44 | 35.7 |

TABLE 43

$^{13}$C NMR Branching Analysis for MA Copolymers of Table 42

| Ex. | Total Me | Me | Et | Pr | Bu | Hex+ & eoc | Am+ & eoc | Bu+ & eoc |
|---|---|---|---|---|---|---|---|---|
| 277 | 72.5 | 42.6 | 10.0 | 3.8 | 3.9 | 7.1 | 13.1 | 16.2 |
|  |  | 58.7% | 13.8% | 5.2% | 5.4% | 9.8% | 18.1% | 22.4% |
| 278 | 82.7 | 48.9 | 10.3 | 4.4 | 4.2 | 10.3 | 15.0 | 19.2 |
|  |  | 59.1% | 12.5% | 5.3% | 5.0% | 12.5% | 18.2% | 23.2% |
| 279 | 94.9 | 54.5 | 13.4 | 5.2 | 5.3 | 12.7 | 17.0 | 21.8 |
|  |  | 57.5% | 14.1% | 5.5% | 5.6% | 13.4% | 18.0% | 22.9% |
| 282 | 50.4 | 32.0 | 5.7 | 2.6 | 2.5 | 6.7 | 8.3 | 10.0 |
|  |  | 63.6% | 11.4% | 5.2% | 5.0% | 13.3% | 16.5% | 19.8% |
| 283 | 58.1 | 37.5 | 6.6 | 3.0 | 2.7 | 6.3 | 8.8 | 11.1 |
|  |  | 64.5% | 11.3% | 5.1% | 4.7% | 10.8% | 15.1% | 19.1% |
| 284 | 68.5 | 44.4 | 6.9 | 3.5 | 3.3 | 7.1 | 10.1 | 13.6 |
|  |  | 64.8% | 10.1% | 5.1% | 4.8% | 10.4% | 14.7% | 19.9% |
| 285 | 97.2 | 65.4 | 10.0 | 4.1 | 4.1 | 9.4 | 13.3 | 17.8 |
|  |  | 67.3% | 10.3% | 4.2% | 4.2% | 4.6% | 13.7% | 18.3% |
| 286 | 46.3 | 29.6 | 5.1 | 2.4 | 1.9 | 5.2 | 6.7 | 9.2 |
|  |  | 64.0% | 11.0% | 5.1% | 4.0% | 11.3% | 14.5% | 19.9% |
| 287 | 30.9 | 20.4 | 4.1 | 1.4 | 1.0 | 2.7 | 3.7 | 5.0 |
|  |  | 66.0% | 13.3% | 4.6% | 3.1% | 8.7% | 12.0% | 16.1% |
| 288 | 37.4 | 24.0 | 4.8 | 1.9 | 1.1 | 3.8 | 4.6 | 6.8 |
|  |  | 64.2% | 12.8% | 5.0% | 3.1% | 10.1% | 12.2% | 18.1% |
| 289 | 48.0 | 32.6 | 4.7 | 2.5 | 1.7 | 4.5 | 5.9 | 8.3 |
|  |  | 67.9% | 9.7% | 5.1% | 3.6% | 9.5% | 12.3% | 17.3% |
| 290 | 78.1 | 53.9 | 7.3 | 3.3 | 3.1 | 7.7 | 10.6 | 13.7 |
|  |  | 69.0% | 9.3% | 4.2% | 3.9% | 9.9% | 13.5% | 17.5% |
| 291 | 35.7 | 23.2 | 4.0 | 1.7 | 1.8 | 4.4 | 5.4 | 6.8 |
|  |  | 35.7% | 11.1% | 4.7% | 5.2% | 12.4% | 15.0% | 19.1% |

TABLE 44

Ethylene/EGPEA Copolymerizations in Chlorobenzene (18 h, 10 mL Total Volume of Chlorobenzene + EGPEA)

| Ex. | Cmpd mmol | EGPEA mL | B(C$_6$F$_5$)$_3$ equiv | NaBAF equiv | Press MPa | Temp °C. | Yield g | Acrylate Incorp mol % | M.W. | Total Me |
|---|---|---|---|---|---|---|---|---|---|---|
| 292 | 45 0.01 | 1 | 40 | 20 | 6.9 | 100 | 10.28 | 0.4 | M$_p$ = 22,374; M$_w$ = 23,126; M$_n$ = 10,630; PDI = 2.18 | 49.5 |
| 293 | 45 0.005 | 1 | 80 | 40 | 6.9 | 100 | 7.84 | 0.5 | M$_p$ = 26,320; M$_w$ = 26,956; M$_n$ = 12,371; PDI = 2.18 | 82.7 |
| 294 | 64 0.005 | 1 | 80 | 40 | 6.9 | 100 | 1.85 | 0.4 | M$_p$ = 83,096; M$_w$ = 81,919; M$_n$ = 39,427; PDI = 2.08 | 71.5 |
| 295 | 55 0.005 | 1 | 80 | 40 | 6.9 | 100 | 1.87 | 0.7 | M$_p$ = 22,984; M$_w$ = 24,347; M$_n$ = 12,365; PDI = 1.97 | 41.3 |
| 296 | 45 0.01 | 1 | 40 | 20 | 3.5 | 120 | 5.59 | 0.6 | M$_p$ = 9,544; M$_w$ = 10,892; M$_n$ = 4,896; PDI = 1.97 | 73.5 |
| 297 | 64 0.01 | 1 | 40 | 20 | 3.5 | 120 | 0.78 | 0.4 | M$_p$ = 26,286; M$_w$ = 26,534; M$_n$ = 13,114; PDI = 2.02 | 134.2 |
| 298 | 55 0.01 | 1 | 40 | 20 | 3.5 | 120 | 1.97 |  | M$_p$ = 7,250; M$_w$ = 8,005; M$_n$ = 3,348; PDI = 2.39 |  |
| 299 | 45 0.01 | 1 | 40 | 20 | 6.9 | 120 | 12.49 | 0.6 | M$_p$ = 14,470; M$_w$ = 15,044; M$_n$ = 6,519; PDI = 2.31 | 70.6 |
| 300 | 45 0.01 | 2 | 40 | 20 | 6.9 | 120 | 6.01 | 1.5 | M$_p$ = 11,778; M$_w$ = 12,804; M$_n$ = 5,707; PDI = 2.24 | 61.2 |
| 301 | 45 0.01 | 3 | 40 | 20 | 6.9 | 120 | 4.14 | 2.4 | M$_p$ = 7,806; M$_w$ = 10,643; M$_n$ = 4,312; PDI = 2.47 | 48.6 |
| 302 | 45 0.005 | 1 | 80 | 40 | 6.9 | 120 | 7.29 | 0.6 | M$_p$ = 11,733; M$_w$ = 13,519; M$_n$ = 5,644; PDI = 2.40 | 67.2 |
| 303 | 45 0.005 | 2 | 80 | 40 | 6.9 | 120 | 5.07 | 1.4 | M$_p$ = 9,852; M$_w$ = 11,599; M$_n$ = 4,755; PDI = 2.44 | 67.1 |
| 304 | 78 0.02 | 2 | 20 | 10 | 6.9 | 120 | 0.96 | 1.4[a] | M$_p$ = 30,063; M$_w$ = 25,126; M$_n$ = 7,262; PDI = 3.46 | 28.0 |
| 305 | 78 0.02 | 4 | 20 | 10 | 6.9 | 120 | 1.06 | 1.1[a] | M$_p$ = 4,852; M$_w$ = 6,734; M$_n$ = 2,384; PDI = 2.82 | 12.5 |
| 306 | 45 0.005 | 1 | 80 | 40 | 3.5 | 120 | 2.64 | 0.8 | M$_p$ = 10,797; M$_w$ = 11,715; M$_n$ = 5,047; PDI = 2.32 | 66.8 |
| 307 | 45 0.005 | 2 | 80 | 40 | 3.5 | 120 | 2.95 | 1.9 | M$_p$ = 8,636; M$_w$ = 9,312; M$_n$ = 4,496; PDI = 2.07 | 67.6 |
| 308 | 45 0.01 | 2 | 40 | 20 | 3.5 | 120 | 2.96 | 1.2 | M$_p$ = 7,616; M$_w$ = 8,630; M$_n$ = 3,709; PDI = 2.33 | 66.3 |
| 309 | 45 0.01 | 3 | 40 | 20 | 3.5 | 120 | 2.70 | 1.9 | M$_p$ = 5,039; M$_w$ = 7,443; M$_n$ = 2,709; PDI = 2.75 | 59.0 |
| 310 | 45 0.0025 | 1 | 160 | 80 | 3.5 | 120 | 1.59 | 0.9 | M$_p$ = 7,737; M$_w$ = 8,732; M$_n$ = 4,051; PDI = 2.16 | 73.0 |
| 311 | 45 0.0025 | 1 | 160 | 80 | 6.9 | 100 | 2.52 | 0.8 | M$_p$ = 25,609; M$_w$ = 25,456; M$_n$ = 11,960; PDI = 2.13 | 27.5 |
| 312 | 45 0.0025 | 2 | 160 | 80 | 6.9 | 100 | 2.02 | 2.1 | M$_p$ = 20,773; M$_w$ = 21,386; M$_n$ = 10,385; PDI = 2.06 | 22.1 |
| 313 | 45 0.0025 | 0.5 | 160 | 80 | 6.9 | 100 | 5.85 | trace | M$_p$ = 23,609; M$_w$ = 25,970; M$_n$ = 12,143; PDI = 2.14 | nd |
| 314 | 45 0.00125 | 1 | 160 | 80 | 6.9 | 100 | 1.67 | 1.0 | M$_p$ = 22,495; M$_w$ = 23,371; M$_n$ = 11,316; PDI = 2.07 | 27.4 |
| 315 | 45 0.00125 | 1 | 160 | 80 | 6.9 | 120 | 2.96 | 0.9 | M$_p$ = 12,729; M$_w$ = 13,757; M$_n$ = 6,189; PDI = 2.22 | 68.2 |
| 316 | 45 0.0025 | 0.5 | 160 | 80 | 6.9 | 120 | 7.27 | 0.4 | M$_p$ = 13,244; M$_w$ = 15,491; M$_n$ = 6,318; PDI = 2.45 | 70.8 |
| 317 | 45 0.0025 | 2 | 160 | 80 | 6.9 | 120 | 3.22 | 1.5 | M$_p$ = 12,047; M$_w$ = 13,044; M$_n$ = 6,043; PDI = 2.16 | 55.6 |
| 318 | 45 0.0025 | 1 | 160 | 80 | 6.9 | 120 | 5.02 | 0.7 | M$_p$ = 12,942; M$_w$ = 13,493; M$_n$ = 6,073; PDI = 2.22 | 58.7 |

[a]Due to the high homopolymer content of the polymer sample, the reported percent acrylate incorporation in the copolymer is an approximation.

TABLE 45

Ethylene/EGPEA Copolymerizations in TCB: Variation of Catalyst Concentration and Structure, and Temperature (6.9 MPa E, 18 h, 10 mL Total Volume of TCB + EGPEA)

| Ex. | Cmpd mmol | EGPEA mL | $B(C_6F_5)_3$ equiv | NaBaF Equiv | Temp °C. | Yield g | Acrylate Incorp mol % | M.W. | Total Me |
|---|---|---|---|---|---|---|---|---|---|
| 319 | 45 0.01 | 1 | 40 | 20 | 140 | 3.01 | 0.5 | $M_p = 7{,}507$; $M_w = 8{,}668$; $M_n = 3{,}753$; PDI = 2.31 | 87.5 |
| 320 | 45 0.01 | 2 | 40 | 20 | 140 | 2.43 | 1.6 | $M_p = 6{,}568$; $M_w = 7{,}865$; $M_n = 3{,}535$; PDI = 2.22 | 80.8 |
| 321 | 45 0.005 | 1 | 80 | 40 | 140 | 2.41 | 0.7 | $M_p = 7{,}192$; $M_w = 8{,}650$; $M_n = 3{,}909$; PDI = 2.21 | 88.7 |
| 322 | 45 0.005 | 2 | 80 | 40 | 140 | 1.66 | 1.6 | $M_p = 6{,}197$; $M_w = 7{,}988$; $M_n = 3{,}234$; PDI = 2.47 | 82.0 |
| 323 | 45 0.0025 | 1 | 160 | 80 | 140 | 4.54 | 0.7 | $M_p = 7{,}443$; $M_w = 8{,}725$; $M_n = 3{,}328$; PDI = 2.62 | 91.6 |
| 324 | 96 0.02 | 1 | 20 | 10 | 120 | 2.14 | 1.2 | $M_p = 9{,}128$; $M_w = 12{,}153$; $M_n = 5{,}089$; PDI = 2.39 | 120.9 |
| 325 | 97 0.02 | 1 | 20 | 10 | 120 | 1.79 | 0.6 | $M_p = 56{,}495$; $M_w = 56{,}319$; $M_n = 25{,}240$; PDI = 2.23 | 18.0 |

TABLE 46

Ethylene/MA Copolymerizations: Variation of Temperature (0.0025 mmol Cmpd, 160 equiv $B(C_6F_5)_3$, 80 equiv NaBAF, 6.9 MPa E, 18 h, 0.5 mL MA, 9.5 mL Chlorobenzene)

| Ex | Cmpd | Temp °C. | Yield g | Acrylate Incorp Mol % | M.W. | Total Me |
|---|---|---|---|---|---|---|
| 326 | 45 | 100 | 2.90 | 0.53 ($^{13}$C) | $M_p = 17{,}308$; $M_w = 18{,}706$; $M_n = 9{,}144$; PDI = 2.05 | 31.8 |
| 327 | 45 | 120 | 2.59 | 0.45 ($^{13}$C) | $M_p = 9{,}967$; $M_w = 10{,}394$; $M_n = 4{,}713$; PDI = 2.21 | 51.8 |

TABLE 47

$^{13}$C NMR Branching Analysis for MA and HA Copolymers of Tables 46, 49 and 50

| Ex. | Total Me | Me | Et | Pr | Bu | Hex+ & eoc | Am+ & eoc | Bu+ & eoc |
|---|---|---|---|---|---|---|---|---|
| 326 | 31.8 | 21.3 | 3.6 | 1.6 | 1.6 | 2.9 | 4.7 | 5.3 |
| 327 | 51.8 | 31.6 | 5.8 | 13.1 | 2.6 | 4.8 | 8.9 | 11.2 |
| 346 | 71.7 | 45.2 | 7.6 | 3.7 | 3.4 | 6.2 | 11.0 | 15.2 |
| 347 | 71.8 | 45.9 | 7.8 | 3.8 | 3.8 | 6.5 | 11.1 | 14.4 |
| 354 | 48.6 | 29.7 | 6.1 | 2.9 | 2.6 | 3.7 | 6.9 | 9.9 |
| 364 | 58.5 | 36.5 | 7.8 | 2.7 | 2.8 |  | 9.6 | 11.6 |
| 366 | 60.2 | 36.0 | 7.9 | 3.4 | 2.6 | 5.7 | 9.5 | 12.8 |
| 383 | 31.1 | 22.0 | 3.5 | 1.2 | 1.6 | 2.8 | 4.0 | 4.5 |
| 384 | 28.5 | 19.1 | 2.6 | 1.6 | 1.4 | 2.0 | 4.4 | 5.3 |
| 388 | 98.6 | 68.1 | 12.2 | 2.5 | 2.8 | 11.2 | 12.1 | 15.8 |

TABLE 48

Ethylene/EGPEA Copolymerizations: Variation of Catalyst Structure and Cocatalyst Concentration (18 h, 6.9 MPa E, 120° C., 0.5 mL EGPEA)

| Ex. | Cmpd mmol | Solvent mL | $B(C_6F_5)_3$ equiv | NaBAF Equiv | Yield g | Acrylate Incorp mol % | M.W. | Total Me |
|---|---|---|---|---|---|---|---|---|
| 328 | 45 0.00125 | CB 9.5 | 320 | 160 | 1.80 | 0.4 | $M_p = 13,525$; $M_w = 13,741$; $M_n = 6,126$; PDI = 2.24 | 59.8 |
| 329 | 45 0.00125 | CB 9.5 | 640 | 160 | 3.72 | 0.3 | $M_p = 11,892$; $M_w = 13,222$; $M_n = 6,184$; PDI = 2.14 | 61.6 |
| 330 | 45 0.00125 | CB 9.5 | 1600 | 160 | 2.90 | 0.4 | $M_p = 11,920$; $M_w = 12,850$; $M_n = 6,419$; PDI = 2.00 | 65.3 |
| 331 | 45 0.00125 | CB 9.5 | 320 | 320 | 3.05 | 0.3 | $M_p = 12,013$; $M_w = 12,568$; $M_n = 5,783$; PDI = 2.17 | 66.8 |
| 332 | 45 0.00125 | Toluene 9.5 | 320 | 160 | 3.52 | 0.3 | $M_p = 10,810$; $M_w = 12,116$; $M_n = 5,518$; PDI = 2.20 | 65.4 |
| 333 | 45 0.00125 | CB 4.5 | 320 | 160 | 1.47 | 0.7 | $M_p = 13,399$; $M_w = 14,553$; $M_n = 7,141$; PDI = 2.04 | 53.4 |
| 334 | 61 0.0025 | CB 9.5 | 320 | 160 | 1.70 | 0.4 | $M_p = 6,206$; $M_w = 7,385$; $M_n = 3,287$; PDI = 2.25 | 65.7 |
| 335 | 57 0.0025 | CB 9.5 | 320 | 160 | 0.76 | 0.3 | $M_p = 15,079$; $M_w = 15,975$; $M_n = 8,241$; PDI = 1.94 | 68.5 |
| 336 | 74 0.0025 | CB 9.5 | 320 | 160 | 3.58 | 0.2 | $M_p = 29,889$; $M_w = 34,141$; $M_n = 17,674$; PDI = 1.93 | 72.6 |
| 337 | 71 0.0025 | CB 9.5 | 320 | 160 | 0.055 | 0.2 | $M_p = 13,750$; $M_w = 15,066$; $M_n = 7,535$; PDI = 2.00 | 91.2 |

TABLE 49

Ethylene/Acrylate Copolymerizations: Variation of Catalyst Structure, Catalyst and Cocatalyst Concentration (18 h, 6.9 MPa E, 120° C.)

| Ex. | Cmpd mmol | Solvent/mL Acrylate/mL | $B(C_6F_5)_3$ Equiv | NaBAF equiv | Yield g | Acrylate Incorp mol % | M.W. | Total Me |
|---|---|---|---|---|---|---|---|---|
| 338 | 45, 0.00125 | CB/9, EGPEA/1 | 640 | 160 | 1.79 | 0.6 | $M_p = 11,857$; $M_w = 12,974$; $M_n = 5,887$; PDI = 2.20 | 59.4 |
| 339 | 45, 0.0025 | CB/14, EGPEA/1 | 640 | 160 | 3.47 | 0.4 | $M_p = 11,853$; $M_w = 12,966$; $M_n = 5,513$; PDI = 2.35 | 64.2 |
| 340 | 45, 0.00125 | CB/14, EGPEA/1 | 640 | 160 | 2.02 | 0.5 | $M_p = 12,305$; $M_w = 12,062$; $M_n = 5,229$; PDI = 2.31 | 67.1 |
| 341 | 45, 0.00125 | CB/14, EGPEA/1 | 960 | 320 | 2.26 | 0.4 | $M_p = 11,788$; $M_w = 12,131$; $M_n = 5,524$; PDI = 2.20 | 60.9 |
| 342 | 45, 0.0025 | CB/13, EGPEA/2 | 960 | 160 | 2.54 | 0.7 | $M_p = 10,220$; $M_w = 11,156$; $M_n = 5,349$; PDI = 2.09 | 62.1 |
| 343 | 74, 0.00125 | CB/14, EGPEA/1 | 960 | 160 | 0.77 | 0.2 | $M_p = 29,720$; $M_w = 32,471$; $M_n = 17,281$; PDI = 1.88 | 66.1 |
| 344 | 74, 0.0025 | CB/13, EGPEA/2 | 960 | 160 | 1.35 | 0.5 | $M_p = 26,232$; $M_w = 27,641$; $M_n = 14,194$; PDI = 1.95 | 69.6 |
| 345 | 74, 0.00125 | Toluene/14, EGPEA/1 | 960 | 160 | 1.55 | 0.2 | $M_p = 30,222$; $M_w = 32,909$; $M_n = 18,006$; PDI = 1.83 | 69.6 |
| 346 | 74, 0.00125 | CB/14.5, MA/0.5 | 960 | 160 | 0.82 | 0.3 ($^{13}$C) | $M_p = 23,118$; $M_w = 23,916$; $M_n = 10,009$; PDI = 2.39 | 71.7 ($^{13}$C) |
| 347 | 74, 0.0025 | CB/14, MA/1 | 960 | 160 | 1.32 | 0.4 ($^{13}$C) | $M_p = 11,962$; $M_w = 13,390$; $M_n = 6,417$; PDI = 2.09 | 71.8 ($^{13}$C) |
| 348 | 45, 0.00125 | TCB/9.5, EGPEA/0.5 | 640 | 320 | 2.33 | trace | $M_p = 14,132$; $M_w = 15,668$; $M_n = 6,596$; PDI = 2.38 | nd |
| 349 | 45, 0.00125 | TCB/9, EGPEA/1 | 640 | 320 | 2.03 | 0.9 | $M_p = 11,996$; $M_w = 13,748$; $M_n = 6,235$; PDI = 2.21 | 51.9 |
| 350 | 45, 0.0019 | TCB/9.5, EGPEA/0.5 | 421 | 210 | 4.71 | 0.4 | $M_p = 13,326$; $M_w = 15,974$; $M_n = 6,186$; PDI = 2.58 | 57.4 |
| 351 | 45, 0.0019 | TCB/9, EGPEA/1 | 421 | 210 | 3.29 | 0.8 | $M_p = 11,534$; $M_w = 13,641$; $M_n = 5,635$; PDI = 2.42 | 60.2 |
| 352 | 45, 0.0019 | TCB/9.5, EGPEA/0.5 | 210 | 210 | 4.43 | 0.4 | $M_p = 12,953$; $M_w = 13,730$; $M_n = 5,116$; PDI = 2.68 | nd |
| 353 | 45, 0.0019 | p-Xylene/9.5, EGPEA/0.5 | 421 | 210 | 5.62 | 0 | $M_p = 14,910$; $M_w = 32,190$; $M_n = 8,859$; PDI = 3.63 | 71.8 |
| 354 | 45, 0.0019 | TCB/9.75, MA/0.25 | 421 | 210 | 0.81 | 0.3 ($^{13}$C) | $M_p = 11,398$; $M_w = 13,504$; $M_n = 5,827$; PDI = 2.32 | 48.6 ($^{13}$C) |
| 355 | 78, 0.01 | TCB/9, EGPEA/1 | 80 | 40 | 0.59 | Nd[a] | $M_p = 64,840$; $M_w = 57,576$; $M_n = 24,348$; PDI = 2.36 | nd |
| 356 | 78, 0.01 | TCB/9, EGPEA/1 | 80 | 40 | 0.56 | Nd[a] | $M_p = 64,496$; $M_w = 59,869$; $M_n = 30,765$; PDI = 1.95 | nd |
| 357 | 76, 0.0019 | TCB/9.5, EGPEA/0.5 | 421 | 210 | 3.95 | 0.5 | $M_p = 21,762$; $M_w = 23,924$; $M_n = 12,118$; PDI = 1.97 | 67.5 |
| 358 | 45, 0.0019 | TCB/9, EGPEA/1 | 421 | 210 | 3.74 | 0.6 | $M_p = 12,616$; $M_w = 15,891$; $M_n = 6,055$; PDI = 2.62 | 57.1 |
| 359 | 45, 0.0019 | p-Xylene/8, Butyl Ether/1 EGPEA/1 | 421 | 210 | 1.24 | 0.7 | $M_p = 8,918$; $M_w = 9,634$; $M_n = 4,250$; PDI = 2.27 | 62.8 |
| 360 | 45, 0.0019 | p-Xylene/4.5, Butyl Ether/4.5, EGPEA/1 | 421 | 210 | 0.91 | 0.8 | $M_p = 6,913$; $M_w = 8,108$; $M_n = 4,024$; PDI = 2.02 | 67.6 |
| 361 | 45, 0.0019 | Butyl Ether/9, EGPEA/1 | 421 | 210 | 0.97 | 1.0 | $M_p = 6,100$; $M_w = 6,969$; $M_n = 3,626$; PDI = 1.92 | 66.8 |
| 362 | 45, 0.00125 | p-Xylene/9, EGPEA/1 | 640 | 320 | 0.98 | 0.5 | $M_p = 21,762$; $M_w = 23,924$; $M_n = 12,118$; PDI = 1.97 | 67.5 |
| 363 | 45, 0.0019 | TCB/9, HA/1 | 421 | 210 | 0.025 | Nd | Nd | Nd |
| 364 | 45, 0.00125 | p-Xylene/9, HA/1 | 640 | 320 | 2.53 | 0.6 ($^{13}$C) | $M_p = 11,816$; $M_w = 11,804$; $M_n = 5,225$; PDI = 2.26 | 58.5 ($^{13}$C) |
| 365 | 45, 0.0019 | TCB/9.5, MA/0.5 | 421 | 210 | 0.083 | Nd | Nd | Nd |
| 366 | 45, 0.00125 | p-Xylene/9.5, MA/0.5 | 640 | 320 | 2.58 | 0.75 ($^{13}$C) | $M_p = 10,362$; $M_w = 10,505$; $M_n = 5,123$; PDI = 2.05 | 67.5 ($^{13}$C) |
| 367 | 79, 0.0019 | TCB/9, EGPEA/1 | 421 | 105 | 0.018 | Nd | Nd | Nd |
| 368 | 59, 0.0019 | TCB/9, EGPEA/1 | 421 | 105 | 0.51 | 1.1 | $M_p = 6,858$; $M_w = 7,745$; $M_n = 3,968$; PDI = 1.95 | 47.2 |

TABLE 49-continued

Ethylene/Acrylate Copolymerizations: Variation of Catalyst Structure, Catalyst and Cocatalyst Concentration (18 h, 6.9 MPa E, 120° C.)

| Ex. | Cmpd mmol | Solvent/mL Acrylate/mL | $B(C_6F_5)_3$ Equiv | NaBAF equiv | Yield g | Acrylate Incorp mol % | M.W. | Total Me |
|---|---|---|---|---|---|---|---|---|
| 369 | 80, 0.0019 | TCB/9, EGPEA/1 | 421 | 105 | 0.59 | 0.6 | $M_p$ = 11,196; $M_w$ = 14,898; $M_n$ = 6,228; PDI = 2.39 | 60.0 |
| 370 | 81, 0.0019 | TCB/9, EGPEA/1 | 421 | 105 | 0.004 | Nd | Nd | Nd |
| 371 | 45, 0.0019 | p-Xylene/9, EGPEA/1 | 421 | 105 | 3.20 | 0.6 | $M_p$ = 14,259; $M_w$ = 14,764; $M_n$ = 6,250; PDI = 2.36 | 55.6 |
| 372 | 45, 0.0019[c] | TCB/9, EGPEA/1 | 421 | 105 | 2.64 | 0.6 | $M_p$ = 13,840; $M_w$ = 15,593; $M_n$ = 7,075; PDI = 2.20 | 57.1 |
| 373 | 82, 0.0019 | TCB/9, EGPEA/1 | 421 | 105 | 0.32 | Nd | $M_p$ = 35,840; $M_w$ = 37,957; $M_n$ = 20,356; PDI = 1.86 | Nd |
| 374 | 45, 0.0019 | TCB/9, EGPEA/1 | 421 | 105 | 0.18 | 2.0 | $M_p$ = 13,679; $M_w$ = 15,497; $M_n$ = 7,382; PDI = 2.10 | 60.4 |
| 375 | 45, 0.0019 | p-Xylene/9, EGPEA/1 | 421 | 105 | 0.86 | 1.2 | $M_p$ = 6,984; $M_w$ = 8,147; $M_n$ = 3,927; PDI = 2.07 | 55.6 |
| 376 | 64, 0.002 | p-Xylene/3, EGPEA/2 | 200 | 100 | 0.25 | 4.2[b] | $M_p$ = 13,668; $M_w$ = 14,464; $M_n$ = 6,967; PDI = 2.08 | 59.4 |
| 377 | 64, 0.002 | p-Xylene/8, EGPEA/2 | 200 | 100 | 0.76 | 3.1 | $M_p$ = 25,728; $M_w$ = 26,593; $M_n$ 13,836; PDI = 1.92 | 87.2 |
| 378 | 64, 0.002 | p-Xylene/4.5, MA/0.5 | 200 | 100 | 0.52 | 2.3 ($^{13}$C) | $M_p$ = 30,000; $M_w$ = 31,999; $M_n$ = 14,434; PDI = 2.22 | 98.6 ($^{13}$C) |
| 379 | 64, 0.002 | p-Xylene/4.5, MA/0.5 | 800 | 100 | 0.68 | Nd | $M_p$ = 28,722; $M_w$ = 31,214; $M_n$ = 13,352; PDI = 2.34 | Nd |

[a]Any copolymer resonances are obscured by the homopolymer resonances.
[b]Percent acrylate incorporation in the copolymer is an estimate due to the high homopolymer content of the sample.
[c]+100 equiv MeAl((BHT)$_2$

TABLE 50

Ethylene/Acrylate Copolymerizations: Variation of Solvent and Acrylate Substituent (18 h, 6.9 MPa E, 100° C.)

| Ex. | Cmpd mmol | Solvent/mL Acrylate/mL | $B(C_6F_5)_3$ Equiv | NaBAF equiv | Yield g | Acrylate Incorp mol % | M.W. | Total Me |
|---|---|---|---|---|---|---|---|---|
| 380 | 45 0.0019 | Toluene/9 EGPEA/1 | 421 | 105 | 1.28 | 1.1 | $M_p$ = 20,773; $M_w$ = 21,618; $M_n$ = 10,131; PDI = 2.13 | 38.0 |
| 381 | 45 0.0019 | Toluene/9 HA/1 | 421 | 105 | 1.40 | 0.4 | $M_p$ = 20,340; $M_w$ = 20,560; $M_n$ = 9,573; PDI = 2.15 | 49.2 |
| 382 | 45 0.0019 | CB/9 HA/1 | 421 | 105 | 0.57 | 0.5 | $M_p$ = 18,173; $M_w$ = 18,605; $M_n$ = 8,670; PDI = 2.15 | 43.4 |
| 383 | 45 0.0019 | Toluene/9.5 MA/0.5 | 421 | 105 | 1.99 | 0.6 ($^{13}$C) | $M_p$ = 20,997; $M_w$ = 21,705; $M_n$ = 10,684; PDI = 2.03 | 31.1 ($^{13}$C) |
| 384 | 45 0.0019 | CB/9.5 MA/0.5 | 421 | 105 | 1.33 | 0.4 | $M_p$ = 13,279; $M_w$ = 15,028; $M_n$ = 7,635; PDI = = 1.97 | 28.5 |

TABLE 51

Ethylene/Hexyl Acrylate Copolymerizations: Variation of Catalyst Structure (18 h, 6.9 MPa E, 120° C., 1 mL Hexyl Acrylate, 9 mL p-Xylene)

| Ex. | Cmpd 0.005 mmol | $B(C_6F_5)_3$ equiv | $LiB(C_6F_5)_4$ equiv | Yield g | Acrylate Incorp mol % | M.W. | Total Me |
|---|---|---|---|---|---|---|---|
| 385 | 79 | 80 | 40 | 1.92 | 1.3 | $M_p$ = 20,773; $M_w$ = 21,618; $M_n$ = 10,131; PDI = 2.13 | 78.4 |
| 386 | 81 | 80 | 40 | 0.011 | Nd | Nd | Nd |
| 387 | 53 | 80 | 40 | 0.41 | 2.3 | $M_p$ = 782; $M_w$ = 1,183; $M_n$ = 409; PDI = 2.89 | 98.4 |

TABLE 52

Ethylene/EGPEA Copolymerizations: Variation of p-Substituent on the N-Aryl Ring
(0.0019 mmol Cmpd, 18 h, 6.9 MPa E, 120° C., 1 mL EGPEA, 9 mL TCB)

| Ex. | Cmpd mmol | $B(C_6F_5)_3$ equiv | $LiB(C_6F_5)_4$ equiv | Yield g | Acrylate Incorp mol % | M.W. | Total Me |
|---|---|---|---|---|---|---|---|
| 388 | 45 | 211 | 105 | 3.98 | 0.8 | $M_p$ = 14,113; $M_w$ = 16,389; $M_n$ = 6,722; PDI = 2.44 | 53.2 |
| 389 | 83 | 211 | 105 | 3.78 | 0.8 | $M_p$ = 15,156; $M_w$ = 16,926; $M_n$ = 7,557; PDI = 2.24 | 54.4 |
| 390 | 84 | 211 | 105 | 2.80 | 1.1 | $M_p$ = 14,422; $M_w$ = 15,390; $M_n$ = 6,960; PDI = 2.21 | 48.7 |

TABLE 53

Ethylene/2,2,3,3,3-Pentafluoropropyl acrylate (PPA) Copolymerizations
(0.0019 mmol Cmpd, 18 h, 10 mL Total Volume of p-Xylene + PPA, 100° C., 6.9 MPa E)

| Ex. | Cmpd | PPA mL | $B(C_6F_5)_3$ equiv | NaBAF equiv | Yield g | Acrylate Incorp mol % | M.W. | Total Me |
|---|---|---|---|---|---|---|---|---|
| 391 | 45 | 1 | 211 | 105 | 5.93 | 0.2 | $M_p$ = 25,838; $M_w$ = 26,041; $M_n$ = 10,736; PDI = 2.43 | 31.3 |
| 392 | 74 | 1 | 211 | 105 | 4.09 | 0.3 | $M_p$ = 67,066; $M_w$ = 64,176; $M_n$ = 32,073; PDI = 2.00 | 45.5 |
| 393 | 45 | 2 | 211 | 105 | 3.76 | 0.3 | $M_p$ = 22,227; $M_w$ = 22,623; $M_n$ = 10,036; PDI = 2.25 | 28.6 |
| 394 | 74 | 2 | 211 | 105 | 3.36 | 0.3 | Bimodal: $M_p$ = 56,152; $M_w$ = 49,560; $M_n$ = 18,664; PDI = 2.66 | 48.4 |

TABLE 54

Ethylene/EGPEA Copolymerizations: Variation of Catalyst Structure,
Pressure and Temperature (18 h, 1 mL EGPEA, 2 mL
p-xylene, 0.0019 mmold Cmpd, 211 equiv $B(C_6F_5)_3$, 105 equiv NaBAF)

| Ex. | Cmpd | Press MPa | Temp ° C. | Yield g | Acrylate Incorp mol % | M.W. | Total Me |
|---|---|---|---|---|---|---|---|
| 395 | 85 | 3.5 | 80 | 0.016 | trace | Nd | 39.9 |
| 396 | 86 | 3.5 | 80 | 0.437 | 0.8 0.6 IC 0.2 EG | $M_p$ = 916; $M_w$ = 1,670; $M_n$ = 739; PDI = 2.26 | 39.9 |
| 397 | 87 | 3.5 | 80 | 0.429 | 2.1 | $M_p$ = 26,665; $M_w$ = 28,284; $M_n$ = 13,707; PDI = 2.06 | 31.1 |
| 398 | 88 | 3.5 | 80 | 0.203 | 2.2 | $M_p$ = 2,832; $M_w$ = 3,358; $M_n$ = 1,754; PDI = 1.92 | 44.4 |
| 399 | 89 | 3.5 | 80 | 0 | — | — | — |
| 400 | 85 | 6.9 | 120 | 0.318 | 0.7 | $M_p$ = 327; $M_w$ = 1,150; $M_n$ = 305; PDI = 3.77 | 57.7 |
| 401 | 86 | 6.9 | 120 | 1.49 | 0.6, 0.4 IC, 0.2 EG | $M_p$ = 488; $M_w$ = 864; $M_n$ = 364; PDI = 2.37 | 82.1 |
| 402 | 87 | 6.9 | 120 | 3.14 | 0.5 | $M_p$ = 15,311; $M_w$ = 15,880; $M_n$ = 7,213; PDI = 2.20 | 65.7 |
| 403 | 88 | 6.9 | 120 | 0.565 | 1.1 | $M_p$ = 1,702; $M_w$ = 2,418; $M_n$ = 1,148; PDI = 2.11 | 95.7 |
| 404 | 89 | 6.9 | 120 | 0 | — | — | — |
| 405 | 90 | 6.9 | 120 | 1.86 | 1.3 | $M_p$ = 4,834; $M_w$ = 5,311; $M_n$ = 2,530; PDI = 2.10 | 52.5 |
| 406 | 91 | 6.9 | 120 | 0.50 | 1.6, 1.3 IC, 0.3 EG | $M_p$ = 1,382; $M_w$ = 2,217; $M_n$ = 982; PDI = 2.26 | 78.4 |
| 407 | 92 | 6.9 | 120 | 1.32 | 0.8 | $M_p$ = 22,852; $M_w$ = 24,968; $M_n$ = 12,472; PDI = 2.00 | 69.9 |
| 408 | 93 | 6.0 | 120 | 0 | — | — | — |
| 409 | 94 | 6.9 | 120 | 1.24 | 1.4 | $M_p$ = 4,172; $M_w$ = 4,579; $M_n$ = 2,254; PDI = 2.03 | 60.9 |
| 410 | 95 | 6.9 | 120 | 0 | — | — | — |
| 411 | 78 | 6.9 | 130 | 0.047 | Nd[b] | $M_p$ = 20,248; $M_w$ = 20,678; $M_n$ = 7,869; PDI = 2.63 | Nd |

TABLE 54-continued

Ethylene/EGPEA Copolymerizations: Variation of Catalyst Structure,
Pressure and Temperature (18 h, 1 mL EGPEA, 2 mL
p-xylene, 0.0019 mmold Cmpd, 211 equiv B($C_6F_5$)$_3$, 105 equiv NaBAF)

| Ex. | Cmpd | Press MPa | Temp °C. | Yield g | Acrylate Incorp mol % | M.W. | Total Me |
|---|---|---|---|---|---|---|---|
| 412 | 64 | 6.9 | 130 | 0.336 | 0.7 | $M_p$ = 31,486; $M_w$ = 32,872; $M_n$ = 14,840; PDI = 2.22 | 108.5 |
| 413 | 74 | 6.9 | 130 | 2.87 | 1.0, 0.7 IC, 0.3 EG | $M_p$ = 19,881; $M_w$ = 20,567; $M_n$ = 8,185; PDI = 2.51 | 97.0 |

[a]Predominant alpha olefin end groups; some internal olefin end groups also present.
[b]Diagnostic $^1$H NMR copolymer resonances, if present, are obscured by homopolymer resonances.

TABLE 55

Ethylene/EGPEA Copolymerizations: Variation of Catalyst Structure,
Cocatalyst Concentration, and Borate Counterion and Structure
(0.0019 mmol Cmpd, 18 h, 2 mL EGPEA, 8 mL p-Xylene, 100° C., 6.9 MPa E)

| Ex. | Cmpd | B($C_6F_5$)$_3$ equiv | Borate 105 equiv | Yield G | Acrylate Incorp mol % | M.W. | Total Me |
|---|---|---|---|---|---|---|---|
| 414 | 74 | 211 | NaBAF | 0.746 | 3.4[a] | $M_p$ = 28,528; $M_w$ = 29,829; $M_n$ = 11,409; PDI = 2.61 | 32.1 |
| 415 | 74 | 211 | LiBArF | 0.647 | 1.9 | $M_p$ = 39,148; $M_w$ = 36,313; $M_n$ = 14,745; PDI = 2.46 | 41.3 |
| 416 | 74 | 421 | NaBAF | 0.217 | 1.3 | $M_p$ = 26,280; $M_w$ = 27,880; $M_n$ = 13,106; PDI = 2.13 | 36.9 |
| 417 | 74 | 421 | LiBArF | 0.358 | 1.2 | $M_p$ = 33,089; $M_w$ = 33,479; $M_n$ = 15,943; PDI = 1.57 | 44.6 |
| 418 | 76 | 421 | LiBArF | 0.738 | 1.2 | $M_p$ = 29,924; $M_w$ = 29,685; $M_n$ = 12,971; PDI = 2.29 | 36.1 |
| 419 | 92 | 421 | LiBArF | 0.385 | 1.1 | $M_p$ = 34,623; $M_w$ = 35,775; $M_n$ = 18,240; PDI = 196 | 33.4 |
| 420 | 64 | 421 | LiBArF | 0.009 | 0.7 | $M_n$ ($^1$H): No olefins | 58.8 |
| 421 | 93 | 421 | LiBArF | 0.021 | 1.5 | $M_n$ ($^1$H): No olefins | 33.2 |
| 422 | 96 | 421 | LiBArF | 0.109 | Nd | Nd | Nd |
| 423 | 90 | 421 | LiBArF | 0.982 | 2.5 | $M_p$ = 7,599; $M_w$ = 8,271; $M_n$ = 3,746; PDI = 2.21 | 26.3 |
| 424 | 74 | 211 | LiBArF | 0.86 | 1.6 | $M_p$ = 26,306; $M_w$ = 28,886; $M_n$ = 10,439; PDI = 2.77 | 37.6 |
| 425 | 74 | 105 | LiBArF | 1.23 | 2.2 | $M_p$ = 16,233; $M_w$ = 21,189; $M_n$ = 8,573; PDI = 2.47 | 38.5 |
| 426 | 74 | 53 | LiBArF | 4.75 | 0 | $M_p$ = 76,091; $M_w$ = 76,631; $M_n$ = 24,522; PDI = 3.13 | Nd |

[a]There is overlap of copolymer and homopolymer resonances in the $^1$H NMR spectrum due to the relatively large amount of homopolymer formed. Therefore, the percent acrylate incorporation in the copolymer is an approximation.

TABLE 56

Ethylene/EGPEA Copolymerizations: Variation of Catalyst Structure
and Concentration (18 h, 1 mL EGPEA, 9 mL p-Xylene, 80° C., 6.9 MPa E)

| Ex. | Cmpd mmol | B($C_6F_5$)$_3$ equiv | LiB($C_6F_5$)$_4$ equiv | MeAl(BHT)$_2$ equiv | Yield g | Acrylate Incorp mol % | M.W. | Total Me |
|---|---|---|---|---|---|---|---|---|
| 427 | 59 0.01 | 40 | 20 | 0 | 6.73 | 1.6 0.9 IC 0.7 EG | $M_p$ = 21,259; $M_w$ = 21,724; $M_n$ = 10,233; PDI = 2.12 | 15.3 |
| 428 | 59 0.0019 | 211 | 105 | 20 | 0.739 | 1.1 | $M_p$ = 19,634; $M_w$ = 20,285; $M_n$ = 8,383; PDI = 2.42 | 10.9 |
| 429 | 94 0.01 | 40 | 20 | 0 | 3.87 | 1.3 0.9 IC 0.4 EG | $M_p$ = 11,047; $M_w$ = 11,998; $M_n$ = 4,529; PDI = 2.65 | 24.5 |

TABLE 56-continued

Ethylene/EGPEA Copolymerizations: Variation of Catalyst Structure
and Concentration (18 h, 1 mL EGPEA, 9 mL p-Xylene, 80° C., 6.9 MPa E)

| Ex. | Cmpd mmol | $B(C_6F_5)_3$ equiv | $LiB(C_6F_5)_4$ equiv | $MeAl(BHT)_2$ equiv | Yield g | Acrylate Incorp mol % | M.W. | Total Me |
|---|---|---|---|---|---|---|---|---|
| 430 | 94 0.0019 | 211 | 105 | 20 | 1.22 | 0.7 | $M_p$ = 9,998; $M_w$ = 12,341; $M_n$ = 4,993; PDI = 2.47 | 17.1 |
| 431 | 53 0.01 | 40 | 20 | 0 | 2.26 | 1.0 0.9 IC 0.1 EG | $M_p$ = 1,562; $M_w$ = 2,097; $M_n$ = 818; PDI = 2.56 | 31.8 |

TABLE 57

Ethylene/Acrylate Copolymerizations: Variation of Catalyst Structure,
Acrylate Structure and Temperature (0.004 mmol Cmpd, 18 h, 100 equiv
$B(C_6F_5)_3$, 50 equiv $LiB(C_6F_5)_4$, 9 mL p-Xylene, 6.9 MPa E)

| Ex. | Cmpd | Temp. ° C. | Acrylate 1 mL | Yield G | Acrylate Incorp mol % | M.W. | Total Me |
|---|---|---|---|---|---|---|---|
| 432 | 45 | 80 | EGPEA | 0.070 | 0.6 0.5 IC 0.1 EG | $M_p$ = 24,391; $M_w$ = 28,348; $M_n$ = 11,007; PDI = 2.58 | 8.5 |
| 433 | 45 | 80 | HA | 0.294 | 1.0 | $M_p$ = 45,116; $M_w$ = 71,337; $M_n$ = 14,837; PDI = 4.81 | 14.2 |
| 434 | 94 | 80 | EGPEA | 0.074 | 0.5 | $M_p$ = 9,723; $M_w$ = 13,173; $M_n$ = 6,276; PDI = 2.10 | 8.0 |
| 435 | 94 | 80 | HA | 0.362 | 0.8 | $M_p$ = 14,965; $M_w$ = 15,692; $M_n$ = 6,605; PDI = 2.38 | 12.4 |
| 436 | 90 | 80 | HA | 0.286 | 0.8 | $M_p$ = 17,982; $M_w$ = 17,990; $M_n$ = 6,559; PDI = 2.74 | 9.7 |
| 437 | 45 | 40 | EGPEA | 0 | — | — | — |
| 438 | 91 | 40 | EGPEA | 0 | — | — | — |
| 439 | 94 | 40 | EGPEA | 0 | — | — | — |

EXAMPLES 440–555

In these Examples sometimes alkylaluminum compounds are used as cocatalysts. These alkylaluminums were purchased from commercial sources, PMAO-IP (97) (polymethylaluminoxane from Akzo-Nobel, Inc., 12.7 wt % aluminum in toluene, (0.88 g/ml at 30° C.)) or synthesized by literature methods, $(AlMe_2(Et_2O)_2)(MeB(C_6F_5)_3)$ (98) (WO0011006), $AlMe(2,6-t-Bu-4-Me(OC_6H_2))_2$ (99) (A. P. Shreve, et al., *Organometallics*, vol. 7, p. 409 (1988)), and $(Al-i-Bu_2(OC_6F_5))_2$ (100) (D. G. Hendershot, et al., *Organometallics*, vol. 10 p. 1917 (1991)).

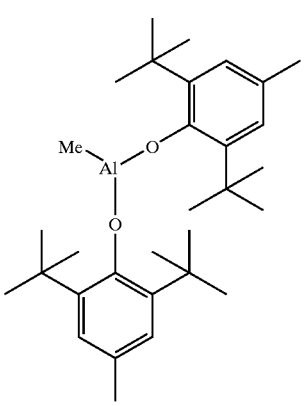

99

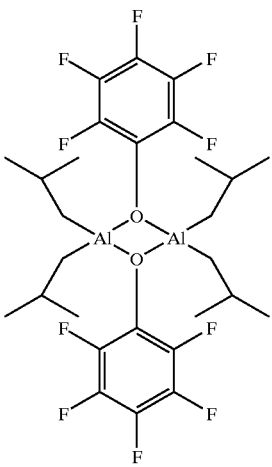

100

The transition metal complexes (101–117) are either isolated compounds or in situ generated from a combination of compounds. Such combinations are shown under the compound designation (number). Syntheses of compounds other than α-diimines or their complexes are described in the following references:

45–97, 101, 102, 103, 104, 105, 109, 110, 116 and 117, are α-diimines and/or Ni complexes the same as or similar to those described in U.S. Pat. No. 6,034,259 and references therein, and U.S. Pat. No. 6,103,658, and these α-diimines and/or Ni complexes are made by methods similar to those described therein. The synthesis of the ligand for 79 is reported in Y. Yamamoto et al., *J. Organometal. Chem.*, vol. 489, p. 21–29 (1995), and K. Sugano, et al., *Chem. Lett.*, vol. 1991 p. 921–924.

The synthesis of the α-diimine for 110 is described in U.S. Pat. No. 6,103,658.

Methods for making 115 are found in U.S. Pat. No. 6,174,975.

A method for the synthesis of 108 is disclosed in previously incorporated U.S. patent application Ser. No. 09/871,100 filed 31 May 2001, now U.S. Pat. No. 6,506,861.

Syntheses of 106 and 107 are found herein. All of the immediately documents are hereby included by reference.

Metal complexes or ingredients for in situ preparations are shown below:

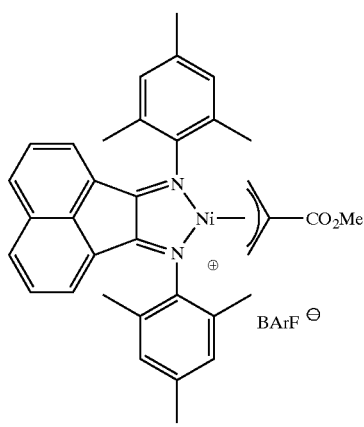

101

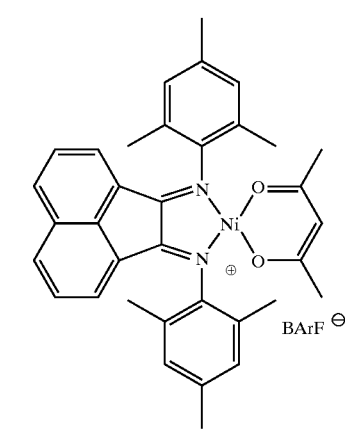

102

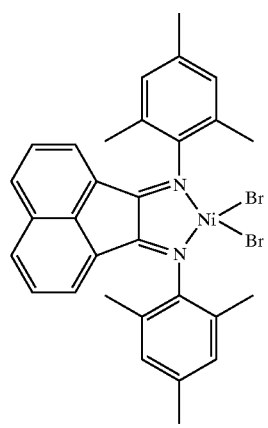

103

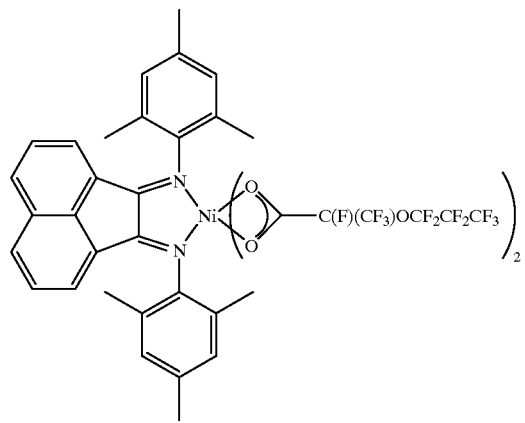

104

105

106

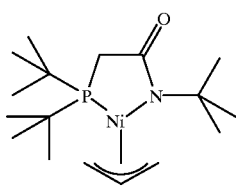
106

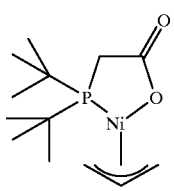
107

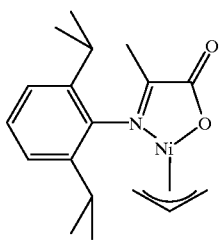
108

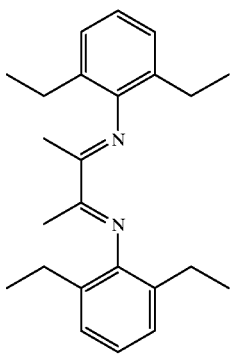
+ Ni(acac)₂ + Ph₃CBArF

109

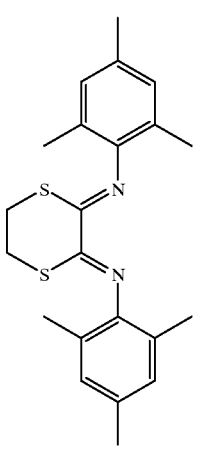
+ Ni(acac)₂

110

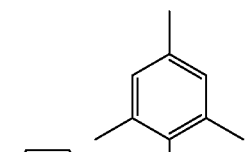
+ {TMEDA}Ni(acac)₂

116

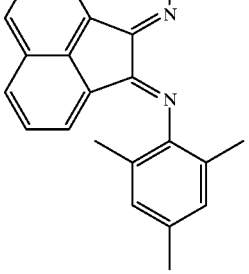
+ {TMEDA}Ni(acac)₂

117

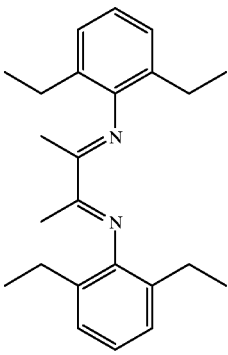

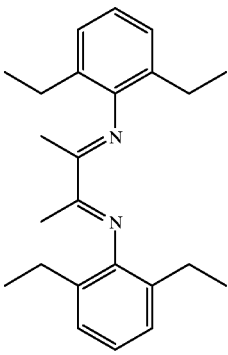

General Polymerization Procedure for Examples 440–555

In a drybox, a glass insert was loaded with a combination of ligand and metal precursor or an isolated metal precatalyst and 2 mL of solvent. The solution was cooled to −30° C. and a solid portion of aluminum cocatalyst (such as 98, 99 or 100) or solution of PMAO-IP (97) was added followed by 4 mL of solvent and the solution was cooled to −30° C. This cooling was done to prevent any polymerization catalyst decomposition prior to contact with the monomers, in case the catalyst was thermally unstable. A solution was made with salt (see below), comonomer and 3 mL of solvent. The solution was added to the glass insert and then cooled to −30° C. The insert was capped and placed into double ziplock bags. Outside the drybox the rack was transferred to a pressure tube and flushed with ethylene. The pressure tube was pressurized with ethylene and heated to the desired temperature and mechanically shaken for the duration of time listed in the table. The reaction solution was quenched with 30 mL of methanol or acidic methanol (10:90 HCl methanol solution) and the polymer was isolated by filtration, rinsed with additional methanol and dried under vacuum.

Polymerization results are presented in Tables 58–64. A short description/explanation for each table is given below. "Salt" in these tables indicates the addition of NaBAF or LiB(C₆F₅)₄ to the polymerization solution and it appeared to inhibit or prevent acrylate homopolymerization, and will be shown as simply Na or Li in the table.

Table 58: Table 58 contains examples with Ni catalysts, diimine with Ni(acac)$_2$, and alkylaluminum cocatalysts for EG-PEA and ethylene copolymerization. At these high ratios of Ni to salt and Al cocatalysts we had some significant acrylate homopolymerization. The acrylate homopolymer was found in two forms, a powder which was a mixture of copolymer with some acrylate homopolymer as identified by $^1$H NMR, and a gelatin consisting of acrylate homopolymer which was physically separated and not included in the polymer weight in the tables. The solution volume was approximately 10 mL in each case, therefore, the solvent added was 10 mL minus the volume added for the liquid comonomer.

Table 59: Table 59 shows examples of some of the better catalysts under conditions with low concentration of Ni and high concentration of salt and Al cocatalysts. In these examples consistently good yields of EGPEA/ethylene copolymer were obtained. Further characterization of these polymers is indicated by Mw from GPC as well as incorporation of acrylate (mole %) in the copolymer that was calculated from $^1$H NMR spectra of the polymer.

Table 60: This table has very low Ni concentrations and more acrylate homopolymer and low yields of polymer are obtained overall.

Table 61: Different combinations of Ni compounds and cocatalysts are used.

Table 62: Examples for E-10-U copolymerizations with ethylene.

Table 63: Hexyl acrylate copolymerization with Ni catalyst.

Table 64: Other catalysts for EGPEA copolymerization.

TABLE 58

Ethylene and EGPA copolymerization (18 h, 6.9 MPa E, 0.02 mmol Ni)

| Ex. | Catalyst mmol | Salt (eq) | Al (eq) | EGPEA | solvent | Temp | Yield (g) |
|---|---|---|---|---|---|---|---|
| 440 | 104 | Li (5) | 100 (50) | 1 mL | 1,2,4-TCB | 120° C. | 1.439 |
| 441 | 104 | Li (5) | 100 (50) | 2 mL | 1,2,4-TCB | 120° C. | 1.033 |
| 442 | 104 | Na (5) | 97 (200) | 2 mL | 1,2,4-TCB | 120° C. | 6.011 |
| 443 | 104 | Li (5) | 100 (50) | 2 mL | p-xylene | 120° C. | 2.982 |
| 444 | 104 | Li (5) | 99 (50) | 1 mL | 1,2,4-TCB | 120° C. | 6.522 |
| 445 | 103 | Li (5) | 100 (50) | 1 mL | p-xylene | 100° C. | 1.287 |
| 446 | 103 | Na (5) | 97 (200) | 1 mL | p-xylene | 100° C. | 5.077 |
| 447 | 104 | Li (5) | 100 (50) | 1 mL | p-xylene | 100° C. | 9.073 |
| 448 | 104 | Na (5) | 97 (200) | 1 mL | p-xylene | 100° C. | 3.96 |
| 449 | 104 | Na (5) | 100 (50) | 1 mL | 1,2,4-TCB | 100° C. | 2.179 |
| 450 | 103 | Li (5) | 100 (50) | 1 mL | 1,2,4-TCB | 100° C. | 3.053 |
| 451 | 103 | Li (5) | 97 (200) | 1 mL | 1,2,4-TCB | 100° C. | 5.977 |
| 452 | 104 | Li (5) | 97 (200) | 1 mL | 1,2,4-TCB | 100° C. | 6.114 |
| 453 | 105 | Li (5) | 97 (200) | 1 mL | 1,2,4-TCB | 100° C. | 1.109 |
| 454 | 105 | Li (5) | 100 (50) | 1 mL | 1,2,4-TCB | 100° C. | 3.392 |
| 455 | 116 | Na (5) | 100 (50) | 1 mL | 1,2,4-TCB | 100° C. | 1.931 |
| 456 | 103 | Na (5) | 100 (50) | 1 mL | 1,2,4-TCB | 100° C. | 1.269 |
| 457 | 103 | Na (5) | 97 (200) | 1 mL | 1,2,4-TCB | 100° C. | 5.066 |
| 458 | 105 | Na (5) | 100 (50) | 1 mL | 1,2,4-TCB | 100° C. | 4.628 |
| 459 | 104 | Na (10) | 100 (50) | 1 mL | 1,2,4-TCB | 100° C. | 0.387 |
| 460 | 104 | Na (5) | 97 (200) | 1 mL | 1,2,4-TCB | 100° C. | 6.538 |
| 461 | 104 | Li (5) | 100 (50) | 1 mL | 1,2,4-TCB | 100° C. | 1.131 |
| 462 | 104 | Li (5) | 100 (50) | 1 mL | 1,2,4-TCB | 100° C. | 4.477 |
| 463 | 104 | no salt | 100 (50) | 1 mL | 1,2,4-TCB | 100° C. | 1.198 |
| 464 | 104 | Na (1) | 100 (50) | 1 mL | 1,2,4-TCB | 120° C. | 0.50 |
| 465 | 104 | Na (1) | 100 (50) | 1 mL | 1,2,4-TCB | 120° C. | 0.260 |
| 466 | 104 | Na (1) | 97 (200) | 1 mL | 1,2,4-TCB | 120° C. | 5.411 |
| 467 | 104 | Na (5) | 100 (50) | 1 mL | 1,2,4-TCB | 120° C. | 0.176 |
| 468 | 104 | Na (1) | 100 (50) | 1 mL | 1,2,4-TCB | 100° C. | 0.254 |
| 469 | 104 | Na (1) | 97 (200) | 1 mL | 1,2,4-TCB | 100° C. | 4.231 |
| 470 | 104 | Na (5) | 100 (50) | 1 mL | 1,2,4-TCB | 100° C. | 1.460 |

TABLE 59

Ethylene and EGPEA Copolymerization (6.9 MPa E, p-xylene solvent)

| Ex. | Catalyst | mmol Ni | Salt eq | Al eq | mL acrylate | Hrs | Temp | Yield | Kg/g Ni | Mw | Mol % Ac |
|---|---|---|---|---|---|---|---|---|---|---|---|
| 471 | 101 | 0.002 | Li (250) | 98 (250) | 1.0 | 18 | 120 | 4.766 | 41 | 19051 | 0.36 |
| 472 | 101 | 0.002 | Li (250) | 98 (250) | 1.5 | 18 | 120 | 3.170 | 27 | 16830 | 0.64 |
| 473 | 106 | 0.002 | Li (250) | 98 (250) | 1.0 | 18 | 120 | 8.332 | 71 | 5539 | 0.17[i]/0.19[e] |
| 474 | 101 | 0.001 | Li (750) | 98 (500) | 1.0 | 18 | 120 | 2.576 | 44 | 16000 | 0.57 |
| 475 | 101 | 0.004 | Li (125) | 98 (125) | 1.0 | 18 | 100 | 7.24 | 31 | 27476 | 0.70 |
| 476 | 101 | 0.002 | Li (250) | 98 (250) | 1.0 | 18 | 100 | 4.749 | 40 | 25432 | 0.42 |
| 477 | 101 | 0.002 | Li (250) | 98 (250) | 1.5 | 18 | 100 | 3.213 | 27 | 22992 | 0.61 |
| 478 | 106 | 0.002 | Li (250) | 98 (250) | 1.0 | 18 | 100 | 4.398 | 37 | 7262 | 0.19[i]/0.16[e] |
| 479 | 101 | 0.001 | Li (750) | 98 (500) | 1.0 | 18 | 100 | 3.374 | 57 | 24042 | 0.30 |
| 480 | 101 | 0.004 | Li (125) | 98 (125) | 1.0 | 64 | 120 | 15.08 | 64 | 17153 | 0.29 |
| 481 | 101 | 0.002 | Li (250) | 98 (250) | 1.0 | 64 | 120 | 10.521 | 90 | 16817 | 0.47 |
| 482 | 101 | 0.002 | Li (250) | 98 (250) | 1.5 | 64 | 120 | 9.455 | 80 | 17930 | 0.8 |
| 483 | 106 | 0.002 | Li (250) | 98 (250) | 1.0 | 64 | 120 | 7.833 | 67 | 5469 | 0.20[i]/0.18[e] |
| 484 | 107 | 0.002 | Li (250) | 98 (500) | 1.0 | 64 | 120 | 1.191 | 10 | 2045 | ND |
| 485 | 101 | 0.004 | Li (125) | 98 (125) | 1.0 | 64 | 100 | 13.073 | 56 | 26512 | 0.41 |
| 486 | 101 | 0.002 | Li (250) | 98 (250) | 1.0 | 64 | 100 | 8.807 | 75 | 25472 | 1.2 |
| 487 | 101 | 0.002 | Li (250) | 98 (250) | 1.5 | 64 | 100 | 6.183 | 53 | 23585 | 0.84 |
| 488 | 106 | 0.002 | Li (250) | 98 (250) | 1.0 | 64 | 100 | 7.100 | 60 | 6803 | 0.15[i]/0.13[e] |
| 489 | 107 | 0.002 | Li (250) | 98 (500) | 1.0 | 64 | 100 | 0.834 | 7 | 3135 | ND |
| 490 | 102 | 0.004 | Li (125) | 100 (250) | 1.0 | 18 | 120 | 7.259 | 31 | 13945 | 0.25 |
| 491 | 102 | 0.004 | Li (125) | 98 (125) | 1.0 | 18 | 120 | 9.147 | 39 | 14056 | 0.35 |

TABLE 59-continued

Ethylene and EGPEA Copolymerization (6.9 MPa E, p-xylene solvent)

| Ex. | Catalyst | mmol Ni | Salt eq | Al eq | mL acrylate | Hrs | Temp | Yield | Kg/g Ni | Mw | Mol % Ac |
|---|---|---|---|---|---|---|---|---|---|---|---|
| 492 | 102 | 0.004 | Li (125) | 98 (125) | 2.0 | 18 | 120 | 3.23 | 14 | 11652 | 0.94 |
| 493 | 101 | 0.004 | Li (125) | 100 (250) | 1.0 | 18 | 120 | 6.165 | 26 | 13988 | 0.33 |
| 494 | 101 | 0.004 | Li (125) | 98 (125) | 1.0 | 18 | 120 | 9.355 | 40 | 15724 | 0.49 |
| 495 | 102 | 0.02 | Li (10) | 100 (25) | 1.0 | 18 | 120 | 6.58 | 6 | N/A | 0.55 |
| 496 | 102 | 0.02 | Li (10) | 98 (25) | 1.0 | 18 | 120 | 18.921 | 16 | N/A | 0.34 |
| 497 | 106 | 0.004 | Li (25) | 98 (50) | 1.0 | 18 | 100 | 4.190 | 18 | N/A | 0.22[i]/0.29[e] |
| 498 | 108 | 0.004 | Li (25) | 98 (50) | 1.0 | 18 | 100 | 0.123 | 0.5 | N/A | ND |
| 499 | 107 | 0.004 | Li (25) | 98 (50) | 1.0 | 18 | 100 | 2.114 | 9 | N/A | 0.38[i]/0.37[e] |
| 500 | 101 | 0.004 | Li (25) | 98 (50) | 1.0 | 18 | 100 | 2.750 | 12 | N/A | 0.42 |
| 501 | 102 | 0.004 | Li (25) | 98 (50) | 1.0 | 18 | 100 | 1.547 | 7 | 10621 | 0.48 |

Footnotes for Table 59:
N/A indicates that a sample was not submitted for $^1$H NMR or GPC. ND (not determined) indicates that the formation of excess acrylate homopolymer overlaps the region for determining copolymer content. For the incorporation of acrylate in the ethylene copolymer (Mol % Ac) the in chain (i) and end of chain (e) position is indicated.

TABLE 60

Ethylene and acrylate Copolymerization (18 h, 120° C., 6.9 MPa E, p-xylene solvent, Al compound 98)

| Ex. | Catalyst | mmol Ni | Salt eq | Al eq | mL acrylate | Yield | Kg/g Ni | Mw | Mol % Ac |
|---|---|---|---|---|---|---|---|---|---|
| 502 | 101 | 0.001 | Li (500) | (500) | 1.0 EGPEA | 3.443 | 59 | 17680 | copoly |
| 503 | 101 | 0.0005 | Li (1000) | (1000) | 1.0 EGPEA | 1.998 | 34 | 16178 | copoly |
| 504 | 106 | 0.001 | Li (500) | (500) | 1.0 EGPEA | 1.560 | 27 | 5500 | copoly |
| 505 | 106 | 0.0005 | Li (1000) | (1000) | 1.0 EGPEA | 1.08 | 37 | 5550 | ND |
| 506 | 109 | 0.001 | Li (500) | (500) | 1.0 EGPEA | 0.576 | 10 | 17704 | ND |
| 507 | 101 | 0.001 | Li (500) | (500) | 0.5 MA | 3.024 | 52 | 15041 | Copoly |
| 508 | 101 | 0.0005 | Li (1000) | (1000) | 0.5 MA | 1.507 | 51 | N/A | N/A |
| 509 | 106 | 0.001 | Li (500) | (500) | 0.5 MA | 0.225 | 4 | N/A | N/A |
| 510 | 106 | 0.0005 | Li (1000) | (1000) | 0.5 MA | 0.390 | 13 | N/A | N/A |
| 511 | 109 | 0.001 | Li (500) | (500) | 0.5 MA | 0.553 | 9 | N/A | N/A |
| 512 | 101 | 0.001 | Li (500) | (500) | 0.5 HA | 1.08 | 18 | N/A | N/A |
| 513 | 101 | 0.0005 | Li (1000) | (1000) | 0.5 HA | 0.982 | 33 | N/A | N/A |
| 514 | 106 | 0.001 | Li (500) | (500) | 0.5 HA | 0.314 | 5 | N/A | N/A |
| 515 | 106 | 0.0005 | Li (1000) | (1000) | 0.5 HA | 0.303 | 10 | N/A | N/A |
| 516 | 109 | 0.001 | Li (1000) | (1000) | 0.5 HA | 0.672 | 11 | N/A | N/A |

N/A indicates that a sample was not submitted for $^1$H NMR or GPC.
ND (not determined) indicates that the formation of excess acrylate homopolymer overlaps the region for determining copolymer content.
copoly = acrylate-ethylene copolymer detected by $^1$H NMR.

TABLE 61

Ethylene and EGPEA Copolymerization (18 h, 120° C., 6.9 MPa E, p-xylene solvent, 1.0 ml EGPEA)

| Ex. | Catalyst | Mmol Ni | Salt eq | Al eq | Yield | Mw |
|---|---|---|---|---|---|---|
| 517 | 104 | 0.004 | Li (125) | 98 (125) | 8.451 | 17004 |
| 518 | 117 | 0.004 | Li (125) | 98 (125) | 0.543 | 17988, 26687 |
| 519 | 106 | 0.002 | Li (250) | 98 (250) | 2.644 | 4787 |
| 520 | 115 | 0.01 | Li (30) | 99 (20)/B(C$_6$F$_5$)$_3$ (10) | 0.307 | N/A |
| 521 | 110 | 0.01 | Li (30) | 99 (20)/B(C$_6$F$_5$)$_3$ (10) | 1.417 | 26934 |
| 522 | 102 | 0.01 | Li (30) | 99 (20)/B(C$_6$F$_5$)$_3$ (10) | 8.456 | 14038 |
| 523 | 101 | 0.01 | Li (30) | 99 (20)/B(C$_6$F$_5$)$_3$ (10) | 8.283 | 13607 |
| 524 | 111 | 0.01 | Li (30) | 100 (50) | 0.897 | N/A |
| 525 | 101 | 0.01 | Li (30) | 98 (25) | 11.741 | 11838 |
| 526 | 101 | 0.01 | Li (30) | 99 (25) | 2.647 | 11370 |
| 527 | 102 | 0.01 | Li (30) | 99 (25) | 2.412 | 11766 |
| 528 | 106 | 0.002 | Li (150) | 98 (250) | 1.612 | 4235 |
| 529 | 106 | 0.002 | Li (150) | 100 (500) | 1.559 | 3812, 6321 |
| 530 | 106 | 0.002 | Li (150) | 99 (500) | 0.450 | N/A |
| 531 | 107 | 0.002 | Li (150) | 98 (250) | 0.929 | N/A |
| 532 | 107 | 0.002 | Li (150) | 100 (500) | 1.595 | 1785 |
| 533 | 107 | 0.002 | Li (150) | 99 (500) | 0.782 | N/A |
| 534 | 108 | 0.002 | Li (150) | 98 (250) | 0.263 | N/A |
| 535 | 108 | 0.002 | Li (150) | 100 (500) | 0.839 | N/A |
| 536 | 108 | 0.002 | Li (150) | 99 (500) | 0.387 | N/A |

TABLE 61-continued

Ethylene and EGPEA Copolymerization (18 h, 120° C., 6.9 MPa E, p-xylene solvent, 1.0 ml EGPEA)

| Ex. | Catalyst | Mmol Ni | Salt eq | Al eq | Yield | Mw |
|-----|----------|---------|---------|-------|-------|-----| copoly = acrylate-ethylene copolymer detected by $^1$H NMR, ND (not determined) indicates that the polyacrylate region swamped out the region of intrest for the copolymer therefore it is not determined. N/A indicates that a sample for $^1$H NMR or GPC was not submitted.

TABLE 62

Ethylene and E-10-U Copolymerization (18 h, p-xylene solvent

| Ex. | Catalyst | mmol Ni | Salt eq | Al eq | mL-E-10-U | T °C. | Pres. MPa | Yield | Mw |
|-----|----------|---------|---------|-------|-----------|-------|-----------|-------|-----|
| 537 | 102 | 0.01 | 0 | 98 (50) | 2.0 | 60 | 1.0 | 2.50 | N/A |
| 538 | 106 | 0.002 | Li (150) | 98 (250) | 1.0 | 120 | 6.9 | 8.525 | 6043 |
| 539 | 106 | 0.004 | Li (75) | 98 (125) | 1.7 | 120 | 6.9 | 0.531 | 4820 |
| 540 | 115 | 0.01 | Li (30) | 99 (50) | 1.7 | 120 | 6.9 | 0.101 | N/A |
| 541 | 106 | 0.004 | Li (75) | 98 (125) | 1.7 | 60 | 3.5 | 0.018 | N/A |
| 542 | 115 | 0.01 | Li (30) | 99 (50) | 1.7 | 60 | 3.5 | 0.091 | N/A |
| 543 | 111 | 0.02 | Na (1) | 100 (50) | 1.1 | 80 | 5.2 | 9.770 | N/A |
| 544 | 112 | 0.02 | Na (1) | 100 (50) | 1.1 | 80 | 5.2 | 0.160 | N/A |

N/A indicates that a sample for $^1$H NMR or GPC was not submitted.

TABLE 63

Copolymerization of ethylene and HA (18 h, 100° C., 6.9 MPa E)

| Ex. | Catalyst | mmol Ni | Salt eq | Al eq | mL acrylate | solvent | Yield | Mw |
|-----|----------|---------|---------|-------|-------------|---------|-------|-----|
| 545 | 104 | 0.02 | Na (5) | 97 (200) | 1.0 HA | 1,2,4TCB | 4.881 | 4177 |
| 546 | 104 | 0.02 | Na (5) | 97 (200) | 2.0 HA | 1,2,4TCB | 3.392 | 21281 |
| 547 | 104 | 0.02 | Li (5) | 99 (50) | 1.0 HA | 1,2,4TCB | 6.443 | 21943 |
| 548 | 104 | 0.02 | Li (5) | 99 (50) | 1.0 HA | p-xylene | 7.655 | 29495 |

TABLE 64

Copolymerization of Ethylene and EGPEA (18 h, 120° C., 6.9 MPa E, 0.01 mmol Ni)

| Ex. | Catalyst | Salt eq | Al eq | mL acrylate | solvent | Yield | Mw |
|-----|----------|---------|-------|-------------|---------|-------|-----|
| 549 | 103 | Li (50) | 98 (50) | 1.0 | p-xylene | 19.010 | 13399 |
| 550 | 116 | Li (50) | 98 (50) | 1.0 | p-xylene | 16.671 | 15559 |
| 551 | 102 | Li (50) | 98 (50) | 1.0 | p-xylene | 11.724 | 12804 |
| 552 | 102 | Na (50) | 97 (100) | 1.0 | 1,2,4-TCB | 5.848 | 26061 |
| 553 | 102 | Na (50) | 97 (50) | 1.0 | 1,2,4-TCB | 5.550 | 11620 |
| 554 | 103 | Na (50) | 97 (100) | 1.0 | 1,2,4-TCB | 10.108 | 12359 |
| 555 | 103 | Na (50) | 97 (50) | 1.0 | 1,2,4-TCB | 9.116 | 14836 |

EXAMPLES 556–651

Various isocyanates were used with a single precursor, di-t-butylphosphinomethyl lithium to prepare variously substituted ligands (see below). Nickel complexes were then prepared in situ, and polymerizations carried out.

All reactions were performed under an atmosphere of nitrogen. The isocyanates for the catalyst preparation were obtained from commercial sources, and were purified by distillation, sublimation, or recrystallization; the compounds were stored under nitrogen before use. TCB was purchased anhydrous and used as is. Additional solvents were distilled from drying agents under nitrogen using standard procedures: chlorobenzene from $P_2O_5$; and THF, from sodium benzophenone ketyl, Ni(II) allyl chloride and NaBAF were prepared according to the literature.

Ninety-five isocyanates were prepared as THF solutions (0.0500 M) and are listed in Table 65. These solutions were prepared in glass vials capped with Teflon® lined silicone septa to maintain an inert atmosphere and prevent evaporation.

Preparation of catalyst solutions was performed according to equation 1.

(Eq. 1)

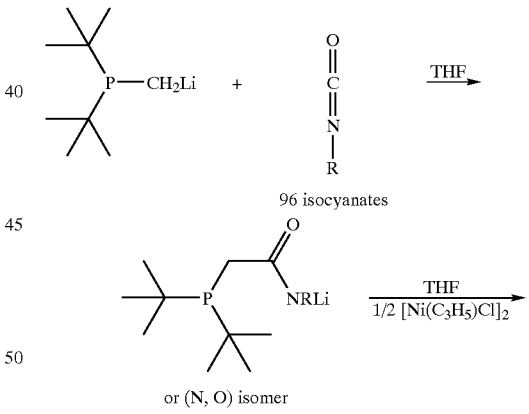

or (N, O) isomer

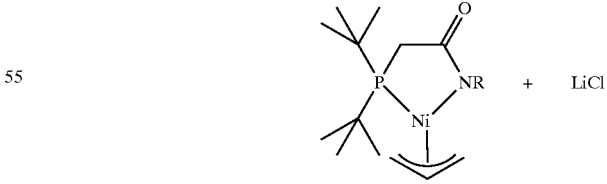

In a typical procedure, each sample was prepared by adding sequentially 150(±3) µL of an isocyanate solution (0.0500 M in THF) followed by 150(±3) µL of a solution of (t-Bu)$_2$PCH$_2$Li (0.0500 M in THF), followed by 150(±3) µL of a solution of (NiCl($\eta^3$-C$_3$H$_5$))$_2$ (0.0250 M in THF) to a septa sealed 2 mL glass vial. The solvent was then removed from each vial by purging with a nitrogen gas stream and each vial was then dried for 2 h in a vacuum chamber. A solution of cocatalyst (B(C$_6$F$_5$)$_3$, B(C$_6$H$_5$)$_3$ or NaBAF) 300 µL (0.1250 M in chlorobenzene or TCB) was added into each vial. Each vial was placed in a high-pressure reactor. The reactor was pressurized to the desired pressure (typically 6.9 MPa or 1.0 MPa) with ethylene and kept at that pressure for 18 h. At the end of the run, the solvent was removed from each vial under vacuum. After this operation each vial was weighed to obtain a polymer yield. To rapidly determine the presence of copolymer, a sample was taken out of each vial and placed in an NMR tube, CDCl$_3$ was added and the solution was analyzed submitted by $^1$H NMR spectroscopy. In some (usually promising) cases, samples were dissolved in TCE and submitted for high temperature $^{13}$C NMR spectroscopy.

Condition 1

Run at room temperature and 6.9 MPa of ethylene. Five equivalents of tris(pentafluorophenyl)borane were present as a cocatalyst. Eighteen hours was chosen as the run time to allow for comparison of the lowest and highest yielding catalysts. Results are presented in Table 65. The experimental procedure was repeated several times and despite some changes in yields, activity trends remained the same.

Condition 2

This was the same as Condition 1, except the ethylene pressure was 1.0 MPa. Results are shown in Table 65.

Condition 3

This was the same as Condition 1, except 5 equivalents of triphenylborane was used as a cocatalyst and the polymerization was run at 1.0 MPa ethylene pressure. This condition was repeated several times with similar results each time. Results are shown in Table 65.

Condition 4

This was run under the same conditions as Condition 1 except, one equivalent of NaBAF was added (150 µl of a 0.05M solution in THF) after the addition of nickel allyl chloride.

Condition 5

Run at room temperature and under 6.9 MPa of ethylene. Five equivalents of tri(pentafluorophenyl)borane were used. The cocatalyst, instead of being dissolved in pure TCB was dissolved in a 1:5 (v:v) mixture of EGPEA and TCB. Because EGPEA has a high boiling point, vials were weighed out immediately after the polymerization reaction without drying. Relative yields were obtained by difference of the weights of the "wet" vials and the pre-tared vials. Results are presented in Table 65. This condition was repeated several times and despite some changes in yields, activity trends remain the same.

Condition 6

This was the same as Condition 5 except the polymerization was run at 100° C. Results are presented in Table 65. This condition was repeated several times and despite some changes in yields, activity trends remain the same.

Condition 7

This was run in the same manner as Condition 6 except 1 equivalent of NaBAF added (150 µl of a 0.05M solution in THF) was also added after the nickel allyl chloride was added. Results are given in Table 65. $^{13}$C NMR analysis indicates that the polymer in Example 582 gives a copolymer with 1.04 mol % incorporation under this condition.

Condition 8

This condition was the same as Condition 7, except the EGPEA contained 250 ppm of benzoquinone as a free radical polymerization inhibitor. Results are given in Table 65. $^{13}$C NMR analysis indicates that the polymers produced in Examples 583 and 591 gave copolymers with trace incorporation of EGPEA, the polymer of Example 585 had 0.17 mol % incorporation of EGPEA, the polymer of Example 632 had 0.51 mol % incorporation of EGPEA, and the polymer of Example 640 had 0.90 mol % incorporation of EGPEA, all under this condition.

TABLE 65

| | | CONDITION | | | | | | | |
|---|---|---|---|---|---|---|---|---|---|
| Ex. | NAME | 1 | 2 | 3 | 4 | 5 | 6 | 7 | 8 |
| 556 | TRANS-2-PHENYLCYCLOPROPYL ISOCYANATE | 1.2262 | 0.3589 | 0.0875 | 0.1950 | 0.4978 | 0.4518 | 0.249 | 0.3437 |
| 557 | PHENYL ISOCYANATE | 0.6409 | 0.1067 | 0.046 | 0.0982 | 0.4686 | 0.6287 | 0.3906 | 0.3762 |
| 558 | 2-BROMOPHENYL ISOCYANATE | 0.5133 | 0.1321 | 0.0485 | 0.0994 | 0.4733 | 0.7043 | 0.3068 | 0.3811 |
| 559 | 2-FLUOROPHENYL ISOCYANATE | 0.3426 | 0.1074 | 0.0703 | 0.1568 | 0.437 | 0.5479 | 0.4299 | 0.4407 |
| 560 | 2,4-DIFLUOROPHENYL ISOCYANATE | 0.5988 | 0.1008 | 0.0615 | 0.1875 | 0.4797 | 0.7257 | 0.448 | 0.4373 |
| 561 | 2,6-DIFLUOROPHENYL ISOCYANATE | 0.3429 | 0.1111 | 0.0392 | 0.0974 | 0.4859 | 0.6638 | 0.4485 | 0.4626 |
| 562 | 2-CHLOROPHENYL ISOCYANATE | 0.4882 | 0.1215 | 0.0462 | 0.1257 | 0.5097 | 0.6995 | 0.4705 | 0.4645 |
| 563 | 2,3-DICHLOROPHENYL ISOCYANATE | 0.4516 | 0.1075 | 0.0434 | 0.1196 | 0.413 | 0.7917 | 0.4686 | 0.4702 |
| 564 | 2,6-DICHLOROPHENYL ISOCYANATE | 0.4058 | 0.1061 | 0.0506 | 0.1088 | 0.4688 | 0.7486 | 0.4394 | 0.3883 |
| 565 | 2-METHOXYPHENYL ISOCYANATE | 1.0975 | 0.113 | 0.0584 | 0.1183 | 0.4762 | 0.5993 | 0.5925 | 0.4257 |
| 566 | 2,4-DIMETHOXYPHENYL ISOCYANATE | 1.0943 | 0.1198 | 0.0415 | 0.1243 | 0.5168 | 0.6874 | 0.561 | 0.3869 |
| 567 | 2-ETHOXYPHENYL ISOCYANATE | 1.1473 | 0.1133 | 0.044 | 0.1469 | 0.4535 | 0.7136 | 0.4882 | 0.4019 |
| 568 | 2-(TRIFLUOROMETHYL)PHENYL ISOCYANATE | 0.4246 | 0.1013 | 0.0424 | 0.2715 | 0.5181 | 0.7255 | 0.4381 | 0.4564 |
| 569 | O-TOLYL ISOCYANATE | 0.6267 | 0.1229 | 0.0862 | 0.1757 | 0.4151 | 0.7253 | 0.5005 | 0.4611 |
| 570 | 2,6-DIMETHYLPHENYL ISOCYANATE | 0.5454 | 0.1198 | 0.0603 | 0.1429 | 0.4016 | 0.6963 | 0.4101 | 0.3991 |
| 571 | 2-ETHYLPHENYL ISOCYANATE | 0.6052 | 0.1166 | 0.0781 | 0.1382 | 0.4254 | 0.6031 | 0.4255 | 0.4705 |
| 572 | 3-BROMOPHENYL ISOCYANATE | 0.587 | 0.1001 | 0.0761 | 0.1376 | 0.4664 | 0.6937 | 0.3257 | 0.4718 |
| 573 | 3,4-DICHLOROPHENYL ISOCYANATE | 0.813 | 0.0945 | 0.0536 | 0.1796 | 0.4698 | 0.7749 | 0.5005 | 0.5852 |
| 574 | 4-BROMOPHENYL ISOCYANATE | 0.6361 | 0.1074 | 0.0577 | 0.1428 | 0.4594 | 0.7041 | 0.5411 | 0.4898 |
| 575 | 4-FLUOROPHENYL ISOCYANATE | 0.8563 | 0.1152 | 0.0986 | 0.1222 | 0.4424 | 0.6754 | 0.5557 | 0.3903 |
| 576 | 4-CHLOROPHENYL ISOCYANATE | 0.7498 | 0.1242 | 0.0641 | 0.1239 | 0.4887 | 0.3319 | 0.4404 | 0.4185 |
| 577 | 4-METHOXYPHENYL ISOCYANATE | 0.5989 | 0.1302 | 0.0778 | 0.1245 | 0.4746 | 0.7178 | 0.6034 | 0.5034 |
| 578 | 4-(TRIFLUOROMETHYL)PHENYL ISOCYANATE | 0.651 | 0.0773 | 0.0539 | 0.1410 | 0.469 | 0.7685 | 0.4609 | 0.4037 |
| 579 | P-TOLYL ISOCYANATE | 0.7736 | 0.1045 | 0.0744 | 0.1335 | 0.4849 | 0.6127 | 0.2255 | 0.5482 |
| 580 | TERT-BUTYL ISOCYANATE | 1.0498 | 0.0808 | 0.1742 | 0.3829 | 0.422 | 1.3345 | 0.6914 | 0.6516 |
| 581 | (S)-(−)-1-PHENYLETHYL ISOCYANATE | 0.873 | 0.1171 | 0.0923 | 0.1276 | 0.4037 | 0.8667 | 0.6858 | 0.6728 |
| 582 | ISOPROPYL ISOCYANATE | 0.2012 | 0.0777 | 0.0107 | 0.1421 | 0.2749 | 0.6658 | 0.394 | 0.5266 |
| 583 | ETHYL ISOCYANATE | 1.3347 | 0.1538 | 0.0805 | 0.1814 | 0.4434 | 1.2218 | 0.5436 | 0.6256 |
| 584 | ALLYL ISOCYANATE | 0.9033 | 0.1644 | 0.0976 | 0.1347 | 0.6952 | 1.0612 | 0.4884 | 0.6627 |

TABLE 65-continued

| Ex. | NAME | CONDITION | | | | | | | |
|---|---|---|---|---|---|---|---|---|---|
| | | 1 | 2 | 3 | 4 | 5 | 6 | 7 | 8 |
| 585 | N-BUTYL ISOCYANATE | 1.1664 | 0.1843 | 0.0637 | 0.1220 | 0.4643 | 1.8471 | 0.4761 | 0.6228 |
| 586 | CYCLOHEXYL ISOCYANATE | 0.8991 | 0.0932 | 0.1353 | 0.2726 | 0.488 | 1.791 | 0.6514 | 0.6029 |
| 587 | 1-NAPHTHYL ISOCYANATE | 0.7214 | 0.0943 | 0.1161 | 0.1352 | 0.4344 | 0.7355 | 0.3902 | 0.4148 |
| 588 | 2,6-DIISOPROPYLPHENYL ISOCYANATE | 0.4853 | 0.1204 | 0.0914 | 0.1423 | 0.3988 | 0.6511 | 0.329 | 0.077 |
| 589 | BENZYL ISOCYANATE | 1.1479 | 0.1492 | 0.1403 | 0.2398 | 0.5289 | 0.7776 | 0.5322 | 0.62 |
| 590 | 3,5-BIS(TRIFLUOROMETHYL)PHENYL ISOCYANATE | 0.7095 | 0.1125 | 0.1214 | 0.1271 | 0.4763 | 0.8135 | 0.4492 | 0.4084 |
| 591 | 2,5-DIFLUOROPHENYL ISOCYANATE | 0.4158 | 0.1146 | 0.0131 | 0.1836 | 0.4606 | 0.4177 | 0.3512 | 0.4228 |
| 592 | 2,4,5-TRICHLOROPHENYL ISOCYANATE | 0.3766 | 0.1572 | 0.0236 | 0.2077 | 0.4821 | 0.8006 | 0.4808 | 0.5625 |
| 593 | 2,4,6-TRICHLOROPHENYL ISOCYANATE | 0.5539 | 0.1011 | 0.0304 | 0.1775 | 0.4748 | 0.7127 | 0.4425 | 0.4596 |
| 594 | 2-ISOPROPYLPHENYL ISOCYANATE | 0.6127 | 0.1362 | 0.0693 | 0.1165 | 0.4707 | 0.6892 | 0.4572 | 0.4482 |
| 595 | 2,3-DIMETHYLPHENYL ISOCYANATE | 0.8057 | 0.1345 | 0.0872 | 0.1027 | 0.4844 | 0.7251 | 0.4875 | 0.4715 |
| 596 | 4-METHOXY-2-METHYLPHENYL ISOCYANATE | 0.6799 | 0.1668 | 0.0762 | 0.1207 | 0.4756 | 0.7112 | 0.3862 | 0.6706 |
| 597 | 5-CHLORO-2,4-DIMETHOXYPHENYL ISOCYANATE | 0.7214 | 0.1385 | 0.0716 | 0.1091 | 0.4337 | 0.7176 | 0.4579 | 0.6935 |
| 598 | 3,5-DICHLOROPHENYL ISOCYANATE | 0.6604 | 0.106 | 0.0931 | 0.1802 | 0.4473 | 0.7304 | 0.4414 | 0.6873 |
| 599 | 5-CHLORO-2-METHOXYPHENYL ISOCYANATE | 0.5286 | 0.113 | 0.057 | 0.1062 | 0.4621 | 0.7468 | 0.4694 | 0.4146 |
| 600 | 3,4,5-TRIMETHOXYPHENYL ISOCYANATE | 0.636 | 0.1275 | 0.0592 | 0.1148 | 0.4942 | 0.7509 | 0.523 | 0.7049 |
| 601 | 3,5-DIMETHOXYPHENYL ISOCYANATE | 0.6032 | 0.1015 | 0.0839 | 0.1171 | 0.4479 | 0.7324 | 0.5068 | 0.6608 |
| 602 | 3-(METHYLTHIO)PHENYL ISOCYANATE | 0.7208 | 0.0708 | 0.0715 | 0.0954 | 0.4626 | 0.7488 | 0.4867 | 0.3239 |
| 603 | 3,5-DIMETHYLPHENYL ISOCYANATE | 0.7576 | 0.1096 | 0.088 | 0.1073 | 0.4382 | 0.6381 | 0.4942 | 0.5342 |
| 604 | 2-METHOXY-5-METHYLPHENYL ISOCYANATE | 0.721 | 0.0987 | 0.0217 | 0.1216 | 0.4154 | 0.6463 | 0.4118 | 0.3875 |
| 605 | 4-IODOPHENYL ISOCYANATE | 0.5297 | 0.0883 | 0.0413 | 0.0881 | 0.4478 | 0.6757 | 0.1696 | 0.4612 |
| 606 | 4-PHENOXYPHENYL ISOCYANATE | 0.5906 | 0.1005 | 0.0936 | 0.0609 | 0.4485 | 0.6619 | 0.4136 | 0.4024 |
| 607 | 4-(METHYLTHIO)PHENYL ISOCYANATE | 0.4779 | 0.0937 | 0.1195 | 0.1086 | 0.4006 | 0.737 | 0.4584 | 0.5003 |
| 608 | 4-ISOPROPYLPHENYL ISOCYANATE | 0.5101 | 0.0769 | 0.0509 | 0.2092 | 0.4664 | 0.6183 | 0.407 | 0.4313 |
| 609 | OCTYL ISOCYANATE | 0.9398 | 0.2845 | 0.1001 | 0.1300 | 0.486 | 1.4104 | 0.4526 | 0.4872 |
| 610 | 2,4,6-TRIMETHYLPHENYL ISOCYANATE | 0.7957 | 0.1156 | 0.067 | 0.1761 | 0.3983 | 0.6478 | 0.2829 | 0.2392 |
| 611 | 2-ISOPROPYL-6-METHYLPHENYL ISOCYANATE | 0.6618 | 0.1211 | 0.0738 | 0.0693 | 0.3989 | 0.577 | 0.3896 | 0.186 |
| 612 | 2,6-DIETHYLPHENYL ISOCYANATE | 0.5731 | 0.1098 | 0.0834 | 0.1372 | 0.4013 | 0.5009 | 0.4077 | 0.3754 |
| 613 | 4-(TRIFLUOROMETHOXY)PHENYL ISOCYANATE | 0.3959 | 0.0939 | 0.094 | 0.1096 | 0.4692 | 0.7275 | 0.454 | 0.4577 |
| 614 | 4-(TRIFLUOROMETHYLTHIO)PHENYL ISOCYANATE | 0.5944 | 0.1932 | 0.0353 | 0.0783 | 0.4089 | 0.7622 | 0.4608 | 0.4214 |
| 615 | 2-CHLORO-5-(TRIFLUOROMETHYL)PHENYL ISOCYANATE | 0.7326 | 0.105 | 0.0647 | 0.0876 | 0.4005 | 0.7298 | 0.2464 | 0.4005 |
| 616 | 2-CHLORO-6-METHYLPHENYL ISOCYANATE | 0.5883 | 0.1192 | 0.0613 | 0.1059 | 0.486 | 0.7034 | 0.3467 | 0.0977 |
| 617 | 2,4,5-TRIMETHYLPHENYL ISOCYANATE | 0.5944 | 0.1185 | 0.0966 | 0.1776 | 0.4417 | 0.6765 | 0.6212 | 0.4493 |
| 618 | 2-TERT-BUTYL-6-METHYLPHENYL ISOCYANATE | 0.8171 | 0.1604 | 0.0643 | 0.0848 | 0.4026 | 0.4572 | 0.1104 | 0.1466 |
| 619 | 3-CHLORO-2-METHOXYPHENYL ISOCYANATE | 0.5302 | 0.1404 | 0.0814 | 0.1427 | 0.459 | 0.782 | 0.4478 | 0.4052 |
| 620 | 3-CHLORO-4-FLUOROPHENYL ISOCYANATE | 0.4591 | 0.0945 | 0.1072 | 0.1099 | 0.4595 | 0.7624 | 0.4699 | 0.4507 |
| 621 | 4-BROMO-2,6-DIMETHYLPHENYL ISOCYANATE | 0.5464 | 0.13 | 0.1132 | 0.1166 | 0.4638 | 0.6462 | 0.4518 | 0.4093 |
| 622 | 2,6-DIBROMO-4-FLUOROPHENYL ISOCYANATE | 0.391 | 0.1774 | 0.0342 | 0.1319 | 0.401 | 0.7821 | 0.4095 | 0.4055 |
| 623 | PHENETHYL ISOCYANATE | 0.8483 | 0.2427 | 0.1198 | 0.1491 | 0.4586 | 1.256 | 0.4523 | 0.4349 |
| 624 | 2,4-DICHLOROBENZYL ISOCYANATE | 0.8151 | 0.1546 | 0.1385 | 0.1366 | 0.5296 | 0.7782 | 0.5995 | 0.7227 |
| 625 | 2-(METHYLTHIO)PHENYL ISOCYANATE | 0.5143 | 0.0504 | 0.0428 | 0.2408 | 0.4157 | 0.7048 | 0.4431 | 0.2206 |
| 626 | 2-BIPHENYLYL ISOCYANATE | 0.5349 | 0.0985 | 0.0553 | 0.0910 | 0.4516 | 0.6602 | 0.2644 | 0.3317 |
| 627 | 3-IODOPHENYL ISOCYANATE | 0.6515 | 0.1149 | 0.0254 | 0.1153 | 0.4593 | 0.6019 | 0.4004 | 0.4163 |
| 628 | 4-BIPHENYLYL ISOCYANATE | 0.6505 | 0.1266 | 0.0859 | 0.1763 | 0.4478 | 0.6759 | 0.5337 | 0.6352 |
| 629 | 1-(4-BROMOPHENYL)ETHYL ISOCYANATE | 0.6759 | 0.1045 | 0.1104 | 0.1413 | 0.3993 | 0.8374 | 0.5492 | 0.639 |
| 630 | 3-ISOCYANATOPROPYLTRIETHOXYSILANE | 0.781 | 0.1447 | 0.0601 | 0.1449 | 0.4447 | 0.7711 | 0.68 | 0.63 |
| 631 | 2,6-DICHLOROPYRID-4-YLISOCYANATE | 0.3357 | 0.0929 | 0.0374 | 0.2234 | 0.464 | 0.4699 | 0.4956 | 0.4817 |
| 632 | 2-BROMO-4,6-DIFLUOROPHENYL ISOCYANATE | 0.3853 | 0.3034 | 0.0332 | 0.1377 | 0.4981 | 0.7634 | 0.3552 | 0.4703 |
| 633 | (R)-(+)-1-PHENYLETHYL ISOCYANATE | 1.1374 | 0.0968 | 0.1314 | 0.1229 | 0.3998 | 0.7987 | 0.6867 | 0.6773 |
| 634 | 1-(1-NAPHTHYL)ETHYL ISOCYANATE | 0.6728 | 0.096 | 0.1357 | 0.0961 | 0.3994 | 0.776 | 0.6416 | 0.6752 |
| 635 | 3,4-DIFLUOROPHENYL ISOCYANATE | 0.5316 | 0.0918 | 0.1369 | 0.1027 | 0.3697 | 0.6019 | 0.3812 | 0.3829 |
| 636 | 3-ISOPROPENYL-ALPHA,ALPHA-DIMETHYLBENZYL ISOCYANATE | 0.8534 | 0.0668 | 0.1206 | 0.1723 | 0.3914 | 0.807 | 0.5119 | 0.5786 |
| 637 | 2-(TRIFLUOROMETHOXY)PHENYL ISOCYANATE | 0.4523 | 0.1001 | 0.1084 | 0.1736 | 0.4919 | 0.7178 | 0.3949 | 0.3472 |
| 638 | 1-ADAMANTYL ISOCYANATE | 1.1437 | 0.1182 | 0.1838 | 0.3750 | 0.5557 | 1.0394 | 0.6603 | 0.6336 |
| 639 | 1,1,3,3-TETRAMETHYLBUTYL ISOCYANATE | 1.109 | 0.1097 | 0.0803 | 0.1382 | 0.387 | 1.0645 | 0.6671 | 0.6077 |
| 640 | 4-BROMO-2-FLUOROPHENYL ISOCYANATE | 0.3947 | 0.1083 | 0.0481 | 0.1094 | 0.4643 | 0.763 | 0.4426 | 0.5667 |
| 641 | 2-FLUORO-5-METHYLPHENYL ISOCYANATE | 0.4424 | 0.1073 | 0.0694 | 0.1698 | 0.4776 | 0.7708 | 0.4446 | 0.5312 |
| 642 | 2,3,4-TRIFLUOROPHENYL ISOCYANATE | 0.9257 | 0.163 | 0.0954 | 0.1493 | 0.4571 | 0.7804 | 0.4449 | 0.5111 |
| 643 | 4-(DIMETHYLAMINO)PHENYL ISOCYANATE | 0.5244 | 0.1365 | 0.0726 | 0.1531 | 0.4774 | 0.7787 | 0.6345 | 0.6669 |
| 644 | 2-(DIFLUOROMETHOXY)PHENYL ISOCYANATE | 0.6934 | 0.1497 | 0.0594 | 0.2253 | 0.4678 | 0.7701 | 0.532 | 0.3925 |
| 645 | 4-(DIFLUOROMETHOXY)PHENYL ISOCYANATE | 0.7621 | 0.1233 | 0.0703 | 0.1651 | 0.4521 | 0.7201 | 0.558 | 0.6245 |
| 646 | 2-CHLOROBENZYL ISOCYANATE | 0.8213 | 0.2136 | 0.1897 | 0.1704 | 0.6774 | 1.0548 | 0.5373 | 0.7148 |
| 647 | 4-FLUOROBENZYL ISOCYANATE | 0.9973 | 0.2161 | 0.1757 | 0.1925 | 0.5137 | 0.7897 | 0.4974 | 0.6074 |
| 648 | 4-METHOXYBENZYL ISOCYANATE | 0.7301 | 0.2021 | 0.1636 | 0.2216 | 0.4744 | 0.8084 | 0.5537 | 0.719 |
| 649 | 4-FLUORO-2-(TRIFLUOROMETHYL)PHENYL-ISOCYANATE | 0.4066 | 0.0944 | 0.0717 | 0.1451 | 0.5543 | 0.7581 | 0.1094 | 0.5099 |
| 650 | 2,6-DIBROMO-4-ISOPROPYLPHENYL ISOCYANATE | 0.3894 | 0.125 | 0.0461 | 0.1033 | 0.4346 | 0.7307 | 0.1975 | 0.4574 |
| 651 | 3-PYRIDYL ISOCYANATE | 0.3692 | 0.1585 | 0.066 | 0.3655 | 0.491 | 0.6084 | 0.2017 | 0.069 |

EXAMPLE 652

Synthesis of Catalyst Derived from t-Butyl Isocyanate

A 500-mL round-bottomed flask was charged with 536 mg (5.40 mmol) of t-butylisocyanate dissolved in ca. 30 mL THF. Then $(t-Bu)_2P-CH_2Li$ (898 mg, 5.40 mmol) dissolved in ca. 30 mL THF was added. The reaction was stirred for one h after which time, a solution of $(Ni(C_3H_5)Cl)_2$ (730 mg, 2.70 mmol) in THF (ca. 30 mL) was added and stirred for an additional one h and the solvent removed. The residue was washed with hexane and dried in vacuo to yield 1.80 g (83%) of a purple powder. $^1$H-NMR ($CD_2Cl_2$, 23° C., 300 MHz): d 6.0–4.0 (broad signals), 4.0–2.0 (broad signals), 1.0–0.0 (broad signals, t-Bu) $^{31}$P-NMR ($CD_2Cl_2$, 23° C., 300 MHz): δ 46.7 (s).

EXAMPLES 653–673

Figure 3:
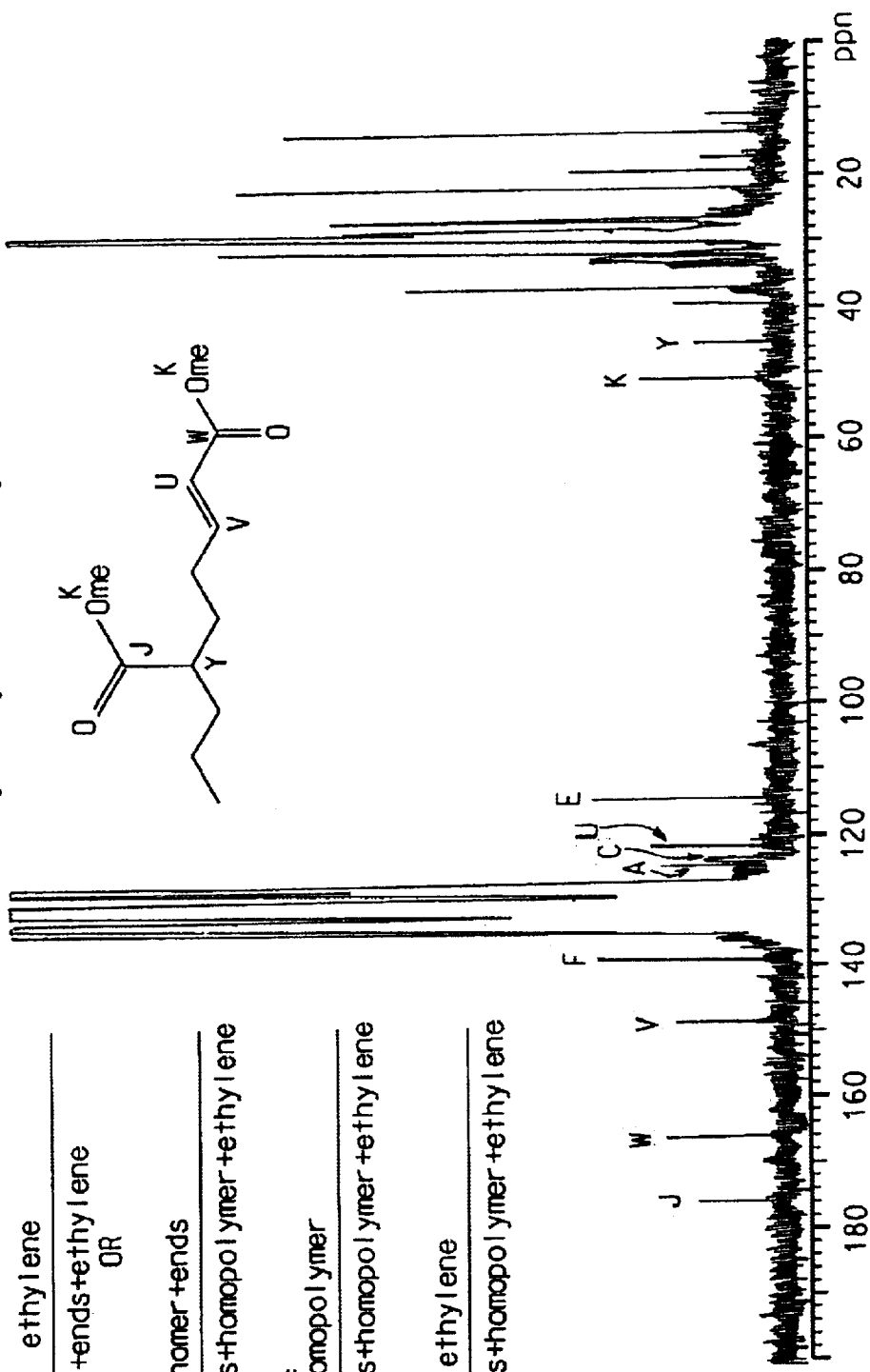
FIG. 3 shows the $^{13}C$ NMR of a copolymer of ethylene and methyl acrylate (MA) which also contains some homopolymer of MA, and which shows assignments of various NMR peaks. Also shown are formulas for calculations of the amount of homopolymer present and the amount of MA incorporated in the copolymer.

Toluene was purified according to R. H. Grubbs et. al., *Organometallics*, 1996, 15, p. 1518–1520. Methyl acrylate was sparged with nitrogen and passed through a column of activated neutral alumina in the drybox before use. In a drybox 1.77 g NaBAF, $B(C_6F_5)_3$ (see Table 66), methyl acrylate (see Table 66) and all but 20 mL of the toluene were combined. The total volume of the reaction mixture was 100 mL and the amount of methyl acrylate and toluene were calculated on this basis. This solution was transferred to a metal addition cylinder in the drybox, and the solution was then charged to a nitrogen-purged 450 mL jacketed autoclave. In the drybox 45 (0.0286 g) was dissolved in the remaining 20 mL of toluene and mixed for 30 minutes on a lab Vibramixer®. This solution was transferred via cannula under positive nitrogen pressure to a small metal addition cylinder attached to the autoclave. While stirring, the autoclave was charged with ethylene to 350 kPa and vented three times. The reactor and its contents were heated to the reaction temperature (Table 66) using a steam/water mixture in the autoclave jacket. After achieving the desired operating temperature, the autoclave was pressurized with ethylene to 350 to 690 kPa below the desired operating pressure (Table 66). The catalyst addition cylinder was charged with ethylene to the desired operating pressure, and the catalyst solution was then pressure injected to begin the polymerization. Ethylene was fed to maintain a constant pressure. After 6 h, the reaction was cooled to RT. All volatiles were removed from the reaction solution using a rotary evaporator. The evaporated residue was washed with three 50–100 mL portions of methanol with decanting of the methanol into a fritted glass filter after each wash. The methanol insoluble solids were then transferred to the filter with methanol and washed on the filter with additional methanol. The solids were dried for 18 hours at 60° C. in a vacuum oven. Molecular weights of the isolated polymer samples were determined by GPC. $^{13}$C NMR of the dried polymers was used to calculate the weight % of homopoly(methyl acrylate), the mole % MA content of the ethylene/methyl acrylate copolymer, and the amount of branching in the polymer. (See FIG. 3 for $^{13}$C peak assignments and formulas for the mole % calculations.) Weight % calculations were done using the mole % values and the molecular weights of the components.

TABLE 66

| Ex. | Temp (° C.) | E Press. (MPa) | Methyl Acrylate (vol %) | $B(C_6F_5)_3$ (mole equiv/Ni) | Isolated Yield (g) | Wt % Homopoly MA | Mole % MA in copolymer | Branching $CH_3$/1000 $CH_2$ | Mw | Mw/Mn |
|---|---|---|---|---|---|---|---|---|---|---|
| 653 | 100 | 4.1 | 20.0 | 200 | 0.7 | 65.65 | 1.60 | 32.3 | 2353 | 1.96 |
| 654 | 140 | 6.9 | 5.0 | 100 | 13.5 | 3.26 | 0.68 | 88.1 | 6273 | 2.11 |
| 655 | 100 | 6.9 | 5.0 | 200 | 3.67 | 0.01 | 0.57 | 33.0 | 17478 | 2.02 |
| 656 | 140 | 6.9 | 5.0 | 300 | 24.96 | 2.22 | 0.31 | 86.7 | 6031 | 2.00 |
| 657 | 100 | 6.9 | 20.0 | 300 | 0.72 | 14.46 | 1.17 | 59.2 | 4427 | 1.98 |
| 658 | 100 | 6.9 | 20.0 | 100 | 1.94 | 69.63 | 1.89 | 52.9 | 6494 | 2.33 |
| 659 | 140 | 6.9 | 20.0 | 200 | 7.3 | 48.59 | 1.41 | 86.9 | 3896 | 2.53 |
| 660 | 140 | 6.9 | 5.0 | 100 | 13.67 | 5.60 | 0.58 | 94.6 | 5850 | 2.15 |
| 661 | 100 | 6.9 | 20.0 | 100 | 1.85 | 74.44 | 1.96 | 37.1 | 5678 | 2.42 |
| 662 | 100 | 4.1 | 5.0 | 100 | 1.16 | 2.14 | 0.92 | 47.3 | 13332 | 1.97 |
| 663 | 100 | 4.1 | 5.0 | 300 | 1.59 | 2.13 | 1.04 | 46.2 | 11085 | 2.07 |
| 664 | 120 | 5.5 | 12.5 | 100 | 6.05 | 22.72 | 1.69 | 56.0 | 5888 | 1.95 |
| 665 | 120 | 4.1 | 5.0 | 200 | 7.59 | 2.71 | 0.88 | 68.8 | 7429 | 2.03 |
| 666 | 100 | 5.5 | 5.0 | 200 | 2.74 | 1.53 | 0.76 | 37.3 | 13347 | 2.02 |
| 667 | 140 | 4.1 | 5.0 | 200 | 14.44 | 6.91 | 1.00 | 99.2 | 4192 | 2.36 |
| 668 | 140 | 4.1 | 20.0 | 300 | 4.86 | 54.01 | 3.20 | 97.4 | 2298 | 1.99 |
| 669 | 140 | 4.1 | 20.0 | 100 | 4.0 | 74.77 | 1.15 | 121.5 | 2144 | 2.17 |
| 670 | 100 | 4.1 | 5.0 | 100 | 1.47 | 7.61 | 1.24 | 45.2 | 11389 | 2.57 |
| 671 | 100 | 4.1 | 5.0 | 300 | 2.58 | 1.82 | 0.64 | 42.1 | 8923 | 2.25 |
| 672 | 100 | 4.1 | 12.5 | 200 | 0.71 | 13.88 | 1.93 | 43.2 | 4858 | 1.82 |
| 673 | 140 | 4.1 | 20.0 | 100 | 4.6 | 75.97 | 2.60 | 110.5 | 2200 | 3.07 |

EXAMPLES 674–769

All reactions were performed under a nitrogen atmosphere. The additives were obtained from commercial sources and used as received. Solvents were purchased anhydrous and distilled from $P_2O_5$ (chlorobenzene), sodium benzophenone ketyl (THF), $CaH_2$ (acetonitrile) or used as received (TCB, methanol).

The additives were prepared as solutions (0.0375 M) in THF (Ex. 674–722), acetonitrile (Ex. 723–739), methanol (Ex. 740–754) and water (Ex. 755–758). These solutions were prepared in glass vials capped with Teflon® lined silicone septa to maintain inert atmosphere and prevent evaporation.

The nickel compounds used are shown below.

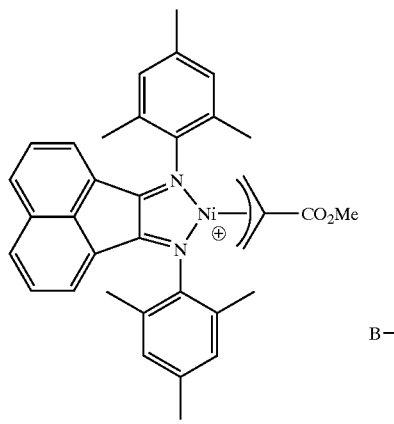
A

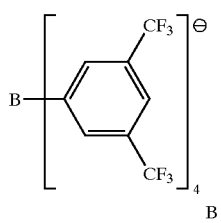
B

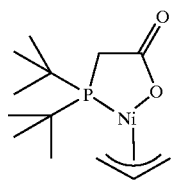
C

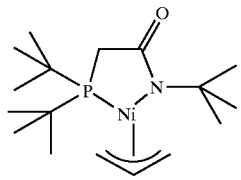

General Polymerization Procedure: In a nitrogen flushed box, a 150 μL or 750 μL of additive solution (0.0375 M) was added to a septum sealed 2 mL glass vial. The septum cap was removed and the solvent was removed under a nitrogen gas stream and the sample was dried for 20 min in a vacuum chamber. Additives for Ex. 763–773 were added to separate 2 mL glass vials by weighing solid (0.0056 mmol or 0.028 mmol) directly into the vial. The vial was recapped and a solution (3 mL of THF) of catalyst A, B or C was added to the vial. Catalysts B and C may contain 0–2 equiv of LiCl and we have assumed 1 equiv for the purposes of calculating a molecular weight. The septum cap was removed and the solvent was removed under a nitrogen gas stream and the sample was dried for 20 min in a vacuum chamber. The vial was recapped with a septum cap. A 0.300 mL polymerization solution containing solvent, cocatalyst(s) and acrylate monomer, if any, was added into each vial. Each vial was placed into a high-pressure reactor and pressurized with ethylene to the desired pressure and temperature for a total of 18 h. For ethylene polymerization experiments the volatiles were removed from each vial in a heated (approx. 50° C.) vacuum chamber. The weight of the vial was measured and the tare weight of the vial was subtracted to calculate the weight of polymer generated (catalyst residue is not taken into consideration). For ethylene copolymerization experiments the vial is weighed directly and the tare weight of the vial was subtracted to calculate the relative weight of polymer generated (the solvent, monomer and catalyst residue are not subtracted from this weight). The amounts of polymers produced (in g) are given in Table 67. Polymerization conditions are given below.

Condition 1: Catalyst B with 5 equiv of additive and 0.300 mL of chlorobenzene. The polymerization was conducted at 6.9 MPa of ethylene at RT for 18 h.

Condition 2: Catalyst B with 1 equiv of additive, 5 equiv of $B(C_6F_5)_3$ and 0.300 mL of chlorobenzene. The polymerization was conducted at 1.0 MPa of ethylene at RT for 18 h.

Condition 3: Catalyst B with 5 equiv of additive, 1 equiv of NaBAF and 0.300 mL of chlorobenzene solution (the chlorobenzene solution contained 2.5 volume % of diethyl ether). The polymerization was conducted at 6.9 MPa ethylene at RT for 18 h.

Condition 4: Catalyst A with 1 equiv of additive, 5 equiv of $B(C_6F_5)_3$, 5 equiv of $LiB(C_6F_5)_4$ and 0.300 mL of TCB solution (the TCB solution contained 20 volume % of EGPEA). The polymerization was conducted at 6.9 MPa of ethylene at 100° C. for 18 h.

Condition 5: Catalyst B with 1 equiv of additive, 5 equiv of $B(C_6F_5)_3$, 5 equiv of $LiB(C_6F_5)_4$ and 0.300 mL of 1,2,4-TCB solution (the 1,2,4-TCB solution contained 20 volume % of EGPEA). The polymerization was conducted at 6.9 MPa of ethylene at 100° C. for 18 h.

Condition 6: Catalyst A with 5 equiv of additive, 5 equiv of $LiB(C_6F_5)_4$ and 0.300 mL of TCB solution (the TCB solution contained 20 volume % of EGPEA). The polymerization was conducted at 6.9 MPa of ethylene at 100° C. for 18 h.

Condition 7: Catalyst C with 1 equiv of additive, 5 equiv of $B(C_6F_5)_3$ and 0.300 mL of chlorobenzene. The polymerization was conducted at 3.5 MPa of ethylene at RT for 18 h.

TABLE 67

| Ex. | ADDITIVE | CONDITION | | | | | | |
|---|---|---|---|---|---|---|---|---|
| | | 1 | 2 | 3 | 4 | 5 | 6 | 7 |
| 674 | 4-CHLOROPHENYLBORONIC ACID | 0.090 | 0.568 | 0.123 | 0.635 | 0.707 | 0.428 | 0.125 |
| 675 | ALUMINUM CHLORIDE | 0.296 | 0.076 | 0.138 | 0.472 | 0.405 | 0.100 | 0.261 |
| 676 | ALUMINUM ISOPROPOXIDE | 0.009 | 0.188 | 1.000 | 0.668 | 0.597 | 0.430 | 0.177 |
| 677 | ALUMINUM PHENOXIDE | 0.020 | 0.706 | 0.482 | 0.614 | 0.694 | 0.412 | 0.175 |
| 678 | ALUMINUM TRIS(2,2,6,6-TETRAMENTYL-3,5-HEPTANEDIONATE) | 0.105 | 0.067 | 0.059 | 0.572 | 0.612 | 0.422 | 0.133 |
| 679 | ALUMINUM TRI-SEC-BUTOXIDE | 0.028 | 0.169 | 0.348 | 0.691 | 0.691 | 0.439 | 0.162 |
| 680 | BORON TRIFLUORIDE TERT-BUTYL METHYL ETHERATE | 0.187 | 0.814 | 0.256 | 0.684 | 0.736 | 0.414 | 0.312 |
| 681 | COPPER(I) ACETATE | 0.004 | 0.402 | 0.011 | 0.680 | 0.749 | 0.409 | 0.150 |
| 682 | COPPER(I) BROMIDE | 0.005 | 0.426 | 0.032 | 0.671 | 0.667 | 0.423 | 0.134 |
| 683 | COPPER(II) ACETATE | 0.009 | 0.296 | 0.013 | 0.685 | 0.681 | 0.429 | 0.073 |
| 684 | COPPER(II) BROMIDE | 0.005 | 0.174 | 0.012 | 0.602 | 0.456 | 0.390 | 0.123 |
| 685 | COPPER(II) CHLORIDE | 0.004 | 0.218 | 0.072 | 0.603 | 0.137 | 0.449 | 0.146 |

TABLE 67-continued

| Ex. | ADDITIVE | CONDITION 1 | 2 | 3 | 4 | 5 | 6 | 7 |
|---|---|---|---|---|---|---|---|---|
| 686 | COPPER(II) TRIFLUOROMETHANESULFONATE | 0.057 | 0.052 | 0.042 | 0.618 | 0.789 | 0.460 | 0.073 |
| 687 | DIBUTYLTIN DICHLORIDE | 0.011 | 0.414 | 0.209 | 0.623 | 0.559 | 0.431 | 0.126 |
| 688 | DIBUTYLTIN DIACETATE | 0.012 | 0.525 | 0.324 | 0.501 | 0.775 | 0.424 | 0.107 |
| 689 | DIETHYL(3-PYRIDYL)BORANE | 0.008 | 0.392 | 0.018 | 0.654 | 0.752 | 0.433 | 0.249 |
| 690 | DIMESITYLBORON FLUORIDE | 0.330 | 0.237 | 0.471 | 0.685 | 0.759 | 0.478 | 0.249 |
| 691 | DIPHENYLZINC | 0.011 | 0.431 | 0.242 | 0.499 | 0.571 | 0.432 | 0.635 |
| 692 | INDIUM(III) TRIFLUOROMETHANESULFONATE | 0.494 | 0.094 | 0.598 | 0.532 | 0.767 | 0.445 | 0.257 |
| 693 | LITHIUM TRIFLUOROMETHANESULFONATE | 0.018 | 0.532 | 0.019 | 0.694 | 0.765 | 0.451 | 0.152 |
| 694 | SODIUM TETRAPHENYLBORATE | 0.237 | 0.081 | 0.046 | 0.610 | 0.775 | 0.494 | 0.183 |
| 695 | TIN(II) ACETATE | 0.015 | 0.233 | 0.385 | 0.453 | 0.454 | 0.416 | 0.089 |
| 696 | TIN(II) BROMIDE | 0.104 | 0.461 | 0.410 | 0.548 | 0.430 | 0.423 | 0.112 |
| 697 | TIN(II) FLUORIDE | 0.001 | 0.568 | 0.028 | 0.648 | 0.734 | 0.439 | 0.179 |
| 698 | TRIMESITYLBORANE | 0.014 | 0.536 | 0.032 | 0.645 | 0.725 | 0.456 | 0.258 |
| 699 | TRIS(4-ETHOXYPHENYL)BISMUTH | 0.019 | 0.095 | 0.035 | 0.620 | 0.742 | 0.438 | 0.145 |
| 700 | TRIS(DIMETHYLAMINO)BORANE | 0.002 | 0.109 | 0.022 | 0.639 | 0.735 | 0.421 | 0.116 |
| 701 | ZINC(II) BROMIDE | 0.381 | 0.104 | 0.291 | 0.588 | 0.519 | 0.436 | 0.211 |
| 702 | ZINC(II) CHLORIDE | 0.207 | 0.106 | 0.196 | 0.538 | 0.483 | 0.434 | 0.121 |
| 703 | 1-NAPHTHALENEBORONIC ACID | 0.010 | 0.090 | 0.044 | 0.706 | 0.795 | 0.517 | 0.092 |
| 704 | PHENYLBORONIC ACID | 0.011 | 0.082 | 0.204 | 0.622 | 0.688 | 0.522 | 0.147 |
| 705 | TRIPHENYLBISMUTH | 0.015 | 0.054 | 0.025 | 0.560 | 0.719 | 0.429 | 0.248 |
| 706 | SAMARIUM(II) IODIDE | 0.030 | 0.100 | 0.028 | 0.504 | 0.411 | 0.438 | 0.156 |
| 707 | SODIUM TETRAKIS(P-TOLYL)BORATE | 0.064 | 0.327 | 0.024 | 0.703 | 0.839 | 0.470 | 0.142 |
| 708 | AMMONIUM CERIUM(IV) NITRATE | 0.019 | 0.094 | 0.026 | 0.609 | 0.425 | 0.440 | 0.123 |
| 709 | 2-METHOXY PHENYLBORONIC ACID | 0.009 | 0.121 | 0.392 | 0.690 | 0.762 | 0.490 | 0.120 |
| 710 | 4-FLUOROPHENYL BORONIC ACID | 0.049 | 0.825 | 0.144 | 0.705 | 0.757 | 0.528 | 0.109 |
| 711 | 4-METHOXYPHENYL BORONIC ACID | 0.016 | 0.574 | 0.121 | 0.732 | 0.786 | 0.494 | 0.104 |
| 712 | ALUMINUM ACETYLACETONATE | 0.017 | 0.088 | 0.019 | 0.644 | 0.664 | 0.432 | 0.115 |
| 713 | ALUMINUM HEXAFLUOROACETYLACETONATE | 0.153 | 0.479 | 0.562 | 0.654 | 0.716 | 0.445 | 0.071 |
| 714 | ALUMINUM TRIFLUOROMETHANESULFONATE | 0.021 | 0.078 | 0.027 | 0.633 | 0.594 | 0.422 | 0.105 |
| 715 | DIMETHYLANILINIUMTETRAKIS(PENTAFLUORO PHENYL)BORATE | 0.210 | 0.852 | 0.548 | 0.638 | 0.713 | 0.403 | 0.308 |
| 716 | LITHIUMTETRAKIS(PENTAFLUOROPHENYL) BORATE DIETHERATE | 0.064 | 0.967 | 0.037 | 0.667 | 0.736 | 0.461 | 0.138 |
| 717 | YTTERBIUM (III) TRIFLUOROMETHANESULFONATE HYDRATE | 0.672 | 0.094 | 0.242 | 0.660 | 0.484 | 0.453 | 0.087 |
| 718 | TIN(II) ACETYLACETONATE | 0.079 | 0.253 | 0.424 | 0.358 | 0.450 | 0.423 | 0.233 |
| 719 | TIN (II) HEXAFLUOROACETYLACETONATE | 0.231 | 0.260 | 0.608 | 0.429 | 0.417 | 0.431 | 0.372 |
| 720 | P-TOLYLBORONIC ACID | 0.010 | 0.632 | 0.221 | 0.669 | 0.749 | 0.509 | 0.128 |
| 721 | TRIS(4-TOLYL)BISMUTH | 0.016 | 0.191 | 0.028 | 0.689 | 0.736 | 0.428 | 0.143 |
| 722 | TRIPHENYL ALUMINUM | 0.670 | 0.370 | 0.418 | 0.664 | 0.513 | 0.430 | 1.036 |
| 723 | ALUMINUM (III) PHENOXIDE | 0.003 | 0.552 | 0.039 | 0.664 | 0.774 | 0.452 | 0.420 |
| 724 | CERIUM(III) FLUORIDE | 0.002 | 0.597 | 0.038 | 0.603 | 0.714 | 0.435 | 0.177 |
| 725 | COPPER(I) BROMIDE | 0.047 | 0.279 | 0.133 | 0.625 | 0.463 | 0.449 | 0.217 |
| 726 | COPPER(I) CHLORIDE | 0.009 | 0.193 | 0.147 | 0.683 | 0.517 | 0.464 | 0.158 |
| 727 | COPPER(I) IODIDE | 0.118 | 0.642 | 0.030 | 0.655 | 0.684 | 0.453 | 0.136 |
| 728 | COPPER(II) ACETATE | 0.007 | 0.201 | 0.010 | 0.663 | 0.686 | 0.418 | 0.055 |
| 729 | COPPER(II) BROMIDE | 0.009 | 0.091 | 0.015 | 0.661 | 0.419 | 0.429 | 0.088 |
| 730 | COPPER(II) CHLORIDE | 0.005 | 0.185 | 0.012 | 0.741 | 0.435 | 0.419 | 0.111 |
| 731 | COPPER(II) TRIFLUOROMETHANESULFONATE | 0.018 | 0.061 | 0.022 | 0.739 | 0.833 | 0.459 | 0.065 |
| 732 | SAMARIUM(III) CHLORIDE | 0.003 | 0.437 | 0.140 | 0.699 | 0.727 | 0.432 | 0.143 |
| 733 | TIN(II)TRIFLUOROMETHANESULFONATE | 0.849 | 0.084 | 0.661 | 0.421 | 0.530 | 0.442 | 0.106 |
| 734 | YTTRIUM(III) CHLORIDE | 0.151 | 0.101 | 0.060 | 0.442 | 0.351 | 0.377 | 0.212 |
| 735 | ZINC(II) TRIFLUOROMETHANESULFONATE | 0.651 | 0.364 | 0.529 | 0.652 | 0.599 | 0.444 | 0.172 |
| 736 | YTTRIUM(III) TRIFLUOROMETHANESULFONATE | 0.561 | 0.105 | 0.234 | 0.723 | 0.564 | 0.463 | 0.169 |
| 737 | TIN(II) OXIDE | 0.002 | 0.656 | 0.028 | 0.699 | 0.766 | 0.450 | 0.145 |
| 738 | TRIFLUOROMETHANESULFONIMIDE | 0.014 | 0.299 | 0.019 | 0.714 | 0.760 | 0.438 | 0.107 |
| 739 | CALCIUM(II) TRIFLUOROMETHANESULFONATE | 0.335 | 0.101 | 0.057 | 0.728 | 0.783 | 0.454 | 0.125 |
| 740 | CERIUM(III) CHLORIDE | 1.028 | 0.091 | 0.491 | 0.635 | 0.418 | 0.167 | 0.202 |
| 741 | COPPER(II) CHLORIDE | 0.008 | 0.072 | 0.014 | 0.780 | 0.428 | 0.444 | 0.085 |
| 742 | COPPER(II) TRIFLUOROMETHANESULFONATE | 0.018 | 0.065 | 0.017 | 0.709 | 0.844 | 0.449 | 0.086 |
| 743 | LANTHANUM(III) CHLORIDE | 1.143 | 0.085 | 0.634 | 0.643 | 0.469 | 0.448 | 0.133 |
| 744 | LANTHANUM(III) TRIFLUOROMETHANESULFONATE | 0.420 | 0.124 | 0.332 | 0.613 | 0.726 | 0.417 | 0.116 |
| 745 | MAGNESIUM(II) TRIFLUOROMETHANESULFONATE | 0.342 | 0.125 | 0.499 | 0.644 | 0.744 | 0.458 | 0.129 |
| 746 | SCANDIUM(III) TRIFLUOROMETHANESULFONATE | 0.469 | 0.082 | 0.401 | 0.637 | 0.270 | 0.444 | 0.118 |
| 747 | TIN(II) TRIFLUOROMETHANESULFONATE | 0.681 | 0.094 | 0.933 | 0.464 | 0.507 | 0.440 | 0.090 |
| 748 | TRIETHANOLAMINE BORATE | 0.010 | 0.128 | 0.013 | 0.494 | 0.583 | 0.426 | 0.081 |
| 749 | SAMARIUM(III) TRIFLUOROMETHANESUFFONATE | 0.717 | 0.095 | 0.599 | 0.727 | 0.685 | 0.455 | 0.124 |
| 750 | SODIUM TETRAKIS(1-IMIDAZOYL)BORATE | 0.012 | 0.746 | 0.019 | 0.476 | 0.432 | 0.437 | 0.120 |
| 751 | YTTRIUM(III) TRIFLUOROMETHANESULFONATE | 0.506 | 0.091 | 0.313 | 0.751 | 0.563 | 0.468 | 0.111 |
| 752 | TRIFLUOROMETHANESULONIMIDE | 0.012 | 0.363 | 0.017 | 0.738 | 0.779 | 0.446 | 0.077 |
| 753 | TIN(II) ACETYLACETONATE | 0.006 | 0.079 | 0.011 | 0.451 | 0.361 | 0.430 | 0.104 |
| 754 | LANTHANIUM(III) TRISTRIFLUOROACETATE | 0.882 | 0.130 | 0.428 | 0.489 | 0.720 | 0.427 | 0.200 |
| 755 | SAMARIUM(III) CHLORIDE | 0.015 | 0.267 | 0.270 | 0.421 | 0.418 | 0.438 | 0.138 |
| 756 | TIN(II) FLUORIDE | 0.018 | 0.581 | 0.350 | 0.616 | 0.755 | 0.440 | 0.169 |
| 757 | YTTRIUM(III) TRIFLUOROMETHANESULFONATE | 0.277 | 0.107 | 0.248 | 0.699 | 0.536 | 0.465 | 0.105 |
| 758 | CALCIUM(II) TRIFLUOROMETHANESULFONATE | 0.020 | 0.300 | 0.085 | 0.712 | 0.745 | 0.457 | 0.140 |
| 759 | LITHIUM TETRAKIS(PENTAFLUOROPHENYL) BORATE DIETHERATE | 0.074 | 0.233 | 0.028 | 0.700 | 0.709 | 0.469 | 0.199 |
| 760 | SODIUM TETRAKIS(3,5-BIS(TRIFLUOROMETHYL)PHENYL)BORATE | 0.094 | 0.135 | 0.068 | 0.664 | 0.753 | 0.442 | 0.191 |

TABLE 67-continued

| | | CONDITION | | | | | | |
|---|---|---|---|---|---|---|---|---|
| Ex. | ADDITIVE | 1 | 2 | 3 | 4 | 5 | 6 | 7 |
| 761 | DIMETHYLANILINIUM TETRAKIS(PENTAFLUOROPHENYL)BORATE | 0.220 | 0.167 | 0.431 | 0.662 | 0.758 | 0.433 | 0.114 |
| 762 | [AliBu2(Et2O)] + [B(C6F5)3R]−[a] | 1.689 | 0.232 | 1.640 | 0.783 | 0.798 | 0.785 | 1.356 |
| 763 | Li[Al(OC6F5)4][b] | 0.747 | 0.049 | 0.121 | 0.646 | 0.617 | 0.429 | 0.238 |
| 764 | AlMes3THF[c] | 0.395 | 0.090 | 0.316 | 0.297 | 0.383 | 0.424 | 0.301 |
| 765 | AlMe(2,6-t-Bu-4-Me(OC6H2))2[d, g, h] | 0.450 | 0.462 | 0.846 | 0.654 | 0.608 | 0.421 | 0.303 |
| 766 | Al-i-Bu2(OC6F5)[e] | 1.132 | 0.247 | 1.385 | 0.720 | 0.799 | 0.299 | 0.630 |
| 767 | NO ADDITIVE | 0.011 | 0.502 | 0.032 | 0.686 | 0.755 | 0.412 | 0.249 |
| 768 | TRITYL TETRAKIS(3,5-BIS(TRIFLUOROMETHYL)PHENYL)BORATE[f, i] | 0.174 | 0.447 | 0.049 | 0.680 | 0.829 | 0.571 | 0.208 |
| 769 | TRIPHENYLBORON | | 0.610 | 0.648 | 0.685 | 0.625 | 0.429 | 0.268 |

Footnotes for Table 67:
Additives for 762–766 and 768 were synthesized by literature methods:
[a]modification of preparation from WO0011006;
[b]Y. Sun, et al., Organometallics, vol. 19, p. 1625 (2000);
[c]V. Srini, et al., Organometallics, vol. 8, p. 827 (1989);
[d]M. Skowronska-Ptasinska, et al., Journal of Organometallic Chemistry, vol. 160, p. 403 (1978);
[e]D. G. Hendershot, et al., Organometallics, vol. 10, p. 1917 (1991);
[f]S. R. Bahr and P. Boudjouk, Journal of Organic Chemistry, vol. 57, p. 5545 (1992). Substitutions for additives were made in the following experiments:
[g]Conditions 4–7 additive is Li[Al(OCPh(CF3)2)4] synthesized by a literature method, T. J. Barbarich, Thesis, 1998, Colorado State University;
[h]Conditions 5–7.

TABLE 68

Copolymerization Using 0.02 mmole Catalyst, 40 eq B(C6F5)3, 8 mL TCB, 2 mL HA, at 120° C. under 6.9 MPa E for 18 h

| Ex | Catalyst | Sm(OTf)3 | Yield (g) | #Me/ 1000 CH2 | Mole % Comonomer | m.p. (° C.) (ΔHf) | Mw/PDI |
|---|---|---|---|---|---|---|---|
| 770 | 5 | 1 eq | 1.429 | 28 | 0.6 | 118 (96.0) | 9,859/8.8 |
| 771 | 21 | 1 eq | 8.184 | 31 | 1.28 ($^{13}$C) 0.40 IC 0.88 EG | 112 (182.7) | 1,628/2.4 |
| 772 | 39 | 0 eq | 0.216 | 28 | 0.8 | 111 (158.3) 97 | Bimodal First 497,946/2.3 Second MP = 887 |

TABLE 69

Copolymerization Using 0.02 mmole Catalyst, 40 eq B(C6F5)3, 20 eq LiB(C6F5)4, 8 mL TCB, 2 mL HA, at 120° C. under 6.9 MPa E for 18 h

| Ex | Catalyst | Yield (g) | #Me/ 1000CH2 | Mole % Comonomer | m.p. (° C.) (ΔHf) | Mw/PDI |
|---|---|---|---|---|---|---|
| 773 | 5 | 3.998 | 10 | 0.54 ($^{13}$C) 0.25 IC 0.29 EG | 124 (209.5) | 3,567/2.2 |
| 774 | 7 | 1.075 | 19 | 0.38 ($^{13}$C) 0.19 IC 0.19 EG | 112 (191.2) | 1,405/1.8 |
| 775 | 6 | 1.253 | 13 | 0.53 ($^{13}$C) 0.25 IC 0.28 EG | 122 (190.6) | 11,123/10.8 |
| 776 | 2 | 0.461 | 9 | 0.41 ($^{13}$C) 0.20 IC 0.21 EG | 125 (186.6) | 22,311/10.8 |
| 777 | 26 | 0.897 | 11 | 0.61 ($^{13}$C) 0.39 IC 0.22 EG | 118 (172.3) | 3,595/2.1 |

TABLE 70

$^{13}$C NMR Branching Analysis for EGPEA Copolymers

| Ex | Total Me | Me | Et | Pr | Bu | Hex+ & EOC | Am+ & EOC | Bu+ & EOC |
|---|---|---|---|---|---|---|---|---|
| 773 | 10.0 | 1.8 | 1.3 | 0.1 | 1.5 | 8.4 | 6.7 | 6.8 |
| 774 | 18.7 | 3.8 | 1.8 | 0.4 | 0.7 | 11.6 | 11.7 | 12.8 |
| 775 | 12.7 | 2.0 | 1.6 | 0.4 | 0.7 | 7.9 | 8.2 | 8.6 |
| 776 | 9.2 | 1.8 | 2.0 | 0.5 | 1.4 | 7.8 | 4.3 | 4.9 |
| 777 | 11 | 1.5 | 2.5 | 0.4 | 1.1 | 8.2 | 6.9 | 6.8 |

118

EXAMPLE 778

Synthesis of 118

In drybox, 0.3009 40 and 0.487 g tris(3,5-bis(trifluoromethyl))borane were dissolved in 25 mL toluene. This mixture was allowed to stir at RT for 1 h. The mixture was filtered through Celite® and the solvent was evaporated. Brown solid (0.160 g) was obtained. A single crystal was obtained by slowly evaporate the methylene chloride/heptane solution of 40. X-Ray single crystal analysis confirmed the Zwitterionic structure of this catalyst.

TABLE 71

Copolymerization Using 0.02 mmole Catalyst, with a Total Volume of 10 mL of TCB and Polar Monomer, at 80° C. under 3.4 MPa of Ethylene

| Ex. | Catalyst | B(C$_6$F$_5$)$_3$ | Polar Monomer | Polar Monomer Volume (mL) | Yield (g) |
|---|---|---|---|---|---|
| 779 | 2 | 40 eq | (allyl-C(CH$_3$)$_2$-CH$_2$OH) | 2 | 0.010 |
| 780 | 118 | 0 eq | (allyl-C(CH$_3$)$_2$-epoxide) | 3 | 0.345 |
| 781 | 2 | 40 eq | CH$_2$=CH(CH$_2$)$_2$C(O)CH$_3$ | 3 | 0.020 |
| 782 | 2 | 40 eq | (allyl-CH(CO$_2$Et)$_2$) | 3 | 0.556 |
| 783 | 2 | 40 eq | CH$_2$=CH(CH$_2$)$_7$C(CH$_2$O)$_3$CCH$_3$ | 3 | 10.269 |

TABLE 72

Ethylene Polymerization Using 0.01 mmole Catalyst, 20 eq LiB(C$_6$F$_5$)$_4$, 10 mL TCB, at 60° C. under 3.4 MPa Ethylene for 18 h

| Ex | Catalyst | Yield (g) | #Me/1000CH$_2$ | m.p. (° C.) (ΔH$_f$) | Mw/PDI |
|---|---|---|---|---|---|
| 784 | 2 | 1.842 | 8 | 126 (166.2) | 35,425/2.8 |
| 785 | 6 | 1.698 | 5 | 128 (172.7) | 43,111/2.2 |
| 786 | 5 | 4.377 | 16 | 123 (173.9) | 17,351/3.0 |
| 787 | 7 | 9.143 | 70 | 105 (157.2) | 1,636/4.3 |
| 788 | 30 | 0.281 | 17 | 123 (195.5) | 12,383/9.6 |

TABLE 73

Ethylene/CO Copolymerization Using 0.02 mmole Catalyst, 40 eq B(C$_6$F$_5$)$_3$, 10 mL TCB, at 100° C. under 2.8 MPa Ethylene/CO (9:1 molar ratio) for 16 h

| Ex | Catalyst | Yield (g) |
|---|---|---|
| 789 | 21 | 0.345 |
| 790 | 2 | 0.108 |
| 791 | 5 | 0.201 |
| 792 | 4 | 0.024 |
| 793 | 40 | 0.480 |

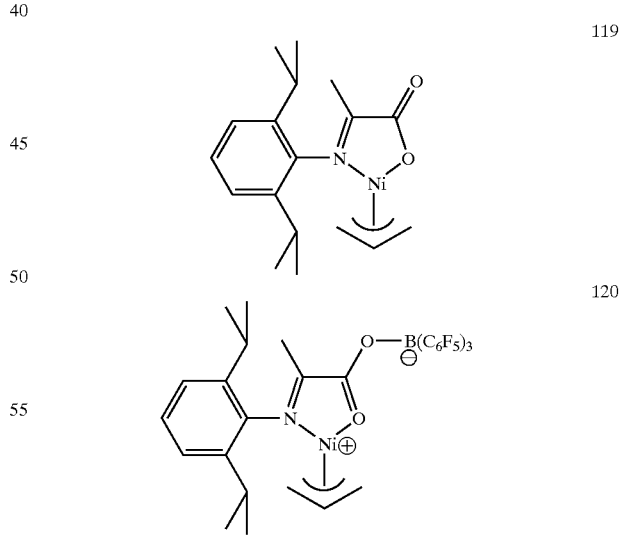

119

120

Methods for the synthesis of these compounds are disclosed in previously incorporated U.S. patent application Ser. No. 09/871,100 filed 31 May 2001, now U.S. Pat. No. 6,506,861, and in U.S. Provisional Patent Application 60/294,794, filed 31 May 2001, the disclosures of which are hereby incorporated by reference herein for all purposes as if fully set forth.

TABLE 74

Copolymerization Using 0.02 mmole Catalyst, 40 eq B(C₆F₅)₃, 6 mL TCB, 4 mL HA, at 100° C. under 6.9 MPa E for 18 h

| Ex. | Catalyst | Yield (g) | #Me/ 1000 CH$_2$ | Mole % HA in Polymer | m.p., (° C.) [ΔH$_f$] | Mw/PDI | TON E/HA |
|---|---|---|---|---|---|---|---|
| 794 | 120 | 2.067* | 24 | 3.9 | 106 [120] | 7,664/2.3 | 3,009/121 |

*In addition to 2.067 g copolymer, HA homopolymer (0.567 g) was also produced.

TABLE 75

Copolymerization Using 0.02 mmole Catalyst, 40 eq B(C₆F₅)₃, 6 mL TCB, 4 mL HA, or EGPEA at 120° C. under 6.9 MPa E for 18 h

| Ex. | Catalyst | Co-Monomer (Mole %) | Yield (g) | #Me/ 1000 CH$_2$ | m.p. (° C.) [ΔH$_f$] | Mw/PDI | TON E/Comonomer |
|---|---|---|---|---|---|---|---|
| 795 | 120 | HA (4.4) | 2.543* | 29 | 97 [86.3] | 6,688/2.7 | 3,587/170 |
| 796 | 120 | EGPEA (2.0) | 3.182** | 22 | 100 [88.8] | 9,821/3.3 | 4,989/100 |

*Contained 2.543 g copolymer and 0.772 g homopolymer of HA
**Contained 3.182 g copolymer and 1.963 g homopolymer of EGPEA

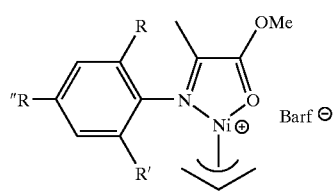

121. R, R' = iPr; R" = H
122. R, R' = Me, R" = H
123. R, R', R" = Me
124. R, R" = Me; R' = Cl
124. R, R' = Me; R" = Br

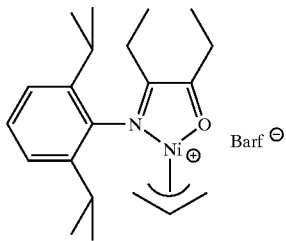

126

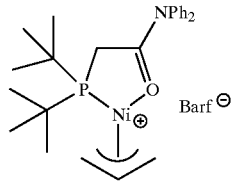

127

TABLE 76

E/HA Copolymerization Using 0.02 mmole Catalyst, 40 eq B(C₆F₅)₃, , 20 eq Li B(C₆F₅)₄, 6 mL TCB, 4 mL HA, at 100° C. under 6.9 MPa E for 18 h

| Ex. | Catalyst | Mole % HA in Polymer | Yield (g) | #Me/ 1000 CH$_2$ | m.p. (° C.) (ΔH$_f$) | Mw/PDI | TON E/Comonomer |
|---|---|---|---|---|---|---|---|
| 797 | 121 | 23 | 0.356[a] | 13 | 122 (138.6) | 4,864/2.6 | 477/11 |
| 798 | 126 | 0.2[b] | 0.403[c] | 3 | 126 (181.4) | 19,918/8.0 | 659/6 |

[a]Contained 0.302 g copolymer and 0.054 g homopolymer of HA
[b]1 mL HA was used rather than 4 mL
[c]Contained 0.380 g copolymer and 0.023 g homopolymer of HA

TABLE 77

Copolymerization Using 0.02 mmole Catalyst, 40 eq B(C$_6$F$_5$)$_3$, 20 eq Li B(C$_6$F$_5$)$_4$, 8 mL TCB, 2 mL HA, at 100° C. under 6.9 MPa E for 18 h

| Ex. | Catalyst | Yield (g)[a] | #Me/1000CH$_2$ | Mole % HA in Polymer | m.p. (° C.) (ΔH$_f$) | Mw/PDI |
|---|---|---|---|---|---|---|
| 799 | 121 | 1.750 | 27 | 0.8 | 124 (160.1) | 10,049/3.47 |
| 800 | 122 | 1.710 | 26 | 1.2 | 118 (176.1) | 3,422/2.42 |
| 801 | 123 | 0.834 | 34 | 1.8 | 120 (147.9) | 3,605/1,521 |
| 802 | 124 | 0.478 | 52 | 2.2 | 95 (132.9) | 2,392/2.37 |
| 803 | 125 | 0.804 | 36 | 1.8 | 119 (153.5) | 3,275/2.40 |
| 804 | 127[b] | 4.257 | 8 | 1.1 | 123 (158.1) | 7,725/1.97 |

[a]All of the copolymer products contained a small amount of homopolymer of HA
[b]20 eq of NaBArF was used here rather than 20 eq of LiB(C$_6$F$_5$)$_4$; toluene was used as solvent here rather than TCB

EXAMPLES 805–833

The reaction mixture including catalyst, solvent, acrylate and cocatalysts was assembled inside a nitrogen filled drybox and placed in a 50 mL stainless steel pressure vessel. A stir bar was added and the vessel sealed and removed from the drybox where it was pressurized with ethylene to the desired pressure. The vessel was heated and stirred with a constant pressure of ethylene for the duration of the reaction.

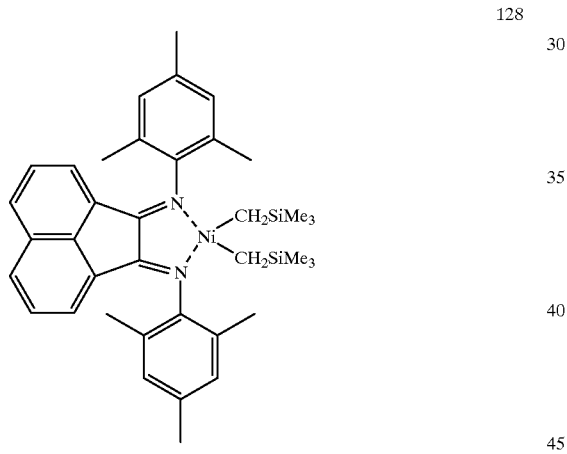

128

TABLE 78

| Ex. | Catalyst | mmol Ni | NaBArf eq | B(C$_6$F$_5$)$_3$ eq | C$_6$H$_5$Cl mL | EGPEA mL | Time h | Temp | Yield | Kg/g Ni | Mw | Mol % EGPEA |
|---|---|---|---|---|---|---|---|---|---|---|---|---|
| 805 | 45 | 0.001659 | 166 | 767 | 15 | 1.5 | 66 | ~127° C. | 15.74 | 161 | 13761 | 0.36/0.40 |
| 806 | 45 | 0.001875 | 150 | 680 | 15.5 | MA 1.0 | 18 | ~124° C. | 4.65 | 42 | | 0.43 |
| 807 | 45 | 0.0015 | 188 | 850 | 15 | 2.1 | 63 | 125° C. | 10.9 | 124 | | 0.45/0.47 |
| 808 | 45 | 0.0015 | 188 | 850 | 15 | 1.5 | 63 | 117° C. | 3.3 | 38 | 9948 | 0.7 |
| 809 | 76 | 0.0015 | 188 | 850 | 15 | 1.5 | 17 | 125° C. | 2.3 | 26 | 19213 | 0.6 |
| 810 | 76 | 0.0015 | 188 | 850 | 15 | 1.5 | 17 | 120° C. | 1.9 | 22 | 30124 | low |
| 811 | 128 | 0.0015 | 188 | 850 | 15 | 1.5 | 17 | 80° C. | 4.5 | 51 | 39600 | low (0.2–0.3) |
| 812 | 128 | 0.00075 | 380 | 1700 | 17 | 2.1 | 18 | 82° C. | 1.34 | 31 | | low |
| 813 | 74 | 0.00125 | 225 | 1017 | 15 tol. | MA 1.0 | 66 | 120° C. | 2.82 | 38 | | |
| 814 | 45 | 0.0015 | 188 | 850 | 15 | 1.5 | 18 | 120° C. | 4.65 | 51 | 12758 | 0.5 |
| 815 | 45 | 0.0015 | 188 | 850 | 15 | MA 1.0 | 72 | 123° C. | 7.3 | 83 | 32036 | 0.24 (13C) |
| 816 | 128 | 0.0015 | 188 | 850 | 15 | MA 1.0 | 72 | 100° C. | 4.2 | 48 | 13082 | 0.29 (13C) |
| 817 | 51 | 0.0015 | 188 | 850 | 15 | 1.5 | 18 | 120° C. | 0.7 | 8 | 20294 | 0.3 |
| 818 | 45 | 0.0015 | 188 | 850 (Al + B–)[a] | 15 | 1.5 | 18 | 120° C. | 4.1 | 47 | 12133 | 0.3 |
| 819 | 45 | 0.0015 | 188 | 430 (Al + B–)[a] | 16 | 1.5 | 18 | 120° C. | 2.8 | 32 | 14634 | 0.6 |

TABLE 78-continued

| Ex. | Catalyst | mmol Ni | NaBArf eq | B(C$_6$F$_5$)$_3$ eq | C$_6$H$_5$Cl mL | EGPEA mL | Time h | Temp | Yield | Kg/g Ni | Mw | Mol % EGPEA |
|---|---|---|---|---|---|---|---|---|---|---|---|---|
| 820 | 45 | 0.0015 | 188 | 850 | 15 | 1.5 | 18 | 122° C. | 3.5 | 40 | | |
| 821 | 45 | 0.0015 | 188 | 850 | 15 | MA 2 | 66 | 122° C. | 8.5 | 97 | 13162 | 0.41 (13C) |
| 822 | 45 | 0.0015 | 188 | 850 | 15 | MA 3 | 17 | 123° C. | 4.9 | 56 | 8305 | 0.88 (13C) |
| 823 | 74 | 0.0015 | 188 | 850 | 15 | MA 2 | 125 | 125° C. | 4.1 | 47 | 23003 | |
| 824 | 45 | 0.0015 | 188 | MAO 1 ml | 15 | 1 | 18 | 125° C. | 4.4 | 50 | 10011 | Low |
| 825 | 45 | 0.0015 | 188 | MAO 0.3 ml | 15 | 1.5 | 18 | 100° C. | 4.2 | 48 | | 0.29 |
| 826 | 45 | 0.0015 | 188 LiB[b] | 850 | 15 | 1.5 | 18 | 122° C. | 2.9 | 33 | | 0.53 |
| 827 | 45 | 0.0015 | 188 LiB | MAO 0.2 ml | 15 | 1.5 | 18 | 100° C. | 1 | 11 | 12507 | 0.52 |
| 828 | 45 | 0.0015 | 188 LiB | MAO 0.3 ml | 15 | 1.5 | 18 | 100° C. | 1.3 | 15 | 11851 | 0.63 |
| 829 | 45 | 0.0015 | 188 | MAO 0.3 ml | 15 | 1.5 | 18 | 100° C. | 6.6 | 75 | 20849 | 0.27 |
| 830 | 74 | 0.0015 | 188 | 1300 | 15 | MA 3 | 115 | 120° C. | 3.4 | 39 | 15103 | 0.56 |
| 831 | 40 | 0.00166 | 170 | 766 | 15 | 1.5 | 18 | ~118° C. | 5.94 | 61 | | 0.5* |
| 832 | 21 | 0.00166 | 170 | 766 | 16 | 1.5 | 18 | ~125° C. | 3.74 | 38 | | ~0.5 |
| 833 | 40 | 0.0015 | 188 | 850 | 15 | 1.5 | 66 | 123° C. | 5.2 | 59 | | 1.2* |

[a]Al(OEt)$_2$(Me$_2$)BMe(C$_6$F$_5$)$_3$.
[b]LiB = Li(B(C$_6$F$_5$)$_4$2Et$_2$O used in place of NaBArf.
[c]In chain and end-of-chain acrylate.
MA = methyl acrylate; MAO = MMAO-12 (12.9 wt % Al in toluene, Akzo-Nobel); EGPEA added before borane

EXAMPLES 829–846

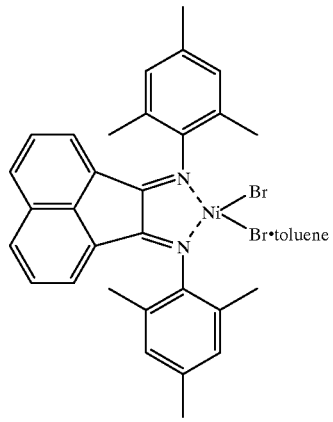

129

Preparation of Supports

Support A: Inside a nitrogen filled drybox, dehydrated, spray-dried spherical silica (2 g, Grace XPO-2402, dehydrated to ~1 mmol OH/g silica) was placed in 6 mL dry toluene and AlMe3 (3 mL, 2M in hexane, Aldrich) added. The slurry was agitated by shaking for 30 min after which the solids were filtered, washed with pentane and dried under vacuum.

Support B: Inside a nitrogen filled drybox, spray-dried spherical silica-alumina (1 g, Grace MS 13-1.10, dehydrated at 500° C.) was placed in 6 mL dry toluene and AlMe$_3$ (1.8 mL, 2M in hexane, Aldrich) added. The slurry was agitated by shaking for 30 min after which the solids were filtered, washed with pentane and dried under vacuum.

Preparation of Catalysts

Catalyst I: Support A (0.5 g) was added to a solution of 45 (76 mg, 0.05 mmol) in anhydrous toluene. The slurry was agitated by shaking for 30 min after which the solids were filtered away from the brown filtrate and dried under vacuum.

Catalyst II: Silica supported MAO (Albemarle Corp, 18 wt % Al on spherical silica) was added to a solution of 45 (76 mg, 0.05 mmol) and B(C$_6$F$_5$)$_3$ (0.133 g, 5eq) in anhydrous toluene. The slurry was agitated by shaking for 30 min after which the solids were filtered away from the black/brown filtrate and dried under vacuum. ICP: % Ni=0.43%.

Catalyst III: Support A (0.5 g) was added to a solution of 45 (76 mg, 0.05 mmol) and B(C$_6$F$_5$)$_3$ (0.133 g, 5 eq) in anhydrous toluene. The slurry was agitated by shaking for 30 min after which the solids were filtered away from the green/brown filtrate and dried under vacuum. ICP: % Ni=0.42%.

Catalyst IV: Inside a nitrogen filled drybox, spray-dried spherical silica alumina (0.5 g, Grace MS 13-1.10, dehydrated at 500° C. under flowing N$_2$), was placed in anhydrous toluene (8 mL) and 45 (38 mg, 0.025 mmol) added. The slurry was agitated by shaking for 30 minutes after which the orange brown solids were filtered, washed with toluene and finally pentane and dried under vacuum. ICP: % Ni=0.28%.

Catalyst V: Inside a nitrogen filled drybox, spray-dried spherical silica alumina (0.5 g, Grace MS 13-1.10, dehydrated at 500° C. under flowing N$_2$), was placed in anhydrous methylene chloride (8 mL) and 129 (16 mg, 0.022 mmol) added. The slurry was agitated by shaking for 45 min after which the orange solids were filtered, washed with toluene and finally pentane and dried under vacuum. ICP: % Ni=0.24%.

Catalyst VI: Support B (0.25 g) was added to a solution of 45 (19 mg, 0.013 mmol) in anhydrous toluene. The slurry was agitated by shaking for 45 min after which the solids were filtered away from the dark green filtrate, washed with toluene and dried under vacuum.

Catalyst VII: Support A (0.25 g) was added to a solution of 45 (19 mg, 0.013 mmol in anhydrous toluene. The slurry was agitated by shaking for 45 min after which the solids were filtered away from the light brown filtrate, washed with toluene and dried under vacuum.

Catalyst VIII: Silica supported MAO (0.25 g, Al-bemarle, 18 wt % Al) was added to a toluene solution of 45 (19 mg, 0.013 mmol in 10 mL). The slurry was agitated by shaking for 30 min after which the solids were filtered away from the blue filtrate, washed with toluene and dried under vacuum. ICP; % Ni=0.36%.

Catalyst IX: Support B (0.25 g) was added to a solution of 45 (19 mg, 0.013 mmol) in anhydrous toluene. $B(C_6F_5)_3$ (56 mg, Boulder Scientific) was added and the slurry was agitated by shaking for 30 min after which the solids were filtered away from the brown filtrate, washed with toluene and dried under vacuum. ICP % Ni=0.28%.

Catalyst X: Support A (0.25 g) was added to a solution of 45 (19 mg, 0.013 mmol) in anhydrous toluene. The slurry was agitated by shaking for 60 min after which the brown solids were filtered away from the green filtrate, washed with toluene and dried under vacuum.

Catalyst XI: Support A was added to a solution of 45 (19 mg, 0.013 mmol) in anhydrous toluene. The slurry was agitated by shaking for 60 min after which the orange solids were filtered away from the orange filtrate, washed with toluene and dried under vacuum.

Catalyst XII: Support A (0.25 g) was added to a solution of 129 (9.6 mg, 0.013 mmol) in anhydrous toluene. The slurry was agitated by shaking for 60 min after which the gray solids were filtered away from the purple filtrate, washed with toluene and dried under vacuum.

Catalyst XIII: Support A (0.25 g) was added to a solution of 40 (5.6 mg, 0.013 mmol) in anhydrous toluene. The slurry was agitated by shaking for 60 min after which the orange solids were filtered away from the orange filtrate, washed with toluene and dried under vacuum.

Catalyst XIV: Support A (0.25 g) was added to a solution of 21 (4.5 mg, 0.013 mmol) in anhydrous toluene. The slurry was agitated by shaking for 60 min after which the beige solids were filtered away from the filtrate, washed with toluene and dried under vacuum.

Copolymerization of Ethylene with EGPEA

The solid catalyst and cocatalyst components (catalyst ~0.004 mmol, 0.177 g NaBAF, and optionally $B(C_6F_5)_3$) were added to a glass insert. Solvent (anhydrous chlorobenzene, 9 mL) and EGPEA, (1 mL, filtered through basic alumina, Aldrich) were added last and the insert placed in a metal pressure vessel. Some ethylene was admitted and the vessel was heated to 120° C. and then pressurized to 6.9 MPa with ethylene and agitated for 18 h. After this time the reactor was cooled, the pressure released and the contents of the insert placed in stirring methanol to precipitate polymer product. The polymeric product was then filtered, washed well and dried. Results are given in Table 79.

Inside a nitrogen filled drybox the solid catalyst and cocatalyst components (2.5 mg NaBAF, and optionally $B(C_6F_5)_3$) were added to glass inserts. Solvent (anhydrous chlorobenzene, 0.25 mL) and EGPEA, (0.05 mL, filtered through basic alumina, Aldrich) were added last and the inserts placed in a metal pressure vessel. The vessel was sealed, removed from the drybox and placed under an atmosphere of ethylene at 6.9 MPa and heated to 110–120° C. for 16 h. After cooling the vessel was opened and the reactions quenched with methanol, and the polymeric product filtered, washed with methanol and dried. Results are given in Table 80.

TABLE 80

| Ex. | Catalyst (mmol) | Yield (mg) | % EGPEA[3] incorporated | End Groups Int:Term. |
|---|---|---|---|---|
| 841 | 45[1] (0.002) | 0.36 | 1.5 | 9:1 |
| 842 | II (0.002) | 0.13 | 1.3 | 1:1.1 |
| 843 | III (0.002) | 0.13 | 1.9 | 1:1.1 |
| 844 | 45[1] (0.001) | 0.22 | 1.5 | 2:1 |
| 845 | VI (0.001) | 0.08 | 1.9[2] | 1:1.3 |
| 846 | VII (0.001) | 0.07 | 1.2 | 1:1.3 |

[1]20 mg $B(C_6F_5)_3$ added as activator. No support
[2]Incorporation may be high due to presence of homopolymer which makes calculation of % incorporation less accurate

EXAMPLES 847–850

General Procedure for Polymerizations in Tables 81–86

The polymerizations were carried out according to General Polymerization Procedure A. Varying amounts of acrylate homopolymer are present in some of the isolated polymers. For acrylate copolymers, the yield of the polymer is reported in grams and includes the yield of the dominant ethylene/acrylate copolymer as well as the yield of any acrylate homopolymer that was formed. Molecular weights were determined by GPC, unless indicated otherwise. Mole percent acrylate incorporation and total Me were determined by $^1$H NMR spectroscopy, unless indicated otherwise. Mole percent acrylate incorporation is typically predominantly IC, unless indicated otherwise. The $LiB(C_6F_5)_4$ used (LiBArF) included 2.5 equiv of $Et_2O$.

TABLE 79

| Ex | Catalyst (mg) | $B(C_6H_5)_3$ 98 eq | AlMe(BHT)$_2$ 20 eq | Yield (g) | % EGPEA[3] incorporated | kg PE/g Ni[1] |
|---|---|---|---|---|---|---|
| 829 | 45 (5.8 mg)[4] | 0.2 g | — | 6.6 | 0.5 | 28 |
| 830 | 45 (5.8 mg)[4] | 0.2 g | 40 mg | 5.4 | 0.5 | 23 |
| 831 | 45 (5.8 mg)[4] | — | 40 mg | 2.7 | 0.7[2] | 11 |
| 832 | VIII (77 mg) | — | — | 0.6 | 0.4 | 3 |
| 833 | I (40 mg) | 0.2 g | | 3.4 | 0.5 | 14 |
| 834 | IV (77 mg) | 0.2 g | | 5.3 | 0.4 | 22 |
| 835 | V (77 mg) | 0.2 g | | 2.1 | 0.5 | 9 |
| 836 | X (80 mg) | 0.2 g | — | 3.6 | 0.7 | 15 |
| 837 | XI (80 mg) | — | 40 mg | 3.0 | 0.8[2] | 13 |
| 838 | XII (80 mg) | — | 40 mg | 2.1 | 0.9[2] | 9 |
| 839 | XIII (80 mg) | — | 40 mg | 6.9 | 0.5 | 29 |
| 840 | XIV (80 mg) | — | 40 mg | 0.1 | 0.3 | 0.5 |

[1]This is calculated based on the amount of nickel added when the catalyst was prepared. As substantial amounts of color washed away from the support this value represents a minimum activity,
[2]Incorporation may be high due to presence of homopolymer which makes calculation of % incorporation less acurate,
[3]Determined by H-NMR at 120° C. in TCE-d$_2$.
[4]No support.

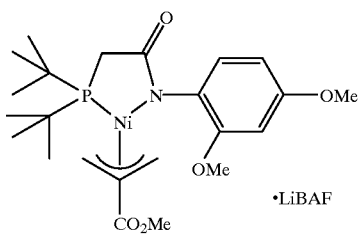

A-1

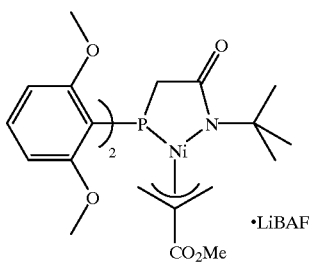

A-3

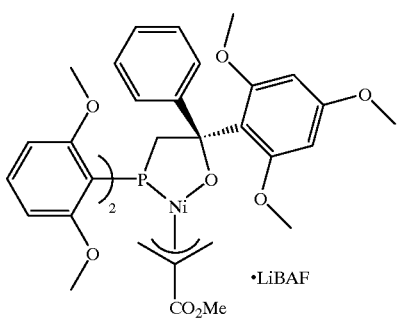

A-4

2,6-Bis-dimethoxyphenyllithium was prepared from 14.18 g (0.103 mole) of 1,3-dimethoxybenzene, 77 mL of a 1.6 M solution of BuLi in hexanes and 0.23 mL of N,N,N', N'-tetramethylethylenediamine in dry diethyl ether (72 mL). Dichloromethylphosphine (5.0 g, 0.04276 mole) was added at 0° C., and the reaction mixture was stirred at room temperature overnight. Methanol (20 mL) was added, and the mixture was concentrated to about half its original volume under reduced pressure. The resulting white precipitates were filtered and were recrystallized from methanol to give white crystals of bis-(2,6-dimethoxyphenyl)(methyl)-phosphine with 48% yield (6.6 g) and melting point at 112.33° C. $^1$H NMR (CDCl$_3$) δ 1.75 (s (broad), 3H, Me-P), 3.55 (s, 12H, Me-O), 6.4–7.2 (m, 6H, aromatic protons); $^{31}$P NMR (CDCl$_3$) δ −51.5 ppm. LS/MS: found m/w is 321, calculated m/w is 321. Anal. found: C, 64.30%; H, 6.45%; calculated for $C_{17}H_{22}O_4P$: C, 63.49%; H, 6.85%.

Synthesis of A-3. Bis-(2,6-dimethoxyphenyl)phosphino]-methyllithium (2,6-MeO-Ph)$_2$P—CH$_2$-Li) (0.33 g, 0.001 mole) was prepared from a 7 mL THF solution of equi-molar amounts of bis-(2,6-dimethoxyphenyl)-(methyl)phosphine and a 1.6 M solution of butyllithium in hexanes with a catalytic amount of TMEDA added. tert-Butylisocyanate (0.125 g, 0.001 mole) in 3 mL of THF was added to the reaction mixture, which was then stirred for 12 hours. Next, 0.24 g (0.0005 mole) of 2-methoxycarbonyl-allyl nickel bromide dimer [(CH$_2$=C(CO$_2$Me)CH$_2$)Ni($\mu$-Br)]$_2$ and 0.89 g (0.001 mole) of NaBAF in 4 mL of THF was added to the reaction mixture, which was stirred overnight. The next day, the solvent was pumped off and the residue was redissolved in diethyl ether. The solution was filtered through Celite®, and solvent was removed under vacuum. Viscous brown product (0.92 g) was obtained. $^{31}$P NMR (CD$_2$Cl$_2$): one major peak at 26.49 ppm.

Synthesis of A-1 and A-4. Synthesis was in a fashion analogous to that reported for A-3 in above, except that (t-Bu)$_2$PCH$_2$Li was employed as the base for the synthesis of A-1 and different electrophiles were employed. The electrophiles employed and compound characterization follow:

| Cmpd | Electrophile | $^{31}$P NMR[a] (CD$_2$Cl$_2$) δ |
|------|--------------|----------------------------------|
| A-1 | 2,4-Dimethoxy-phenylisocyanate | 60.6 ppm (major); 62.1 ppm (minor) |
| A-4 | 2,4,6-Trimethoxy-benzophenone | 22.5 (major) |

[a] In some cases, additional minor resonances were present in the $^{31}$P NMR spectrum.

TABLE 81

Ethylene Homopolymerizations and Ethylene/Acrylate Co-polymerizations (18 h)

| Ex | Cmpd (mmol) | Acrylate mL (Solvent mL) | B(C$_6$F$_5$)$_3$ (Borate) | Press MPa | Temp ° C. | Yield g | Acrylate Incorp. mol % | M.W. | Total Me |
|---|---|---|---|---|---|---|---|---|---|
| 847 | A-1 (0.004) | EGPEA 1 (p-Xylene 9) | 100 equiv (NaBAF 50 equiv) | 3.4 | 60 | 0.64 | 0.5 0.3 IC 0.2 EG | M$_p$ = 13,148; M$_w$ = 14,087; M$_n$ = 6,487; PDI = 2.17 | 7.1 |
| 848 | A-1 (0.02) | EGPEA 1 (p-Xylene 9) | 20 equiv (NaBAF 10 equiv) | 1 | 60 | 0.09 | 1.4 0.7 IC 0.7 EG | M$_p$ = 5,447; M$_w$ = 8,088; M$_n$ = 3,454; PDI = 2.17 | 13.3 |
| 849 | A-3 (0.02) | None (p-Xylene 10) | 10 equiv (None) | 3.4 | 60 | 0.80 | — | M$_p$ = 801; M$_w$ = 37,894; M$_n$ = 500; PDI = 75.77 | 119 |

TABLE 81-continued

Ethylene Homopolymerizations and Ethylene/Acrylate Co-polymerizations (18 h)

| Ex | Cmpd (mmol) | Acrylate mL (Solvent mL) | B(C₆F₅)₃ (Borate) | Press MPa | Temp °C. | Yield g | Acrylate Incorp. mol % | M.W. | Total Me |
|---|---|---|---|---|---|---|---|---|---|
| 850 | A-4 (0.02) | None (p-Xylene 10) | 10 equiv (None) | 3.4 | 60 | 0.33 | — | $M_p$ = 956; $M_w$ = 52,382; $M_n$ = 817; PDI = 64.09 | 76.4 |

TABLE 82

Ethylene/Acrylate Copolymerizations (0.004 mmol Cmpd, 18 h, 100 equiv B (C₆F₅)₃, 50 equiv LiB (C₆F₅)₄, 1 mL EGPEA, 9 mL p-Xylene)

| Ex | Cmpd | Press MPa | Temp. °C. | Yield g | Acrylate Incorp Mol % | M.W. | Total Me |
|---|---|---|---|---|---|---|---|
| 851 | 45 | 2.1 | 60 | 0.008 | 0.7 | $M_n$($^1$H): No Olefins | 11.9 |
| 852 | 91 | 2.1 | 60 | 0.008 | 1.5 | $M_n$($^1$H): No Olefins | 13.6 |
| 853 | 94 | 2.1 | 60 | 0.011 | 1.2 | $M_n$($^1$H): No Olefins | 9.4 |
| 854[a] | 53 | 2.1 | 60 | 0.041 | 2.4 2.0 IC 0.4 EG | $M_n$($^1$H) = 3,528.3 | 24.7 |

[a]Predominant alpha olefin end groups; some internal olefin end groups also present.

TABLE 83

Ethylene/E-10-U Copolymerizations: Variation of Temperature and Pressure (0.02 mmol Cmpd; 2 mL E-10-U; 8 mL TCB; 40 equiv B(C₆F₅)₃; 18 h)

| Ex | Cmpd | Press MPa | Temp °C. | Yield g | Comonomer Incorp mol % | M.W. |
|---|---|---|---|---|---|---|
| 855 | 46 | 1 | 25 | 3.24 | 3.3 | $M_p$ = 67,355; $M_w$ = 74,377; $M_n$ = 39,452; PDI = 1.89 |
| 856 | 46 | 3.4 | 60 | 11.14 | 2.8 | $M_p$ = 67,243; $M_w$ = 69,152; $M_n$ = 34,553; PDI = 2.00 |
| 857 | 46 | 6.9 | 120 | 6.09 | 1.1 | $M_p$ = 13,731; $M_w$ = 20,516; $M_n$ = 5,477; PDI = 3.75 |

TABLE 84

Ethylene/Zonyl TAN (ZTAN) Copolymerization (0.002 mmol Cmpd; 200 equiv B (C₆F₅)₃; 100 equiv NaBAF; 18 h)

| Ex | Cmpd | ZTAN g (p-Xylene mL) | Press MPa | Temp °C. | Yield g | Comonomer Incorp Mol % | M.W. | Total Me |
|---|---|---|---|---|---|---|---|---|
| 858 | 45 | 2 (8) | 6.9 | 120 | 17.90 | Trace | $M_p$ = 11,579; $M_w$ = 12,467; $M_n$ = 4,226; PDI = 2.95 | Nd |
| 859 | 45 | 3 (7) | 4.1 | 80 | 0.613 | 0.52 ($^{13}$C NMR) | $M_p$ = 24,805; $M_w$ = 23,507; $M_n$ = 10,500; PDI = 2.24 | 20.3[a] ($^{13}$C NMR) |

TABLE 84-continued

Ethylene/Zonyl TAN (ZTAN) Copolymerization (0.002 mmol Cmpd; 200 equiv B (C$_6$F$_5$)$_3$; 100 equiv NaBAF; 18 h)

| Ex | Cmpd | ZTAN g (p-Xylene mL) | Press MPa | Temp °C. | Yield g | Comonomer Incorp Mol % | M.W. | Total Me |
|----|------|----------------------|-----------|----------|---------|------------------------|------|----------|
| 860 | 45 (0.002) | 3 (7) | 6.9 | 100 | 1.75 | 0.30 ($^{13}$C NMR) | $M_p$ = 20,490; $M_w$ = 21,489; $M_n$ = 10,466; PDI = 2.05 | 27.4[b] ($^{13}$C NMR) |

[a]Branches as determined by $^{13}$C NMR spectroscopy: 20.3 Total Me; 14.8 Me; 1.9 Et; 0.8 Pr, 1.2 Bu; 1.6 Hex+ and eoc; 2.7 Am+ and eoc; 2.8 Bu+ and eoc.
[b]Branches as determined by $^{13}$C NMR spectroscopy: 27.4 Total Me; 18.9 Me; 2.9 Et; 1.3 Pr, 1.5 Bu; 3.5 Hex+ and eoc; 3.8 Am+ and eoc; 4.2 Bu+ and eoc.

TABLE 85

Ethylene/Acrylate/alpha-Olefin Terpolymerizations (0.002 mmol Cmpd; 18 h; 6.9 MPa E; 120° C.; 8 mL p-Xylene; 200 equiv B (C$_6$F$_5$)$_3$; 100 equiv NaBAF; alpha-Olefins: 1-Hexene, 1-H; Ethyl-10-Undecylenate, E-10-U)

| Ex | Cmpd | Acrylate mL | α-Olefin mL | Yield g | Acrylate Incorp[a] mol % | E-10-U Incorp[a] mol % | Total Me[a] |
|----|------|-------------|-------------|---------|--------------------------|------------------------|-------------|
| 861 | 45 | EGPEA 1 | 1-H 1 | 1.64 | 0.57 | [b] | 57.2[c] |
| 862 | 45 | EGPEA 1 | E-10-U 1 | 2.24 | 0.86 | 0.80 | 45.0[d] |
| 863 | 40 | EGPEA 1 | 1-H 1 | 6.33 | 0.51 0.23 IC 0.28 EG | [b] | 11.7[e] |
| 864 | 40 | EGPEA 1 | E-10-U 1 | 3.48 | 0.42 0.21 IC 0.21 EG | 0.33 | 8.7[f] |

[a]Acrylate incorporation, E-10-U incorporation, and Total Me were determined by $^{13}$C NMR spectroscopy. For 1-H terpolymers, acrylate incorporation was determined by assuming that the copolymer was derived from just ethylene and acrylate.
[b]The larger number of butyl branches relative to ethyl branches is consistent with 1-hexene incorporation.
[c]57.2 Total Me; 31.6 Me; 7.2 Et; 2.9 Pr, 7.4 Bu; 4.5 Hex+ and eoc; 8.7 Am+ and eoc; 15.4 Bu+ and eoc; Me$_{sBu}$ = 1.8%; Et$_{sBu}$ = 16.4%.
[d]45.0 Total Me; 23.8 Me; 5.6 Et; 6.6 Pr, 2.3 Bu; 4.1 Hex+ and eoc; 0.7 Am+ and eoc; 9.0 Bu+ and eoc; Me$_{sBu}$ = 2.7%; Et$_{sBu}$ = 18.4%.
[e]11.7 Total Me; 2.0 Me; 0.8 Et; 0.3 Pr, 1.5 Bu; 5.9 Hex+ and eoc; 5.5 Am+ and eoc; 8.6 Bu+ and eoc.
[f]8.7 Total Me; ~0 Me; 0.6 Et; 1.4 Pr, 0.3 Bu; 6.7 Hex+ and eoc; 1.5 Am+ and eoc; 6.7 Bu+ and eoc.

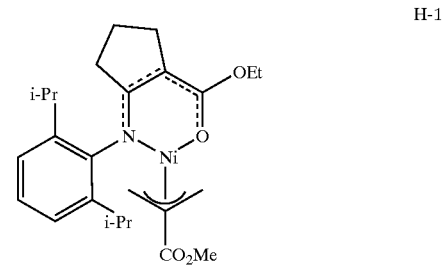

H-1

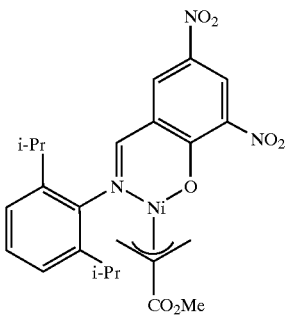

H-2

TABLE 86

Ethylene/Acrylate Copolymerizations (0.02 mmol Cmpd; 6.9 MPa E; 1 mL EGPEA; 9 mL TCB; 18 h)

| Ex | Cmpd | Borane equiv | Borate equiv | Temp °C. | Yield G | Comonomer Incorp mol % | M.W. | Total Me |
|---|---|---|---|---|---|---|---|---|
| 865 | H-1 | $B(C_6F_5)_3$ 20 | NaBAF 10 | 120 | 1.28 | 0.2 IC & EG | $M_p = 5,017; M_w = 6,796;$ $M_n = 1,840; PDI = 3.69$ | 54.3 |
| 866 | H-2 | $BPh_3$ 20 | none | 80 | 0.14 | 5.3 | Bimodal UV: $M_p = 21,679;$ RI $M_p = 20,271;$ | 22.0 |

EXAMPLE 867

Synthesis of $(t-Bu)_2PCH_2N(2,6-C_6F_2H_3)OLi$

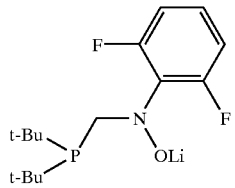

1001

In a dry box, to a 50 mL flask containing 10 mL of THF solution of 1,3-difluoro-2-nitrosobenzene (0.0276 g, 0.193 mmol), was added slowly to a THF solution of (t-Bu)$_2$PCH$_2$Li (0.0321 g, 0.193 mmol) at −30° C. The solution was stirred 2 hours and it turned brown. After removal of the solvent, the purple residue was rinsed with pentane and dried under vacuum. A brown powder was obtained.

EXAMPLE 868

Synthesis of $(t-BU)_2PCH_2N(2-(3-OLi)C_{10}H_6)OLi$

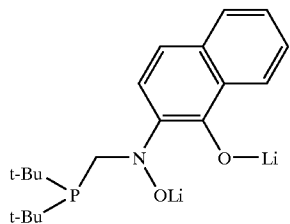

1002

In a dry box, to a 100 mL flask containing 20 mL of THF solution of 2-nitroso-1-naphthol (0.1044 g, 0.603 mmol), NaH (0.016 g, 1.1 equiv.) powder was added slowly at room temperature. When no more H$_2$ was released, a THF solution of (t-Bu)$_2$PCH$_2$Li (0.1002 g, 0.603 mmol) at −30° C. was added slowly. The solution was stirred 2 hours and turned brown from yellow. After removing the solvent, a brown powder (0.1402 g, 0.388 mmol) was obtained in 64% yield. $^1$H NMR (C$_6$D$_6$): complicated. $^{31}$P NMR (C$_6$D$_6$): major peak 29.5636 ppm.

EXAMPLE 869

Synthesis of $(t-Bu)_2PCH_2N(C_6H_5)OLi$

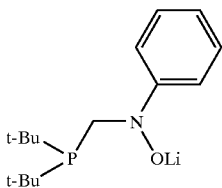

1003

In a dry box, to a 100 mL flask containing 20 mL of THF solution of nitrosobenzene (0.0682 g, 0.64 mmol), was added slowly a THF solution of (t-Bu)$_2$PCH$_2$Li (0.1058 g, 0.64 mmol) at −30° C. The solution was stirred overnight and turned purple from yellow. After removing the solvent, a purple powder (0.1321 g, 0.483 mmol) was obtained in 76% yield. $^1$H NMR (C$_6$D$_6$): complicated; $^{31}$P NMR (C$_6$D$_6$): major peak 38.1167 ppm.

EXAMPLE 870

Synthesis of $(t-Bu)_2PCH_2N(2-CH_3—C_6H_4)OLi$

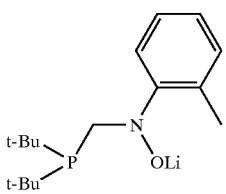

1004

In dry box, to a 100 mL flask containing 20 mL of THF solution of o-nitrosotoluene (0.0763 g, 0.63 mmol) was added slowly a THF solution of (t-Bu)$_2$PCH$_2$Li (0.1046 g, 0.63 mmol) at −30° C. The solution was stirred overnight and turned purple from yellow. After removing the solvent and rinsing with petane, a purple powder (0.1538 g, 0.54 mmol) was obtained in 85% yield. $^1$H NMR (C$_6$D$_6$): complicated; $^{31}$P NMR (C$_6$D$_6$): complicated, indicating the desired product, but also additional products.

EXAMPLES 871–874

Polymerizations of Ethylene at 1000 psi of $C_2H_4$ in Shaker Tube:

| Ex | Ligand | PE (g) | TO (molPE/mol cat) |
|---|---|---|---|
| 871 | 1001 | 3.0595 | 5110.9 |
| 872 | 1002 | 7.9434 | 13827.2 |
| 873 | 1003 | 6.8919 | 13165.7 |
| 874 | 1004 | 3.9511 | 7226.8 |

Conditions: 0.02 mmol ligand, 1 equiv. Allyl-Ni complex, 10 equiv. B$(C_6F_5)_3$, 5 ml TCB, RT, 18 h.

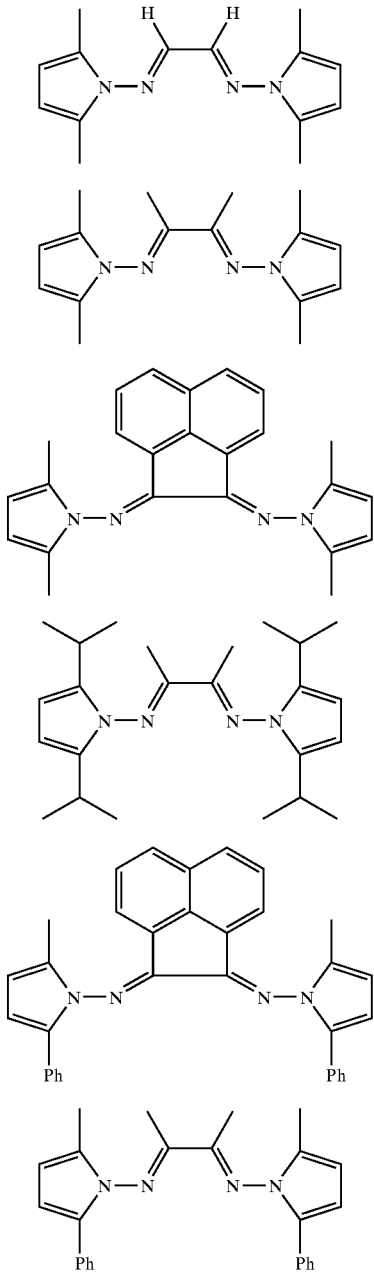

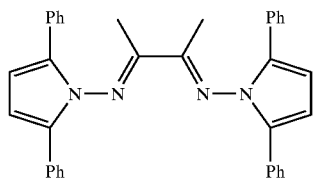

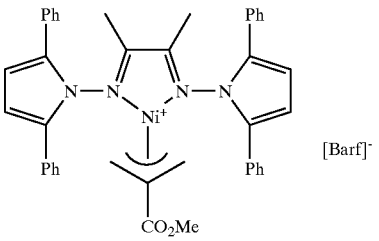

The syntheses of aminopyrrole ligands is published in WO00/50470.

EXAMPLE 875

Synthesis of Ligand 1005

A 50 mL round bottom flask was charged with 0.3988 g (2.745 mmol) of 40 wt. % glyoxal solution in water, 0.6045 g (5.49 mmol) of 1-amino-2,5-dimethylpyrrole, 15 ml methanol and 1 drop of formic acid. The mixture was stirred overnight and light brown precipitate formed. The solid was collected by filtration, rinsed with hexane and dried under vacuum. 0.46 g (1.9 mmol) of product was obtained in 69% yield. $^1$H NMR (CDCl$_3$) 8.18 (s, 2, C—H), 5.8 (s, 4, Hpy), 2.3 (s, 12, CH$_3$).

EXAMPLE 876

Synthesis of Ligand 1006

A 50 mL round bottom flask was charged with 0.25 g (2.9 mmol) of 2,3-butadione, 0.696 g (6.318 mmol) of 1-amino-2,5-dimethylpyrrole, 20 ml methanol and 1 drop of formic acid. The reaction was monitored by TLC with elute of 10% ethyl acetate in hexane. Two major spots were showed on the TLC even after overnight stirring. The clear yellow mixture was stirred 2 days and the solvent was removed. The yellow residue was recrystallized with hexane. 0.26 g (0.96 mmol) of bis-substituted product and 0.3652 g (2.0 mmol) of mono-substituted product were obtained. $^1$H NMR (CDCl$_3$) for bis-: δ 5.83 (s, 4, Hpy), 2.12 (s, 6, CH$_3$), 2.0 (s, 12, CH$_3$-Py). $^1$H NMR (CDCl$_3$) for mono-: δ 5.83 (s, 4, H-py), 2.52 (s, 3, CH$_3$), 1.96 (s, 12, CH$_3$-py), 1.92 (s, 3, CH$_3$).

EXAMPLE 877

Synthesis of Ligand 1007

A 150 mL round bottom flask was charged with 0.6 g (2.9 mmol) of acenaphthenequinone, 0.6488 g (5.89 mmol) of 1-amino-2,5-dimethylpyrrole, 50 ml methanol and 1 drop of formic acid. The reaction was monitored by TLC with elute of 30% ethyl acetate in hexane and stirred 3 days. The solvent was removed under vacuum and the red residue was separated on a silica gel column with 30% ethyl acetate in hexane. 0.07 g (0.19 mmol) of dark red crystals bis-substituted product and 0.06 g (0.2 mmol) of orange powder mono-substituted product were obtained. $^1$H NMR (CDCl$_3$)

for bis-: δ 7.96 (d, 2, H-acen), 7.5 (t, 2, H-acen), 6.74 (d, 2, H-acen), 5.99 (s; 4, H-py), 2.08 (s, 12, $CH_3$-Py). $^1$H NMR ($CDCl_3$) for mono-: δ 8.17 (d-d, 2, H-acen), 8.08 (d, 1, H-acen), 7.8 (t, 1, H-acen), 7.54 (t, 1, H-acen), 6.91 (d, 1, H-acen), 5.97 (a, 2, H-py), 2.02 (8, 6, $CH_3$-Py). If the reaction was carried out in toluene with p-toluenesulfonic acid as catalyst under reflux, the exclusive product was bis-substituted but it was isolated in very low yield.

EXAMPLE 878

Synthesis of Ligand 1008

A 50 mL round bottom flask was charged with 0.1418 g (1.65 mmol) of 2,3-butadione, 0.5478 g (3.29 mmol) of 1-amino-2,5-diisopropylpyrrole, 20 ml methanol and 1 drop of formic acid. The reaction was monitored by TLC with elute of 10% ethyl acetate in hexane and stirred 2 days at 50° C. The solvent was removed under vacuum and the yellow oily residue was separated on a silica gel column with 5% ethyl acetate in hexane. 0.226 g (0.59 mmol) of yellow crystalline product was obtained in 36% yield. $^1$H NMR ($CDCl_3$): 5.86 (s, 4, H-py), 2.53 (m, 4, H-Pr-i), 2.11 (s, 6, $CH_3$)$_2$, 1.10 (d, 24, $CH_3$-Pr-i).

EXAMPLE 879

Synthesis of Ligand 1009

A 100 mL round bottom flask was charged with 0.4418 g (2.43 mmol) of acenaphthenequinone, 0.907 g (4.85 mmol) of 1-amino-2-methyl-5-phenylpyrrole, 50 ml methanol and 1 drop of formic acid. The reaction was monitored by TLC with elute of 30% ethyl acetate in hexane and stirred 7 days at RT. The solvent was removed under vacuum and the red solid residue was separated on a silica gel column with 10% ethyl acetate in hexane. 0.15 g (0.30 mmol) of dark red crystals were obtained in 13% yield. $^1$H NMR ($CD_2Cl_2$): δ 8.06 (m, 2H), 7.72–7.6 (m, 6H), 7.32 (m, 4H), 7.18 (m, 2H), 6.92 (d, 1H), 6.86 (d, 1H), 6.66 (d-d, 2H), 6.38 (d, 2H), 2.32 (d, 6, $CH_3$).

EXAMPLE 880

Synthesis of Ligand 1010

A 100 mL round bottom flask was charged with 0.1881 g (2.18 mmol) of 2,3-butadione, 0.817 g (4.37 mmol) of 1-amino-2-methyl-5-phenylpyrrole, 50 ml methanol and 1 drop of formic acid. The reaction was stirred 7 days at RT and yellow precipitate formed. The reaction mixture was filtered through a frit to collect the yellow solid that then was dissolved in ether and dried over $Na_2SO_4$. The ether was removed and the yellow solid was dried under high vacuum. 0.46 g (1.17 mmol) yellow powder was obtained in 53% yield. $^1$H NMR ($CD_2Cl_2$): δ 7.20 (m, 8, Ph-H), 7.10 (t, 2, Ph-H), 6.20 (d, 2, Py-H), 5.95 (m, 2, Py-H), 2.05 (s, 6, $CH_3$), 1.80 (s, 6, $CH_3$).

EXAMPLE 881

Synthesis of Ligand 1011

A 100 mL round bottom flask was charged with 0.129 g (1.5 mmol) of 2,3-butanedione, 0.7021 g (3.0 mmol) of 1-amino-2,5-diphenylpyrrole, 50 ml methanol and 1 drop of formic acid. The reaction was monitored by TLC with elute of 30% ethyl acetate in hexane and stirred 7 days at RT. The solvent was removed under vacuum and the red solid residue was separated on a silica gel column with 10% ethyl acetate in hexane. 0.4963 g (0.97 mmol) of yellow powder was obtained in 64% yield. $^1$H NMR ($CD_2Cl_2$): δ 7.37(m, 4, ph-H), 7.28 (m, 6, ph-H), 6.49 (s, 2, py-H), 1.76 (s, 6, $CH_3$).

EXAMPLE 882

Synthesis of Catalyst 1012

The ligand 7 (0.1102 g, 0.212 mmol), allyl-Ni dimer ([(2-MeO$_2$C—C$_3$H$_4$)NiBr]$_2$) (0.0505 g, 0.106 mmol) and Na(tetra[3,5-bis(trifluoromethyl)]-phenylborane) (0.1879 g, 0.212 mmol) were mixed in 20 mL of ether in a 50 mL of round bottom flask. The reaction mixture was stirred at room temperature for one hour and filtered through a Celite plug on a frit. Removal of the solvent yields a brown powder that was then rinsed with pentane and dried under high vacuum 0.3069 g (0.199 mmol) product was collected in 94% yield. $^1$H NMR ($CD_2Cl_2$): δ 7.58–7.06 (m, 6, Ar—H), 6.46 (d, 2, Py-H), 6.40 (d, 2, Py-H), 3.65 (s, 2, allyl-H), 3.42 (B, 3, MeO), 1.90 (s, 6, $CH_3$), 1.85 (s, 2, allyl-H).

EXAMPLES 883–898

Copolymerization of Ethylene and Polar-comonomers

Into a glass vial used for shaker reaction, were weighed 0.02 mmol of the ligand, 1 equivalent of allyl-Ni dimer ([(2-MeO$_2$C—C$_3$H$_4$)NiBr]$_2$) and 10 equivalent of NaBaf. 2 ml of ether was added into the vial and shaken well. After two hours during which time the most of the ether was evaporated off, 20 equivalent of tri(pentafluorophenyl)-borane cocatalyst, 9 ml of 1,2,4-trichlorobenzene and 1 ml of ethylene glycol phenyl ether acrylate was added into the vial. The vials were placed into a shaker tube, sealed, and taken out from the dry box. The shaker tube was connected to a high pressure, ethylene shaker reaction unit.

Reaction conditions for polymerization were: 1000 psi ethylene, 120° C., 18 hours.

TABLE 87

Results of shaker tube copolymerizations

| Ex | Ligand | Polymer yield (g) | Catalyst Productivity (Kg/g) | $M_w$ | $M_n$ | $M_n/M_w$ | Me/1000 $CH_2$ | Comon. Incorp. (Mol %) | Peak MP (° C.) ΔH (J/g) |
|---|---|---|---|---|---|---|---|---|---|
| 883 | 1007 | 1.4967 | 1.37 | 2482 | 992 | 2.5 | 29.2 | 0.35 | 89 broad |
| 884 | 1006 | 1.0752 | 0.88 | 3586 | 1306 | 2.75 | 28.5 | 0.27 | 114 shoulder |

TABLE 87-continued

Results of shaker tube copolymerizations

| Ex | Ligand | Polymer yield (g) | Catalyst Productivity (Kg/g) | $M_w$ | $M_n$ | $M_n/M_w$ | Me/1000 $CH_2$ | Comon. Incorp. (Mol %) | Peak MP (° C.) ΔH (J/g) |
|---|---|---|---|---|---|---|---|---|---|
| 885 | 1008 | 2.3451 | 2.07 | 38156 | 20004 | 1.91 | — | Trace | 86 shoulder |
| 886 | 1008 | 2.6151 | 2.75 | 22933 | 1106 | 20.74 b | — | Trace | 93 109 |
| 887 | 1011 | 1.5141 | 1.09 | 5371 | 1209 | 4.44 b | — | trace | 127 shoulder |
| 888 | 1009 | 2.674 | 2.24 | 2754 | 1082 | 2.55 b | | trace | 66 158 |
| 889 | 1010 | 1.6429 | 1.33 | 3860 | 1166 | 3.31 b | | trace | 117 shoulder |
| 890 | 1007 | 0.6397 | 0.78 | 20928 | 2232 | 9.37 b | | trace | 120 shoulder |
| 891 | 1009 | 0.6282 | 0.53 | 208622 | 1615 | 129.15 b bimodal | | | 85 broad |
| 892 | 1010 | 0.7601 | 0.61 | 4855 | 1644 | 2.95 b | | | 110 broad |
| 893 | 1012 | 1.4557 | 1.22 | 16467 | 1116 | 14.76 b | | | 125 160 |
| 894 | 1012 | 1.2511 | 1.06 | 17343 | 844 | 20.55 b | — | Trace | 124 154.0 |
| 895 | 1007 | 1.1725 | 1.38 | 2832 | 1207 | 2.35 b | | | 120 shoulder |
| 896 | 1006 | 1.5382 | 0.97 | 29780 | 1160 | 25.68 | — | 0.15 | 122 185 |
| 897 | 1008 | 2.0138 | 2.08 | 14466 | 1293 | 11.19 | — | trace | |
| 898 | 1012 | 1.8074 | 1.56 | 54346 | 1881 | 28.9 | — | 0 | 125 shoulder |

Notes:
a. 20 equivalent of NaBarf,
b. RI data for GPC in THF, dual detector RI-UV,
c. $[AlMe_2(Et_2O)]^+[MeB(C_6F_5)_3]^-$ cocatalyst and p-xylene solvent,
d. No allyl-Ni dimer needed,
e. Hexyl acrylate comonomer.

What is claimed is:

1. A process for the polymerization of olefins, comprising the step of contacting, at a temperature of about −100° C. to about +200° C., at least one polymerizable olefin with an active polymerization catalyst comprising a Group 3 through 11 (IUPAC) transition metal or a lanthanide metal complex of a ligand of the formula (I), (II) or (XII)

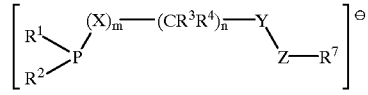
(I)

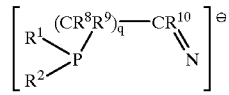
(II)

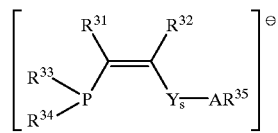
(XII)

wherein:
R$^1$ and R$^2$ are each independently hydrocarbyl, substituted hydrocarbyl or a functional group;
Y is CR$^{11}$R$^{12}$, S(T), P(T)Q, NR$^{36}$ or NR$^{36}$NR$^{36}$;
X is O, CR$^5$R$^6$ or NR$^5$;
A is O, S, Se, N, P or As;
Z is O, Se, N, P or As;
each Q is independently hydrocarbyl or substituted hydrocarbyl;
R$^3$, R$^4$, R$^5$, R$^6$, R$^{11}$ and R$^{12}$ are each independently hydrogen, hydrocarbyl, substituted hydrocarbyl or a functional group;
R$^7$ is hydrogen, hydrocarbyl, substituted hydrocarbyl or a functional group, provided that when Z is O or Se, R$^7$ is not present;
R$^8$ and R$^9$ are each independently hydrogen, hydrocarbyl, substituted hydrocarbyl or a functional group;
R$^{10}$ is hydrogen, hydrocarbyl, substituted hydrocarbyl or a functional group;
each T is independently =O or =NR$^{30}$;
R$^{30}$ is hydrogen, hydrocarbyl, substituted hydrocarbyl or a functional group;
R$^{31}$ and R$^{32}$ are each independently hydrogen, hydrocarbyl, substituted hydrocarbyl or a functional group;
R$^{33}$ and R$^{34}$ are each independently hydrocarbyl or substituted hydrocarbyl, provided that each is independently an aryl substituted in at least one position vicinal to the free bond of the aryl group, or each independently has an E$_s$ of −1.0 or less;
R$^{35}$ is hydrogen, hydrocarbyl, substituted hydrocarbyl or a functional group, provided that when A is O, S or Se, R$^{35}$ is not present;

each $R^{36}$ is independently hydrogen, hydrocarbyl, substituted hydrocarbyl or a functional group;

m is 0 or 1;

s is 0 or 1;

n is 0 or 1; and q is 0 or 1;

and provided that:

any two of $R^3$, $R^4$, $R^5$, $R^6$, $R^8$, $R^9$, $R^{11}$ and $R^{12}$ bonded to the same carbon atom taken together may form a functional group;

any two of $R^1$, $R^2$, $R^3$, $R^4$, $R^5$, $R^6$, $R^7$, $R^8$, $R^9$, $R^{11}$, $R^{12}$, $R^{31}$, $R^{32}$, $R^{33}$, $R^{34}$, $R^{35}$, and $R^{36}$ bonded to the same atom or vicinal to one another taken together may form a ring; and when said ligand is (I), Y is C(O), Z is O, and $R^1$ and $R^2$ are each independently hydrocarbyl, then $R^1$ and $R^2$ are each independently an aryl substituted in one position vicinal to the free bond of the aryl group, or $R^1$ and $R^2$ each independently have an $E_s$ of −1.0 or less.

2. The process of claim 1, wherein said transition metal is Ni, Pd, Pt, Fe, Co, Ti, Zr, V, Hf, Cr or Cu.

3. The process of claim 2, wherein said transition metal is Ni, Pd, Ti or Zr.

4. The process of claim 1, wherein the ligand is (I) and:

the transition metal is Ni, m is 0, n is 1, $R^3$ and $R^4$ are hydrogen, Y is $CR^{11}R^{12}$, $R^{11}$ is hydrocarbyl or substituted hydrocarbyl, $R^{12}$ is hydrocarbyl, substituted hydrocarbyl or a functional group, and Z is O; or the transition metal is Ti, m is 0, n is 1, $R^3$ and $R^4$ are hydrogen, Y is $CR^{11}R^{12}$, $R^{11}$ is hydrocarbyl or substituted hydrocarbyl, $R^{12}$ is hydrocarbyl, substituted hydrocarbyl or a functional group, and Z is O; or the transition metal is Zr, m is 0, n is 1, $R^3$ and $R^4$ are hydrogen, Y is $CR^{11}R^{12}$, $R^{11}$ is hydrocarbyl or substituted hydrocarbyl, $R^{12}$ is hydrocarbyl, substituted hydrocarbyl or a functional group, and Z is O; or the transition metal is Ni, m is 0, n is 1, $R^3$ and $R^4$ are hydrogen, $R^7$ is hydrocarbyl or substituted hydrocarbyl, Y is $CR^{11}R^{12}$, $R^{11}$ is hydrogen, $R^{12}$ is hydrocarbyl or substituted hydrocarbyl, and Z is N; or the transition metal is Ni, m is 0, n is 1, $R^3$ and $R^4$ are hydrogen, Y is $CR^{11}R^{12}$, $R^{11}$ and $R^{12}$ taken together are oxo, and Z is O; or the transition metal is Ni, m is 0, n is 1, $R^3$ and $R^4$ are hydrogen, $R^7$ is hydrocarbyl or substituted hydrocarbyl, Y is $CR^{11}R^{12}$, $R^{11}$ and $R^{12}$ taken together are oxo, and Z is N; or the transition metal is Ni, m is 0, n is 1, $R^3$ and $R^4$ are hydrogen, Y is S(T), T is =O and Z is O; or the transition metal is Ni, m is 0, n is 1, $R^3$ and $R^4$ are hydrogen, Y is S(T), T is =N-silyl, Z is N and $R^7$ is silyl; or the transition metal is Ni, m is 0, n is 1, $R^3$ and $R^4$ are hydrogen, Y is S(T), T is =O, Z is N, and $R^7$ is hydrocarbyl or substituted hydrocarbyl; or the transition metal is Ni, m is 0, n is 1, $R^3$ and $R^4$ are hydrogen, Y is $CR^{11}R^{12}$, $R^{11}$ and $R^{12}$ taken together are a ring and Z is O; or the transition metal is Ni, m is 0, n is 1, $R^3$ and $R^4$ are hydrogen, Y is $CR^1R^{12}$, $R^{11}$ and $R^{12}$ taken together are N-hydrocarbyl- or N-substituted hydrocarbylimino, Z is N and $R^7$ is hydrocarbyl or substituted hydrocarbyl; or the transition metal is Ni, m is 0, n is 1, $R^3$ and $R^4$ are hydrogen, Y is S(T), T is =O and Z is O; or the transition metal is Ni, m is 0, n is 1, $R^3$ and $R^4$ are hydrogen, Y is $CR^{11}R^{12}$, $R^{11}$ and $R^{12}$ taken together are sulfo, Z is N and $R^7$ is hydrocarbyl or substituted hydrocarbyl.

5. A process for the polymerization of olefins, comprising the step of contacting, at a temperature of about −100° C. to about +200° C., at least one polymerizable olefin with a compound of the formula (IV), (V) or (XIII)

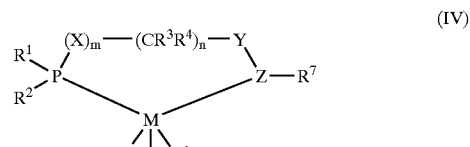

(IV)

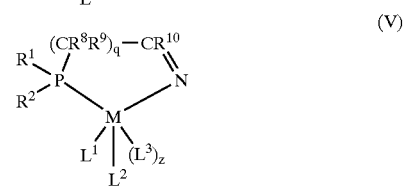

(V)

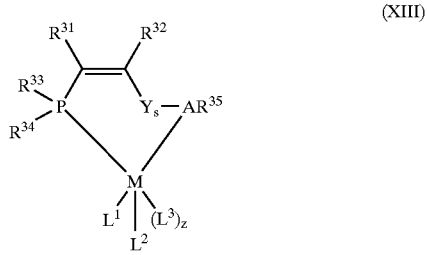

(XIII)

wherein:

$R^1$ and $R^2$ are each independently hydrocarbyl, substituted hydrocarbyl or a functional group;

Y is $CR^{11}R^{12}$, S(T), P(T)Q, $NR^{36}$ or $NR^{36}NR^{36}$;

X is O, $CR^5R^6$ or $NR^5$;

A is O, S, Se, N, P or As;

Z is O, Se, N, P or As;

each Q is independently hydrocarbyl or substituted hydrocarbyl;

$R^3$, $R^4$, $R^5$, $R^6$, $R^{11}$ and $R^{12}$ are each independently hydrogen, hydrocarbyl, substituted hydrocarbyl or a functional group;

$R^7$ is hydrogen, hydrocarbyl, substituted hydrocarbyl or a functional group, provided that when Z is O or Se, $R^7$ is not present;

$R^8$ and $R^9$ are each independently hydrogen, hydrocarbyl, substituted hydrocarbyl or a functional group;

$R^{10}$ is hydrogen, hydrocarbyl, substituted hydrocarbyl or a functional group;

each T is independently =O or =$NR^{30}$;

$R^{30}$ is hydrogen, hydrocarbyl, substituted hydrocarbyl or a functional group;

$R^{31}$ and $R^{32}$ are each independently hydrogen, hydrocarbyl, substituted hydrocarbyl or a functional group;

$R^{33}$ and $R^{34}$ are each independently hydrocarbyl or substituted hydrocarbyl, provided that each is independently an aryl substituted in at least one position vicinal to the free bond of the aryl group, or each independently has an $E_s$ of −1.0 or less;

$R^{35}$ is hydrogen, hydrocarbyl, substituted hydrocarbyl or a functional group, provided that when A is O, S or Se, $R^{35}$ is not present;

each $R^{36}$ is independently hydrogen, hydrocarbyl, substituted hydrocarbyl or a functional group;

m is 0 or 1;

s is 0 or 1;

n is 0 or 1; and q is 0 or 1;

M is a Group 3 through Group 11 transition metal or a lanthanide metal; and $L^1$ is a monodentate monoanionic ligand into which an ethylene molecule may insert between $L^1$ and M, and $L^2$ is a monodentate neutral ligand which may be displaced by ethylene or an empty coordination site, or $L^1$ and $L^2$ taken together are a monoanionic bidentate ligand into which ethylene may insert between said monoanionic bidentate ligand and said nickel atom, and each $L^3$ is independently a monoanionic ligand and z is the oxidation state of M minus 2;

and provided that;

any two of $R^3$, $R^4$, $R^5$, $R^6$, $R^8$, $R^9$, $R^{11}$ and $R^{12}$ bonded to the same carbon atom taken together may form a functional group;

any two of $R^1$, $R^2$, $R^3$, $R^4$, $R^5$, $R^6$, $R^7$, $R^8$, $R^9$, $R^{11}$, $R^{12}$, $R^{31}$, $R^{32}$, $R^{33}$, $R^{34}$, $R^{35}$ and $R^{35}$ bonded to the same atom or vicinal to one another taken together may form a ring; and when said compound is (IV), Y is C(O), Z is O, and $R^1$ and $R^2$ are each independently hydrocarbyl, then $R^1$ and $R^2$ are each independently an aryl substituted in one position vicinal to the free bond of the aryl group, or $R^1$ and $R^2$ each independently have an $E_s$ of −1.0 or less.

6. The process of claim 5, wherein M is Ni, Pd, Pt, Fe, Co, Ti, Zr, V, Hf, Cr or Cu.

7. The process of claim 6, wherein M is Ni, Pd, Ti or Zr.

8. The process of claim 5, wherein the compound is (IV) and:

M is Ni, m is 0, n is 1, $R^3$ and $R^4$ are hydrogen, Y is $CR^{11}R^{12}$, $R^{11}$ is hydrocarbyl or substituted hydrocarbyl, $R^{12}$ is hydrocarbyl, substituted hydrocarbyl or a functional group, and Z is O; or M is Ti, m is 0, n is 1, $R^3$ and $R^4$ are hydrogen, Y is $CR^{11}R^{12}$, $R^{11}$ is hydrocarbyl or substituted hydrocarbyl, $R^{12}$ is hydrocarbyl, substituted hydrocarbyl or a functional group, and Z is O; or M is Zr, m is 0, n is 1, $R^3$ and $R^4$ are hydrogen, Y is $CR^{11}R^{12}$, $R^{11}$ is hydrocarbyl or substituted hydrocarbyl, $R^{12}$ is hydrocarbyl, substituted hydrocarbyl or a functional group, and Z is O; or M is Ni, m is 0, n is 1, $R^3$ and $R^4$ are hydrogen, $R^7$ is hydrocarbyl or substituted hydrocarbyl, Y is $CR^{11}R^{12}$, $R^{11}$ is hydrogen, $R^{12}$ is hydrocarbyl or substituted hydrocarbyl, and Z is N; or M is Ni, m is 0, n is 1, $R^3$ and $R^4$ are hydrogen, Y is $CR^{11}R^{12}$, $R^{11}$ and $R^{12}$ taken together are oxo, and Z is O; or M is Ni, m is 0, n is 1, $R^3$ and $R^4$ are hydrogen, $R^7$ is hydrocarbyl or substituted hydrocarbyl, Y is $CR^{11}R^{12}$, $R^{11}$ and $R^{12}$ taken together are oxo, and Z is N; or M is Ni, m is 0, n is 1, $R^3$ and $R^4$ are hydrogen, Y is S(T), T is =O and Z is O; or M is Ni, m is 0, n is 1, $R^3$ and $R^4$ are hydrogen, Y is S(T), T is =N-silyl, Z is N and $R^7$ is silyl; or M is Ni, m is 0, n is 1, $R^3$ and $R^4$ are hydrogen, Y is S(T), T is =O, Z is N, and $R^7$ is hydrocarbyl or substituted hydrocarbyl; or M is Ni, m is 0, n is 1, $R^3$ and $R^4$ are hydrogen, Y is $CR^{11}R^{12}$, $R^{11}$ and $R^{12}$ taken together are a ring and Z is O; or M is Ni, m is 0, n is 1, $R^3$ and $R^4$ are hydrogen, Y is $CR^{11}R^{12}$, $R^{11}$ and $R^{12}$ taken together are N-hydrocarbyl- or N-substituted hydrocarbylimino, Z is N and $R^7$ is hydrocarbyl or substituted hydrocarbyl; or M is Ni, m is 0, n is 1, $R^3$ and $R^4$ are hydrogen, Y is S(T), T is =O and Z is O; or the transition metal is Ni, m is 0, n is 1, $R^3$ and $R^4$ are hydrogen, Y is $CR^{11}R^{12}$, $R^{11}$ and $R^{12}$ taken together are sulfo, Z is N and $R^7$ is hydrocarbyl or substituted hydrocarbyl.

* * * * *